US011459548B2

(12) United States Patent
Boer et al.

(10) Patent No.: US 11,459,548 B2
(45) **Date of Patent: *Oct. 4, 2022**

(54) UDP-GLYCOSYLTRANSFERASES

(71) Applicant: DSM IP ASSETS B.V., Heerlen (NL)

(72) Inventors: Viktor Marius Boer, Echt (NL); Johannes Gustaaf Ernst Van Leeuwen, Echt (NL); Priscilla Zwartjens, Echt (NL); Catharina Petronella Antonia Maria Kolen, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/159,962

(22) Filed: Jan. 27, 2021

(65) Prior Publication Data

US 2021/0147815 A1 May 20, 2021

Related U.S. Application Data

(60) Continuation of application No. 16/777,427, filed on Jan. 30, 2020, now Pat. No. 10,947,515, which is a (Continued)

(51) Int. Cl.
*C12N 1/14* (2006.01)
*C12N 1/16* (2006.01)
(Continued)

(52) U.S. Cl.
CPC .............. *C12N 9/1048* (2013.01); *A23L 2/60* (2013.01); *A23L 27/36* (2016.08); *C12N 1/14* (2013.01);
(Continued)

(58) Field of Classification Search
None
See application file for complete search history.

(56) References Cited

U.S. PATENT DOCUMENTS 4,590,160 A 5/1986 Nishihashi et al.
5,204,253 A 4/1993 Sanford et al.
(Continued)

FOREIGN PATENT DOCUMENTS

CN 101720910 A 6/2010
CN 102216313 A 10/2011
(Continued)

OTHER PUBLICATIONS

Flores et al., "Permeabilization of yeast cells (*Kluyveromyces lactis*) with organic solvents," Enzyme Microb Technol. 16(4):340-6 (1994).
(Continued)

*Primary Examiner* — Richard C Ekstrom
(74) *Attorney, Agent, or Firm* — McBee Moore & Vanik IP, LLC; Susan McBee; Chester Moore

(57) ABSTRACT

The present invention relates to a recombinant host comprising a recombinant nucleic acid sequence encoding a polypeptide having at least about: a. 85% identity to the amino acid sequence set forth in SEQ ID NO: 1; b. 85% identity to the amino acid sequence set forth in SEQ ID NO: 3; c. 85% identity to the amino acid sequence set forth in SEQ ID NO: 6; d. 85% identity to the amino acid sequence set forth in SEQ ID NO: 9; e. 85% identity to the amino acid sequence set forth in SEQ ID NO: 11; f. 85% identity to the amino acid sequence set forth in SEQ ID NO: 14; g. 85% identity to the amino acid sequence set forth in SEQ ID NO: 17; h. 85% identity to the amino acid sequence set forth in SEQ ID NO: 20; i. 85% identity to the amino acid sequence set forth in SEQ ID NO: 22; or j. 85% identity to the amino acid sequence set forth in SEQ ID NO: 25.

34 Claims, 32 Drawing Sheets

Specification includes a Sequence Listing.

Related U.S. Application Data division of application No. 15/558,133, filed as application No. PCT/EP2016/055734 on Mar. 16, 2016, now Pat. No. 10,604,743.

(60) Provisional application No. 62/133,606, filed on Mar. 16, 2015.

(51) Int. Cl.

| | |
|---|---|
| ***C12N 1/20*** | (2006.01) |
| ***C12N 15/52*** | (2006.01) |
| ***C12N 15/63*** | (2006.01) |
| ***C12P 5/00*** | (2006.01) |
| ***C12P 19/56*** | (2006.01) |
| ***C12N 9/10*** | (2006.01) |
| ***A23L 27/30*** | (2016.01) |
| ***A23L 2/60*** | (2006.01) |

(52) U.S. Cl.

CPC ................. *C12N 1/16* (2013.01); *C12N 1/20* (2013.01); *C12N 9/1051* (2013.01); *C12N 15/52* (2013.01); *C12N 15/63* (2013.01); *C12P 5/007* (2013.01); *C12P 19/56* (2013.01); *C12Y 204/01017* (2013.01)

(56) References Cited

U.S. PATENT DOCUMENTS 5,306,862 A 4/1994 Chappell et al.
5,460,949 A 10/1995 Saunders et al.
5,538,880 A 7/1996 Lundquist et al.
5,876,988 A 3/1999 Selten et al.
6,013,863 A 1/2000 Lundquist et al.
6,215,051 B1 4/2001 Yu et al.
6,255,557 B1 7/2001 Brandle
6,284,493 B1 9/2001 Roth
6,284,506 B1 9/2001 Hoshino et al.
6,329,571 B1 12/2001 Hiei
6,432,672 B1 8/2002 Selten et al.
6,586,202 B2 6/2003 Hoshino et al.
6,660,507 B2 12/2003 Cheng et al.
6,806,076 B1 10/2004 Miyake et al.
6,969,595 B2 11/2005 Brzostowicz et al.
7,034,140 B2 4/2006 Bramucci et al.
7,056,717 B2 6/2006 Cheng et al.
7,098,000 B2 8/2006 Cheng et al.
7,129,392 B2 10/2006 Hahn et al.
7,132,268 B2 11/2006 Miyake et al.
7,172,886 B2 2/2007 Keasling et al.
7,183,089 B2 2/2007 Keasling et al.
7,186,891 B1 3/2007 Chappell et al.
7,208,298 B2 4/2007 Miyake et al.
7,335,815 B2 2/2008 Boronat et al.
7,364,885 B2 4/2008 Miyake et al.
7,422,884 B2 9/2008 Bai et al.
7,514,597 B2 4/2009 Nakamura et al.
7,569,389 B2 8/2009 Feldmann et al.
7,622,284 B2 11/2009 Op et al.
7,692,065 B2 4/2010 Harper et al.
7,838,287 B2 11/2010 Goldsmith et al.
7,923,541 B2 4/2011 Yang et al.
7,927,851 B2 4/2011 Brandle et al.
7,943,366 B2 5/2011 Rajgarhia et al.
7,981,647 B2 7/2011 Berry et al.
8,034,591 B2 10/2011 Winkler et al.
8,129,171 B2 3/2012 Boles et al.
9,562,251 B2 2/2017 Hansen et al.
9,738,890 B2 8/2017 Roubos et al.
10,604,743 B2 3/2020 Boer et al.
10,947,515 B2 * 3/2021 Boer ........................ C12N 1/20
2002/0142408 A1 10/2002 Dicosimo et al.
2003/0033626 A1 2/2003 Hahn et al.
2003/0148416 A1 8/2003 Berry et al.
2003/0148479 A1 8/2003 Keasling et al.
2003/0190734 A1 10/2003 Hoshino et al.
2003/0219798 A1 11/2003 Gokarn et al.
2004/0010815 A1 1/2004 Lange et al.
2004/0072311 A1 4/2004 Dicosimo et al.
2004/0078846 A1 4/2004 Desouza et al.
2004/0176570 A1 9/2004 Bacher et al.
2004/0194162 A1 9/2004 Hahn et al.
2005/0003474 A1 1/2005 Desouza et al.
2005/0032169 A1 2/2005 Miyake et al.
2005/0142648 A1 6/2005 Boles et al.
2006/0014264 A1 1/2006 Sauer et al.
2006/0079476 A1 4/2006 Keasling et al.
2006/0083838 A1 4/2006 Jackson et al.
2006/0127972 A1 6/2006 Nieboer et al.
2007/0004000 A1 1/2007 Miyake et al.
2007/0077616 A1 4/2007 Keasling et al.
2007/0099261 A1 5/2007 Keasling et al.
2007/0118916 A1 5/2007 Puzio et al.
2007/0128311 A1 6/2007 Prakash et al.
2007/0166782 A1 7/2007 Keasling et al.
2007/0202579 A1 8/2007 Berry et al.
2007/0238157 A1 10/2007 Millis et al.
2007/0238159 A1 10/2007 Millis et al.
2007/0238160 A1 10/2007 Millis et al.
2007/0254354 A1 10/2007 Millis et al.
2007/0269857 A1 11/2007 Miyake et al.
2007/0286850 A1 12/2007 Bai et al.
2008/0064063 A1 3/2008 Brandle et al.
2008/0081358 A1 4/2008 Viitanen et al.
2008/0131926 A1 6/2008 Miyake et al.
2008/0261280 A1 10/2008 Hahn et al.
2008/0271205 A1 10/2008 Yamaguchi et al.
2008/0286870 A1 11/2008 Viitanen et al.
2008/0292775 A1 11/2008 Prakash et al.
2008/0318227 A1 12/2008 Bacher et al.
2009/0004724 A1 1/2009 Keasling et al.
2009/0047718 A1 2/2009 Blaschek et al.
2009/0055974 A1 2/2009 Tanksley et al.
2009/0074935 A1 3/2009 Lee
2009/0143308 A1 6/2009 Monk et al.
2009/0286262 A1 11/2009 Slack
2010/0112156 A1 5/2010 Abelyan et al.
2010/0120096 A1 5/2010 Kitaoka et al.
2010/0221801 A1 9/2010 Van Dyk
2010/0297722 A1 11/2010 Anterola et al.
2010/0316782 A1 12/2010 Shi et al.
2011/0087011 A1 4/2011 Chiang et al.
2011/0092684 A1 4/2011 Abelyan et al.
2011/0126318 A1 5/2011 Allen et al.
2011/0160311 A1 6/2011 Prakash et al.
2012/0021111 A1 1/2012 Pfister et al.
2012/0083593 A1 4/2012 Liu et al.
2012/0164678 A1 6/2012 Stephanopoulos et al.
2012/0178169 A1 7/2012 Voytas et al.
2013/0076280 A1 3/2013 Yoo
2013/0137138 A1 5/2013 Hansen
2014/0303036 A1 10/2014 Roubos et al.
2014/0329281 A1 11/2014 Houghton-Larsen et al.
2014/0357588 A1 12/2014 Markosyan et al.
2015/0031868 A1 1/2015 Lehmann et al.
2015/0037892 A1 2/2015 Wiessenhaan et al.
2015/0128306 A1 5/2015 Ono
2015/0159188 A1 6/2015 Ono et al.
2015/0218533 A1 8/2015 Ono
2015/0252401 A1 9/2015 Wang et al.
2015/0342234 A1 12/2015 Hicks et al.
2016/0010133 A1 1/2016 Park et al.
2016/0102331 A1 4/2016 Boer et al.
2016/0153017 A1 6/2016 Van Der Hoeven et al.
2016/0177360 A1 6/2016 Boer et al.
2016/0186225 A1 6/2016 Mikkelsen et al.
2016/0213039 A1 7/2016 Kumar et al.
2016/0251635 A1 9/2016 Mao et al.
2017/0218419 A1 8/2017 Kishore et al.
2017/0275666 A1 9/2017 Prakash et al.
2017/0314011 A1 11/2017 Roubos et al.
2017/0332673 A1 11/2017 Philippe et al.

(56) References Cited

U.S. PATENT DOCUMENTS

| | | | | |
|---|---|---|---|---|
| 2018/0073050 | A1 | 3/2018 | Boer et al. | |
| 2021/0147815 | A1* | 5/2021 | Boer | C12P 19/56 |

FOREIGN PATENT DOCUMENTS

| | | | |
|---|---|---|---|
| CN | 103179850 | A | 6/2013 |
| CN | 103397064 | A | 11/2013 |
| CN | 103732753 | A | 4/2014 |
| CN | 104845990 | A | 8/2015 |
| EP | 0955363 | A2 | 11/1999 |
| EP | 1072683 | A1 | 1/2001 |
| EP | 1171610 | A1 | 1/2002 |
| EP | 1198575 | A1 | 4/2002 |
| EP | 1383864 | A2 | 1/2004 |
| EP | 1392824 | A2 | 3/2004 |
| EP | 1499708 | B1 | 1/2006 |
| EP | 1897951 | A2 | 3/2008 |
| EP | 1947189 | A2 | 7/2008 |
| EP | 2575432 | A1 | 4/2013 |
| EP | 2902410 | A1 | 8/2015 |
| JP | 58-149697 | A | 9/1983 |
| JP | 03-277275 | A | 12/1991 |
| JP | 05-115298 | A | 5/1993 |
| JP | 10-001408 | A | 1/1998 |
| JP | 2009-034080 | A | 2/2009 |
| KR | 2015-0000258 | A | 1/2015 |
| WO | 00/36081 | A2 | 6/2000 |
| WO | 00/37663 | A2 | 6/2000 |
| WO | 00/37671 | A2 | 6/2000 |
| WO | 00/63389 | A1 | 10/2000 |
| WO | 00/63400 | A2 | 10/2000 |
| WO | 01/11055 | A1 | 2/2001 |
| WO | 01/12828 | A1 | 2/2001 |
| WO | 01/83769 | A2 | 11/2001 |
| WO | 01/94561 | A2 | 12/2001 |
| WO | 02/20728 | A2 | 3/2002 |
| WO | 02/20815 | A2 | 3/2002 |
| WO | 02/24865 | A2 | 3/2002 |
| WO | 02/26933 | A2 | 4/2002 |
| WO | 02/55709 | A2 | 7/2002 |
| WO | 02/99095 | A2 | 12/2002 |
| WO | 03/08540 | A2 | 1/2003 |
| WO | 03/062430 | A1 | 7/2003 |
| WO | 2004/029255 | A2 | 4/2004 |
| WO | 2004/099381 | A2 | 11/2004 |
| WO | 2005/079183 | A2 | 8/2005 |
| WO | 2006/009434 | A1 | 1/2006 |
| WO | 2006/016395 | A1 | 2/2006 |
| WO | 2006/093289 | A1 | 9/2006 |
| WO | 2006/096392 | A2 | 9/2006 |
| WO | 2006096130 | A1 | 9/2006 |
| WO | 2007/136847 | A2 | 11/2007 |
| WO | 2008/008256 | A2 | 1/2008 |
| WO | 2008/034648 | A1 | 3/2008 |
| WO | 2008/039499 | A2 | 4/2008 |
| WO | 2008/051349 | A2 | 5/2008 |
| WO | 2008/091547 | A2 | 7/2008 |
| WO | 2009/005704 | A1 | 1/2009 |
| WO | 2009/071277 | A1 | 6/2009 |
| WO | 2009/086049 | A2 | 7/2009 |
| WO | 2009/105612 | A2 | 8/2009 |
| WO | 2009/108680 | A2 | 9/2009 |
| WO | 2009/111513 | A1 | 9/2009 |
| WO | 2009/140394 | A1 | 11/2009 |
| WO | 2010/021001 | A2 | 2/2010 |
| WO | 2010/038911 | A1 | 4/2010 |
| WO | 2010/044960 | A1 | 4/2010 |
| WO | 2010/142305 | A1 | 12/2010 |
| WO | 2010/146463 | A2 | 12/2010 |
| WO | 2011/028671 | A1 | 3/2011 |
| WO | 2011/037959 | A1 | 3/2011 |
| WO | 2011/046423 | A1 | 4/2011 |
| WO | 2011/056834 | A | 5/2011 |
| WO | 2011/060057 | A1 | 5/2011 |
| WO | 2011/140329 | A1 | 11/2011 |
| WO | 2011/151326 | A2 | 12/2011 |
| WO | 2011/153144 | A1 | 12/2011 |
| WO | 2011/153378 | A1 | 12/2011 |
| WO | 2012/075030 | A1 | 6/2012 |
| WO | 2013/007657 | A1 | 1/2013 |
| WO | 2013/019050 | A2 | 2/2013 |
| WO | 2013/021261 | A2 | 2/2013 |
| WO | 2013/022989 | A2 | 2/2013 |
| WO | 2013/076280 | A1 | 5/2013 |
| WO | 2013/076577 | A1 | 5/2013 |
| WO | 2013/096420 | A1 | 6/2013 |
| WO | 2013/102793 | A2 | 7/2013 |
| WO | 2013/110673 | A1 | 8/2013 |
| WO | 2013/135728 | A1 | 9/2013 |
| WO | 2013/144257 | A1 | 10/2013 |
| WO | 2013/176738 | A1 | 11/2013 |
| WO | 2014/086890 | A1 | 6/2014 |
| WO | 2014/122227 | A2 | 8/2014 |
| WO | 2014/122328 | A1 | 8/2014 |
| WO | 2014/191580 | A1 | 12/2014 |
| WO | 2014/191581 | A2 | 12/2014 |
| WO | 2014/193934 | A1 | 12/2014 |
| WO | 2014/195944 | A1 | 12/2014 |
| WO | 2015/007748 | A1 | 1/2015 |
| WO | 2015/011209 | A1 | 1/2015 |
| WO | 2015/014959 | A1 | 2/2015 |
| WO | 2015/014969 | A1 | 2/2015 |
| WO | 2015/016393 | A1 | 2/2015 |
| WO | 2015/028324 | A2 | 3/2015 |
| WO | 2015/051454 | A1 | 4/2015 |
| WO | 2015/132411 | A2 | 9/2015 |
| WO | 2016/023844 | A1 | 2/2016 |
| WO | 2016/038095 | A2 | 3/2016 |
| WO | 2016/120486 | | 8/2016 |
| WO | 2017/025362 | A1 | 2/2017 |

OTHER PUBLICATIONS

Fowler et al., "Effects of Dimethylsulfoxide on the Lactose Operon in *Escherichia coli*," J Bacteriol. 92(2):353-7 (1966).
Freire, "Differential scanning calorimetry," Methods Mol Biol. 40:191-218 (1995).
Fukunaga et al., "Enzymatic transglucosylation products of stevioside: separation and sweetness-evaluation," Agric. Biol. Chem. 53(6):1603-7 (Jan. 1989).
Garber et al., "Computational methods for transcriptome annotation and quantification using RNA-seq," Nat Methods 8(6):469-77 (2011).
GenBank Accession No. AAB62280, dated Jul. 2, 1997 (2 pages).
GenBank Accession No. AAB87091, dated Mar. 22, 2000 (2 pages).
GenBank Accession No. AAC28895.1, dated Aug. 6, 1998 (2 pages).
GenBank Accession No. AAC39505, dated Jul. 26, 1998 (1 page).
GenBank Accession No. AAF61439.1, dated Sep. 25, 2000 (2 pages).
GenBank Accession No. AAM53963.1, dated Jun. 17, 2002 (2 pages).
GenBank Accession No. AAR06912, dated Dec. 28, 2004 (2 pages).
GenBank Accession No. AAS07253.1, dated Jan. 31, 2004 (3 pages).
GenBank Accession No. AAT93110.1, dated Apr. 24, 2007 (2 pages).
GenBank Accession No. ABA42921, dated Jun. 21, 2006 (1 page).
GenBank Accession No. ABC98596, dated Jan. 31, 2014 (2 pages).
GenBank Accession No. ABD60225, dated May 28, 2008 (2 pages).
GenBank Accession No. ABD92926, dated Oct. 10, 2007 (2 pages).
GenBank Accession No. AC133334, dated Jan. 31, 2004 (44 pages).
GenBank Accession No. ACD93722, dated Jun. 10, 2008 (1 page).
GenBank Accession No. ACE87855.1, dated Jun. 24, 2008 (1 page).
GenBank Accession No. ACM47734.1, dated Feb. 7, 2009 (1 page).
GenBank Accession No. ACT33422.1, dated Jul. 17, 2009 (1 page).
GenBank Accession No. AEE36246, dated Oct. 6, 2014 (3 pages).
GenBank Accession No. AF034774, dated Apr. 17, 1998 (2 pages).
GenBank Accession No. AF515727.1, dated Jun. 17, 2002 (2 pages).

(56) References Cited

OTHER PUBLICATIONS

GenBank Accession No. AY345974.1, dated Dec. 28, 2004 (2 pages).
GenBank Accession No. AY345978.1, dated Dec. 28, 2004 (2 pages).
Genbank Accession No. AY345980.1, dated Dec. 28, 2004 (2 pages).
GenBank Accession No. AY345982.1, dated Dec. 28, 2004 (2 pages).
GenBank Accession No. AY562490, dated May 23, 2006 (3 pages).
GenBank Accession No. AZF53544, dated Apr. 14, 2011 (2 pages).
GenBank Accession No. BAA43200, dated Mar. 13, 1999 (2 pages).
GenBank Accession No. BAB59027, dated Jan. 30, 2002 (1 page).
GenBank Accession No. BAF61135, dated May 9, 2007 (2 pages).
GenBank Accession No. BAG30962, dated Nov. 12, 2012 (2 pages).
GenBank Accession No. BC153262, dated Oct. 4, 2007 (3 pages).
GenBank Accession No. BG521726.1, dated May 13, 2000 (2 pages).
GenBank Accession No. CAA23011.1, dated Oct. 23, 2008 (2 pages).
GenBank Accession No. CAA46815.1, dated Apr. 18, 2005 (2 pages).
GenBank Accession No. CAA75568, dated Nov. 14, 2006 (2 pages).
GenBank Accession No. CAA76703, dated Nov. 14, 2006 (1 page).
GenBank Accession No. CAE09055, dated Nov. 14, 2006 (2 pages).
GenBank Accession No. CAG41604, dated Feb. 6, 2015 (2 pages).
GenBank Accession No. DQ269454.4, dated May 28, 2008 (2 pages).
GenBank Accession No. DQ398871.3, dated May 28, 2008 (2 pages).
GenBank Accession No. EDY51667, dated Sep. 2, 2008 (2 pages).
GenBank Accession No. EU263989, dated Jun. 11, 2008 (2 pages).
GenBank Accession No. EU722415.1, dated Jun. 10, 2008 (2 pages).
GenBank Accession No. EU751291.1, dated Jun. 24, 2008 (2 pages).
Orihara et al., "Biotransformation of steviol by cultured cells of eucalyptus perriniana and Coffea Arabica," Phytochemistry 30(12):3989-92 (1991).
Osmani et al., "Catalytic key amino acids and UDP-sugar donor specificity of a plant glucuronosyltransferase, UGT94B1: molecular modeling substantiated by site-specific mutagenesis and biochemical analyses," Plant Phys. 148(3):1295-1308 (2008).
Osmani et al., "Substrate specificity of plant UDP-dependent glycosyltransferases predicted from crystal structures and homology modeling," Phytochemistry 70(3):325-47 (2009).
Paradise et al., "Redirection of flux through the FPP branch-point in *Saccharomyces cerevisiae* by down-regulating squalene synthase," Biotechnol Bioeng. 100(2):371-8 (2008).
Partow et al., "Characterization of different promoters for designing a new expression vector in *Saccharomyces cerevisiae*," Yeast 27:955-64 (2010).
Pearson et al., "Improved tools for biological sequence comparison," Proc Natl Acad Sci. 85(8):2444-8 (1998).
Piirainen et al., "Glycoengineering of yeasts from the perspective of glycosylation efficiency," N Biotechnol. 31(6):532-7 (Dec. 2014).
Pompon et al., "Yeast Expression of Animal and Plant P450s in Optimized Redox Environments," Methods Enzymol 272:51-64 (1996).
Prelich, Gregory, "Gene overexpression: uses, mechanisms, and interpretation," Genetics 190(3):841-54 (Mar. 2012).
Presecki et al., "Production of L-malic acid by permeabilized cells of commercial *Saccharomyces* sp. strains," Biotechnol Lett. 27(23-24):1835-9 (2005).
Prisic et al, "Synergistic substrate inhibition of ent-copalyl diphosphate synthase: a potential feed-forward inhibition mechanism limiting gibberellin metabolism," Plant Physiol. 144(1):445-54 (2007).
Rice et al., EMBOSS: The European Molecular Biology Open Software Suite, Resource Internet, 16(6):276-277 (2000).
Richman et al., "Functional genomics uncovers three glucosyltransferases involved in the synthesis of the major sweet glucosides of Stevia rebaudiana," Plant J. 41(1):56-67 (2005).
Riesmeier et al., "Isolation and characterization of a sucrose carrier cDNA from spinach by functional expression in yeast," EMBO J 11(13):4705-13 (1992).
Ro et al., "Production of the antimalarial drug precursor artemisinic acid in engineered yeast," Nature 440(7086):940-3 (2006).
Robinson et al., "A scaling normalization method for differential expression analysis of RNA-seq data," Genome Bioi. 11(3):R25 (2010).
Rodriguez-Concepcion et al., "Elucidation of the methylerythritol phosphate pathway for isoprenoid biosynthesis in bacteria and plastids. A metabolic milestone achieved through genomics," Plant Physiol. 130(3):1079-89 (2002).
Rudinger et al., "Characteristics of the amino acids as components of a peptide hormone sequence," Peptide Hormones. Biol. Council. pp. 5-7 (1976).
Saenge et al., "Potential use of oleaginous red yeast *Rhodotorula glutinis* for the bioconversion of crude glycerol from biodiesel plant to lipids and carotenoids," Process Biochemistry 46(1):210-8 (Jan. 2011).
Saier et al., "The Transporter Classification Database: recent advances," Nucleic Acids Res. 37:D274-8 (Jan. 2009).
Saier Jr et al., "The major facilitator superfamily," J. Mol. Microbiol. Biotechnol. 1(2):257-79 (Nov. 1999).
Saier Jr. et al., "The transporter classification database," Nucl. Acids Res., 42(1):D251-258 (2014).
Saier, "Families of transmembrane sugar transport proteins," Mol Microbiol., 35(4):699-710 (2000).
Sauer et al., "The soluble and membrane-bound transhydrogenases UdhA and PntAB have divergent functions in NADPH metabolism of *Escherichia coli*," J Biol Chem. 279(8):6613-9 (2004).
Sawada et al., "UDP-glucuronic acid:anthocyanin glucuronosyltransferase from red daisy (*Bellis perennis*) flowers. Enzymology and phylogenetics of a novel glucuronosyltransferase involved in flower pigment biosynthesis," J Biol Chem. 280(2):899-906 (2005).
Schwab et al., Poster, "Watchmaker®—Compound Generation by Combinatorial Genetics and Screening in Yeast," 141st Annual Conference in St. Louis, 2008, 1 page.
Sen et al., "Developments in Directed Evolution for Improving Enzyme Functions," Appl Biochem Biotechnol. 143(3):212-23 (2007).
Senthilraja et al., "RNA secondary structure prediction: Analysis of *Saccharomyces cerevisiae* RNAs," Int. J. Pharm. Rev. Res. 25(2):287-91 (Mar.-Apr. 2014).
Shao et al., "Crystal structures of a multifunctional triterpene/flavonoid glycosyltransferase from Medicago truncatula," Plant Cell 17(11):3141-54 (2005).
Shao et al., "Enhanced production of alpha-galactosyl epitopes by metabolically engineered Pichia pastoris," Appl Environ Microbiol. 69(9):5238-42 (2003).
Shibata et al., "Glucosylation of Steviol and Steviol-Glucosides in Extracts from Stevia rebaudiana Bertoni" Plant Physiol. 95(1):152-56 (1991).
Singh et al., "Compendium of Transgenic Crop Plants: Transgenic Sugar, Tuber and Fiber," Ed. Kole & Hall, Blackwell Publishing Ltd. pp. 97-115 (2008).
Son et al., "Production of flavonoid o-glucoside using sucrose synthase and flavonoid o-glucosyltransferase fusion protein," J Microbiol Biotechnol. 19(7):709-12 (2009).
Song et al., "The Aspergillus fumigatus 1-29 damage resistance protein family coordinately regulates ergosterol biosynthesis and azole susceptibility," MBIO, 7:1-13 (2016).
Sonnhammer et al., "Pfam: a comprehensive database of protein domain families based on seed alignments," Proteins 28(3):405-420 (1997).
Sonnhammer et al., "Pfam: multiple sequence alignments and HMM-profiles of protein domains," Nucleic Acids Res. 26(1):320-2 (1998).
Starratt et al., "Rebaudioside F, a diterpene glycoside from Stevia redaudiana", Phytochemistry, 59(4):367-370. (Feb. 2002). Abstract.

(56) References Cited

OTHER PUBLICATIONS

Sun et al., "Regulation and Function of *Escherichia coli* Sugar Efflux Transporter A (SetA) during Glucose-Phosphate Stress" Journal of Bacteriology, 193(1):143-55 (Jan. 2011).
Tiwari et al., "Plant secondary metabolism linked glycosyltransferases: An update on expaning knowledge and scopes", Biotechnology Advances, 34:714-739 (May 2016).
U.S Food and Drug Administration GRAS Notice Notice 329, "Notice to the U.S. Food and Drug Administration that the use of Rebpure™ (Rebaudioside A) derived from Stevia rebaudiana, as a Food Ingredient is Generally Recognized as Safe (GRAS)," pp. 1-275 (Mar. 2010).
U.S. Food and Drug Administration GRAS Notice 323, "GRAS Assessment of High Purity Steviol Glycosides; Food Usage Conditions for General Recognition of Safety for PureCircle USA, Inc.," pp. 1-262 (Feb. 2010).
UniProt Accession No. B5MEX6, Nov. 4, 2008 (1 page).
UniProt Accession No. E4MW7, Feb. 8, 2011 (1 page).
UniProt Accession No. F2DG34, May 2011 (pp. 1-4).
UniProt Accession No. Q6VAA8, 2004 (pp. 1-6).
UniProt Accession No. Q7FPQ4, 2004 (pp. 1-6).
Unitprot Accession No. Q75183, dated Jul. 22, 2008 (pp. 1-2).
Unitprot Accession No. Q75183, dated Jul. 5, 2004 (pp. 1-4).
Unligil et al., "Glycosyltransferase structure and mechanism," Curr Opin Struct Biol. 10(5):510-7 (2000).
Vazquez De Aldana et al., "Nucleotide sequence of the exo-1,3-beta-glucanase-encoding gene, EXG1, of the yeast *Saccharomyces cerevisiae*," Gene 97(2):173-82 (1991).
Abraham et al., "Permeabilization of baker's yeast with N-lauroyl sarcosine," J Ind Microbial Biotechnol. 35(8):799-804 (2008).
Ageitos et al., "Oily yeasts as oleaginous cell factories," Appl Microbiol Biotechnol. 90(4):1219-27 (May 2011).
Agrawal Pawan K., "NMR spectroscopy in the structural elucidation of oligosaccharides and glycosides," Phytochemistry 31(10):3307-30 (1992).
Ajikumar et al., "Terpenoids: opportunities for biosynthsis of natural product drugs using engineered microorganisms," Molecular Pharmaceuticals 5(2):167-90 (2008).
Alakomi et al., "Lactic acid permeabilizes gram-negative bacteria by disrupting the outer membrane," Appl Environ Microbiol. 66(5):2001-5 (2000).
Ali et al., "Biochemical investigation during different stages of in vitro propagation of Stevia rebaudiana," Pak J Bot. 42(4):2827-37 (2010).
Altschul et al., Basic Local Alignment Search Tool, J. Mol. Biol., 215:403-410 (1990).
Altschul et al., Gapped BLAST and PSI-BLAST: a new generation of protein database search programs, Nucleic Acids Research, 25(17):3389-3402 (1997).
Bankar et al., "Environmental and industrial applications of Yarrowia lipolytica," Appl Microbiol Biotechnol. 84(5):847-65 (Oct. 2009).
Bateman et al., "Pfam 3.1: 1313 multiple alignments and profile HMMs match the majority of proteins," Nucl Acids Res. 27(1):260-2 (1999).
Bay et al., "Diversity and evolution of the small multidrug resistance protein family," BMC Evol. Biol. 9:140 (Jun. 2009).
Baykov et al., "A malachite green procedure for orthophosphate determination and its use in alkaline phosphatase-based enzyme immunoassay," Anal Biochem. 171(2):266-70 (Jun. 1988).
Beopoulos et al., "Yarrowia lipolytica: A model and a tool to understand the mechanisms implicated in lipid accumulation," Biochimie 91(6):692-6 (Jun. 2009).
Brachmann et al., "Designer deletion strains derived from *Saccharomyces cerevisiae* S288C: a useful set of strains and plasmids for PCR-mediated gene disruption and other applications," Yeast 14:115-32 (1998).
Brandle et al., "Leaf ESTs from Stevia rebaudiana: A Resource for Gene Discovery in Diterpene Synthesis," Plant Mol Biol. 50(4-5):613-22 (2002).
Brandle et al., "Steviol glycoside biosynthesis," Phytochemistry 68(14):1855-63 (2007).
Brochado et al. "Improved vanillin production in baker's yeast through in silico design," Microb Cell Fact. 9:84-98 (2010).
Budiman, Muhammad A. et al., "A deep-coverage tomato BAC library and prospects toward development of an STC framework for genome sequencing", Genome Research, Jan. 1, 2000, pp. 129-136, http://www.ncbi.nlm.nih.gov/pubmed/10645957.
Carretero-Paulet et al., "Expression and Molecular Analysis of the *Arabidopsis* DXR Gene Encoding 1-Deoxy-d-Xylulose 5-Phosphate Reductoisomerase, the First Committed Enzyme of the 2-C-Methyl-D-Erythritol 4-Phosphate Pathway," Plant Physiol. 129(4):1581-91 (2002).
Ceunen et al., "Steviol glycosides: chemical diversity, metabolism, and function," J. Nat. Prod. 76(6):1201-28 (Jun. 2013).
Chemler et al., "Biosynthesis of isoprenoids, polyunsaturated fatty acids and flavonoids in *Saccharomyces cerevisiae*," Microb Cell Fact. 5:20 (2006).
Chen et al., "Fusion protein linkers: Property, design, and functionality", Advanced Drug Delivery reviews, 65(0):1257-69 (2013).
Chen et al., "Progress in the Application of Affinity Tags for the Expression and Purification of Recombinant Proteins," China Biotechnology, vol. 32, No. 12, pp. 93-103, Dec. 15, 2012 (English Abstract).
Chen et al., "Sugar transporters for intercellular exchange and nutrition of pathogens," Nature 468(7323):527-32 (2010).
Chen et al., "Transferring a biosynthetic cycle into a productive *Escherichia coli* strain: large-scale synthesis of galactosides," J Am Chem Soc. 123(36):8866-7 (2001).
Chen et al., "MolProbity: all-atom structure validation for macromolecular crystallography," Acta Crystallogr D Biol Crystallogr 66(Pt 1):12-21 (Jan. 2010).
Chen, "Summary on Study of Stevioside," China Pharmacist, vol. 10, No. 6, p. 598-599 (2007).
Chenna et al., "Multiple sequence alignment with the Clustal series of programs," Nucleic Acids Res. 31(13):3497-500 (2003).
Chica et al., "Semi-rational approaches to engineering enzyme activity: combining the benefits of directed evolution and rational design," Curr Opin Biotechnol. 16(4):378-84 (2005).
Chow et al., "Enzyme encapsulation in permeabilized *Saccharomyces cerevisiae* cells," Biotechnol Prog. 20(2):449-56 (2004).
Correa et al., "Genetic mapping of 1,3-beta-glucanase-encoding genes in *Saccharomyces cerevisiae*," Current Genet. 22(4):283-8 (1992).
Daran et al., "Genetic and biochemical characterization of the UGP1 gene encoding the UDP-glucose pyrophosphorylase from *Saccharomyces cerevisiae*," Eur J Biochem. 233(2):520-30 (1995).
Darise et al., "Enzymic Transglucosylation of Rubusoside and the Structure-Sweetness Relationship of Steviol-Bisglycosides," Agric. Biol. Chem. 48(10):2483-8 (Jan. 1984).
Davis et al., "MolProbity: all-atom contacts and structure validation for proteins and nucleic acids," Nucleic Acids Res. 35:W375-83 (Apr. 2007).
Del Sorbo et al., "Fungal transporters involved in efflux of natural toxic compounds and fungicides," Fungal. Genet. Biol. 30(1):1-15 (Jun. 2000).
Diener et al., "*Arabidopsis* ALF5, a multidrug efflux transporter gene family member, confers resistance to toxins," Plant Cell 13(7):1625-38 (Jul. 2001).
Dodhia et al., "Engineering human cytochrome P450 enzymes into catalytically self-sufficient chimeras using molecular Lego," J Biol Inorg Chem. 11(7):903-16 (Oct. 2006).
Dubey, et al., An overview of the non-mevalonate pathway for terpenoid biosynthesis in plants, J. Biosci. 28(5):637-46 (2003).
Dubois et al., "Diterpenoid sweeteners. Synthesis and sensory evaluation of stevioside analogues with improved organoleptic properties," J. Med. Chem. 28(1):93-8 (Jan. 1985).
EBI accession GSP BBR03844, Stevia rebaudiana UGT1 protein, seq 88, Data base accession BBR03844, Jan. 29, 2015.
EBI Accession No. AAY05902, "Jerusalem artichoke in-chain hydroxylase CYP81B1" (1 page), Jun. 15, 2009.
EBI Accession No. ABM86477, "Rice abiotic stress responsive polypeptide SEQ ID No. 4723" (1 page), dated Jun. 2, 2005.

(56) References Cited

OTHER PUBLICATIONS

EBI accession Uniprot K4BW0, Glycosyltransferase, Feb. 4, 2015.
EBI accession Uniprot K4D509_02-2015, Glycosyltransferase, Apr. 2, 2015.
EBI accession Uniprot K4D509_07-2015, Glycosyltransferase, Jul. 22, 2015.
EFSA Panel on Food Additives and Nutrient Sources added to Food (ANS), "Scientific Opinion on the safety of steviol glycosides for the proposed uses as a food additive," EFSA Journal 8(4):1537 (2010).
Eisenreich et al., "Biosynthesis of isoprenoids via the non-mevalonate pathway," Cell Mol Life Sci. 61(12):1401-6 (2004).
EMBOSS Needle results for Alignment of SEQ ID No. 5 of EP'432 and UGT91D1, dated Apr. 4, 2016 (2 pages).
Emmerstorfer et al., "Over-expression of ICE2 stabilizes cytochrome P450 reductase in *Saccharomyces cerevisiae* and Pichia pastoris," Biotechnol J. 10(4):623-35 (Apr. 2015).
Fernandez et al., "Activation of chitin synthetase in permeabilized cells of a *Saccharomyces cerevisiae* mutant Tacking proteinase B," J Bacteriol. 152(3):1255-64 (1982).
Lin et al., "Arrestin-related ubiquitin-ligase adaptors regulate endocytosis and protein turnover at the cell surface," Cell 135(4):714-25 (2008).
Liu et al., "Biosynthesis of Rebaudioside A by Whole Cell of Recombinant *Saccharomyces cerevisiae*," Food and Fermentation Industries, 38(7) : 6-10 (2012) (Abstract translation).
Liu et al., "Functional and biochemical characterization of *Escherichia coli* sugar efflux transporters" Journal of Biological Chemistry, 274(33):22977-84 (Aug. 1999).
Liu et al., "Preparation of high-activity whole cell biocatalysts by permeabilization of recombinant yeasts with alcohol," J Biosci Bioeng. 89(6):554-8 (2000).
Louveau, Thomas et al., "Predicting the substrate specificity of a glycosyltransferase implicated in the production of phenolic volatiles in tomato fruit", Febs Journal, Jan. 17, 2011, pp. 390-400, vol. 278, No. 2.
Ma "Part 1. Molecular Cloning and Functional Analysis of UDPG Glucosyltransferase Gene. Part 2. Molecular Cloning, Sequence Analysis and Evolution of Actin and EF1a Genes in Stevia Rebaudiana." Chinese Doctor and Master Dissertations Full-Text Database, Agricultural Technology Part, vol. 2; pp. 1-74 (2004).
Ma et al., "Molecular cloning and characterization of Stevia Rebaudiana UDP-glucosyltransferase," Acta Biologiae Experimentalis Sinica 36(2):123-9 (2003).
Madan et al., "*Stevia rebaudiana* (Bert.) Bertoni—A Review," Indian Journal of Natural Products and Resources 1(3):267-86 (2010).
Madhav et al., "Functional and structural variation of uridine diphosphate glycosyltransferase (UGT) gene of Stevia rebaudiana—UGTSr involved in the synthesis of rebaudioside A," Plant Physiol. Biochem. 63:245-53 (Feb. 2013).
Mahe et al., "The ATP Binding Cassette Transporters Pdr5 and Snq2 of *Saccharomyces cerevisiae* Can Mediate Transport of Steriods via in Vivo", JBC, 271(41):25167-25172. (Oct. 1996).
Malonek et al., "The NADPH-cytochrome P450 Reductase Gene from Gibberalla fujikuroi is Essential for Gibberellin Biosynthesis," J Bio Chem. 279(24):25075-84 (2004).
Mantovaneli et al., "The effect of temperature and flow rate on the clarification of the aqueous stevia-extract in a fixed-bed column with zeolites," Braz J Chem Eng. 21(3):449-58 (2004).
Mao et al., "Produce steviol glycosides in engineered yeast", 2015 Synthetic Biology: Engineering, Evolution & Design (SEED), Poster Abstract (Jun. 2015).
Martin et al., "Ice2p is important for the distribution and structure of the cortical ER network in *Saccharomyces cerevisiae*," J Cell Sci. 118(Pt 1):65-77 (Oct. 2006).
Masada et al., "An efficient chemoenzymatic production of small molecule glucosides with in situ UDP-glucose recycling," FEBS Lett. 581(13):2562-6 (2007).
Mattanovich et al., "Recombinant protein production in yeasts," Methods Mol Biol. 824:329-58 (2012).
Megeji et al., "Introducing *Stevia rebaudiana*, a natural zero-calorie sweetener," Current Science 88(5):801-4 (2005).
Mikayama et al., "Molecular cloning and functional expression of a cDNA encoding glycosylation-inhibiting factor," Proc Natl Acad Sci U S A. 90(21):10056-60 (1993).
Mohamed et al., "UDP-dependent glycosyltransferases involved in the biosynthesis of steviol glycosides" Journal of Plant Physiology 168(10):1136-1141 (Jul. 2011; Epub Apr. 7, 2011).
Morita et al., "Japanese morning glory dusky mutants displaying reddish-brown or purplish-gray flowers are deficient in a novel glycosylation enzyme for anthocyanin biosynthesis, UDP-glucose:anthocyanidin 3-O-glucoside-2"-O-glucosyltransferase, due to 4-bp insertions in the gene," Plant J. 42(3):353-63 (2005).
Mumberg et al., "Yeast vectors for the controlled expression of heterologous proteins in different genetic backgrounds," Gene 156(1):119-22 (1995).
Naesby et al., "Yeast artificial chromosomes employed for random assembly of biosynthetic pathways and production of diverse compounds in *Saccharomyces cerevisiae*," Microb Cell Fact. 8:45 (2009).
Nagalakshmi et al., "The transcriptional landscape of the yeast genome defined by RNA sequencing," Science 320(5881 ): 1344-9 (2008).
Nagatoshi et al., "UGT75L6 and UGT94E5 mediate sequential glucosylation of crocetin to crocin in Gardenia jasminoides", FEBS Letters, 586:1055-1061 (2012).
Naglak et al., "Rapid protein release from *Escherichia coli* by chemical permeabilization under fermentation conditions," Biotechnol Bioeng. 39(7):732-40 (1991).
Nagy et al., "Role of the yeast ABC transporter Yor1p in cadmium detoxification," Biochimie 88(11):1665-71 (Jun. 2006).
Nakagiri et al., "cDNA cloning, functional expression and characterization of ent-copalyl diphosphate synthase from *Scoparia dulcis* L.," Plant Sci. 169:760-7 (2005).
NCBI Crocetin glucoside Solanum lycopersicum, Crocetin glucoside glucosyltransferase-like [Solanum lycopersicum], Nov. 19, 2014., Accession No. XP_004249995.
NCBI Reference Sequence XP 009770958.1, "Crocetin glucoside glucosyltransferase-like [Nicotiana sylvestris]", Oct. 21, 2014.
NCBI Reference Sequence XP 009795814.1, "Crocetin Glucoside glucosyltransferase-like [Nicotiana sylvestris]", Oct. 21, 2014.
NCBI Reference Sequence XP 009796593.1, "Crocetin glucoside glucosyltransferas-like [Nicotiana sylvestris]", Oct. 21, 2014.
Nelson et al., "P450 superfamily: update on new sequences, gene mapping, accession numbers and nomenclature," Pharmacogenetics 6:1-42 (1996).
Newman et al., "High-level production of amorpha-4,11-diene in a two-phase partitioning bioreactor of metabolically engineered *Escherichia coli*," Biotechnol Bioeng 95(4):684-91 (2006).
Ni et al., "Outer membrane mutation effects on UDP-glucose permeability and whole-cell catalysis rate," Appl Microbiol Biotechnol. 73(2):384-93 (2006).
Nicaud, "Yarrowia lipolytica," Yeast 29(10):409-18 (Oct. 2012).
Nielsen et al., "Efficient PCR-based gene targeting with a recyclable marker for Aspergillus nidulans," Fungal Genet Biol. 43(1):54-64 (2006).
Nikaido et al., "Mechanisms of RND multidrug efflux pumps," Biochim. Biophys. Acta. 1794(5):769-81 (May 2009).
Nikko et al. "Arrestin-like proteins mediate ubiquitination and endocytosis of the yeast metal transporter Smf1," EMBO Rep. 9(12):1216-21 (2008).
Nikko et al., "Arrestin-mediated endocytosis of yeast plasma membrane transporters," Traffic 10(12):1856-67 (2009).
Nour-Eldin et al., "USER cloning and USER fusion: the ideal cloning techniques for small and big laboratories," Methods Mol Biol. 643:185-200 (2010).
Office Action received for European Application No. 16710728, dated Aug. 14, 2018, 11 pages.
Ohta et al., "Characterization of Novel Steviol Glycosides from Leaves of Stevia rebaudiana Morita," J. Applied Glycosides 57(3):199-209 (Mar. 2010).

(56) References Cited

OTHER PUBLICATIONS

Ohta et al., MassBank Accession No. FU000299 (May 2016).
Ohta et al., MassBank Accession No. FU000332 (May 2016).
Ohta et al., MassBank Accession No. FU000341 (May 2011).
Ohta et al., MassBank Accession No. FU000342 (May 2011).
Ohta et al., MassBank Accession No. FU000343 (May 2011).
Ohtani et al., "Further Study on the 1,4-alpha-Transglucosylation of Rubusoside, a Sweet Steviol-Bisglucoside from Rubus suavissimus," Agric Biol Chem. 55(2):449-53 (1991).
Oka et al., "Reconstruction of de novo pathway for synthesis of UDP-glucuronic acid and UDP-xylose from intrinsic UDP-glucose in *Saccharomyces cerevisiae*," FEBS J. 273(12):2645-57 (2006).
Ooyen et al., "Heterologous protein production in the yeast *Kluyveromyces lactis*," FEMS Yeast Res. 6(3):381-92 (May 2006).
GenBank Accession No. NM_116512, dated Jan. 22, 2014 (3 pages).
GenBank Accession No. NP_001105097, dated Aug. 4, 2015 (2 pages).
GenBank Accession No. NP_013636.1 (YML075C), dated Jul. 16, 2015 (3 pages).
GenBank Accession No. NP_194183, dated Jan. 22, 2014 (4 pages).
GenBank Accession No. NP_195399, dated Jan. 22, 2014 (3 pages).
GenBank Accession No. NP_197872.1, dated Jan. 22, 2014 (2 pages).
GenBank Accession No. Q9UVY5.1, dated Apr. 1, 2015 (3 pages).
GenBank Accession No. XM_001467423, dated Jul. 16, 2015 (2 pages).
GenBank Accession No. XP_002282091, dated Dec. 7, 2011 (1 page).
GenBank Accession No. XP_002288339, dated Jul. 15, 2009 (2 pages).
GenBank Accession No. XP_002311286, dated Dec. 31, 2013 (2 pages).
GenBank Accession No. ZP_05004570, dated Jun. 8, 2010 (2 pages).
Geuns Jan M.C., "Stevioside," Phytochemistry 64(5):913-21 (2003).
Giaever et al., "The yeast deletion collection: a decade of functional genomics," Genetics 197(2):451-65 (Jun. 2014).
Gietz et al., "High-efficiency yeast transformation using the LiAc/SS carrier DNA/PEG method," Nat Protoc. 2(1):31-4 (2007).
Girvan et al., "Flavocytochrome P450 BM3 mutant W1046A is a NADH-dependent fatty acid hydroxylase: implications for the mechanism of electron transfer in the P450 BM3 dimer," Arch Biochem Biophys. 507(1):75-85 (Mar. 2011).
Gloster, Tracey M. "Advances in understanding glycosyltransferases from a structural perspective," Curr Opin Struct Biol. 28:131-41 (2014).
Goralczyk, "Compounds from Stevia for Improving and Maintaining Mental Performance," Stevia World Forum, Feb. 24-25, 2010, 17 pages.
Gossen et al., "Studying gene function in eukaryotes by conditional gene inactivation," Ann Rev Genet. 36:153-73 (2002).
Gritz et al., "Plasmid-encoded hygromycin B resistance: the sequence of hygromycin B phosphotransferase gene and its expression in *Escherichia coli* and *Saccharomyces cerevisiae*," Gene 25(2-3):179-88 (Nov. 1983).
Gunel et al., "Metabolic Engineering for Production of Geranylgeranyl Pyrophosphate Synthase in Non-Carotenogenic Yeast *Schizosaccharomyces pombe*," Biotechnol. & Biotechnol. Eq. 20(3):76-82 (2006).
Guo et al., "Protein tolerance to random amino acid change", Proceedings of the National Academy of Sciences USA, vol. 101, No. 25, pp. 9205-9210 (2004).
Hallstrom et al., "Divergent transcriptional control of multidrug resistance genes in *Saccharomyces cerevisiae*," J. Biol. Chem. 273(4):2098-104 (Jan. 1998).
Hansen et al., "De novo biosynthesis of vanillin in fission yeast (*Schizosaccharomyces pombe*) and baker's yeast (*Saccharomyces cerevisiae*)," Appl Environ Microbiol. 75(9):2765-74 (2009).
Hansen et al., "Versatile Enzyme Expression and Characterization System for Aspergillus nidulans, with the Penicillium brevicompactum Polyketide Synthase Gene from the Mycophenolic Acid Gene Cluster as a Test Case," Appl Environ Microbiol. 77(9):3044-51 (2011).
Hellfritsch et al., "Human psychometric and taste receptor responses to steviol glycosides," J. Agric. Food Chem. 60(27):6782-93 (Jul. 2012).
Humphrey et al., "Spatial organisation of four enzymes from Stevia rebaudiana that are involved in steviol glycoside synthesis," Plant Mol Bio. 61(1-2):47-62 (2006).
Husar et al., Overexpression of the UGT73C6 alters brassinosteriod glucoside formation in *Arabidopsis thaliana*, BMC Plant Biology, 11:1-14 (2011).
Iandolino et al., " High-Quality RNA, cDNA, and Derived EST Libraries From Grapevine (*Vitis vinifera* L.)," Plant Mol Biol Reporter 22:269-78 (2004).
International Preliminary Report on Patentability received for PCT Patent Application No. PCT/EP2016/055734, dated Sep. 28, 2017, 18 pages.
International Search Report and Written Opinion received for PCT Patent Application No. PCT/EP2016/055734, dated Aug. 23, 2016, 26 pages.
Irmler et al., "Indole alkaloid biosynthesis in Catharanthus roseus: new enzyme activities and identification of cytochrome P450 CYP72A1 as secologanin synthase," Plant J. 24(6):797-804 (2000).
Jennewein et al., "Taxol biosythesis: baxane 13 alpha-hydroxylase is a cytochrome P450-dependent monooxygenase," Proc Natl Acad Sci U S A 98(24):13595-600 (2001).
Jewett et al. "An integrated cell-free metabolic platform for protein production and synthetic biology," Mol Syst Biol. 4:220 (2008).
Johnstone et al., "Cloning an Aspergillus nidulans developmental gene by transformation," EMBO J. 4(5):1307-11 (1985).
Katzmann et al., "Expression of an ATP-binding cassette transporter-encoding gene (YOR1) is required for oligomycin resistance in *Saccharomyces cerevisiae*," Mol. Cell Biol. 15(12):6875-83 (Dec. 1995).
Kawai et al., "Transformation of *Saccharomyces cerevisiae* and other fungi: methods and possible underlying mechanism," Bioeng Bugs. 1(6):395-403 (2010).
Khan et al., "Physical and chemical mutagenesis in Stevia rebaudiana: variant generation with higher UGT expression and glycosidic profile but with low photosynthetic capabilities," Acta Physiologiae Plantarum 38(1) (2016).
Khoury et al., "Computational design of Candida boidinii xylose reductase for altered cofactor specificity," Protein Sci. 18(10):2125-38 (Oct. 2009).
Kim et al., ""Hydroxylation of ent-Kaurenoic Acid to Steviol in Stevia rebaudiana Bertoni—Purification and Partial Characterization of the Enzyme,"" Arch Biochem Biophys. 332(2):223-30 (1996).
Kim et al., "Characterization of ent-kaurenoic acid 13-hydroxylase in steviol biosynthesis of Stevia rebaudiana Bertoni," Journal of the Korean Agriculturalchemical Society 40(6):501-7 (1997).
Knowles et al., "Genetic Transformation and Plant Regeneration in Stevia rebaudiana Using Microprojectile Bombardment," In Vitro Cellular & Developmental Biology 39(abstract):23-A (2003).
Kohda et al., "New Sweet Diterpene glucoside from Stevia Rebaudiana," Phytochemistry 15(6):981-3 (1976).
Kondo et al., "Preparation of high activity whole cell biocatalyst by permeabilization of recombinant flocculent yeast with alcohol," Enzyme Microb Technol. 27(10),806-11 (2000).
Kumar et al., "A comprehensive analysis of fifteen genes of steviol glycosides biosynthesis pathway in *Stevia rebaudiana* (Bertoni)," Gene 492:276-84 (Epub Oct. 20, 2011).
Kusama et al., "Transglucosylation into stevioside by the enzyme system from *Streptomyces* sp.," Agric. Biol. Chem. 50(10):2445-51 (Oct. 1986).
Li et al., "Crystal structure of Medicago truncatula UGT85H2—insights into the structural basis of a multifunctional (iso)flavonoid glycosyltransferase," J Mol Biol. 370(5):951-63 (2007).

(56) References Cited

OTHER PUBLICATIONS

Li et al., "Phylogenetic analysis of the UDP-glycosyltransferase multigene family of *Arabidopsis thaliana*," J Biol Chem. 276(6):4338-43 (2001).
Li et al., "Systematic Mutational Analysis of Peptide Inhibition of the p53-MDM2/MDMX," J Mol Biol. 398(2):200-13 (2010).
Li et al., "High-density cultivation of oleaginous yeast *Rhodosporidium toruloides* Y4 in fed-batch culture," Enzyme and Microbial Technology 41(3):312-7 (Aug. 2007).
Verwaal et al., "High-Level Production of Beta-Carotene in *Saccharomyces cerevisiae* by Successive Transformation with Carotenogenic Genes from Xanthophyllomyces dendrorhous," Appl Environ Microbiol. 73(13):4342-50 (2007).
Wallin, "Steviol Glycosides," Chem. Tech Assessment—63rd JECFA, pp. 1-5 (2004).
Wallin, "Steviol Glycosides," Chem. Tech Assessment—69th JECFA, pp. 1-7 (2007).
Wallner et al., "Can correct protein models be identified?," Protein Sci. 12(5):1073-86 (May 2003).
Wanchao et al., "Advances on the Steviol Glycoside Biosynthesis and Its Key Enzymes," Biotechnology Bulletin, Feb. 2008 (English Abstract Translation).
Wang et al., "Efficient enzymatic production of rebaudioside A from stevioside", Bioscience, Biotechnology, and Biochemistry, 80:67-73 (Aug. 2015).
Wang et al., "Characterics of the tomato nuclear genome as determined by sequencing undermethylated EcoRI digested fragments," Theoretical and Applied Genetics, 112(1):72-84 (2005).
Wang et al., "Design and construction of artificial biological systems for complex natural products biosynthesis," Chinese Journal of Biotechnology, 29(8):1146-60 (2013).
Wang et al., "Pathway mining-based integration of critical enzyme parts for de novo biosynthesis of steviolglycoside sweetener in *Escherichia coli*", Cell Research, 26:258-261 (Sep. 2015).
Wang et al., "RNA-Seq: a revolutionary tool for transcriptomics," Nat Rev Genet. 10(1):57-63 (2009).
Wang, "Structure, mechanism and engineering of plant natural product glycosyltransferases," FEBS Letters 583(20):3303-9 (2009).
Warth et al., "Hydrophilic interaction liquid chromatography coupled with tandem mass spectrometry for the quantification of uridine diphosphate-glucose, uridine diphosphate-glucuronic acid, deoxynivalenol and its glucoside: In-house validation and application to wheat," Journal of Chromatography A, 1423, pp. 183-189 (2015).
Wilhelm et al., "Defining transcribed regions using RNA-seq," Nature Protocols 5:255-66 (2010).
Xu et al., "Generation of hepatitis B virus PreS2-S antigen in Hansenula polymorpha," Virol Sin. 29(6):403-9 (Dec. 2014).
Yadav et al., "A review on the improvement of stevia [*Stevia rebaudiana* (Bertoni)]," Can J Plant Sci. 91:1-27 (2011).
Yadav et al., "Steviol Glycosides from Stevia: Biosynthesis Pathway Review and their Application in Foods and Medicine.", CritRev. 52(11):988-998 (2012).
Yang et al., Base substitution mutations in uridinediphosphate-dependent glycosyltransferase 76G1 gene of Stevia rebaudiana causes the low levels of rebaudioside A: mutations in UGT76G1, a key gene of steviol glycosides synthesis, Plant Physiol Biochem. 80:220-5 (2014).
Yang Quanhua et.al., "Analysis of the Chemical constituents of Stevia rebaudiana and its sweetness," Journal of Beijing University of Chemical Technology, vol. 39, No. 2., p. 28-32 (2012) (English Abstract).
Yao et al., "A genetic linkage map for Stevia rebaudiana," Genome 42:657-61 (1999).
Yazaki, "ABC transporters involved in the transport of plant secondary metabolites," FEBS Lett. 580(4):1183-91 (Feb. 2006).
Yu et al., "Bioconversion of ethyl 4-chloro-3-oxobutanoate by permeabilized fresh brewer's yeast cells in the presence of allyl bromide," J Ind Microbiol Biotechnol. 34(2)151-6 (2007).
Yuan et al., "Kinetics and activation parameters for oxidations of styrene by Compounds I from the cytochrome P450(BM-3) (CYP102A1) heme domain and from CYP119," Biochemistry 48(38):9140-6 (Sep. 2009).
Zheng et al. "An efficient one-step site-directed and site-saturation mutagenesis protocol," Nucleic Acids Res. 32(14):e115 (Aug. 2004).
Zhu et al., "A multi-omic map of the lipid-producing yeast *Rhodosporidium toruloides*," Nature Commun. 3:1112 (Oct. 2012).
Csernetics et al. "Expression of three isoprenoid biosynthesis genes and their effects on the carotenoid production of the zygomycete *Mucor circinelloides*", Fungal Genetics and Biology, No. 24 (2011) pp. 696-703.
Velayos et al. "Expression of the carG gene, encoding geranylgeranyl pyrophosphate synthase, is up-regulated by blue light in Mucor circinelloides", Curr Genet (2003) vol. 43, pp. 112-120.
Database Geneseq [Online] (Mar. 12, 2015), "S. Rebaudiana Derived Polypeptide (UGT2 4) SEQ:106.", XP-002760405, retrieved from EBI accession No. GSP:BBU04074, Database accession No. BBU04074 L: Sequence information for W02015007748; sequence.
Database Geneseq [Online] (Sep. 12, 2013), "Stevia Rebaudiana UGT2 gene, SEQ: 87.", XP002757289, retrieved from EBI accession No. GSN:BAR69149 Database accession No. BAR69149, L: Sequence Information for W02013/110673; sequence.
Database Geneseq [Online] (Sep. 12, 2013), "Stevia Rebaudiana UGT2 protein, SEQ: 88.", XP002757288, retrieved from EBI accession No. GSP:BAR69150, Database accession No. BAR69150 L: Sequence Information for W02013/110673; sequence.
Database Geneseq [Online] (Apr. 11, 2013), "Stevia rebaudiana UGT 91d2e polypeptide, SEQ ID:5.", XP002757294, retrieved from EBI accession No. GSP:BAK52046, Database accession No. BAK52046 L: Sequence Information for W02013/022989; sequence.
Database Geneseq [Online] (Jan. 29, 2015), "Stevia rebaudiana UDP-glycosyltransferase (UGT) protein (UGT2 la) SEQ 88.", XP002757290, retrieved from EBI accession No. GSP:BBQ97923 Database accession No. BBQ97923 L: Sequence Information for W02014/191580; sequence.
Database Geneseq [Online] (Jan. 29, 2015), "S. rebaudiana UDP-glycosyltransferase (UGT) protein (UGT2 lb), SEQ 100.", XP002757291, retrieved from EBI accession No. GSP:BBQ97935, Database accession No. BBQ97935 L: Sequence Information for W02014/191580; sequence.
Database Geneseq [Online] (Jan. 29, 2015), "Stevia rebaudiana UGT2 protein, SEQ: 88.", XP002757293, retrieved from EBI accession No. GSP:BBR03844 Database accession No. BBR03844 L: Sequence Information for W02014/191581; sequence.
Database Geneseq [Online] (Mar. 26, 2015), "Stevia rebaudiana UDP-glycosyltransferase (UGT) protein, SEQ ID 100.", XP002757292, retrieved from EBI accession No. GSP:BBU39053 Database accession No. BBU39053 L: Sequence Information for W02015/014969; sequence.
Praveen Guleria et al: "Insights into Steviol Glycoside Biosynthesis Pathway Enzymes Through Structural Homology Modeling", American Journal of Biochemistry and Molecular Biology, vol. 3, No. 1, (Oct. 4, 2012), pp. 1-19, XP055270235.
Praveen Guleria et al: "Agrobacterium Mediated Transient Gene Silencing (AMTS) in Stevia rebaudiana: Insights into Steviol Glycoside Biosynthesis Pathway", PLOS One, vol. 8, No. 9, (Sep. 4, 2013), p. e74731, XP055269932.
Gueldener, Ulrich et al., "A new efficient gene disruption cassette for repeated use in budding yeast", Nucleic Acids Research, 1996, pp. 2519-2524, vol. 24, No. 13.
Lambert, Jolanda M. et al., "Cre-lox-Based System for Multiple Gene Deletions and Selectable-Marker Removal in Lactobacillus plantarum", Applied and Environmental Microbiology, Feb. 2007, pp. 1126-1135, vol. 73, No. 4.
Wang, Jun et al., "Glycosylation and Glycosyltransferase of Small Molecular Compounds of Plant", China Academic Journal Electronic Publishing House, Oct. 2008, pp. 997-1003, vol. 44, No. 5.
"Predicted: Solanum lycopersicum beta-D-glucosyl crocetin beta-1,6-glucosyltransferase (LOC101260725), mRNA", NCIB, Aug. 8, 2018, pp. 1-2, XM_004238649.2.

* cited by examiner

SEQUENCE LISTING

```
<160> NUMBER OF SEQ ID NOS: 84

<210> SEQ ID NO 1
<211> LENGTH: 473
<212> TYPE: PRT
<213> ORGANISM: Artificial sequence
<220> FEATURE:
<223> OTHER INFORMATION: UGT2_1b variant

<400> SEQUENCE: 1

Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Gln
            20                  25                  30

Leu Ala Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Phe Val Lys Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Leu Ala Ser Asp Gly Leu Gln Glu Pro Leu Thr Arg Phe Leu Glu Ser
            100                 105                 110

Ser Ser Pro Asp Trp Ile Ile Tyr Asp Tyr Thr His Tyr Trp Leu Pro
        115                 120                 125

Glu Ile Ala Ala Ser Leu Gly Val Ala Arg Ala His Phe Ser Val Thr
    130                 135                 140

Thr Pro Trp Ala Leu Ala Phe Met Gly Pro Ser Ala Asp Ala Met Ile
145                 150                 155                 160

Asn Gly Ser Asp Gly Arg Thr Glu Val Glu Asp Phe Thr Val Pro Pro
                165                 170                 175

Lys Trp Ile Pro Phe Pro Thr Thr Val Ala Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Cys Asp Cys Leu Leu Ser Arg Thr Tyr
    210                 215                 220

His Glu Phe Gly Thr Gln Trp Leu Pro Leu Leu Glu Glu Leu His Gln
225                 230                 235                 240

Val Pro Val Val Pro Val Gly Leu Leu Pro Pro Ser Ile Pro Gly Asp
                245                 250                 255

Glu Lys Asp Glu Asn Trp Val Ser Ile Lys Asp Trp Leu Asp Lys Gln
            260                 265                 270

Glu Lys Gly Ser Val Val Tyr Val Ala Leu Gly Ser Glu Val Leu Leu
```

-continued

```
        275                 280                 285

Thr Glu Glu Glu Val Val Glu Leu Ala Leu Gly Leu Glu Leu Ser Gly
    290                 295                 300

Leu Pro Phe Phe Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Gly Gly Phe Val Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Glu Ser Leu Arg Leu Val Val Val Glu Lys Glu Gly Glu Ile Tyr
            420                 425                 430

Arg Glu Lys Ala Arg Glu Met Ser Lys Val Tyr Ser Asp Thr Lys Arg
        435                 440                 445

Glu Lys Glu Tyr Val Asp Gln Phe Val Asp Tyr Leu Glu Lys Asn Ala
    450                 455                 460

Arg Ala Val Ala Ile Asp His Glu Ser
465                 470


<210> SEQ ID NO 2
<211> LENGTH: 1419
<212> TYPE: DNA
<213> ORGANISM: Artificial sequence
<220> FEATURE:
<223> OTHER INFORMATION: UGT2_1b CpO for S. cerevisiae

<400> SEQUENCE: 2

atggccactt ctgactccat cgttgatgac agaaagaagt tgcacatcgt tatgttccca      60

tggttagctt tcggtcacat tatcccatac ttgcaattgg ctaaattgat tgctgaaaag     120

ggtcacaaag tctctttctt gtccaccacc agaaacatcc aaagattatc ttctcacatt     180

tctccattga tcaacttcgt caagttgact ttaccaagag ttcaagaatt gccagaagat     240

gctgaagcta ccaccgatgt ccatccagaa gatatcccat acttgaagtt ggcttctgat     300

ggtttgcaag aaccattgac tagattcttg gaatcttctt ctccagactg gattatctac     360

gactacactc actactggtt accagaaatt gctgcctctt tgggtgttgc tcgtgctcat     420

ttctccgtta ccactccatg ggctttggct ttcatgggtc catctgctga tgctatgatc     480

aacggttctg atggtagaac cgaagtcgaa gacttcaccg ttccaccaaa atggatccca     540

ttcccaacca ctgtcgcttg gagaaagcac gatttggcca gattagttcc atacaaggcc     600

ccaggtatct ctgacggtta cagaatgggt ttagtcttga agggttgtga ctgtttgttg     660

tccagaactt accatgaatt cggtactcaa tggttacctt tgttggaaga attgcaccaa     720

gtcccagttg ttccagttgg tttgttgcct ccttctatcc caggtgacga aaaggacgaa     780

aactgggttt ccatcaagga ctggttagat aagcaagaaa agggttccgt tgtctacgtt     840

gctttgggtt ctgaagtctt gttgactgaa gaagaagttg ttgaattggc tttgggtttg     900

gaattgtccg gtctaccatt tttctgggct tacagaaagc caaagggtcc agctaagtct     960
```

-continued

```
gactctgttg aattgccaga tggtttcgtc gaaagaacca gagacagagg tttggtctgg   1020

acttcctggg ctccacaatt gagaattttg tcccacgaat ctgttggtgg tttcgttacc   1080

cactgtggtt ctggttccat tgtcgaaggt ttgatgttcg gtcacccatt gatcatgttg   1140

ccaatcttcg gtgaccaacc attgaacgct agattattgg aagacaagca agtcggtatt   1200

gaaatcccaa gaaacgaaga agacggttgt ttgaccaagg aatctgttgc cgaatctcta   1260

agattggttg ttgtcgaaaa ggaaggtgaa atctacagag aaaaggctag agaaatgtcc   1320

aaggtttact ctgataccaa gagagaaaag gaatatgtcg accaatttgt tgactacttg   1380

gaaaagaacg ctcgtgccgt tgccattgac cacgaaagc                          1419
```

```
<210> SEQ ID NO 3
<211> LENGTH: 473
<212> TYPE: PRT
<213> ORGANISM: Artificial sequence
<220> FEATURE:
<223> OTHER INFORMATION: UGT2_2b variant

<400> SEQUENCE: 3

Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Gln
            20                  25                  30

Leu Ala Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Phe Val Lys Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125

Ser Ile Ala Thr Lys His Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160

Asn Gly Ser Asp Gly Arg Thr Thr Pro Glu Asp Phe Thr Val Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Cys Asp Cys Leu Leu Ser Arg Thr Tyr
    210                 215                 220

His Glu Phe Gly Thr Gln Trp Leu Pro Leu Leu Glu Glu Leu His Gln
225                 230                 235                 240

Val Pro Val Val Pro Val Gly Leu Leu Pro Pro Ser Ile Pro Gly Asp
                245                 250                 255

Glu Lys Asp Glu Asn Trp Val Ser Ile Lys Asp Trp Leu Asp Lys Gln
            260                 265                 270

Glu Lys Gly Ser Val Val Tyr Val Ala Leu Gly Ser Glu Val Leu Leu
```

-continued

```
        275                 280                 285

Thr Glu Glu Glu Val Val Glu Leu Ala Leu Gly Leu Glu Leu Ser Gly
    290                 295                 300

Leu Pro Phe Phe Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Gly Gly Phe Val Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Gln Arg Asn Glu Glu Asp Gly Cys Leu Thr Lys Glu Ser Val
                405                 410                 415

Ala Glu Ser Leu Arg Leu Val Val Val Glu Lys Glu Gly Glu Ile Tyr
            420                 425                 430

Arg Glu Lys Ala Arg Glu Met Ser Lys Val Tyr Ser Asp Thr Lys Arg
        435                 440                 445

Glu Lys Glu Tyr Val Asp Gln Phe Val Asp Tyr Leu Glu Lys Asn Ala
    450                 455                 460

Arg Ala Val Ala Ile Asp His Glu Ser
465                 470


<210> SEQ ID NO 4
<211> LENGTH: 1419
<212> TYPE: DNA
<213> ORGANISM: Artificial sequence
<220> FEATURE:
<223> OTHER INFORMATION: UGT2_2b CpO for S. cerevisiae

<400> SEQUENCE: 4

atggccactt ctgactccat cgttgatgac agaaagaagt tgcacatcgt tatgttccca     60

tggttagctt tcggtcacat tatcccatac ttgcaattgg ctaaattgat tgctgaaaag    120

ggtcacaaag tctctttctt gtccaccacc agaaacatcc aaagattatc ttctcacatt    180

tctccattga tcaacttcgt caagttgact ttaccaagag ttcaagaatt gccagaagat    240

gctgaagcta ccaccgatgt ccatccagaa gatatcccat acttgaagaa ggcttctgat    300

ggtttgcaac cagaagtcac tgaattcttg gaacaacact ctccagactg gattatctac    360

gactacactc actactggtt accatccatt gctactaagc acggtgtttc tcgtgctcat    420

ttctccgtta ccactccatg ggctattgct tacatgggtc caactgctga tgctatgatc    480

aacggttctg atggtagaac cactccagaa gacttcaccg ttccaccaaa atggttccca    540

ttcccaacca aggtctgttg gagaaagcac gatttggcca gattagttcc atacaaggcc    600

ccaggtatct ctgacggtta cagaatgggt ttagtcttga agggttgtga ctgtttgttg    660

tccagaactt accatgaatt cggtactcaa tggttacctt tgttggaaga attgcaccaa    720

gtcccagttg ttccagttgg tttgttgcct ccttctatcc caggtgacga aaaggacgaa    780

aactgggttt ccatcaagga ctggttagat aagcaagaaa agggttccgt tgtctacgtt    840

gctttgggtt ctgaagtctt gttgactgaa gaagaagttg ttgaattggc tttgggtttg    900

gaattgtccg gtctaccatt tttctgggct tacagaaagc caaagggtcc agctaagtct    960
```

-continued gactctgttg aattgccaga tggtttcgtc gaaagaacca gagacagagg tttggtctgg 1020
acttcctggg ctccacaatt gagaattttg tcccacgaat ctgttggtgg tttcgttacc 1080
cactgtggtt ctggttccat tgtcgaaggt ttgatgttcg gtcacccatt gatcatgttg 1140
ccaatcttcg gtgaccaacc attgaacgct agattattgg aagacaagca agtcggtatt 1200
gaaatccaaa gaaacgaaga agacggttgt ttgaccaagg aatctgttgc cgaatctcta 1260
agattggttg ttgtcgaaaa ggaaggtgaa atctacagag aaaaggctag agaaatgtcc 1320
aaggtttact ctgataccaa gagagaaaag gaatatgtcg accaatttgt tgactacttg 1380
gaaaagaacg ctcgtgccgt tgccattgac cacgaaagc 1419

<210> SEQ ID NO 5
<211> LENGTH: 1419
<212> TYPE: DNA
<213> ORGANISM: Artificial sequence
<220> FEATURE:
<223> OTHER INFORMATION: UGT2_2b CpO for Y. lipolitica

<400> SEQUENCE: 5
atggccacct ccgactccat tgtcgacgac cgaaagaagc tccacattgt catgttcccc 60
tggctcgcct ttggccacat cattccctac ctccagctcg ccaagctcat tgctgagaag 120
ggccacaagg tttctttcct ctccaccacc cgaaacatcc agcgactctc ttcccacatc 180
tctcccctca tcaactttgt caagctcacc ctcccccgag tccaggagct tcccgaggat 240
gctgaggcca ccactgatgt ccaccccgag gacatcccct acctcaagaa ggcttccgac 300
ggtctgcagc ccgaggtcac tgagtttctc gagcagcact ctcccgactg gatcatctac 360
gactacaccc actactggct cccctccatt gccaccaagc acggtgtctc tcgagcccac 420
ttctccgtca ccacccccctg ggccattgct tacatgggtc ccactgccga tgccatgatc 480
aacggttccg acggccgaac cactcccgag gacttcactg tccctcccaa gtggttcccc 540
ttccccacca aggtctgctg gcgaaagcac gatctcgccc gactcgtccc ctacaaggcc 600
cccggtatct ccgacggtta ccgaatgggt ctggtcctca agggctgtga ctgcctcctc 660
tctcgaacct accacgagtt cggcacccag tggctccccc tccttgagga gctgcaccag 720
gtccccgttg tccccgtcgg tctgctccct ccctccatcc ccggtgacga gaaggacgag 780
aactgggttt ccatcaagga ctggctcgac aagcaggaga agggctctgt tgtctacgtt 840
gctctcggct ccgaggttct gctcaccgag gaagaggttg ttgagctggc tctcggtctg 900
gagctgtccg gcctcccctt cttctgggcc taccgaaagc ccaagggccc cgccaagtcc 960
gactccgtcg agctgcccga cggtttcgtc gagcgaaccc gagatcgagg tctggtctgg 1020
acctcttggg ctccccagct ccgaatcctc tcccacgagt ccgttggtgg tttcgtcacc 1080
cactgcggtt ccggctccat cgtcgagggt ctgatgttcg gccaccctct catcatgctc 1140
cccatcttcg gtgaccagcc cctcaacgcc cgactgctcg aggataagca ggtcggtatc 1200
gagatccagc gaaacgaaga ggacggctgt ctgaccaagg agtccgtcgc cgagtctctc 1260
cgactcgttg ttgtcgagaa agagggtgag atctaccgag agaaggcccg agagatgtcc 1320
aaggtctact ccgacaccaa gcgtgagaag gagtacgtcg accagttcgt cgactacctc 1380
gagaagaacg cccgagctgt tgccattgac cacgagtct 1419

<210> SEQ ID NO 6
<211> LENGTH: 473
<212> TYPE: PRT

<213> ORGANISM: Artificial sequence
<220> FEATURE:
<223> OTHER INFORMATION: UGT2_3b variant

<400> SEQUENCE: 6

```
Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Gln
            20                  25                  30

Leu Ala Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Phe Val Lys Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125

Ser Ile Ala Thr Lys His Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160

Asn Gly Ser Asp Gly Arg Thr Thr Pro Glu Asp Phe Thr Val Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Ser Asp Leu Leu Leu Ser Arg Ser Tyr
    210                 215                 220

His Glu Phe Gly Thr Glu Trp Leu Arg Leu Leu Glu Thr Leu His Arg
225                 230                 235                 240

Val Pro Val Val Pro Val Gly Leu Leu Pro Pro Glu Ile Pro Gly Asp
                245                 250                 255

Gly Glu Asp Glu Ser Trp Val Ser Ile Lys Asp Trp Leu Asp Lys Lys
            260                 265                 270

Glu Lys Gly Ser Val Val Tyr Val Ala Leu Gly Ser Glu Val Leu Val
        275                 280                 285

Ser Gln Glu Glu Leu Asn Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Glu Glu Arg Thr Arg Gly Arg
                325                 330                 335

Gly Val Val Trp Thr Ser Trp Ala Pro Gln Leu Arg Ile Leu Ser His
            340                 345                 350

Glu Ser Val Ala Gly Phe Leu Thr His Cys Gly Ser Gly Ser Ile Val
        355                 360                 365

Glu Gly Leu Met Phe Gly His Pro Leu Ile Met Leu Pro Leu Phe Gly
    370                 375                 380

Asp Gln Pro Leu Asn Ala Arg Leu Leu Glu Asp Lys Gln Val Gly Ile
```

-continued

```
385                 390                 395                 400

Glu Ile Pro Arg Asp Glu Glu Asp Gly Cys Leu Thr Lys Glu Ser Val
                405                 410                 415

Ala Arg Ser Leu Arg Leu Val Met Val Glu Lys Glu Gly Glu Ile Tyr
            420                 425                 430

Arg Glu Lys Ala Arg Glu Met Ser Lys Ile Tyr Asn Asn Thr Glu Val
        435                 440                 445

Glu Asp Gln Tyr Val Ser Gln Phe Val Glu Tyr Leu Glu Lys Asn Ala
    450                 455                 460

Arg Ala Val Ala Ile Asp His Glu Ser
465                 470
```

```
<210> SEQ ID NO 7
<211> LENGTH: 1419
<212> TYPE: DNA
<213> ORGANISM: Artificial sequence
<220> FEATURE:
<223> OTHER INFORMATION: UGT2_3b CpO for S. cerevisiae

<400> SEQUENCE: 7

atggccactt ctgactccat cgttgatgac agaaagaagt tgcacatcgt tatgttccca      60

tggttagctt tcggtcacat tatcccatac ttgcaattgg ctaaattgat tgctgaaaag     120

ggtcacaaag tctctttctt gtccaccacc agaaacatcc aaagattatc ttctcacatt     180

tctccattga tcaacttcgt caagttgact ttaccaagag ttcaagaatt gccagaagat     240

gctgaagcta ccaccgatgt ccatccagaa gatatcccat acttgaagaa ggcttctgat     300

ggtttgcaac cagaagtcac tgaattcttg gaacaacact ctccagactg gattatctac     360

gactacactc actactggtt accatccatt gctactaagc acggtgtttc tcgtgctcat     420

ttctccgtta ccactccatg ggctattgct tacatgggtc caactgctga tgctatgatc     480

aacggttctg atggtagaac cactccagaa gacttcaccg ttccaccaaa atggttccca     540

ttcccaacca aggtctgttg gagaaagcac gatttggcca gattagttcc atacaaggcc     600

ccaggtatct ctgacggtta cagaatgggt ttagtcttga agggttctga cttgttgttg     660

tccagatctt accatgaatt cggtactgaa tggttaagat tgttggaaac tttgcacaga     720

gtcccagttg ttccagttgg tttgttgcct cctgaaatcc caggtgacgg tgaagacgaa     780

tcttgggttt ccatcaagga ctggttagat aagaaggaaa agggttccgt tgtctacgtt     840

gctttgggtt ctgaagtctt ggtttctcaa gaagaattga acgaattggc tttgggtttg     900

gaattgtccg gtctaccatt tgtctgggct tacagaaagc caaagggtcc agctaagtct     960

gactctgttg aattgccaga tggtttcgaa gaaagaacca gaggtagagg tgttgtctgg    1020

acttcctggg ctccacaatt gagaattttg tcccacgaat ctgttgctgg tttcttgacc    1080

cactgtggtt ctggttccat tgtcgaaggt ttgatgttcg gtcacccatt gatcatgttg    1140

ccattgttcg gtgaccaacc attgaacgct agattattgg aagacaagca agtcggtatt    1200

gaaatcccaa gagatgaaga agacggttgt ttgaccaagg aatctgttgc ccgttctcta    1260

agattggtta tggtcgaaaa ggaaggtgaa atctacagag aaaaggctag agaaatgtcc    1320

aagatctaca acaacaccga agtcgaagac caatatgtct cccaatttgt tgaatacttg    1380

gaaaagaacg ctcgtgccgt tgccattgac cacgaaagc                           1419

<210> SEQ ID NO 8
<211> LENGTH: 1419
<212> TYPE: DNA
```

<213> ORGANISM: Artificial sequence
<220> FEATURE:
<223> OTHER INFORMATION: UGT2_3b CpO for Y. lipolitica

<400> SEQUENCE: 8

```
atggccacct ccgactccat tgtcgacgac cgaaagaagc tccacattgt catgttcccc     60

tggctcgcct ttggccacat catcccttac ctccagctcg ccaagctcat tgctgagaag    120

ggccacaagg tttccttcct ctccaccacc cgaaacatcc agcgactctc ctcccacatc    180

tctcctctca tcaactttgt caagctcacc ctcccccgag tccaggagct gcccgaggat    240

gctgaggcca ccaccgatgt ccaccccgag gacatcccct acctcaagaa ggcctccgat    300

ggcctccagc ccgaggtcac cgagttcctc gagcagcact ctcccgactg gatcatctac    360

gactacaccc actactggct cccctccatt gccaccaagc acggtgtctc tcgagcccac    420

ttctccgtca ccacccccctg ggccattgcc tacatgggtc ccactgctga cgccatgatc    480

aacggttccg acggccgaac cactcccgag gacttcactg tccctcccaa gtggttcccc    540

ttccccacca aggtctgctg gcgaaagcac gacctcgccc gactcgtccc ctacaaggct    600

cccggtatct ccgacggcta ccgaatgggt ctggtcctca agggctctga tctcctcctc    660

tctcgatctt accacgagtt cggcaccgag tggctccgac tgctcgagac tctccaccga    720

gtccccgttg tccccgtcgg tctgctccct cccgagatcc ccggtgacgg tgaggacgag    780

tcttgggttt ccatcaagga ctggctcgac aagaaggaga agggctccgt tgtctacgtt    840

gctctcggtt ccgaggttct tgtctcccaa gaggagctta acgagctggc tctcggtctg    900

gagctgtccg gtctgccctt tgtctgggcc taccgaaagc ccaagggccc cgccaagtcc    960

gactccgtcg agcttcccga cggtttcgag gagcgaaccc gaggccgagg tgttgtctgg   1020

acctcttggg ctccccagct ccgaatcctc tcccacgagt ccgtcgccgg tttcctcacc   1080

cactgcggtt ccggctccat tgttgagggt ctgatgttcg gccacccccct catcatgctc   1140

cccctcttcg gtgaccagcc cctcaacgcc cgacttctcg aggacaagca ggtcggtatt   1200

gagatccccc gagatgaaga ggacggctgt ctgaccaagg agtctgttgc ccgatctctg   1260

cgactcgtca tggtcgagaa ggaaggtgag atctaccgag agaaggcccg agagatgtcc   1320

aagatctaca acaacaccga ggtcgaggac cagtacgttt cccagttcgt cgagtacctt   1380

gagaagaacg cccgagctgt tgccattgac cacgaatca                           1419
```

<210> SEQ ID NO 9
<211> LENGTH: 473
<212> TYPE: PRT
<213> ORGANISM: Artificial sequence
<220> FEATURE:
<223> OTHER INFORMATION: UGT2_4b variant

<400> SEQUENCE: 9

```
Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Glu
            20                  25                  30

Leu Ser Lys Leu Ile Ala Gln Lys Gly His Lys Val Ser Phe Leu Ser
        35                  40                  45

Thr Thr Lys Asn Ile Asp Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80
```

```
Ala Glu Ala Thr Thr Asp Val His Pro Glu Asp Ile Pro Tyr Leu Lys
                85                  90                  95

Leu Ala Ser Asp Gly Leu Gln Glu Pro Leu Thr Arg Phe Leu Glu Ser
            100                 105                 110

Ser Ser Pro Asp Trp Ile Ile Tyr Asp Tyr Thr His Tyr Trp Leu Pro
        115                 120                 125

Glu Ile Ala Ala Ser Leu Gly Val Ala Arg Ala His Phe Ser Val Thr
    130                 135                 140

Thr Pro Trp Ala Leu Ala Phe Met Gly Pro Ser Ala Asp Ala Met Ile
145                 150                 155                 160

Asn Gly Ser Asp Gly Arg Thr Glu Val Glu Asp Phe Thr Val Pro Pro
                165                 170                 175

Lys Trp Ile Pro Phe Pro Thr Thr Val Ala Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Cys Asp Cys Leu Leu Ser Arg Thr Tyr
    210                 215                 220

His Glu Phe Gly Thr Gln Trp Leu Pro Leu Leu Glu Glu Leu His Gln
225                 230                 235                 240

Val Pro Val Val Pro Val Gly Leu Leu Pro Pro Ser Ile Pro Gly Asp
                245                 250                 255

Glu Lys Asp Glu Asn Trp Val Ser Ile Lys Asp Trp Leu Asp Lys Gln
            260                 265                 270

Glu Lys Gly Ser Val Val Tyr Val Ala Leu Gly Ser Glu Val Leu Leu
        275                 280                 285

Thr Glu Glu Glu Val Val Glu Leu Ala Leu Gly Leu Glu Leu Ser Gly
    290                 295                 300

Leu Pro Phe Phe Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Ala Gly Phe Leu Thr His Cys Gly Ser Gly Ser Ile Val
        355                 360                 365

Glu Gly Leu Met Phe Gly His Pro Leu Ile Met Leu Pro Leu Phe Gly
    370                 375                 380

Asp Gln Pro Leu Asn Ala Arg Leu Leu Glu Asp Lys Gln Val Gly Ile
385                 390                 395                 400

Glu Ile Pro Arg Asp Glu Glu Asp Gly Cys Leu Thr Lys Glu Ser Val
                405                 410                 415

Ala Arg Ser Leu Arg Leu Val Met Val Glu Lys Glu Gly Glu Ile Tyr
            420                 425                 430

Arg Glu Lys Ala Arg Glu Met Ser Lys Ile Tyr Asn Asn Thr Glu Val
        435                 440                 445

Glu Asp Gln Tyr Val Ser Gln Phe Val Glu Tyr Leu Glu Lys Asn Ala
    450                 455                 460

Arg Ala Val Ala Ile Asp His Glu Ser
465                 470

<210> SEQ ID NO 10
<211> LENGTH: 1419
<212> TYPE: DNA
```

<213> ORGANISM: Artificial sequence
<220> FEATURE:
<223> OTHER INFORMATION: UGT2_4b CpO for S. cerevisiae

<400> SEQUENCE: 10

```
atggccactt ctgactccat cgttgatgac agaaagaagt tgcacatcgt tatgttccca     60

tggttagctt tcggtcacat tatcccatac ttggaattgt ccaaattgat tgctcaaaag    120

ggtcacaaag tctctttctt gtccaccacc aagaacatcg acagattatc ttctcacatt    180

tctccattga tcaacgttgt ccaattgact ttaccaagag ttcaagaatt gccagaagat    240

gctgaagcta ccaccgatgt ccatccagaa gatatcccat acttgaagtt ggcttctgat    300

ggtttgcaag aaccattgac tagattcttg gaatcttctt ctccagactg gattatctac    360

gactacactc actactggtt accagaaatt gctgcctctt tgggtgttgc tcgtgctcat    420

ttctccgtta ccactccatg ggctttggct ttcatgggtc catctgctga tgctatgatc    480

aacggttctg atggtagaac cgaagtcgaa gacttcaccg ttccaccaaa atggatccca    540

ttcccaacca ctgtcgcttg gagaaagcac gatttggcca gattagttcc atacaaggcc    600

ccaggtatct ctgacggtta cagaatgggt ttagtcttga agggttgtga ctgtttgttg    660

tccagaactt accatgaatt cggtactcaa tggttacctt tgttggaaga attgcaccaa    720

gtcccagttg ttccagttgg tttgttgcct ccttctatcc caggtgacga aaaggacgaa    780

aactgggttt ccatcaagga ctggttagat aagcaagaaa agggttccgt tgtctacgtt    840

gctttgggtt ctgaagtctt gttgactgaa gaagaagttg ttgaattggc tttgggtttg    900

gaattgtccg gtctaccatt tttctgggct tacagaaagc caaagggtcc agctaagtct    960

gactctgttg aattgccaga tggtttcgtc gaaagaacca gagacagagg tttggtctgg   1020

acttcctggg ctccacaatt gagaattttg tcccacgaat ctgttgctgg tttcttgacc   1080

cactgtggtt ctggttccat tgtcgaaggt ttgatgttcg gtcacccatt gatcatgttg   1140

ccattgttcg gtgaccaacc attgaacgct agattattgg aagacaagca agtcggtatt   1200

gaaatcccaa gagatgaaga agacggttgt ttgaccaagg aatctgttgc ccgttctcta   1260

agattggtta tggtcgaaaa ggaaggtgaa atctacagag aaaaggctag agaaatgtcc   1320

aagatctaca acaacaccga agtcgaagac caatatgtct cccaatttgt tgaatacttg   1380

gaaaagaacg ctcgtgccgt tgccattgac cacgaaagc                          1419
```

<210> SEQ ID NO 11
<211> LENGTH: 473
<212> TYPE: PRT
<213> ORGANISM: Artificial sequence
<220> FEATURE:
<223> OTHER INFORMATION: UGT2_5b variant

<400> SEQUENCE: 11

```
Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Glu
            20                  25                  30

Leu Ser Lys Leu Ile Ala Gln Lys Gly His Lys Val Ser Phe Leu Ser
        35                  40                  45

Thr Thr Lys Asn Ile Asp Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80
```

-continued

```
Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125

Ser Ile Ala Thr Lys His Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160

Asn Gly Ser Asp Gly Arg Thr Thr Pro Glu Asp Phe Thr Val Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Ser Asp Leu Leu Leu Ser Arg Ser Tyr
    210                 215                 220

His Glu Phe Gly Thr Glu Trp Leu Arg Leu Leu Glu Thr Leu His Arg
225                 230                 235                 240

Val Pro Val Val Pro Val Gly Leu Leu Pro Pro Glu Ile Pro Gly Asp
                245                 250                 255

Gly Glu Asp Glu Ser Trp Val Ser Ile Lys Asp Trp Leu Asp Lys Lys
            260                 265                 270

Glu Lys Gly Ser Val Val Tyr Val Ala Leu Gly Ser Glu Val Leu Val
        275                 280                 285

Ser Gln Glu Glu Leu Asn Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Glu Glu Arg Thr Arg Gly Arg
                325                 330                 335

Gly Val Val Trp Thr Ser Trp Ala Pro Gln Leu Arg Ile Leu Ser His
            340                 345                 350

Glu Ser Val Gly Gly Phe Val Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Glu Ser Leu Arg Leu Val Val Val Glu Lys Glu Gly Glu Ile Tyr
            420                 425                 430

Arg Glu Lys Ala Arg Glu Met Ser Lys Val Tyr Ser Asp Thr Lys Arg
        435                 440                 445

Glu Lys Glu Tyr Val Asp Gln Phe Val Asp Tyr Leu Glu Lys Asn Ala
    450                 455                 460

Arg Ala Val Ala Ile Asp His Glu Ser
465                 470
```

<210> SEQ ID NO 12
<211> LENGTH: 1419
<212> TYPE: DNA

<213> ORGANISM: Artificial sequence
<220> FEATURE:
<223> OTHER INFORMATION: UGT2_5b CpO for S. cerevisiae

<400> SEQUENCE: 12
atggccactt ctgactccat cgttgatgac agaaagaagt tgcacatcgt tatgttccca 60
tggttagctt tcggtcacat tatcccatac ttggaattgt ccaaattgat tgctcaaaag 120
ggtcacaaag tctctttctt gtccaccacc aagaacatcg acagattatc ttctcacatt 180
tctccattga tcaacgttgt ccaattgact ttaccaagag ttcaagaatt gccagaagat 240
gctgaagcta ccaccgatgt ccatccagaa gatatcccat acttgaagaa ggcttctgat 300
ggtttgcaac cagaagtcac tgaattcttg gaacaacact ctccagactg gattatctac 360
gactacactc actactggtt accatccatt gctactaagc acggtgtttc tcgtgctcat 420
ttctccgtta ccactccatg ggctattgct tacatgggtc caactgctga tgctatgatc 480
aacggttctg atggtagaac cactccagaa gacttcaccg ttccaccaaa atggttccca 540
ttcccaacca aggtctgttg gagaaagcac gatttggcca gattagttcc atacaaggcc 600
ccaggtatct ctgacggtta cagaatgggt ttagtcttga agggttctga cttgttgttg 660
tccagatctt accatgaatt cggtactgaa tggttaagat tgttggaaac tttgcacaga 720
gtcccagttg ttccagttgg tttgttgcct cctgaaatcc caggtgacgg tgaagacgaa 780
tcttgggttt ccatcaagga ctggttagat aagaaggaaa agggttccgt tgtctacgtt 840
gctttgggtt ctgaagtctt ggtttctcaa gaagaattga acgaattggc tttgggtttg 900
gaattgtccg gtctaccatt tgtctgggct tacagaaagc caaagggtcc agctaagtct 960
gactctgttg aattgccaga tggtttcgaa gaaagaacca gaggtagagg tgttgtctgg 1020
acttcctggg ctccacaatt gagaattttg tcccacgaat ctgttggtgg tttcgttacc 1080
cactgtggtt ctggttccat tgtcgaaggt ttgatgttcg gtcacccatt gatcatgttg 1140
ccaatcttcg gtgaccaacc attgaacgct agattattgg aagacaagca agtcggtatt 1200
gaaatcccaa gaaacgaaga agacggttgt ttgaccaagg aatctgttgc cgaatctcta 1260
agattggttg ttgtcgaaaa ggaaggtgaa atctacagag aaaaggctag agaaatgtcc 1320
aaggtttact ctgataccaa gagagaaaag gaatatgtcg accaatttgt tgactacttg 1380
gaaaagaacg ctcgtgccgt tgccattgac cacgaaagc 1419

<210> SEQ ID NO 13
<211> LENGTH: 1419
<212> TYPE: DNA
<213> ORGANISM: Artificial sequence
<220> FEATURE:
<223> OTHER INFORMATION: UGT2_5b CpO for Y. lipolitica

<400> SEQUENCE: 13
atggccacct ccgactccat tgtcgacgac cgaaagaagc tccacattgt catgttcccc 60
tggctcgcct tcggccacat catcccttac ctggagctgt ccaagctcat tgcccagaag 120
ggccacaagg tttctttcct ctccaccacc aagaacattg accgactctc ctcccacatc 180
tctcctctca tcaacgttgt ccagctcacc ctcccccgag tccaggagct tcccgaggat 240
gctgaggcca ccaccgacgt ccacccccgag gacatcccct acctcaagaa ggcctccgat 300
ggcctccagc ccgaggtcac cgagttcctc gagcagcact cccccgactg gatcatctac 360
gactacaccc actactggct cccctccatt gccaccaagc acggtgtctc tcgagcccac 420
ttctccgtca ccaccccctg ggccattgcc tacatgggtc ccactgccga cgccatgatc 480

-continued

```
aacggttccg acggccgaac cacccccgag gatttcactg tccctcccaa gtggttcccc    540

ttccccacca aggtctgctg gcgaaagcac gacctcgctc gactcgtccc ctacaaggcc    600

cccggtatct ccgacggtta ccgaatgggt ctggttctca agggctccga tctcctcctc    660

tctcgatctt accacgagtt tggtactgag tggctccgac tgctcgagac tctccaccga    720

gtccccgttg tccccgtcgg cctcctccct cccgagatcc ccggtgatgg tgaggacgag    780

tcttgggttt ccatcaagga ctggctcgac aagaaggaga agggctctgt tgtctacgtt    840

gctctcggtt ccgaggtcct tgtctctcaa gaggagctta acgagcttgc tctgggcctc    900

gagctgtccg gcctcccctt cgtctgggcc taccgaaagc ccaagggtcc cgccaagtcc    960

gactccgtcg agctgcccga cggtttcgag gagcgaaccc gaggccgagg tgttgtctgg   1020

acctcttggg ctccccagct ccgaatcctc tcccacgagt ccgtcggtgg ctttgtcacc   1080

cactgcggtt ccggctccat cgtcgagggt ctgatgtttg gccacccccct catcatgctc   1140

cccatcttcg gtgaccagcc cctcaacgcc cgactccttg aggacaagca ggtcggtatt   1200

gagatccccc gaaacgagga agatggttgt ctgaccaagg agtctgttgc tgagtctctg   1260

cgactcgttg ttgtcgagaa agagggtgag atctaccggg agaaggcccg agagatgtcc   1320

aaggtctact ccgacaccaa gcgagagaag gagtacgtcg accagttcgt cgactacctc   1380

gagaagaacg cccgagctgt tgccattgac cacgaatcc                          1419
```

<210> SEQ ID NO 14
<211> LENGTH: 473
<212> TYPE: PRT
<213> ORGANISM: Artificial sequence
<220> FEATURE:
<223> OTHER INFORMATION: UGT2_6b variant

<400> SEQUENCE: 14

```
Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Glu
            20                  25                  30

Leu Ser Lys Leu Ile Ala Gln Lys Gly His Lys Val Ser Phe Leu Ser
        35                  40                  45

Thr Thr Lys Asn Ile Asp Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125

Ser Ile Ala Thr Lys His Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160

Asn Gly Ser Asp Gly Arg Thr Thr Pro Glu Asp Phe Thr Val Pro Pro
                165                 170                 175

Lys Trp Phe Pro Phe Pro Thr Lys Val Cys Trp Arg Lys His Asp Leu
            180                 185                 190
```

-continued

```
Ala Arg Leu Val Pro Tyr Lys Ala Pro Gly Ile Ser Asp Gly Tyr Arg
        195                 200                 205

Met Gly Leu Val Ile Lys Gly Cys Asp Cys Leu Leu Ser Lys Thr Tyr
    210                 215                 220

His Glu Phe Gly Thr Gln Trp Leu Arg Leu Leu Glu Thr Leu His Arg
225                 230                 235                 240

Lys Pro Val Ile Pro Val Gly Leu Leu Pro Pro Ser Ile Pro Gly Ser
                245                 250                 255

Asp Lys Asp Asp Ser Trp Val Ser Ile Lys Glu Trp Leu Asp Gly Gln
            260                 265                 270

Glu Lys Gly Ser Val Val Tyr Val Ala Leu Gly Ser Glu Val Leu Val
        275                 280                 285

Thr Gln Asp Glu Val Val Glu Leu Ala His Gly Leu Glu Leu Ser Gly
    290                 295                 300

Leu Pro Phe Val Trp Ala Tyr Arg Asn Pro Lys Gly Pro Ala Lys Ser
305                 310                 315                 320

Asp Ser Val Glu Leu Pro Asp Gly Phe Val Glu Arg Val Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Ser Phe Thr Arg Asp Ser Val
                405                 410                 415

Ala Glu Ser Leu Arg Leu Val Met Val Glu Glu Glu Gly Lys Ile Tyr
            420                 425                 430

Arg Glu Lys Ala Lys Glu Met Ser Lys Leu Phe Gly Asp Lys Asp Leu
        435                 440                 445

Gln Asp Gln Tyr Val Asp Asp Phe Val Glu Tyr Leu Gln Lys His Arg
    450                 455                 460

Arg Ala Val Ala Ile Asp His Glu Ser
465                 470
```

<210> SEQ ID NO 15
<211> LENGTH: 1419
<212> TYPE: DNA
<213> ORGANISM: Artificial sequence
<220> FEATURE:
<223> OTHER INFORMATION: UGT2_6b CpO for S. cerevisiae

<400> SEQUENCE: 15

```
atggccactt ctgactccat cgttgatgac agaaagaagt tgcacatcgt tatgttccca      60

tggttagctt tcggtcacat tatcccatac ttggaattgt ccaaattgat tgctcaaaag     120

ggtcacaaag tctctttctt gtccaccacc aagaacatcg acagattatc ttctcacatt     180

tctccattga tcaacgttgt ccaattgact ttaccaagag ttcaagaatt gccagaagat     240

gctgaagcta ccaccgatgt ccatccagaa gatatcccat acttgaagaa ggcttctgat     300

ggtttgcaac cagaagtcac tgaattcttg gaacaacact ctccagactg gattatctac     360

gactacactc actactggtt accatccatt gctactaagc acggtgtttc tcgtgctcat     420

ttctccgtta ccactccatg ggctattgct tacatgggtc caactgctga tgctatgatc     480
```

```
aacggttctg atggtagaac cactccagaa gacttcaccg ttccaccaaa atggttccca    540
ttcccaacca aggtctgttg gagaaagcac gatttggcca gattagttcc atacaaggcc    600
ccaggtatct ctgacggtta cagaatgggt ttagtcatca agggttgtga ctgtttgttg    660
tccaagactt accatgaatt cggtactcaa tggttaagat tgttggaaac tttgcacaga    720
aagccagtta tcccagttgg tttgttgcct ccttctatcc caggttctga caaggacgac    780
tcttgggttt ccatcaagga atggttagat ggtcaagaaa agggttccgt tgtctacgtt    840
gctttgggtt ctgaagtctt ggttactcaa gacgaagttg ttgaattggc tcacggtttg    900
gaattgtccg gtctaccatt tgtctgggct tacagaaacc caaagggtcc agctaagtct    960
gactctgttg aattgccaga tggtttcgtc gaaagagtta gagacagagg tttggtctgg   1020
acttcctggg ctccacaatt gagaattttg tcccacgaat ctgtttgtgg tttcttgact   1080
cactgtggtt ctggttctat cgtcgaaggt ttgatgttcg gtcatccttt gatcatgttg   1140
cctatctttg gtgaccaacc attgaacgct agattgttgg aagacaagca agttggtatt   1200
gaaattccaa gaaacgaaga agatggttct ttcaccagag actctgttgc tgaatctttg   1260
agattagtca tggttgaaga agaaggtaag atctacagag aaaaggccaa ggaaatgtcc   1320
aagttgtttg gtgacaaaga tttgcaagac caatacgtcg atgacttcgt cgaatacttg   1380
caaaagcacc gtcgtgccgt tgccattgac cacgaatca                          1419
```

<210> SEQ ID NO 16
<211> LENGTH: 1419
<212> TYPE: DNA
<213> ORGANISM: Artificial sequence
<220> FEATURE:
<223> OTHER INFORMATION: UGT2_6b CpO for Y. lipolitica

<400> SEQUENCE: 16

```
atggctactt ccgactccat tgtcgacgac cgaaagaagc tccacattgt catgttcccc     60
tggctcgcct ttggccacat cattccctac ctcgagcttt ccaagctcat tgcccagaag    120
ggccacaagg tttctttcct ctccaccacc aagaacattg accgactctc ctcccacatc    180
tctcctctca tcaacgttgt ccagctcacc ctcccccgag tccaggagct gcccgaggac    240
gccgaggcca ccaccgatgt ccaccccgag gatatcccct acctcaagaa ggcctccgac    300
ggtctgcagc ccgaggtcac cgagttcctc gagcagcact ctcccgactg gatcatctac    360
gactacaccc actactggct cccctccatt gccaccaagc acggtgtctc tcgagcccac    420
ttctccgtca ccaccccctg ggccattgcc tacatgggcc ccactgctga cgccatgatc    480
aacggttccg atggccgaac cacccccgag gacttcactg tccctcccaa gtggttcccc    540
ttccccacca aggtctgctg gcgaaagcac gatctggccc gactcgttcc ctacaaggcc    600
cccggtatct ccgacggcta ccgaatgggt ctggtcatca agggctgcga ctgtctgctc    660
tccaagacct accacgagtt tggcacccag tggctccgac tcctcgagac tctccaccga    720
aagcccgtca tccccgtcgg tctgctccct ccctccatcc ccggctccga caaggacgac    780
tcttgggttt ccatcaagga gtggctcgac ggccaggaga agggctctgt tgtctacgtt    840
gctctcggtt ccgaggttct cgtcacccag gacgaggttg ttgagctggc ccacggtctg    900
gagctgtccg gcctcccctt cgtctgggct taccgaaacc ccaagggtcc cgccaagtcc    960
gactccgtcg agcttcccga tggtttcgtc gagcgagtcc gagatcgagg tctggtctgg   1020
acctcttggg ctccccagct ccgaatcctc tcccacgagt ccgtctgtgg tttcctcacc   1080
```

-continued cactgcggtt ccggctccat cgtcgagggt ctgatgttcg gccacccccct catcatgctc 1140 cccatcttcg gtgaccagcc cctcaacgcc cgactccttg aggacaagca ggtcggtatc 1200
gagatccccc gaaacgaaga ggacggttcc ttcacccgag actctgttgc tgagtctctc 1260
cgactcgtca tggtcgagga agagggtaag atctaccgag agaaggccaa ggagatgtcc 1320
aagctgttcg gtgacaagga tctccaggac cagtacgtcg acgactttgt cgagtacctc 1380
cagaagcacc gacgagctgt tgccattgac cacgagtct 1419

<210> SEQ ID NO 17
<211> LENGTH: 473
<212> TYPE: PRT
<213> ORGANISM: Artificial sequence
<220> FEATURE:
<223> OTHER INFORMATION: UGT2_7b variant

<400> SEQUENCE: 17

Met Ala Thr Ser Asp Ser Ile Val Asp Asp Arg Lys Lys Leu His Ile
1 5 10 15

Val Met Phe Pro Trp Leu Ala Phe Gly His Ile Ile Pro Tyr Leu Glu
20 25 30

Leu Ser Lys Leu Ile Ala Gln Lys Gly His Lys Val Ser Phe Leu Ser
35 40 45

Thr Thr Lys Asn Ile Asp Arg Leu Ser Ser His Ile Ser Pro Leu Ile
50 55 60

Asn Val Val Gln Leu Thr Leu Pro Arg Val Gln Glu Leu Pro Glu Asp
65 70 75 80

Ala Glu Ala Thr Thr Asp Val His Pro Glu Asp Ile Pro Tyr Leu Lys
85 90 95

Lys Ala Ser Asp Gly Leu Gln Pro Glu Val Thr Glu Phe Leu Glu Gln
100 105 110

His Ser Pro Asp Trp Ile Ile Tyr Asp Tyr Thr His Tyr Trp Leu Pro
115 120 125

Glu Ile Ala Lys Ser Leu Gly Val Ser Arg Ala His Phe Ser Val Thr
130 135 140

Thr Pro Trp Ala Ile Ala Tyr Ile Gly Pro Thr Ala Asp Ala Met Ile
145 150 155 160

Asn Gly Ser Asp Tyr Arg Thr Glu Leu Glu Asp Phe Thr Val Pro Pro
165 170 175

Lys Trp Phe Pro Phe Pro Thr Thr Val Cys Trp Arg Lys His Asp Leu
180 185 190

Ala Arg Leu Val Pro Tyr Lys Ala Pro Gly Ile Ser Asp Gly Tyr Arg
195 200 205

Met Gly Leu Val Ile Lys Gly Cys Asp Cys Leu Leu Ser Lys Thr Tyr
210 215 220

His Glu Phe Gly Thr Gln Trp Leu Arg Leu Leu Glu Thr Leu His Arg
225 230 235 240

Lys Pro Val Ile Pro Val Gly Leu Leu Pro Pro Ser Ile Pro Gly Ser
245 250 255

Asp Lys Asp Asp Ser Trp Val Ser Ile Lys Glu Trp Leu Asp Gly Gln
260 265 270

Glu Lys Gly Ser Val Val Tyr Val Ala Leu Gly Ser Glu Val Leu Val
275 280 285

Thr Gln Asp Glu Val Val Glu Leu Ala His Gly Leu Glu Leu Ser Gly
290 295 300

-continued

```
Leu Pro Phe Val Trp Ala Tyr Arg Asn Pro Lys Gly Pro Ala Lys Ser
305                 310                 315                 320

Asp Ser Val Glu Leu Pro Asp Gly Phe Val Glu Arg Val Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Ser Phe Thr Arg Asp Ser Val
                405                 410                 415

Ala Glu Ser Leu Arg Leu Val Met Val Glu Glu Glu Gly Lys Ile Tyr
            420                 425                 430

Arg Glu Lys Ala Lys Glu Met Ser Lys Leu Phe Gly Asp Lys Asp Leu
        435                 440                 445

Gln Asp Gln Tyr Val Asp Asp Phe Val Glu Tyr Leu Gln Lys His Arg
    450                 455                 460

Arg Ala Val Ala Ile Asp His Glu Ser
465                 470
```

```
<210> SEQ ID NO 18
<211> LENGTH: 1419
<212> TYPE: DNA
<213> ORGANISM: Artificial sequence
<220> FEATURE:
<223> OTHER INFORMATION: UGT2_7b CpO for S. cerevisiae

<400> SEQUENCE: 18

atggccactt ctgactccat cgttgatgac agaaagaagt tgcacatcgt tatgttccca     60

tggttagctt tcggtcacat tatcccatac ttggaattgt ccaaattgat tgctcaaaag    120

ggtcacaaag tctctttctt gtccaccacc aagaacatcg acagattatc ttctcacatt    180

tctccattga tcaacgttgt ccaattgact ttaccaagag ttcaagaatt gccagaagat    240

gctgaagcta ccaccgatgt ccatccagaa gatatcccat acttgaagaa ggcttctgat    300

ggtttgcaac cagaagtcac tgaattcttg gaacaacact ctccagactg gattatctac    360

gactacactc actactggtt accagaaatt gctaagtctt tgggtgtttc tcgtgctcat    420

ttctccgtta ccactccatg ggctattgct tacattggtc caactgctga tgctatgatc    480

aacggttctg attacagaac cgaattggaa gacttcaccg ttccaccaaa atggttccca    540

ttcccaacca ctgtctgttg gagaaagcac gatttggcca gattagttcc atacaaggcc    600

ccaggtatct ctgacggtta cagaatgggt ttagtcatca agggttgtga ctgtttgttg    660

tccaagactt accatgaatt cggtactcaa tggttaagat tgttggaaac tttgcacaga    720

aagccagtta tcccagttgg tttgttgcct ccttctatcc caggttctga caaggacgac    780

tcttgggttt ccatcaagga atggttagat ggtcaagaaa agggttccgt tgtctacgtt    840

gctttgggtt ctgaagtctt ggttactcaa gacgaagttg ttgaattggc tcacggtttg    900

gaattgtccg gtctaccatt tgtctgggct tacagaaacc caaagggtcc agctaagtct    960

gactctgttg aattgccaga tggtttcgtc gaaagagtta gagacagagg tttggtctgg   1020

acttcctggg ctccacaatt gagaattttg tcccacgaat ctgtttgtgg tttcttgact   1080
```

-continued

```
cactgtggtt ctggttctat cgtcgaaggt ttgatgttcg gtcatccttt gatcatgttg   1140

cctatctttg gtgaccaacc attgaacgct agattgttgg aagacaagca agttggtatt   1200

gaaattccaa gaaacgaaga agatggttct ttcaccagag actctgttgc tgaatctttg   1260

agattagtca tggttgaaga agaaggtaag atctacagag aaaaggccaa ggaaatgtcc   1320

aagttgtttg gtgacaaaga tttgcaagac caatacgtcg atgacttcgt cgaatacttg   1380

caaaagcacc gtcgtgccgt tgccattgac cacgaatca                          1419
```

<210> SEQ ID NO 19
<211> LENGTH: 1419
<212> TYPE: DNA
<213> ORGANISM: Artificial sequence
<220> FEATURE:
<223> OTHER INFORMATION: UGT2_7b CpO for Y. lipolitica

<400> SEQUENCE: 19

```
atggccacct ccgactccat tgttgacgac cgaaagaagc tccacattgt catgttcccc     60

tggctcgcct tcggccacat cattccctac ctcgagcttt ccaagctcat tgcccagaag    120

ggccacaagg tttctttcct ctccaccacc aagaacattg accgactctc ctcccacatc    180

tctcctctca tcaacgttgt ccagctcacc ctcccccgag tccaggagct gcccgaggat    240

gctgaggcca ccaccgacgt ccaccccgag gatatcccct acctcaagaa ggcctccgat    300

ggtctgcagc ccgaggtcac cgagttcctc gagcagcact ctcccgactg gatcatctac    360

gactacaccc actactggct ccccgagatt gccaagtctc tcggtgtctc tcgagcccac    420

ttctccgtca ccacccccctg ggccattgct tacatcggtc ccactgctga cgccatgatc    480

aacggctccg actaccgaac tgaactcgag gacttcactg ttcctcccaa gtggttcccc    540

ttccccacca ccgtctgctg gcgaaagcac gatctcgccc gactggtccc ctacaaggct    600

cccggtatct ccgacggcta ccgaatgggt ctggtcatca agggttgcga ctgtctgctc    660

tccaagacct accacgagtt tggcacccag tggctgcgac tcctcgagac tctccaccga    720

aagcccgtca tccccgtcgg tctgctgccc ccttccatcc ccggttccga caaggacgac    780

tcttgggttt ccatcaagga gtggctcgac ggccaggaga agggctctgt tgtctacgtt    840

gctctcggct ccgaggttct cgtcacccag gacgaggttg tcgagctggc ccacggtctg    900

gagctgtccg gtctgccctt cgtctgggcc taccgaaacc ccaagggccc cgccaagtcc    960

gactccgtcg agcttcccga tggtttcgtc gagcgagtcc gagatcgagg tctggtctgg   1020

acctcttggg ctccccagct ccgaatcctc tcccacgagt ccgtctgcgg tttcctcacc   1080

cactgtggtt ccggctccat tgtcgagggt ctgatgttcg gccacccccct catcatgctc   1140

cccatcttcg gtgaccagcc cctcaacgcc cgactccttg aggacaagca ggtcggtatc   1200

gagatccccc gaaacgaaga ggacggctct ttcacccgag actccgttgc cgagtctctc   1260

cgactcgtca tggtcgagga agagggtaag atctaccgag agaaggccaa ggagatgtcc   1320

aagctctttg gtgacaagga tctccaggac cagtacgtcg acgactttgt cgagtacctc   1380

cagaagcacc gacgagctgt tgccatcgac cacgagtcg                          1419
```

<210> SEQ ID NO 20
<211> LENGTH: 473
<212> TYPE: PRT
<213> ORGANISM: Artificial sequence
<220> FEATURE:
<223> OTHER INFORMATION: UGT2_8b

<400> SEQUENCE: 20

-continued

```
Met Ala Thr Ser Asp Ser Ile Val Asp Asp Arg Lys Gln Leu His Ile
1               5                   10                  15

Val Met Phe Pro Trp Leu Ala Phe Gly His Ile Ile Pro Tyr Leu Glu
            20                  25                  30

Leu Ser Lys Leu Ile Ala Glu Lys Gly His Lys Val Ser Phe Leu Ser
        35                  40                  45

Thr Pro Lys Asn Ile Gln Arg Leu Ser Ser His Leu Ser Pro Leu Ile
    50                  55                  60

Asn Val Val Gln Leu Pro Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125

Ser Ile Ala Thr Lys His Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160

Asn Gly Ser Asp Gly Arg Thr Thr Pro Glu Asp Phe Thr Val Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Ile Lys Gly Cys Asp Cys Leu Leu Ser Lys Thr Tyr
    210                 215                 220

His Glu Phe Gly Thr Gln Trp Leu Arg Leu Leu Glu Thr Leu His Arg
225                 230                 235                 240

Lys Pro Val Ile Pro Val Gly Leu Leu Pro Pro Ser Ile Pro Gly Ser
                245                 250                 255

Asp Lys Asp Asp Ser Trp Val Ser Ile Lys Glu Trp Leu Asp Gly Gln
            260                 265                 270

Glu Lys Gly Ser Val Val Tyr Val Ala Leu Gly Ser Glu Val Leu Val
        275                 280                 285

Thr Gln Asp Glu Val Val Glu Leu Ala His Gly Leu Glu Leu Ser Gly
    290                 295                 300

Leu Pro Phe Val Trp Ala Tyr Arg Asn Pro Lys Gly Pro Ala Lys Ser
305                 310                 315                 320

Asp Ser Val Glu Leu Pro Asp Gly Phe Val Glu Arg Val Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Ser Phe Thr Arg Asp Ser Val
                405                 410                 415
```

-continued

```
Ala Glu Ser Leu Arg Leu Val Met Val Glu Glu Glu Gly Lys Ile Tyr
            420                 425                 430

Arg Glu Lys Ala Lys Glu Met Ser Lys Leu Phe Gly Asp Lys Asp Leu
        435                 440                 445

Gln Asp Gln Tyr Val Asp Asp Phe Val Glu Tyr Leu Gln Lys His Arg
    450                 455                 460

Arg Ala Val Ala Ile Asp His Glu Ser
465                 470
```

<210> SEQ ID NO 21
<211> LENGTH: 1419
<212> TYPE: DNA
<213> ORGANISM: Artificial sequence
<220> FEATURE:
<223> OTHER INFORMATION: UGT_8b CpO for S. cerevisiae

<400> SEQUENCE: 21

```
atggccactt ctgactccat cgttgatgac agaaagcaat tgcacatcgt tatgttccca     60

tggttagctt tcggtcacat tatcccatac ttggaattgt ccaaattgat tgctgaaaag    120

ggtcacaaag tctctttctt gtccaccccca aagaacatcc aaagattatc ttctcacttg    180

tctccattga tcaacgttgt ccaattgcca ttaccaagag ttcaagaatt gccagaagat    240

gctgaagcta ccaccgatgt ccatccagaa gatatcccat acttgaagaa ggcttctgat    300

ggtttgcaac cagaagtcac tgaattcttg gaacaacact ctccagactg gattatctac    360

gactacactc actactggtt accatccatt gctactaagc acggtgtttc tcgtgctcat    420

ttctccgtta ccactccatg ggctattgct tacatgggtc caactgctga tgctatgatc    480

aacggttctg atggtagaac cactccagaa gacttcaccg ttccaccaaa atggttccca    540

ttcccaacca aggtctgttg gagaaagcac gatttggcca gattagttcc atacaaggcc    600

ccaggtatct ctgacggtta cagaatgggt ttagtcatca agggttgtga ctgtttgttg    660

tccaagactt accatgaatt cggtactcaa tggttaagat tgttggaaac tttgcacaga    720

aagccagtta tcccagttgg tttgttgcct ccttctatcc caggttctga caaggacgac    780

tcttgggttt ccatcaagga atggttagat ggtcaagaaa agggttccgt tgtctacgtt    840

gctttgggtt ctgaagtctt ggttactcaa gacgaagttg ttgaattggc tcacggtttg    900

gaattgtccg gtctaccatt tgtctgggct tacagaaacc caaagggtcc agctaagtct    960

gactctgttg aattgccaga tggtttcgtc gaaagagtta gagacagagg tttggtctgg   1020

acttcctggg ctccacaatt gagaattttg tcccacgaat ctgtttgtgg tttcttgact   1080

cactgtggtt ctggttctat cgtcgaaggt ttgatgttcg gtcatccttt gatcatgttg   1140

cctatctttg gtgaccaacc attgaacgct agattgttgg aagacaagca agttggtatt   1200

gaaattccaa gaaacgaaga agatggttct ttcaccagag actctgttgc tgaatctttg   1260

agattagtca tggttgaaga agaaggtaag atctacagag aaaaggccaa ggaaatgtcc   1320

aagttgtttg gtgacaaaga tttgcaagac caatacgtcg atgacttcgt cgaatacttg   1380

caaaagcacc gtcgtgccgt tgccattgac cacgaatca                           1419
```

<210> SEQ ID NO 22
<211> LENGTH: 473
<212> TYPE: PRT
<213> ORGANISM: Artificial sequence
<220> FEATURE:
<223> OTHER INFORMATION: UGT2_9b variant

<400> SEQUENCE: 22

-continued

Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Gln
            20                  25                  30

Leu Ser Lys Leu Leu Ala Gln Lys Gly His Lys Val Ser Phe Ile Ser
        35                  40                  45

Thr Pro Arg Asn Ile Gln Arg Leu Ser Ser His Ile Ser Pro Leu Ile
    50                  55                  60

Asn Leu Val Gln Leu Pro Leu Pro Arg Val Asp Asn Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110

His Ser Pro Asp Trp Ile Ile Tyr Asp Tyr Thr His Tyr Trp Leu Pro
        115                 120                 125

Glu Ile Ala Lys Ser Leu Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160

Asn Gly Ser Asp Tyr Arg Thr Glu Leu Glu Asp Phe Thr Val Pro Pro
                165                 170                 175

Lys Trp Phe Pro Phe Pro Thr Thr Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Ser Asp Leu Leu Leu Ser Arg Ser Tyr
    210                 215                 220

His Glu Phe Gly Thr Glu Trp Leu Arg Leu Leu Glu Thr Leu His Arg
225                 230                 235                 240

Val Pro Val Val Pro Val Gly Leu Leu Pro Pro Glu Ile Pro Gly Asp
                245                 250                 255

Gly Glu Asp Glu Ser Trp Val Ser Ile Lys Asp Trp Leu Asp Lys Lys
            260                 265                 270

Glu Lys Gly Ser Val Val Tyr Val Ala Leu Gly Ser Glu Val Leu Val
        275                 280                 285

Ser Gln Glu Glu Leu Asn Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Glu Glu Arg Thr Arg Gly Arg
                325                 330                 335

Gly Val Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Ser Leu Thr Lys Glu Ser Val
                405                 410                 415

-continued

Ala Arg Ser Leu Arg Ser Val Val Val Glu Glu Glu Gly Lys Ile Tyr
420 425 430

Arg Glu Lys Ala Lys Glu Met Ser Lys Leu Phe Gly Asp Lys Asp Leu
435 440 445

Gln Asp Gln Tyr Val Asp Asp Phe Val Glu Tyr Leu Gln Lys His Arg
450 455 460

Arg Ala Val Ala Ile Asp His Glu Ser
465 470

<210> SEQ ID NO 23
<211> LENGTH: 1419
<212> TYPE: DNA
<213> ORGANISM: Artificial sequence
<220> FEATURE:
<223> OTHER INFORMATION: UGT2_9b CpO for S.cerevisiae

<400> SEQUENCE: 23
atggccactt ctgactccat cgttgatgac agaaagaagt tgcacatcgt tatgttccca 60
tggttagctt tcggtcacat tatcccatac ttgcaattgt ccaaattgtt ggctcaaaag 120
ggtcacaaag tctctttcat ctccaccccca agaaacatcc aaagattatc ttctcacatt 180
tctccattga tcaacttggt ccaattgcca ttaccaagag ttgacaactt gccagaagat 240
gctgaagcta ccaccgatgt ccatccagaa gatatcccat acttgaagaa ggcttctgat 300
ggtttgcaac cagaagtcac tgaattcttg gaacaacact ctccagactg gattatctac 360
gactacactc actactggtt accagaaatt gctaagtctt tgggtgtttc tcgtgctcat 420
ttctccgtta ccactccatg ggctattgct tacatgggtc caactgctga tgctatgatc 480
aacggttctg attacagaac cgaattggaa gacttcaccg ttccaccaaa atggttccca 540
ttcccaacca ctgtctgttg gagaaagcac gatttggcca gattagttcc atacaaggcc 600
ccaggtatct ctgacggtta cagaatgggt ttagtcttga agggttctga cttgttgttg 660
tccagatctt accatgaatt cggtactgaa tggttaagat tgttggaaac tttgcacaga 720
gtcccagttg ttccagttgg tttgttgcct cctgaaatcc caggtgacgg tgaagacgaa 780
tcttgggttt ccatcaagga ctggttagat aagaaggaaa agggttccgt tgtctacgtt 840
gctttgggtt ctgaagtctt ggtttctcaa gaagaattga acgaattggc tttgggtttg 900
gaattgtccg gtctaccatt tgtctgggct tacagaaagc caaagggtcc agctaagtct 960
gactctgttg aattgccaga tggtttcgaa gaaagaacca gaggtagagg tgttgtctgg 1020
acttcctggg ctccacaatt gagaattttg tcccacgaat ctgtttgtgg tttcttgact 1080
cactgtggtt ctggttccat tgtcgaaggt ttgatgttcg gtcatccatt gatcatgttg 1140
ccaatctttg gtgaccaacc tttgaacgcc agattattgg aagacaagca agttggtatt 1200
gaaattccaa gaaacgaaga agacggttct ttgaccaagg aatctgttgc cagatctttg 1260
agatctgttg ttgtcgaaga agaaggtaag atctacagag aaaaggccaa ggaaatgtcc 1320
aaattgtttg gtgacaagga tttgcaagat caatatgtcg atgacttcgt cgaatactta 1380
caaaagcacc gtcgtgctgt tgccattgac catgaaagc 1419

<210> SEQ ID NO 24
<211> LENGTH: 1419
<212> TYPE: DNA
<213> ORGANISM: Artificial sequence
<220> FEATURE:
<223> OTHER INFORMATION: UGT2_9b CpO for Y. lipolitica

<400> SEQUENCE: 24

```
atggccacct ccgactccat tgtcgacgac cgaaagaagc tccacattgt catgttcccc     60
tggctcgcct ttggccacat cattccctac ctccagctct ccaagctcct cgcccagaag    120
ggccacaagg tttctttcat ctccactccc cgaaacatcc agcgactctc ctcccacatc    180
tctcctctca tcaacctcgt ccagctcccc ctcccccgag tcgacaacct ccccgaggat    240
gctgaggcca ccaccgatgt ccaccccgag gacatcccct acctcaagaa ggcctccgac    300
ggcctccagc ccgaggtcac cgagttcctc gagcagcact cccccgactg gatcatctac    360
gactacaccc actactggct ccccgagatt gccaagtctc tcggtgtctc tcgagcccac    420
ttctccgtca ccaccccctg ggccattgct tacatgggtc ccactgccga tgccatgatc    480
aacggctccg actaccgaac cgagcttgag gacttcaccg tccctcccaa gtggttcccc    540
ttccccacca ccgtctgctg gcgaaagcac gatctcgccc gactcgtccc ctacaaggct    600
cccggtatct ccgacggtta ccgaatgggc ctcgttctca agggttccga tctgctgctc    660
tcccgatctt accacgagtt tggtactgag tggctgcgac tcctcgagac tctgcaccga    720
gtccccgttg tccccgtcgg tctgctccct cccgagatcc ccggtgacgg tgaggacgag    780
tcttgggttt ccatcaagga ctggctcgac aagaaggaga agggctccgt cgtctacgtt    840
gccctcggct ccgaggttct cgtttcccaa gaggagctta acgagcttgc tctcggcctc    900
gagctgtccg gtctgccctt tgtctgggcc taccgaaagc ccaagggccc cgccaagtcc    960
gactccgtcg agctgcccga cggcttcgag gagcgaaccc gaggtcgagg tgttgtctgg   1020
acctcttggg ctccccagct ccgaatcctc tcccacgagt ccgtctgtgg tttcctgacc   1080
cactgcggtt ccggctctat cgtcgagggt ctgatgttcg gccacccccct catcatgctc  1140
cccatcttcg gtgaccagcc cctcaacgcc cgacttctcg aggacaagca ggtcggtatt   1200
gagatccccc gaaacgaaga ggacggctct ctcaccaagg agtctgttgc tcgatctctg   1260
cgatccgtcg ttgtcgagga agagggtaag atctaccgag agaaggccaa ggagatgtcc   1320
aagctgttcg gtgacaagga tctgcaggac cagtacgtcg acgacttcgt cgagtacctc   1380
cagaagcacc gacgagctgt tgccattgac cacgaatcc                          1419
```

```
<210> SEQ ID NO 25
<211> LENGTH: 473
<212> TYPE: PRT
<213> ORGANISM: Artificial sequence
<220> FEATURE:
<223> OTHER INFORMATION: UGT2_10b variant

<400> SEQUENCE: 25

Met Ala Thr Ser Asp Ser Ile Val Asp Asp Arg Lys Lys Leu His Ile
1               5                   10                  15

Val Met Phe Pro Trp Leu Ala Phe Gly His Ile Ile Pro Tyr Leu Glu
            20                  25                  30

Leu Ser Lys Leu Ile Ala Gln Lys Gly His Lys Val Ser Phe Leu Ser
        35                  40                  45

Thr Thr Lys Asn Ile Asp Arg Leu Ser Ser His Ile Ser Pro Leu Ile
    50                  55                  60

Asn Phe Val Lys Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Glu Phe Leu Glu Gln
            100                 105                 110
```

```
His Ser Pro Asp Trp Ile Ile Tyr Asp Tyr Thr His Tyr Trp Leu Pro
        115                 120                 125

Glu Ile Ala Lys Ser Leu Gly Val Ser Arg Ala His Phe Ser Val Thr
    130                 135                 140

Thr Pro Trp Ala Ile Ala Tyr Met Gly Pro Thr Ala Asp Ala Met Ile
145                 150                 155                 160

Asn Gly Ser Asp Tyr Arg Thr Glu Leu Glu Asp Phe Thr Val Pro Pro
                165                 170                 175

Lys Trp Phe Pro Phe Pro Thr Thr Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Ile Lys Gly Cys Asp Cys Leu Leu Ser Lys Thr Tyr
    210                 215                 220

His Glu Phe Gly Thr Gln Trp Leu Arg Leu Leu Glu Glu Leu His Arg
225                 230                 235                 240

Val Pro Val Ile Pro Val Gly Leu Leu Pro Pro Ser Ile Pro Gly Ser
                245                 250                 255

Asp Lys Asp Asp Ser Trp Val Ser Ile Lys Glu Trp Leu Asp Gly Gln
            260                 265                 270

Glu Lys Gly Ser Val Val Tyr Val Ala Leu Gly Ser Glu Val Leu Val
        275                 280                 285

Thr Gln Glu Glu Val Val Glu Leu Ala His Gly Leu Glu Leu Ser Gly
    290                 295                 300

Leu Pro Phe Phe Trp Ala Tyr Arg Lys Pro Lys Gly Pro Ala Lys Ser
305                 310                 315                 320

Asp Ser Val Glu Leu Pro Asp Gly Phe Val Glu Arg Val Arg Asp Arg
                325                 330                 335

Gly Leu Val Trp Thr Ser Trp Ala Pro Gln Leu Arg Ile Leu Ser His
            340                 345                 350

Glu Ser Val Ala Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Ser Phe Thr Arg Asp Ser Val
                405                 410                 415

Ala Glu Ser Leu Arg Leu Val Met Val Glu Glu Glu Gly Lys Ile Tyr
            420                 425                 430

Arg Glu Lys Ala Lys Glu Met Ser Lys Leu Phe Gly Asp Lys Asp Leu
        435                 440                 445

Gln Asp Gln Tyr Val Asp Asp Phe Val Glu Tyr Leu Gln Lys His Arg
    450                 455                 460

Arg Ala Val Ala Ile Asp His Glu Ser
465                 470
```

<210> SEQ ID NO 26
<211> LENGTH: 1419
<212> TYPE: DNA
<213> ORGANISM: Artificial sequence
<220> FEATURE:
<223> OTHER INFORMATION: UGT2_10b CpO for Y. lipolitica

<400> SEQUENCE: 26

```
atggccacct ccgactccat tgttgacgac cgaaagaagc tccacattgt catgttcccc     60
tggctcgcct ttggccacat catcccctat ctcgagcttt ccaagctcat tgcccagaag    120
ggccacaagg tttccttcct ctccaccacc aagaacattg accgactctc ctcccacatc    180
tctcccctca tcaactttgt caagctcacc ctcccccgag tccaggagct gcccgaggac    240
gccgaggcca ccactgatgt ccaccccgag gatatcccct acctcaagaa ggcctccgac    300
ggcctccagc ccgaggtcac tgagttcctc gagcagcact ctcccgactg gatcatctac    360
gactacaccc actactggct ccccgagatt gccaagtctc tcggtgtctc tcgagcccac    420
ttctccgtca ccaccccctg ggccattgct tacatgggtc ccactgccga tgccatgatc    480
aacggttccg actaccgaac cgagcttgag gacttcaccg tccctcccaa gtggttcccc    540
ttccccacca ccgtctgctg gcgaaagcac gatctggccc gactcgtccc ctacaaggct    600
cccggtatct ccgacggtta ccgaatgggc ctcgtcatca agggctgcga ctgtctgctc    660
tccaagacct accacgagtt cggtactcag tggctccgac ttctcgagga gctgcaccga    720
gtccccgtca tccccgttgg tctgctccct ccctccatcc ccggctctga caaggacgac    780
tcttgggttt ccatcaagga gtggctcgac ggccaggaga agggctccgt tgtctacgtt    840
gctctcggtt ccgaggttct cgtcacccag gaagaggttg tcgagcttgc tcacggtctg    900
gagctgtccg gtctgccctt cttctgggcc taccgaaagc ccaagggtcc cgccaagtcc    960
gactccgtcg agcttcccga tggtttcgtc gagcgagtcc gagatcgagg tctggtctgg   1020
acctcttggg ctccccagct ccgaatcctc tcccacgagt ccgttgctgg tttcctcacc   1080
cactgcggtt ccggctccat tgtcgagggc ctcatgttcg gccaccctct catcatgctc   1140
cccatcttcg gtgaccagcc cctcaacgcc cgactccttg aggacaagca ggtcggtatc   1200
gagatccccc gaaacgagga agatggttct ttcacccgag actctgttgc cgagtctctg   1260
cgactcgtca tggtcgagga agagggtaag atctaccgag agaaggccaa ggagatgtcc   1320
aagctctttg gcgacaagga cctccaggac cagtacgtcg acgactttgt cgagtacctc   1380
cagaagcacc gacgagctgt tgccattgac cacgaaagc                           1419
```

<210> SEQ ID NO 27
<211> LENGTH: 473
<212> TYPE: PRT
<213> ORGANISM: Stevia rebaudiana

<400> SEQUENCE: 27

```
Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
```

-continued

```
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Val Leu Val
        275                 280                 285

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Arg Ser Leu Arg Ser Val Val Val Glu Lys Glu Gly Glu Ile Tyr
            420                 425                 430

Lys Ala Asn Ala Arg Glu Leu Ser Lys Ile Tyr Asn Asp Thr Lys Val
        435                 440                 445

Glu Lys Glu Tyr Val Ser Gln Phe Val Asp Tyr Leu Glu Lys Asn Ala
    450                 455                 460

Arg Ala Val Ala Ile Asp His Glu Ser
465                 470


<210> SEQ ID NO 28
<211> LENGTH: 1422
<212> TYPE: DNA
<213> ORGANISM: Artificial sequence
<220> FEATURE:
<223> OTHER INFORMATION: UGT2_1a CpO for S. cerevisiae

<400> SEQUENCE: 28

atggctacat ctgattctat tgttgatgac aggaagcagt tgcatgtggc tactttccct     60
```

-continued

```
tggcttgctt tcggtcatat actgccttac ctacaactat caaaactgat agctgaaaaa    120
ggacataaag tgtcattcct ttcaacaact agaaacattc aaagattatc ttcccacata    180
tcaccattga ttaacgtcgt tcaattgaca cttccaagag tacaggaatt accagaagat    240
gctgaagcta caacagatgt gcatcctgaa gatatccctt acttgaaaaa ggcatccgat    300
ggattacagc ctgaggtcac tagattcctt gagcaacaca gtccagattg gatcatatac    360
gactacactc actattggtt gccttcaatt gcagcatcac taggcatttc tagggcacat    420
ttcagtgtaa ccacaccttg ggccattgct tacatgggtc catccgctga tgctatgatt    480
aacggcagtg atggtagaac taccgttgaa gatttgacaa ccccaccaaa gtggtttcca    540
tttccaacta aagtctgttg gagaaaacac gacttagcaa gactggttcc atacaaggca    600
ccaggaatct cagacggcta tagaatgggt ttagtcctta aagggtctga ctgcctattg    660
tctaagtgtt accatgagtt tgggacacaa tggctaccac ttttggaaac attacaccaa    720
gttcctgtcg taccagttgg tctattacct ccagaaatcc ctggtgatga gaaggacgag    780
acttgggttt caatcaaaaa gtggttagac gggaagcaaa aaggctcagt ggtatatgtg    840
gcactgggtt ccgaagtttt agtatctcaa acagaagttg tggaacttgc cttaggtttg    900
gaactatctg gattgccatt tgtctgggcc tacagaaaac caaaaggccc tgcaaagtcc    960
gattcagttg aattgccaga cggctttgtc gagagaacta gagatagagg gttggtatgg   1020
acttcatggg ctccacaatt gagaatcctg agtcacgaat ctgtgtgcgg tttcctaaca   1080
cattgtggtt ctggttctat agttgaagga ctgatgtttg gtcatccact tatcatgttg   1140
ccaatctttg gtgaccagcc tttgaatgca cgtctgttag aagataaaca agttggaatt   1200
gaaatcccac gtaatgagga agatggatgt ttaaccaagg agtctgtggc cagatcatta   1260
cgttccgttg tcgttgaaaa ggaaggcgaa atctacaagg ccaatgcccg tgaactttca   1320
aagatctaca atgacacaaa agtagagaag gaatatgttt ctcaatttgt agattaccta   1380
gagaaaaacg ctagagccgt agctattgat catgaatcct aa                      1422
```

```
<210> SEQ ID NO 29
<211> LENGTH: 1422
<212> TYPE: DNA
<213> ORGANISM: Artificial sequence
<220> FEATURE:
<223> OTHER INFORMATION: UGT2_1a CpO for Y. lipolitica

<400> SEQUENCE: 29

atggccacct ccgactccat tgtcgacgac cgaaagcagc tgcacgttgc caccttcccc     60
tggctcgcct ttggccacat tctgccctac ctccagctct ccaagctcat tgctgagaag    120
ggccacaagg tttctttcct gtccaccacc cgaaacatcc agcgactctc ctcccacatc    180
tctcctctca tcaacgttgt ccagctcacc ctcccccgag tccaggagct ccccgaggat    240
gccgaggcca ccactgatgt ccaccccgag gacatcccct acctcaagaa ggcctccgac    300
ggtctgcagc ccgaggtcac ccgattcctc gagcagcact ctcccgactg gatcatctac    360
gactacaccc actactggct cccctccatt gctgcttctc tcggtatctc tcgagcccac    420
ttctccgtca ccaccccctg ggccattgct tacatgggcc cctctgctga cgccatgatc    480
aacggttccg acggccgaac caccgtcgag gatctcacca cccctcccaa gtggttcccc    540
ttccccacca aggtctgctg gcgaaagcac gatctcgccc gactcgtccc ctacaaggcc    600
cccggtatct ccgacggtta ccgaatgggt ctggttctca agggctccga ctgtctgctc    660
```

-continued

```
tccaagtgct accacgagtt tggtacccag tggctccccc tgctcgagac tctgcaccag     720

gtccccgttg tccccgtcgg tctgctccct cccgagatcc ccggtgacga gaaggacgag     780

acttgggttt ccatcaagaa gtggctcgac ggcaagcaga agggctccgt cgtctacgtt     840

gctctcggct ccgaggttct tgtctcccag actgaggtcg tcgagctcgc cctcggtctg     900

gagctctccg gtctgccctt cgtctgggcc taccgaaagc ccaagggtcc cgccaagtcc     960

gactccgtcg agctccccga cggtttcgtc gagcgaactc gagatcgagg tctggtctgg    1020

acctcttggg ctccccagct ccgaatcctc tcccacgagt ccgtctgcgg tttcctgacc    1080

cactgtggtt ccggctccat tgtcgagggc ctcatgttcg gccacccccct catcatgctg   1140

cccatcttcg gtgaccagcc cctcaacgcc cgactcctcg aggacaagca ggtcggtatc    1200

gagatccccc gaaacgaaga ggacggctgc ctcaccaagg agtctgttgc ccgatctctg    1260

cgatctgttg ttgtcgagaa agagggtgag atctacaagg ccaacgcccg agagctctcc    1320

aagatctaca acgacaccaa ggtcgagaag gagtacgttt cccagtttgt cgactacctc    1380

gagaagaacg cccgagctgt cgccattgac cacgagagtt aa                       1422
```

<210> SEQ ID NO 30
<211> LENGTH: 600
<212> TYPE: DNA
<213> ORGANISM: Artificial sequence
<220> FEATURE:
<223> OTHER INFORMATION: ScEno2 promoter

<400> SEQUENCE: 30

```
gtgtcgacgc tgcgggtata gaaagggttc tttactctat agtacctcct cgctcagcat      60

ctgcttcttc ccaaagatga acgcggcgtt atgtcactaa cgacgtgcac caacttgcgg     120

aaagtggaat cccgttccaa aactggcatc cactaattga tacatctaca caccgcacgc     180

ctttttttctg aagcccactt tcgtggactt tgccatatgc aaaattcatg aagtgtgata    240

ccaagtcagc atacacctca ctagggtagt ttctttggtt gtattgatca tttggttcat     300

cgtggttcat taattttttt tctccattgc tttctggctt tgatcttact atcatttgga     360

tttttgtcga aggttgtaga attgtatgtg acaagtggca ccaagcatat ataaaaaaaa     420

aaagcattat cttcctacca gagttgattg ttaaaaacgt atttatagca aacgcaattg     480

taattaattc ttattttgta tcttttcttc ccttgtctca atcttttatt tttattttat     540

ttttcttttc ttagtttctt tcataacacc aagcaactaa tactataaca tacaataata     600
```

<210> SEQ ID NO 31
<211> LENGTH: 1056
<212> TYPE: DNA
<213> ORGANISM: Saccharomyces cerevisiae

<400> SEQUENCE: 31

```
atggcttctg aaaaggaaat cagaagagaa cgtttcttga atgttttccc aaaattggtt      60

gaagaattga acgcttctct attagcttac ggtatgccaa aggaagcttg tgactggtac     120

gctcactctt tgaactacaa caccccaggt ggtaagttga acagaggtct atccgttgtt     180

gacacctacg ccattttgtc caacaagacc gtcgaacaat taggtcaaga agaatacgaa     240

aaggttgcca tcttaggttg gtgtatcgaa ttgttgcaag cttacttctt ggttgctgat     300

gacatgatgg acaaatctat caccagaaga ggtcaaccat gttggtacaa ggttccagaa     360

gtcggtgaaa ttgccatcaa cgatgctttc atgttggaag ctgccatcta caagttgttg     420

aagtctcact tcagaaacga aaagtactac attgacatca ctgaattatt ccacgaagtt     480
```

```
actttccaaa ccgaattggg tcaattgatg gacttgatta ccgctccaga agataaggtc    540

gatttgtcca aattttcctt gaagaaacac tctttcattg tcactttcaa gactgcttac    600

tactcctttt acttgcctgt tgctttggcc atgtatgtcg ctggtatcac cgatgaaaag    660

gacttgaagc aagctcgtga tgtcttgatt ccattaggtg aatacttcca aatccaagat    720

gactacttgg actgtttcgg tactccagaa caaatcggta agattggtac tgatatccaa    780

gacaacaagt gttcctgggt tatcaacaag gctttggaat tggcttctgc tgaacaaaga    840

aagactttgg acgaaaacta cggtaagaag gactctgttg ctgaagctaa gtgtaagaag    900

atcttcaacg atttgaaaat tgaacaatta taccatgaat acgaagaatc tattgccaag    960

gacttgaaag ccaagatctc tcaagtcgac gaatccagag gtttcaaggc tgatgtcttg   1020

actgctttct tgaacaaggt ctacaagaga tcaaaa                             1056
```

```
<210> SEQ ID NO 32
<211> LENGTH: 301
<212> TYPE: DNA
<213> ORGANISM: Artificial sequence
<220> FEATURE:
<223> OTHER INFORMATION: Adh1 terminator

<400> SEQUENCE: 32

agcgaatttc ttatgattta tgatttttat tattaaataa gttataaaaa aaataagtgt     60

atacaaattt taaagtgact cttaggtttt aaaacgaaaa ttcttattct tgagtaactc    120

tttcctgtag gtcaggttgc tttctcaggt atagcatgag gtcgctctta ttgaccacac    180

ctctaccggc atgccgagca aatgcctgca aatcgctccc catttcaccc aattgtagat    240

atgctaactc cagcaatgag ttgatgaatc tcggtgtgta ttttatgtcc tcagaggaca    300

a                                                                    301
```

```
<210> SEQ ID NO 33
<211> LENGTH: 600
<212> TYPE: DNA
<213> ORGANISM: Artificial sequence
<220> FEATURE:
<223> OTHER INFORMATION: Sc Fba1 promoter

<400> SEQUENCE: 33

ctacttggct tcacatacgt tgcatacgtc gatatagata ataatgataa tgacagcagg     60

attatcgtaa tacgtaatag ttgaaaatct caaaaatgtg tgggtcatta cgtaaataat    120

gataggaatg ggattcttct atttttcctt tttccattct agcagccgtc gggaaaacgt    180

ggcatcctct ctttcgggct caattggagt cacgctgccg tgagcatcct ctctttccat    240

atctaacaac tgagcacgta accaatggaa aagcatgagc ttagcgttgc tccaaaaaag    300

tattggatgg ttaataccat ttgtctgttc tcttctgact ttgactcctc aaaaaaaaaa    360

aatctacaat caacagatcg cttcaattac gccctcacaa aaactttttt ccttcttctt    420

cgcccacgtt aaattttatc cctcatgttg tctaacggat ttctgcactt gatttattat    480

aaaaagacaa agacataata cttctctatc aatttcagtt attgttcttc cttgcgttat    540

tcttctgttc ttctttttct tttgtcatat ataaccataa ccaagtaata catattcaaa    600
```

```
<210> SEQ ID NO 34
<211> LENGTH: 1575
<212> TYPE: DNA
<213> ORGANISM: Saccharomyces cerevisiae
```

<400> SEQUENCE: 34
atggaccaat tggtcaagac tgaagtcacc aagaaatctt tcactgctcc agtccaaaag 60
gcttccactc cagttttgac caacaagacc gtcatctccg gttccaaggt taaatctttg 120
tcctctgctc aatcttcctc ctctggtcca tcttcttctt ctgaagaaga tgattccaga 180
gatatcgaat ctttggacaa gaaaatcaga ccattggaag aattggaagc tctattgtcc 240
tctggtaaca ctaagcaatt aaagaacaag gaagttgctg ctttggttat ccacggtaaa 300
ttgccattgt acgctttgga aaagaaatta ggtgacacca ccagagctgt tgctgtcaga 360
agaaaggctt tgtccatttt ggctgaagct ccagtcttgg cttccgacag attaccatac 420
aagaactacg actacgaccg tgtctttggt gcttgttgtg aaaatgtcat tggttacatg 480
ccattaccag ttggtgtcat tggtccattg gttatcgacg gtacttctta ccacatccca 540
atggctacca ctgaaggttg tttggttgct tctgccatga gaggttgtaa ggccatcaac 600
gctggtggtg gtgctaccac cgttttgact aaggatggta tgaccagagg tcctgttgtc 660
agattcccaa ctttgaagag atctggtgct tgtaagatct ggttggattc tgaagaaggt 720
caaaacgcca tcaagaaggc tttcaactcc acttccagat tcgctagatt gcaacacatt 780
caaacttgtt tagctggtga cttgttgttc atgagattca gaaccaccac tggtgacgct 840
atgggtatga acatgatctc caagggtgtt gaatactctt tgaagcaaat ggttgaagaa 900
tacggttggg aagatatgga agttgtctct gtttctggta actactgtac cgacaagaag 960
ccagctgcca tcaactggat cgaaggtcgt ggtaagtccg ttgttgctga agctaccatt 1020
ccaggtgacg ttgtcagaaa ggttttgaaa tctgatgttt ctgctttagt cgaattgaac 1080
attgccaaga acttggtcgg ttctgccatg gctggttccg tcggtggttt caacgctcat 1140
gccgctaact tggtcactgc tgttttcttg gctttaggtc aagatccagc tcaaaatgtc 1200
gaatcctcta actgtatcac tttgatgaag gaagttgacg gtgatttgag aatttctgtt 1260
tccatgccat ccattgaagt cggtactatc ggtggtggta ctgtcttgga accacaaggt 1320
gccatgttgg acttgttggg tgttcgtggt ccacacgcta ccgctccagg tactaacgcc 1380
agacaattgg ccagaattgt tgcctgtgcc gtcttggctg gtgaattgtc tctatgtgcc 1440
gctttggctg ctggtcactt ggttcaatct cacatgaccc acaacagaaa gcctgctgaa 1500
ccaaccaaac caaacaactt ggatgctact gacattaaca gattaaagga cggttctgtc 1560
acctgtatca agtct 1575

<210> SEQ ID NO 35
<211> LENGTH: 301
<212> TYPE: DNA
<213> ORGANISM: Artificial sequence
<220> FEATURE:
<223> OTHER INFORMATION: Adh2 terminator

<400> SEQUENCE: 35
agcggatctc ttatgtcttt acgatttata gttttcatta tcaagtatgc ctatattagt 60
atatagcatc tttagatgac agtgttcgaa gtttcacgaa taaaagataa tattctactt 120
tttgctccca ccgcgtttgc tagcacgagt gaacaccatc cctcgcctgt gagttgtacc 180
cattcctcta aactgtagac atggtagctt cagcagtgtt cgttatgtac ggcatcctcc 240
aacaaacagt cggttatagt ttgtcctgct cctctgaatc gtgtccctcg atatttctca 300
t 301

-continued

<210> SEQ ID NO 36
<211> LENGTH: 600
<212> TYPE: DNA
<213> ORGANISM: Artificial sequence
<220> FEATURE:
<223> OTHER INFORMATION: Sc Tef1 promoter

<400> SEQUENCE: 36
ttggctgata atagcgtata aacaatgcat actttgtacg ttcaaaatac aatgcagtag 60
atatatttat gcatattaca tataatacat atcacatagg aagcaacagg cgcgttggac 120
ttttaatttt cgaggaccgc gaatccttac atcacaccca atcccccaca agtgatcccc 180
cacacaccat agcttcaaaa tgtttctact ccttttttac tcttccagat tttctcggac 240
tccgcgcatc gccgtaccac ttcaaaacac ccaagcacag catactaaat ttcccctctt 300
tcttcctcta gggtgtcgtt aattacccgt actaaaggtt tggaaaagaa aaaagacacc 360
gcctcgtttc tttttcttcg tcgaaaaagg caataaaaat ttttatcacg tttctttttc 420
ttgaaaattt ttttttttga tttttttctc tttcgatgac ctcccattga tatttaagtt 480
aataaacggt cttcaatttc tcaagtttca gtttcatttt tcttgttcta ttacaacttt 540
ttttacttct tgctcattag aaagaaagca tagcaatcta atctaagttt taattacaaa 600

<210> SEQ ID NO 37
<211> LENGTH: 1005
<212> TYPE: DNA
<213> ORGANISM: Saccharomyces cerevisiae

<400> SEQUENCE: 37
atggaagcta agattgacga attgatcaac aacgaccctg tctggtcctc tcaaaacgaa 60
tctttgatct ccaagccata caaccacatc ttgttgaagc caggtaagaa cttcagatta 120
aacttgattg ttcaaatcaa cagagttatg aacttgccaa aggaccaatt ggccattgtt 180
tcccaaattg tcgaattgtt gcacaactcc tctctattga tcgatgacat tgaagataat 240
gctccattaa gaagaggtca aaccacttct catttgattt tcggtgtccc atccaccatc 300
aacactgcta actacatgta cttcagagcc atgcaattgg tttctcaatt gaccaccaag 360
gaaccattat accacaactt gatcactatc tttaacgaag aattgattaa cttgcaccgt 420
ggtcaaggtt tggacatcta ctggagagat ttcttgccag aaattattcc aactcaagaa 480
atgtacttga acatggtcat gaacaagact ggtggtttat tcagattgac tttacgtttg 540
atggaagctt tgtctccatc ttcccaccac ggtcactctt tggttccatt catcaatcta 600
ttaggtatca tctaccaaat cagagatgat tacttgaact tgaaggactt ccaaatgtcc 660
tctgaaaagg gtttcgctga agatatcact gaaggtaaat tgtctttccc aattgtccac 720
gccttgaact ttaccaagac caagggtcaa actgaacaac acaacgaaat tttgagaatc 780
ttattgttga gaacttctga caaggacatc aagttgaaat tgatccaaat cttggaattc 840
gataccaact ctttggctta caccaagaac ttcatcaacc aattggttaa catgatcaag 900
aatgacaacg aaaacaaata cttgccagac ttggcttccc actccgatac cgctaccaac 960
ttgcacgacg aattgttgta cattattgac catttgtctg agtta 1005

<210> SEQ ID NO 38
<211> LENGTH: 301
<212> TYPE: DNA
<213> ORGANISM: Artificial sequence
<220> FEATURE:
<223> OTHER INFORMATION: Sc Gmp1 terminator

<400> SEQUENCE: 38
agtctgaaga atgaatgatt tgatgatttc tttttccctc catttttctt actgaatata 60
tcaatgatat agacttgtat agtttattat ttcaaattaa gtagctatat atagtcaaga 120
taacgtttgt ttgacacgat tacattattc gtcgacatct tttttcagcc tgtcgtggta 180
gcaatttgag gagtattatt aattgaatag gttcattttg cgctcgcata aacagttttc 240
gtcagggaca gtatgttgga atgagtggta attaatggtg acatgacatg ttatagcaat 300
a 301

<210> SEQ ID NO 39
<211> LENGTH: 600
<212> TYPE: DNA
<213> ORGANISM: Artificial sequence
<220> FEATURE:
<223> OTHER INFORMATION: Sc Pgk1 promoter

<400> SEQUENCE: 39
gggccagaaa aaggaagtgt ttccctcctt cttgaattga tgttaccctc ataaagcacg 60
tggcctctta tcgagaaaga aattaccgtc gctcgtgatt tgtttgcaaa aagaacaaaa 120
ctgaaaaaac ccagacacgc tcgacttcct gtcttcctat tgattgcagc ttccaatttc 180
gtcacacaac aaggtcctag cgacggctca caggttttgt aacaagcaat cgaaggttct 240
ggaatggcgg gaaagggttt agtaccacat gctatgatgc ccactgtgat ctccagagca 300
aagttcgttc gatcgtactg ttactctctc tctttcaaac agaattgtcc gaatcgtgtg 360
acaacaacag cctgttctca cacactcttt tcttctaacc aaggggggtgg tttagtttag 420 tagaacctcg tgaaacttac atttacatat atataaactt gcataaattg gtcaatgcaa 480
gaaatacata tttggtcttt tctaattcgt agtttttcaa gttcttagat gctttctttt 540 tctcttttttt acagatcatc aaggaagtaa ttatctactt tttacaacaa atataaaaca 600

<210> SEQ ID NO 40
<211> LENGTH: 1001
<212> TYPE: DNA
<213> ORGANISM: Artificial sequence
<220> FEATURE:
<223> OTHER INFORMATION: Kl prom 12 promoter

<400> SEQUENCE: 40
cgtaaaaact aaaacgagcc cccaccaaag aacaaaaaag aaggtgctgg gcccccactt 60
tcttcccttg cacgtgatag gaagatggct acagaaacaa gaagatggaa atcgaaggaa 120
agagggagac tggaagctgt aaaaactgaa atgaaaaaaa aaaaaaaaaa aaaaaaacaa 180
gaagctgaaa atggaagact gaaatttgaa aaatggtaaa aaaaaaaaag aaacacgaag 240
ctaaaaacct ggattccatt ttgagaagaa gcaagaaagg taagtatggt aacgaccgta 300
caggcaagcg cgaaggcaaa tggaaaagct ggagtccgga agataatcat ttcatcttct 360
tttgttagaa cagaacagtg gatgtccctc atctcggtaa cgtattgtcc atgccctaga 420
actctctgtc cctaaaaaga ggacaaaaac ccaatggttt ccccagcttc cagtggagcc 480
accgatccca ctggaaacca ctggacagga agagaaaatc acggacttcc tctattgaag 540
gataattcaa cactttcacc agatcccaaa tgtcccgccc ctattcccgt gttccatcac 600
gtaccataac ttaccatttc atcacgttct ctatggcaca ctggtactgc ttcgactgct 660
ttgcttcatc ttctctatgg gccaatgagc taatgagcac aatgtgctgc gaaataaagg 720
gatatctaat ttatattatt acattataat atgtactagt gtggttattg gtaattgtac 780

```
ttaattttga tatataaagg gtggatcttt ttcattttga atcagaattg gaattgcaac    840

ttgtctcttg tcactattac ttaatagtaa ttatatttct tattaacctt ttttttaagt    900

caaaacacca aggacaagaa ctactcttca aaggtatttc aagttatcat acgtgtcaca    960

cacgcttcac agtttcaagt aaaaaaaaag aatattacac a                       1001


<210> SEQ ID NO 41
<211> LENGTH: 2229
<212> TYPE: DNA
<213> ORGANISM: Stevia rebaudiana

<400> SEQUENCE: 41

atgtgtaaag ctgtttccaa ggaatactct gacttgttgc aaaaggatga agcctccttc     60

accaaatggg atgatgacaa agttaaggac catttagaca ctaacaagaa cttgtaccca    120

aacgatgaaa tcaaggaatt cgtcgaatct gtcaaagcta tgttcggttc catgaatgat    180

ggtgaaatca acgtttccgc ttacgacacc gcttgggttg ctttggttca agacgttgat    240

ggttccggtt ctccacaatt cccatcttct ttggaatgga ttgccaacaa ccaattgtct    300

gatggttctt ggggtgacca tttgttattc tctgctcacg acagaattat taacacttta    360

gcttgtgtca ttgctttgac ttcctggaat gtccatccat ccaagtgtga aaagggtttg    420

aacttcttga gagaaaacat ctgtaagttg gaagatgaaa atgctgaaca catgccaatt    480

ggtttcgaag ttaccttccc atctttgatt gatatcgcca agaagttgaa catcgaagtc    540

ccagaagaca ccccagcttt gaaggaaatc tacgccagaa gagatatcaa gttgaccaaa    600

atcccaatgg aagttttgca caaggttcca accaccttgt tgcactcttt ggaaggtatg    660

ccagacttgg aatgggaaaa gttgttaaag ttgcaatgta aggacggttc tttcttgttc    720

tctccatctt ctaccgcctt tgctttgatg caaactaagg acgaaaagtg tctacaatac    780

ttaactaata tcgttaccaa attcaacggt ggtgtcccaa acgtttaccc tgttgacttg    840

tttgaacaca tctgggttgt tgacagattg caacgtttgg gtattgctcg ttatttcaag    900

tctgaaatca aggactgtgt tgaatacatc aacaagtact ggactaagaa cggtatctgt    960

tgggctcgta acacccacgt tcaagatatc gacgacactg ctatgggttt cagagtcttg   1020

agagctcatg gttacgatgt caccccagat gtcttcagac aattcgaaaa ggatggtaag   1080

ttcgtttgtt ttgccggtca atccactcaa gccgtcactg gtatgttcaa cgtctacaga   1140

gcttctcaaa tgttgttccc aggtgaaaga atcctagaag acgctaagaa gttctcctac   1200

aactacttga aagaaaagca atctactaac gaattgttgg acaaatggat cattgccaaa   1260

gacttaccag gtgaagtcgg ttacgctttg gatattccat ggtacgcttc tctaccaaga   1320

ttagaaacca gatactactt ggaacaatac ggtggtgaag acgatgtctg gatcggtaag   1380

accttgtaca gaatgggtta cgtttccaac aacacttact tggaaatggc caaattggac   1440

tacaacaact acgtcgccgt cttacaattg gaatggtaca ccattcaaca atggtacgtt   1500

gacattggta ttgaaaagtt tgaatccgac aacatcaagt ccgtcttggt ttcctactac   1560

ttggctgctg cttccatctt tgaaccagaa agatccaagg aaagaattgc ttgggctaag   1620

accaccatct tggttgacaa gatcacttct attttcgact cttcccaatc ttccaaggaa   1680

gatatcaccg ctttcattga caaattcaga aacaagtctt cttccaagaa gcactccatt   1740

aacggtgaac catggcacga agttatggtt gctttgaaga agactttgca cggttttgct   1800

ttggatgctt tgatgactca ctctcaagat attcaccctc aattacacca agcttgggaa   1860
```

-continued

```
atgtggttaa ccaagttgca agatggtgtc gatgtcactg ctgaattgat ggttcaaatg   1920

atcaacatga ctgccggtag atgggtttct aaggaattgt tgactcaccc tcaataccaa   1980

cgtttgtcca ccgtcaccaa ctctgtctgt cacgacatca ctaagttgca caacttcaaa   2040

gaaaactcca ctactgtcga ttctaaggtt caagaattgg ttcaattagt tttctctgac   2100

accccagatg acttggacca agacatgaag caaactttct tgactgtcat gaagaccttc   2160

tactacaagg cttggtgtga cccaaacacc atcaacgacc atatttctaa ggtcttcgaa   2220

attgttatc                                                           2229
```

<210> SEQ ID NO 42
<211> LENGTH: 2271
<212> TYPE: DNA
<213> ORGANISM: Stevia rebaudiana

<400> SEQUENCE: 42

```
atgacttctc acggtggtca aaccaaccca accaacttga ttattgacac caccaaggaa     60

agaatccaaa agcaattcaa gaatgttgaa atctccgttt cctcctacga cactgcttgg    120

gttgccatgg ttccatctcc aaactcccca aagtctccat gtttcccaga atgtttgaac    180

tggttaatca acaaccaatt gaacgatggt tcctggggtt tagtcaatca cacccacaac    240

cacaatcacc cattgttgaa ggactctcta tcctccactt tggcttgtat cgttgctttg    300

aagagatgga acgttggtga agaccaaatc aacaagggtt tgtcctttat tgaatccaac    360

ttggcttctg ctactgaaaa gtcccaacca tctcctatcg gttttgacat cattttccca    420

ggtttattgg aatacgctaa gaacttggac atcaacttat tatctaagca aaccgatttc    480

tccttgatgt tgcacaagag agaattggaa caaaagagat gtcactccaa cgaaatggac    540

ggttacttgg cttacatttc tgaaggtttg ggtaacttgt acgactggaa catggtcaag    600

aaataccaaa tgaagaacgg ttccgttttc aactctccat ctgctaccgc tgctgctttc    660

atcaaccatc aaaacccagg ttgtttgaac tacttgaact ctttgttgga caaattcggt    720

aacgctgttc caactgtcta cccacacgat ttgtttatca gattatccat ggttgacacc    780

attgaacgtt tgggtatttc tcatcacttc agagtcgaaa tcaagaacgt tttggatgaa    840

acttacagat gttgggttga aagagatgaa caaatcttca tggatgtcgt cacttgtgcc    900

ttggccttca gattattgag aattaacggt tacgaagttt ctccagaccc attggctgaa    960

atcactaacg aattggcttt gaaggacgaa tacgccgctt tggaaactta ccatgcctct   1020

cacatcttat accaagaaga cttgtcctct ggtaagcaaa tcttgaagtc tgctgacttc   1080

ttgaaggaaa ttatctctac tgattctaac agattgtcca agttgattca caaggaagtt   1140

gaaaacgcct tgaaattccc aatcaacact ggtttggaaa gaattaacac cagaagaaac   1200

atccaattat acaacgttga caacactaga atcttgaaga ctacttatca ctcttccaac   1260

atctccaaca ctgactactt gagattggct gtcgaagatt tctacacctg tcaatctatt   1320

tacagagaag aattgaaggg tttggaaaga tgggttgtcg aaaacaaatt ggaccaattg   1380

aaatttgcta gacaaaagac cgcctactgt tacttctccg ttgctgccac tttgtcctct   1440

ccagaattat ctgacgccag aatctcctgg gctaagaatg gtatcttgac caccgttgtc   1500

gatgacttct tcgatattgg tggtaccatt gacgaattga ccaacttgat tcaatgtgtt   1560

gaaaagtgga acgtcgatgt cgataaggac tgttgttctg aacacgtcag aatcttattc   1620

ttggctttga aagatgctat ctgttggatc ggtgacgaag ctttcaaatg gcaagctcgt   1680

gacgttacct ctcacgtcat ccaaacctgg ttggaattga tgaactctat gttgagagaa   1740
```

-continued gccatctgga cccgtgatgc ttacgtccca actttgaacg aatacatgga aaatgcttac 1800
gtttctttcg ctttgggtcc aattgtcaag cctgctattt acttcgttgg tccaaagttg 1860
tccgaagaaa ttgttgaatc ttctgaatac cacaacttgt tcaaattgat gtctactcaa 1920
ggtcgtttgt tgaacgatat ccactctttc aagcgtgaat tcaaggaagg taagttgaat 1980
gctgttgctt tgcatttgtc taacggtgaa tctggtaagg tcgaagaaga agttgtcgaa 2040
gaaatgatga tgatgatcaa gaacaagaga aaggaattga tgaagttgat ctttgaagaa 2100
aacggttcta ttgtcccaag agcttgtaag gatgctttct ggaacatgtg tcacgtcttg 2160
aacttcttct acgctaacga tgacggtttc actggtaaca ccatcttaga caccgtcaag 2220
gacatcattt acaacccatt agtcttggtt aacgaaaacg aagaacaaag a 2271

<210> SEQ ID NO 43
<211> LENGTH: 301
<212> TYPE: DNA
<213> ORGANISM: Artificial sequence
<220> FEATURE:
<223> OTHER INFORMATION: Sc Tal1 terminator

<400> SEQUENCE: 43
aggaagtatc tcggaaatat taatttaggc catgtcctta tgcacgtttc ttttgatact 60
tacgggtaca tgtacacaag tatatctata tatataaatt aatgaaaatc ccctatttat 120
atatatgact ttaacgagac agaacagttt tttatttttt atcctatttg atgaatgata 180
cagtttctta ttcacgtgtt atacccacac caaatccaat agcaataccg gccatcacaa 240
tcactgtttc ggcagcccct aagatcagac aaaacatccg gaaccacctt aaatcaacgt 300
c 301

<210> SEQ ID NO 44
<211> LENGTH: 1575
<212> TYPE: DNA
<213> ORGANISM: Gibberella fujikuroi

<400> SEQUENCE: 44
atgtccaagt ctaactccat gaactccact tctcacgaaa ctttattcca acaattggtt 60
ttgggtttgg acagaatgcc attgatggat gtccactggt tgatctacgt tgctttcggt 120
gcttggttat gttcctacgt cattcacgtt ttgtcctctt cttctaccgt caaggttcca 180
gttgtcggtt acagatccgt tttcgaacca acctggttat tgagattaag atttgtctgg 240
gaaggtggtt ccattattgg tcaaggttac aacaaattca aggactctat cttccaagtc 300
agaaagttgg gtactgacat tgttatcatc ccaccaaact acatcgatga agtcagaaag 360
ttgtcccaag acaagaccag atctgttgaa ccattcatca acgatttcgc tggtcaatac 420
accagaggta tggtctttct acaatctgat ttgcaaaacc gtgtcatcca acaaagattg 480
actccaaagt tggtttcttt gactaaggtc atgaaggaag aattggacta cgctttgacc 540
aaggaaatgc cagacatgaa gaacgacgaa tgggttgaag ttgacatttc ttccatcatg 600
gtcagattga tctccagaat ctctgcccgt gttttcttgg gtccagaaca ctgtcgtaac 660
caagaatggt tgaccaccac tgctgaatac tctgaatctt tattcatcac tggtttcatc 720
ttgagagttg tcccacacat cttaagacca ttcattgctc cattgttgcc ttcttacaga 780
actttgttga gaaatgtctc ttctggtaga agagttatcg gtgatatcat cagatctcaa 840
caaggtgatg gtaacgaaga tatcttgtcc tggatgagag atgctgctac cggtgaagaa 900

-continued

```
aagcaaattg acaacattgc tcaaagaatg ttgatcttgt ctttggcttc cattcacacc    960

accgccatga ccatgaccca tgccatgtac gacttgtgtg cctgtccaga atacattgaa   1020

ccattacgtg acgaagtcaa atccgttgtt ggtgcttctg gttgggacaa gactgctttg   1080

aacagattcc acaagttgga ctctttcttg aaggaatctc aaagattcaa cccagttttc   1140

ttgttgactt tcaacagaat ctaccatcaa tccatgactt tgtccgatgg taccaacatt   1200

ccatctggta ccagaattgc tgttccatct cacgctatgt tgcaagattc tgctcacgtt   1260

ccaggtccaa ctcctccaac tgaatttgac ggtttcagat actccaagat cagatctgac   1320

tctaactatg ctcaaaagta cttgttctcc atgaccgatt cttccaacat ggctttcggt   1380

tacggtaagt acgcttgtcc aggtcgtttc tacgcctcca acgaaatgaa attgactttg   1440

gccattttgt tgttgcaatt tgaattcaaa ttgccagatg gtaagggtag accaagaaac   1500

atcactatcg actctgacat gattccagac ccaagagcta gattatgtgt cagaaagaga   1560

tctctacgtg acgaa                                                    1575
```

<210> SEQ ID NO 45
<211> LENGTH: 301
<212> TYPE: DNA
<213> ORGANISM: Artificial sequence
<220> FEATURE:
<223> OTHER INFORMATION: Sc Tpi1 terminator

<400> SEQUENCE: 45

```
agattaatat aattatataa aaatattatc ttcttttctt tatatctagt gttatgtaaa     60

ataaattgat gactacggaa agcttttttta tattgtttct ttttcattct gagccactta    120

aatttcgtga atgttcttgt aagggacggt agatttacaa gtgatacaac aaaaagcaag    180

gcgctttttc taataaaaag aagaaaagca tttaacaatt gaacacctct atatcaacga    240

agaatattac tttgtctcta aatccttgta aaatgtgtac gatctctata tgggttactc    300

a                                                                     301
```

<210> SEQ ID NO 46
<211> LENGTH: 403
<212> TYPE: DNA
<213> ORGANISM: Artificial sequence
<220> FEATURE:
<223> OTHER INFORMATION: Ag lox_TEF1 promoter

<400> SEQUENCE: 46

```
taccgttcgt ataatgtatg ctatacgaag ttatgtcccc gccgggtcac ccggccagcg     60

acatggaggc ccagaatacc ctccttgaca gtcttgacgt gcgcagctca ggggcatgat    120

gtgactgtcg cccgtacatt tagcccatac atccccatgt ataatcattt gcatccatac    180

attttgatgg ccgcacggcg cgaagcaaaa attacggctc ctcgctgcag acctgcgagc    240

agggaaacgc tcccctcaca gacgcgttga attgtcccca cgccgcgccc ctgtagagaa    300

atataaaagg ttaggatttg ccactgaggt tcttctttca tatacttcct tttaaaatct    360

tgctaggata cagttctcac atcacatccg aacataaaca aca                      403
```

<210> SEQ ID NO 47
<211> LENGTH: 810
<212> TYPE: DNA
<213> ORGANISM: Artificial sequence
<220> FEATURE:
<223> OTHER INFORMATION: KANMX

<400> SEQUENCE: 47

```
atgggtaagg aaaagactca cgtttcgagg ccgcgattaa attccaacat ggatgctgat     60

ttatatgggt ataaatgggc tcgcgataat gtcgggcaat caggtgcgac aatctatcga    120

ttgtatggga agcccgatgc gccagagttg tttctgaaac atggcaaagg tagcgttgcc    180

aatgatgtta cagatgagat ggtcagacta aactggctga cggaatttat gcctcttccg    240

accatcaagc attttatccg tactcctgat gatgcatggt tactcaccac tgcgatcccc    300

ggcaaaacag cattccaggt attagaagaa tatcctgatt caggtgaaaa tattgttgat    360

gcgctggcag tgttcctgcg ccggttgcat tcgattcctg tttgtaattg tccttttaac    420

agcgatcgcg tatttcgttt ggctcaggcg caatcacgaa tgaataacgg tttggttgat    480

gcgagtgatt ttgatgacga gcgtaatggc tggcctgttg aacaagtctg gaaagaaatg    540

cataagcttt tgccattctc accggattca gtcgtcactc atggtgattt ctcacttgat    600

aaccttattt ttgacgaggg gaaattaata ggttgtattg atgttggacg agtcggaatc    660

gcagaccgat accaggatct tgccatccta tggaactgcc tcggtgagtt ttctccttca    720

ttacagaaac ggctttttca aaaatatggt attgataatc ctgatatgaa taaattgcag    780

tttcatttga tgctcgatga gtttttctaa                                     810
```

<210> SEQ ID NO 48
<211> LENGTH: 285
<212> TYPE: DNA
<213> ORGANISM: Artificial sequence
<220> FEATURE:
<223> OTHER INFORMATION: Ag Tef1_lox terminator

<400> SEQUENCE: 48

```
atcagtactg acaataaaaa gattcttgtt ttcaagaact tgtcatttgt atagtttttt     60

tatattgtag ttgttctatt ttaatcaaat gttagcgtga tttatatttt ttttcgcctc    120

gacatcatct gcccagatgc gaagttaagt gcgcagaaag taatatcatg cgtcaatcgt    180

atgtgaatgc tggtcgctat actgctgtcg attcgatact aacgccgcca tccagtgtcg    240

aaaacgagct cataacttcg tataatgtat gctatacgaa cggta                    285
```

<210> SEQ ID NO 49
<211> LENGTH: 1575
<212> TYPE: DNA
<213> ORGANISM: Arabidopsis thaliana

<400> SEQUENCE: 49

```
atggaatctt tagtcgttca caccgtcaat gccatctggt gtattgtcat tgttggtatt     60

ttctctgttg gttaccacgt ttacggtcgt gccgttgttg aacaatggag aatgagaaga    120

tctttgaaat tgcaaggtgt caagggtcca ccaccatcca ttttcaacgg taatgtctct    180

gaaatgcaaa gaatccaatc tgaagctaag cactgttccg gtgacaacat catttctcac    240

gattactcct cctctttgtt ccctcacttt gaccactgga gaaagcaata cggtagaatc    300

tacacctact ccactggttt gaaacaacat ttgtacatca accatccaga aatggtcaag    360

gaattatctc aaaccaacac tttgaactta ggtcgtatca ctcacatcac caagagattg    420

aacccaatct taggtaacgg tatcatcact tccaacggtc cacactgggc tcatcaaaga    480

agaattattg cttacgaatt cacccacgac aaaatcaagg gtatggtcgg tttgatggtc    540

gaatctgcca tgccaatgtt gaacaaatgg gaagaaatgg ttaagagagg tggtgaaatg    600

ggttgtgaca tccgtgttga cgaagatttg aaggatgttt ctgctgatgt cattgctaag    660
```

-continued gcttgtttcg gttcctcttt ctccaagggt aaggctatct tctccatgat cagagacttg 720
ttgactgcca tcactaagag atctgttttg ttcagattca acggtttcac cgacatggtt 780
ttcggttcca agaagcatgg tgatgtcgat atcgatgctt tggaaatgga attggaatct 840
tctatctggg aaaccgttaa ggaaagagaa attgaatgta aggacactca caagaaggat 900
ttgatgcaat taatcttgga aggtgccatg agatcttgtg acggtaactt gtgggacaag 960
tctgcttaca gaagatttgt tgtcgacaac tgtaaatcca tctactttgc cggtcacgac 1020
tctactgctg tctccgtttc ctggtgtttg atgttgctag ctttgaaccc atcctggcaa 1080
gtcaagatca gagatgaaat cttatcttct tgtaagaacg gtattccaga tgctgaatcc 1140
attccaaact tgaagaccgt taccatggtc attcaagaaa ctatgagatt gtacccacca 1200
gctccaattg tcggtagaga agcttccaag gacatcagat taggtgactt ggttgttcca 1260
aagggtgttt gtatctggac tttgattcca gctttgcacc gtgacccaga aatctggggt 1320
ccagatgcta acgacttcaa gccagaaaga ttctctgaag gtatttccaa ggcttgtaaa 1380
tacccacaat cttacatccc attcggtttg ggtccaagaa cctgtgtcgg taagaacttc 1440
ggtatgatgg aagtcaaagt tttggtttct ttgattgttt ccaagttctc tttcaccttg 1500
tctccaactt accaacactc tccatctcac aagttgttgg ttgaacctca acacggtgtt 1560
gtcattagag tcgtt 1575

<210> SEQ ID NO 50
<211> LENGTH: 1000
<212> TYPE: DNA
<213> ORGANISM: Artificial sequence
<220> FEATURE:
<223> OTHER INFORMATION: Kl prom 6 promoter

<400> SEQUENCE: 50
caaagggggg gcagggacag ggatacgaca agggctgggg aaaaaaaaaa agatagatac 60
gattggccgg gtaagcctgg ggaaatgtag caagtgcggg taagttaaaa ggtaaccacg 120
tgactccgga agagtcacgt ggttacggac ttttttctct agatctcagc tttttatcgg 180
tcttaccctg ccctcctgcc ccctgcccct tccctttgcc ccaaaaagaa aggaaatctg 240
ttggatttcg ctcaggccat ccctttcgtt aatatcggtt atcgctttac acactgcaca 300
tccttctgtc caaaaggaat ccagaagttt agcttttcct tcctttccca cagacattag 360
cctaggccct ctctcatcat ttgcatgcct cagccaatgt accaagaata acgcaacgag 420
gttgggaaat tttaacccaa caatcgatgc agatgtgaca agagattaga cacgttccag 480
ataccagatt acacagcttg tgctagcaga gtgacatatg gtggtgttgt gtctcgttta 540
gtacctgtaa tcgagagtgt tcaaatcagt cgatttgaac acccttactg ccactgaata 600
ttgattgaat accgtttatt gaaggtttta tgagtgatct tctttcggtc caggacaatt 660
tgttgagctt tttctatgta gagttccgtc cctttttttt ttttttttgc tttctcgcac 720
ttactagcac tatttttttt tcacacacta aaacacttta ttttaatcta tatatatata 780
tatatatata tgtaggaatg gaatcacaga catttgatac tcatcctcat ccttattaat 840
tcttgtttta atttgtttga cttagccaaa ccaccaatct caacccatcg tatttcaggt 900
attgtgtgtc tagtgtgtct ctggtatacg gaaataagtg ccagaagtaa ggaagaaaca 960
aagaacaagt gtctgaatac tactagcctc tcttttcata 1000

<210> SEQ ID NO 51
<211> LENGTH: 2133

-continued

<212> TYPE: DNA
<213> ORGANISM: Arabidopsis thaliana

<400> SEQUENCE: 51
atgtcctctt cttcttcttc ttctacttcc atgattgatt tgatggctgc catcatcaag 60
ggtgaaccag tcattgtctc tgacccagcc aacgcttctg cttacgaatc cgttgctgct 120
gaattgtcct ccatgttgat tgaaaacaga caattcgcta tgattgtcac tacttccatt 180
gctgtcttga ttggttgtat cgtcatgttg gtctggagaa gatccggttc cggtaactcc 240
aagagagttg aaccattgaa gccattagtc atcaagccaa gagaagaaga aattgatgac 300
ggtagaaaga aggtcaccat cttctttggt actcaaaccg gtactgctga aggttttgct 360
aaggctttgg gtgaagaagc caaagctaga tacgaaaaga ccagattcaa gatcgttgac 420
ttggacgact acgctgctga tgacgacgaa tacgaagaaa agttgaagaa ggaagatgtt 480
gccttcttct tcttggctac ttacggtgat ggtgaaccaa ctgacaatgc tgccagattc 540
tacaaatggt tcaccgaagg taacgacaga ggtgaatggt taaagaactt gaaatacggt 600
gttttcggtc taggtaacag acaatacgaa cacttcaaca aggttgccaa ggttgtcgat 660
gacatcttgg ttgaacaagg tgctcaaaga ttagtccaag tcggtttggg tgatgatgac 720
caatgtatcg aagatgactt cactgcttgg agagaagctt tgtggccaga attggacacc 780
atcttaagag aagaaggtga taccgctgtt gccaccccat acactgctgc tgttttggaa 840
tacagagttt ctatccacga ctctgaagat gccaagttca acgacatcaa catggctaac 900
ggtaacggtt acactgtttt cgacgctcaa cacccataca aggccaatgt tgctgtcaag 960
agagaattgc acactccaga atctgatcgt tcttgtatcc acttggaatt tgacattgct 1020
ggttctggtt tgacctacga aaccggtgac cacgtcggtg tcttatgtga caacttgtct 1080
gaaactgtcg atgaagcttt gagattattg gacatgtctc cagacactta tttctccttg 1140
catgctgaaa aggaagatgg tactccaatt tcttcttcct tgcctcctcc attcccacca 1200
tgtaacttga gaaccgcttt aaccagatac gcttgtttgc tatcctctcc aaagaagtcc 1260
gctttggttg ctttggctgc tcacgcttct gacccaactg aagctgaaag attgaaacat 1320
ttggcttccc cagctggtaa ggatgaatac tccaaatggg ttgttgaatc tcaaagatct 1380
ttgttggaag tcatggctga attcccatct gccaagccac cattgggtgt tttcttcgcc 1440
ggtgttgctc caagattgca accaagattt tactccatct cttcttctcc aaagattgct 1500
gaaaccagaa ttcacgttac ctgtgccttg gtctacgaaa agatgccaac cggtagaatt 1560
cacaagggtg tttgttccac ctggatgaag aacgctgttc catacgaaaa gtctgaaaac 1620
tgttcttctg ctccaatctt cgtccgtcaa tccaacttca agttgccatc tgactccaag 1680
gtcccaatca tcatgatcgg tccaggtact ggtttagctc cattcagagg tttcttgcaa 1740
gaaagattgg ccttagttga atctggtgtc gaattgggtc cttctgtttt gttcttcggt 1800
tgtagaaacc gtcgtatgga cttcatctac gaagaagaat tgcaaagatt tgtcgaatct 1860
ggtgctttgg ctgaattgtc cgttgctttc tctcgtgaag gtccaaccaa agaatacgtt 1920
caacacaaga tgatggacaa agcctccgac atctggaaca tgatctccca aggtgcttac 1980
ttgtacgttt gtggtgatgc taaaggtatg gccagagatg tccacagatc tttacatacc 2040
attgcccaag aacaaggttc catggactcc accaaggctg aaggtttcgt taagaacttg 2100
caaacttctg gtcgttactt gagagatgtt tgg 2133

<210> SEQ ID NO 52

<211> LENGTH: 301
<212> TYPE: DNA
<213> ORGANISM: Artificial sequence
<220> FEATURE:
<223> OTHER INFORMATION: Sc Pdc1 terminator

<400> SEQUENCE: 52

```
agcgatttaa tctctaatta ttagttaaag ttttataagc atttttatgt aacgaaaaat      60

aaattggttc atattattac tgcactgtca cttaccatgg aaagaccaga caagaagttg     120

ccgacagtct gttgaattgg cctggttagg cttaagtctg ggtccgcttc tttacaaatt     180

tggagaattt ctcttaaacg atatgtatat tcttttcgtt ggaaaagatg tcttccaaaa     240

aaaaaaccga tgaattagtg gaaccaagga aaaaaaaaga ggtatccttg attaaggaac     300

a                                                                     301
```

<210> SEQ ID NO 53
<211> LENGTH: 1000
<212> TYPE: DNA
<213> ORGANISM: Artificial sequence
<220> FEATURE:
<223> OTHER INFORMATION: Kl prom 3 promoter

<400> SEQUENCE: 53

```
gagcctgtcc aagcaaatgc cttctcataa atggtgccaa agacccgcaa gcccaaagca      60

attacccccc aaaaagaaat gatatagtgc aagatacgta tatgaccatg acttgactag     120

gtgaaacagt gcagaaacag ccgcacaaaa gcagccctaa ccctcagagt cgattttact     180

ctttcaggta ataaagcctc gacatcaatt ttagacagaa gccaggctgg cctcgagatt     240

atagccatag gcaagcaaga ggagagaagg ggaggccccc catgggggc ctcccccccg      300

ctgtcaaggt ttggcagaac ctagcttcat taggccacta gcccagccta aaacgtcaac     360

gggcaggagg aacactccca caagacggcg tagtattctc gattcataac cattttctca     420

atcgaattac acagaacaca ccgtacaaac ctctctatca taactactta atagtcacac     480

acgtactcgt ctaaatacac atcatcgtcc tacaagttca tcaaagtgtt ggacagacaa     540

ctataccagc atggatctct tgtatcggtt cttttctccc gctctctcgc aataacaatg     600

aacactgggt caatcatagc ctacacaggt gaacagagta gcgtttatac agggtttata     660

cggtgattcc tacggcaaaa atttttcatt tctaaaaaaa aaaagaaaaa tttttctttc     720

caacgctaga aggaaaagaa aaatctaatt aaattgattt ggtgattttc tgagagttcc     780

ctttttcata tatcgaattt tgaatataaa aggagatcga aaaaattttt ctattcaatc     840

tgttttctgg ttttatttga tagttttttt gtgtattatt attatggatt agtactggtt     900

tatatgggtt tttctgtata acttcttttt attttagttt gtttaatctt attttgagtt     960

acattatagt tccctaactg caagagaagt aacattaaaa                          1000
```

<210> SEQ ID NO 54
<211> LENGTH: 1443
<212> TYPE: DNA
<213> ORGANISM: Stevia rebaudiana

<400> SEQUENCE: 54

```
atggacgcta tggccaccac tgaaaagaag cctcacgtta tctttattcc attcccagct      60

caatctcata tcaaggctat gttgaaattg gctcaattat tgcaccacaa gggtttgcaa     120

atcacttttg tcaacaccga cttcattcac aaccaattct tggaatcttc tggtcctcac     180

tgtttggacg gtgctccagg tttcagattc gaaaccattc cagatggtgt ttcccactct     240
```

```
ccagaagcct ccatcccaat cagagaatcc ttgttgagat ctattgaaac caacttcttg    300

gaccgtttca tcgatttggt taccaaattg ccagacccac caacctgtat catttctgac    360

ggtttcttgt ccgttttcac catcgatgct gccaagaaat tgggtattcc agtcatgatg    420

tactggactt tggctgcttg tggtttcatg ggtttctacc atattcactc tttgattgaa    480

aagggtttcg ctccattaaa ggatgcttct tacttgacca acggttactt ggacaccgtc    540

attgactggg ttccaggtat ggaaggtatc agattgaaag atttcccatt ggactggtct    600

actgacttga atgacaaggt cttgatgttc actactgaag ctccacaaag atctcataag    660

gtttctcacc acatcttcca cactttcgat gaattagaac catctatcat caagactcta    720

tccttgagat acaaccatat ctacaccatt ggtccattac aattgttgtt ggaccaaatc    780

ccagaagaaa agaagcaaac cggtatcact tctttgcacg gttactcttt agtcaaggaa    840

gaaccagaat gtttccaatg gttacaatcc aaggaaccaa actctgttgt ctacgttaac    900

tttggttcca ccactgttat gtccttggaa gatatgactg aatttggttg ggtttggct    960

aactctaacc actacttctt atggatcatc agatctaact tggtcattgg tgaaaacgcc   1020

gttttgcctc cagaattgga agaacacatc aagaagagag gtttcattgc ttcctggtgt   1080

tctcaagaaa aggtcttgaa gcacccatct gttggtggtt tcttgaccca ctgtggttgg   1140

ggttccacca ttgaatccct atctgctggt gttccaatga tctgttggcc atactcctgg   1200

gaccaattga ctaactgtcg ttacatctgt aaggaatggg aagttggttt ggaaatgggt   1260

actaaggtca agagagatga agtcaagaga ttagtccaag aattgatggg tgaaggtggt   1320

cacaagatga gaaacaaagc caaggactgg aaggaaaagg ccagaattgc tattgctcca   1380

aacggttctt cctccttgaa catcgataaa atggttaagg aaatcactgt cttggctcga   1440

aac                                                                 1443
```

<210> SEQ ID NO 55
<211> LENGTH: 301
<212> TYPE: DNA
<213> ORGANISM: Artificial sequence
<220> FEATURE:
<223> OTHER INFORMATION: Sc TDH1 terminator

<400> SEQUENCE: 55

```
aataaagcaa tcttgatgag gataatgatt ttttttgaa tatacataaa tactaccgtt     60

tttctgctag attttgtgaa gacgtaaata agtacatatt actttttaag ccaagacaag    120

attaagcatt aactttaccc ttttctcttc taagtttcaa tactagttat cactgtttaa    180

aagttatggc gagaacgtcg gcggttaaaa tatattaccc tgaacgtggt gaattgaagt    240

tctaggatgg tttaaagatt tttcctttt gggaaataag taaacaatat attgctgcct    300

t                                                                    301
```

<210> SEQ ID NO 56
<211> LENGTH: 1000
<212> TYPE: DNA
<213> ORGANISM: Artificial sequence
<220> FEATURE:
<223> OTHER INFORMATION: Kl prom 2 promoter

<400> SEQUENCE: 56

```
gagcctgtcc aagcaaatgc cttctcataa atggtgccaa agacccgcaa gcccaaagca     60

attacccccc aaaaagaaat gatatagtgc aagatacgta tatgaccatg acttgactag    120
```

-continued

```
gtgaaacagt gcagaaacag ccgcacaaaa gcagccctaa ccctcagagt cgattttact    180

ctttcaggta ataaagcctc gacatcaatt ttagacagaa gccaggctgg cctcgagatt    240

atagccatag gcaagcaaga ggagagaagg ggaggccccc catgggggc ctccccccg    300

ctgtcaaggt ttggcagaac ctagcttcat taggccacta gcccagccta aaacgtcaac    360

gggcaggagg aacactccca caagacggcg tagtattctc gattcataac cattttctca    420

atcgaattac acagaacaca ccgtacaaac ctctctatca taactactta atagtcacac    480

acgtactcgt ctaaatacac atcatcgtcc tacaagttca tcaaagtgtt ggacagacaa    540

ctataccagc atggatctct tgtatcggtt cttttctccc gctctctcgc aataacaatg    600

aacactgggt caatcatagc ctacacaggt gaacagagta gcgtttatac agggtttata    660

cggtgattcc tacggcaaaa atttttcatt tctaaaaaaa aaaagaaaaa tttttctttc    720

caacgctaga aggaaaagaa aaatctaatt aaattgattt ggtgattttc tgagagttcc    780

ctttttcata tatcgaattt tgaatataaa aggagatcga aaaaattttt ctattcaatc    840

tgttttctgg ttttatttga tagttttttt gtgtattatt attatggatt agtactggtt    900

tatatgggtt tttctgtata acttcttttt attttagttt gtttaatctt attttgagtt    960

acattatagt tccctaactg caagagaagt aacattaaaa                         1000
```

<210> SEQ ID NO 57
<211> LENGTH: 1380
<212> TYPE: DNA
<213> ORGANISM: Stevia rebaudiana

<400> SEQUENCE: 57

```
atggctgaac aacaaaagat caagaaatct ccacacgtct tgttgattcc attcccattg     60

caaggtcaca tcaacccatt catccaattc ggtaagagat tgatttccaa gggtgtcaag    120

accactttag tcaccactat tcacacttta aactccactt taaaccactc taacactact    180

accacctcta ttgaaatcca agccatttct gacggttgtg acgaaggtgg tttcatgtct    240

gctggtgaat cttacttgga aactttcaag caagtcggtt ccaagtcttt ggctgatttg    300

atcaagaaat tgcaatccga aggtactacc atcgatgcta tcatctacga ctccatgact    360

gaatgggttt tggatgttgc cattgaattt ggtattgacg gtggttcttt cttcacccaa    420

gcctgtgttg ttaactcttt gtactaccac gtccacaagg gtttgatctc tctaccatta    480

ggtgaaaccg tttccgtccc aggtttccca gtcttgcaaa gatgggaaac tccattgatc    540

ttacaaaacc atgaacaaat ccaatctcca tggtcccaaa tgttgtttgg tcaattcgct    600

aacattgacc aagctagatg ggttttcacc aactctttct acaagttgga agaagaagtc    660

attgaatgga ccagaaagat ctggaacttg aaggttatcg gtccaactct accatccatg    720

tacttggaca agagattgga tgacgacaag gacaacggtt tcaacttgta caaggctaac    780

catcacgaat gtatgaactg gttggatgac aagccaaagg aatctgttgt ttacgttgct    840

ttcggttctt tggtcaagca tggtccagaa caagttgaag aaatcaccag agctttgatt    900

gactccgatg ttaacttctt atgggttatc aagcacaagg aagaaggtaa attgccagaa    960

aacttgtctg aagttatcaa gaccggtaag ggtttgattg ttgcttggtg taagcaattg   1020

gatgttttgg ctcacgaatc cgtcggttgt ttcgtcactc actgtggttt caactctact   1080

ttggaagcta tctccttggg tgttccagtt gttgccatgc ctcaattctc tgaccaaacc   1140

accaacgcca aattgttgga tgaaatcttg ggtgtcggtg tccgtgtcaa ggctgatgaa   1200

aacggtattg ttagaagagg taacttagct tcctgtatca agatgatcat ggaagaagaa   1260
```

cgtggtgtca ttatcagaaa gaatgctgtc aaatggaagg acttggctaa ggttgctgtc 1320
cacgaaggtg gttcctctga caatgacatt gttgaatttg tctctgaatt gatcaaagcg 1380

<210> SEQ ID NO 58
<211> LENGTH: 1374
<212> TYPE: DNA
<213> ORGANISM: Stevia rebaudiana

<400> SEQUENCE: 58
atggaaaaca agactgaaac cactgttaga agaagaagaa gaatcatctt attcccagtt 60
ccattccaag gtcacattaa cccaatcttg caattggcta acgtcttata ctccaagggt 120
ttctccatca ccatcttcca caccaacttc aacaaaccta aaacttccaa ctacccacac 180
ttcaccttca gatttatctt ggacaacgac ccacaagatg aaagaatttc taacttgcca 240
acccatggtc cattggccgg tatgagaatt ccaatcatca acgaacacgg tgctgacgaa 300
ttgagaagag aattggaatt gttgatgttg gcttctgaag aagatgaaga agtctcttgt 360
ttgatcactg atgctttatg gtactttgct caatctgttg ctgactcttt gaacttgaga 420
agattagtct tgatgacctc ttctttgttc aacttccacg ctcacgtttc tctaccacaa 480
tttgatgaat tgggttactt ggacccagat gacaagacca gattggaaga acaagcctcc 540
ggtttcccaa tgttgaaggt caaggatatc aagtctgcct actccaactg gcaaatcttg 600
aaggaaattt tgggtaagat gatcaagcaa accaaggctt cttctggtgt catctggaac 660
tccttcaagg aattggaaga atctgaattg gaaaccgtca tcagagaaat tccagctcca 720
tctttcttga ttccattacc aaagcatttg actgcttcct cctcttctct attggaccac 780
gacagaactg ttttccaatg gttggaccaa caaccaccat cttccgtctt atacgtttcc 840
tttggttcca cttctgaagt tgacgaaaag gacttcttgg aaattgctcg tggtttggtt 900
gactccaagc aatctttctt atgggttgtc agaccaggtt tcgtcaaggg ttccacctgg 960
gttgaacctt tgccagacgg tttcttgggt gaaagaggta gaattgtcaa atgggttcca 1020
caacaagaag ttttggctca cggtgccatt ggtgctttct ggactcactc tggttggaac 1080
tctactttgg aatccgtttg tgaaggtgtt ccaatgattt tctctgactt cggtttggac 1140
caaccattga atgctcgtta catgtccgat gttttgaagg ttggtgtcta cttggaaaac 1200
ggttgggaac gtggtgaaat tgctaacgcc atcagaagag tcatggtcga tgaagaaggt 1260
gaatacatca gacaaaatgc tcgtgtcttg aaacaaaagg ctgatgtttc tttgatgaag 1320
ggtggttctt cttacgaatc tttggaatct ttggtttcct acatctccag tctc 1374

<210> SEQ ID NO 59
<211> LENGTH: 602
<212> TYPE: DNA
<213> ORGANISM: Artificial sequence
<220> FEATURE:
<223> OTHER INFORMATION: Sc Eno1 terminator

<400> SEQUENCE: 59
aagcttttga ttaagccttc tagtccaaaa aacacgtttt tttgtcattt atttcatttt 60
cttagaatag tttagtttat tcattttata gtcacgaatg ttttatgatt ctatataggg 120
ttgcaaacaa gcatttttca ttttatgtta aaacaatttc aggtttacct tttattctgc 180
ttgtggtgac gcgtgtatcc gcccgctctt ttggtcaccc atgtatttaa ttgcataaat 240
aattcttaaa agtggagcta gtctatttct atttacatac ctctcatttc tcatttcctc 300

-continued

```
caagcttttg attaagcctt ctagtccaaa aaacacgttt ttttgtcatt tatttcattt    360

tcttagaata gtttagttta ttcattttat agtcacgaat gttttatgat tctatatagg    420

gttgcaaaca agcatttttc attttatgtt aaaacaattt caggtttacc ttttattctg    480

cttgtggtga cgcgtgtatc cgcccgctct tttggtcacc catgtattta attgcataaa    540

taattcttaa aagtggagct agtctatttc tatttacata cctctcattt ctcatttcct    600

cc                                                                   602
```

<210> SEQ ID NO 60
<211> LENGTH: 600
<212> TYPE: DNA
<213> ORGANISM: Saccharomyces cerevisiae

<400> SEQUENCE: 60

```
ccgcggaacc gccagatatt cattacttga cgcaaaagcg tttgaaataa tgacgaaaaa     60

gaaggaagaa aaaaaaagaa aaataccgct tctaggcggg ttatctactg atccgagctt    120

ccactaggat agcacccaaa cacctgcata tttggacgac ctttacttac accaccaaaa    180

accactttcg cctctcccgc ccctgataac gtccactaat tgagcgatta cctgagcggt    240

cctcttttgt ttgcagcatg agacttgcat actgcaaatc gtaagtagca acgtgtcaag    300

gtcaaaactg tatggaaacc ttgtcacctc acttaattct agctagccta ccctgcaagt    360

caagaggtgt ccgtgattcc tagccacctc aaggtatgcc tctccccgga aactgtggcc    420

ttttctggca cacatgatct ccacgatttc aacatataaa tagcttttga taatggcaat    480

attaatcaaa tttattttac ttctttcttg taacatctct cttgtaatcc cttattcctt    540

ctagctattt ttcataaaaa accaagcaac tgcttatcaa cacacaaaca ctaaatcaaa    600
```

<210> SEQ ID NO 61
<211> LENGTH: 301
<212> TYPE: DNA
<213> ORGANISM: Kluyveromyces lactis

<400> SEQUENCE: 61

```
aattactctt ttaagttaac gaacgctttt gatgagacta acgatatttc aagtgattcc     60

attttttact tctaagtttt tatcaccttt atcttaacca ttctatgcca gtctttgctt    120

tatggacttt gattcaaatt atgaagggaa gtttttacgc caaataaaaa ctactacaac    180

aaattattaa aaaaaatgac gaataatatg aagtgtctaa cgactgccaa aattattcat    240

tccttttttta tacacataac catttcactt catttactgg tttgagtggt ttattacgtc    300

g                                                                    301
```

<210> SEQ ID NO 62
<211> LENGTH: 803
<212> TYPE: DNA
<213> ORGANISM: Yarrowia lipolytica

<400> SEQUENCE: 62

```
taccaaccac agattacgac ccattcgcag tcacagttca ctagggtttg ggttgcatcc     60

gttgagagtg gtttgttttt aaccttctcc atgtgctcac tcaggttttg ggttcagatc    120

aaatcaaggc gtgaaccact gtttgaggac aaatgtgaca caaccaacca gtgtcagggg    180

caagtccgtg acaaagggga agatacaatg caattactga cagttacgga ctgcctcgat    240

gccctaacct tgccccaaaa taagacaact gtcctcgttt aagcgcaacc ctattcagcg    300

tcacgtcata atagcgtttg gatagcacta gtctatgagg agcgttttat gttgcggtga    360
```

```
gggcgattgg tgctcatatg ggttcaattg aggtggtgga acgagcttag tcttcaattg    420

aggtgcgagc gacacaattg ggtgtcacgt ggcctaattg acctcggatc gtggagtccc    480

cagttataca gcaaccacga ggtgcatgag taggagacgt caccagacaa tagggttttt    540

ttggactgga gagggtaggg caaaagcgct caacgggctg tttggggagc tatgggggag    600

gaattggcga tatttgtgag gttgacggct ccgatttgcg tgttttgtcg cttctgcatc    660

tccccatacc catatcttcc ctccccacct ctttccacga taattttacg gatcagcaat    720

aaggttcctt ctcctagttt ccacgtccat atatatctat gctgcgtcgt ccttttcgtg    780

acatcaccaa aacacataca aaa                                            803


<210> SEQ ID NO 63
<211> LENGTH: 995
<212> TYPE: DNA
<213> ORGANISM: Yarrowia lipolytica

<400> SEQUENCE: 63

ctgtacctgc tgtggaccac gcacggcgga acgtaccgta caaatatttt cttgctcaca     60

tgactctctc tcggccgcgc acgccggtgg caaattgctc ttgcattggc tctgtctcta    120

gacgtccaaa ccgtccaaag tggcagggtg acgtgatgcg acgcacgaag gagatggccc    180

ggtggcgagg aaccggacac ggcgagccgg cgggaaaaaa ggcggaaaac gaaaagcgaa    240

gggcacaatc tgacggtgcg gctgccacca acccaaggag gctattttgg gtcgctttcc    300

atttcacatt cgccctcaat ggccactttg cggtggtgaa catggtttct gaaacaaccc    360

cccagaatta gagtatattg atgtgtttaa gattgggttg ctatttggcc attgtggggg    420

agggtagcga cgtggaggac attccagggc gaattgagcc tagaaagtgg taccattcca    480

accgtctcag tcgtccgaat tgatcgctat aactatcacc tctctcacat gtctacttcc    540

ccaaccaaca tccccaacct cccccacact aaagttcacg ccaataatgt aggcactctt    600

tctgggtgtg ggacagcaga gcaatacgga ggggagatta cacaacgagc cacaattggg    660

gagatggtag ccatctcact cgacccgtcg actttggca acgctcaatt acccaccaaa    720

tttgggctgg agttgagggg accgtgttcc agcgctgtag gaccagcaac acacacggta    780

tcaacagcaa ccaacgcccc cgctaatgca cccagtactg cgcaggtgtg ggccaggtgc    840

gttccagatg cgagttggcg aaccctaagc cgacagtgta ctttttggga cgggcagtag    900

caatcgtggg cggagacccc ggtgtatata aaggggtgga gaggacggat tattagcacc    960

aacacacaca cttatactac atgctagcca caaaa                               995


<210> SEQ ID NO 64
<211> LENGTH: 1004
<212> TYPE: DNA
<213> ORGANISM: Yarrowia lipolytica

<400> SEQUENCE: 64

gtcagaaggg gcagctctaa acgaagaact gcggtcaggt gacacaactt tttccatctc     60

agggtgtgtc gcgtgtgctt catccaaact ttagttgggg ttcgggttcg cgcgagatga    120

tcacgtgccc tgatttggtg tcgtccccccg tcgcgctgcg cacgtgattt atttatttcc   180

ggtggctgct gtctacgcgg ggccttctct gcccttctgt ttcaaccttc gggcggttct    240

cgtaaccagc agtagcaatc catttcgaaa ctcaaagagc taaaaacgtt aaacctcagc    300

agtcgctcga cgaatgggct gcggttggga agcccacgag gcctatagcc agagcctcga    360
```

-continued

```
gttgacagga gcccagacgc cttttccaac ggcaactttt atataaaatg gcaatgtatt    420
catgcaattg cggccgtgtc aggttggaga cactggacca cactctccat tgcttcctga    480
ggagatggat cattgctagt gcatctacgc gcagcaatcc cgcaagctcg acaaccgtag    540
atgggctttg gtgggccaat caattacgca acccgcacgt taaattgtat gaggaaggaa    600
ggccacggta caaagtgggt ggtcttcacc cagtggttgt tggtggcgtc atgcagacca    660
tgcattgggg atagcacagg gttggggtgt cttgtggact caatgggtga aaggagatgg    720
aaaagggcgg tgaaaagtgg tagaatcgaa atccctgacg tcaatttata aagtaaaatg    780
cgtttctgcc attttgctcc cctccttctt tcgcaatcgc ctccccaaaa gttgtcgtgg    840
cagtacacat gcttgcatac aatgaagcta atccggcttg ctcagtagtt gctatatcca    900
ggcatggtgt gaaacccctc aaagtatata taggagcggt gagccccagt ctggggtctt    960
ttctctccat ctcaaaacta ctttctcaca tgctagccac aaaa                    1004
```

<210> SEQ ID NO 65
<211> LENGTH: 1422
<212> TYPE: DNA
<213> ORGANISM: Yarrowia lipolytica

<400> SEQUENCE: 65

```
atttcttgtg tgtgcggcaa acgtagcaat tgcaactgca taaacgatga ttgtaaaagt     60
atcacacttt gctcagacag gttagattca cctggtacga gggcagtgtc ttaaaggttc    120
catctacctc ggcccttgtt tcttgaagag tggtcaatat gtgttttata cagctgaaat    180
ttcccctgta tgttgagatc gtgtatattg gtcataatct gggctcttta gtcgatccca    240
gttttctcgg gcaagttttt ttctccacaa agtaccgctg gaaaactcta tgtgacttgt    300
tgacagatta cttgggttat ctgcgggata tgtcttggat aggcaaccgg gcatatatca    360
ccgggcggac tgttggttct gtacgtacat acagcacttt gagctcatgt ctcacacgca    420
accatggtgc gtggaggctt tggcatcctt tctacttgta gtggctatag tacttgcagt    480
ccaagcaaac atgagtatgt gcttgtatgt actgaaaccc gtctacggta atattttaga    540
gtgtggaact atgggatgag tgctcattcg atactatgtt gtcacccgat ttgccgtttg    600
cgaggtaaga cacattcggt ggttcaggcg gctacttgta tgtagcatcc acgttcatgt    660
tttgtggatc agattaatgg tatggatatg cacggggcgt ttccccggta acgtgtaggc    720
agtccagtgc aacccagaca gctgagctct ctatagccgt gcgtgtgcgg tcatatcacg    780
ctacacttag ctacagaata aagctcggta gcgccaacag cgttgacaaa tagctcaagg    840
gcgtggagca cagggtttag gaggttttaa tgggcgagaa ggcgcgtaga tgtagtcttc    900
ctcggtccca tcggtaatca cgtgtgtgcc gatttgcaag acgaaaagcc acgagaataa    960
accgggagag gggatggaag tccccgaaca gcaaccagcc cttgccctcg tggacataac   1020
ctttcacttg ccagaactct aagcgtcacc acggtataca agcgcacgta gaagattgtg   1080
gaagtcgtgt tggagactgt tgatttgggc ggtggagggg ggtatttgag agcaagtttg   1140
agatttgtgc cattgagggg gaggttattg tggccatgca gtcggatttg ccgtcacggg   1200
accgcaacat gcttttcatt gcagtccttc aactatccat ctcacctccc ccaatggctt   1260
ttaactttcg aatgacgaaa gcaccccccct ttgtacagat gactatttgg gaccaatcca   1320
atagcgcaat tgggtttgca tcatgtataa aaggagcaat cccccactag ttataaagtc   1380
acaagtatct cagtataccc gtctaaccac acatttatca cc                      1422
```

-continued

<210> SEQ ID NO 66
<211> LENGTH: 865
<212> TYPE: DNA
<213> ORGANISM: Yarrowia lipolytica

<400> SEQUENCE: 66

```
atgctcactt ttgttgtcct gatgatctcc cgttatttcg ccgctcctct ggaaaccatc     60
cgcccgcaaa tcccctctgc ccatcttgac aatgcacaat gcatcattct cagcctgcat    120
gaatgcgaaa gatggcaata ttggtggagg aggcgacggc ggtaaacaat ggagatagag    180
accacaaaag agacctggag acccaaaatg gactcacgac aactccccca ctcccccact    240
ccccatctcc ccctgggcat cagttgccca tcggtatctc aactgtcgca ctagttagcg    300
caaccatcac atactttaga cgccaaacaa tgggacaact catcgcgccg aactatgggc    360
agattttaac tcgcacaaca ttaccccaac tctaaaaggt aacctcgacc ggaaaacggg    420
aagacaggat cagcaaccgt gatcgacaga atcttcaggg cactacagtt gatagacata    480
ggttatgttg gtaggtctag acgggcctcg gggaattgac ccccaccagtt gcaagtcacg   540
tgcccctgat acagctagtt tagcacatct gcccactacg tctggacgca ccatggtggt    600
gccagtcgcg tgaactcaaa cacccactag cctcgggaag gattcagtta aatccgcacc    660
ttatttccaa cacaaagaag cggttggcgg acaaagaaca tgtcctttct ggggcactgt    720
acattccagg actctgttca aggtcaaata tacaaaacac agatagagaa acatagacag    780
ctgcggcctt ataaatacct gggcgcactt ctctcttttt ccctcctcat cacacattcg    840
ttcaccacta agtcactcgt tcaaa                                          865
```

<210> SEQ ID NO 67
<211> LENGTH: 880
<212> TYPE: DNA
<213> ORGANISM: Yarrowia lipolytica

<400> SEQUENCE: 67

```
aaacaaaaga gctgaaatca tatccttcag tagtagtata gtcctgttat cacagcatca     60
attacccccg tccaagtaag ttgattggga tttttgttta cagatacagt aatatacttg    120
actatttctt tacaggtgac tcagaaagtg catgttggaa atgagccaca gaccaagaca    180
agatatgaca aaattgcact attcgatgca gaattcgacg gtgtttccat tggtgttatg    240
acattcatct gcattcatac aaaaaagtct tggtagtggt acttttgcgt tattacctcc    300
gatatctacg caccccccaa cccccctgct acagtaaaga gtgtgagtct actgtacatg    360
cttactaaac cacctactgt acagcgaaac ccctcagcaa aatcacacaa tcagctcatt    420
acaacacacc caatgacctc accacaaatt ctatacgcct tttgacgcca ttattacagt    480
agcttgcaac gccgttgtct taggttccat ttttagtgct ctattacctc acttaacccg    540
tataggcaga tcaggccatg gcactaagtg tagagctaga ggttgatatc gccacgagtg    600
ctccatcagg gctagggtgg ggttagaaat acagtccgtg cgcactcaaa aggcgtccgg    660
gttagggcat ccgataatat cgcctggact cggcgccata ttctcgactt ctgggcgcgt    720
tgtattcatc tcctccgctt cccaacactt ccacccgttt ctccatccca accaatagaa    780
tagggtaacc ttattcggga cactttcgtc atacatagtc agatatacaa gcaatgtcac    840
tctccttcgt actcgtacat acaacacaac tacattcaaa                          880
```

<210> SEQ ID NO 68
<211> LENGTH: 1000
<212> TYPE: DNA

<213> ORGANISM: Yarrowia lipolytica

<400> SEQUENCE: 68
caattcatgt atcgtgtcaa ttcatgtatc gtgtcaattc atgtatcgtg tcaatactta 60
tatctcaagt ggttgcatcg caaacagcca tcgcatactc cactctactc tcactgagtt 120
cactcttacc cggctccacc ttctagaagc caccaccgat ccaccgacga tgatcagtcc 180
accacttgct ctgaatgtgc gttggagctg caccatgatt gatgacgtca ccgccattca 240
gatagggcaa aagacgagcg ccaatcgcaa caatgggcga gtgtcgacga ctcccccgct 300
ctctgcggtt tcagcgactc caaccgtcgc caaaagaccg tcattttcgt ctaaagcgca 360
gcccagccca tctcttctaa aagattccag aaagataggg ttcaccaact acgcaccaat 420
atgtacagta tcgtagctac tccggcttgg ctgatctgag agatagagat ggctccgaaa 480
cgcggaaaac ggcggggtcg gaccgatcac gtgacacgta ctcatccgtc gcgccccgag 540
cgccatttca acaccaaata ctcccggtca cgtgccaccc cgcccgctct acccacgaga 600
tgtttctaca ctatacactg ccacgccgtc atacctgcag ctaggttaac attcgattaa 660
ttagtggagt caccagtgta caggactatg gcggaaaccg ggttacacaa accggcccgg 720
aatagcagca ttataccgct ggacgagatc accgtcaata aattgcgtcg ttactcggga 780
caaccattgc tcctccggct acacctgctc aaaggacttg ttccacactc ttccccagct 840
ctcccacgca aacaaagaga gcaaccttaa gtggacagct catgagcact cccctcgttt 900
gctgcccacg ctcgattata taaagaccag cggatcccct tctatttgga cttgcatcaa 960
ccaaccacaa cccacaccaa gcacacaaag cacaagaaca 1000

<210> SEQ ID NO 69
<211> LENGTH: 127
<212> TYPE: DNA
<213> ORGANISM: Yarrowia lipolytica

<400> SEQUENCE: 69
aattaacaga tagtttgccg gtgataattc tcttaacctc ccacactcct ttgacataac 60
gatttatgta acgaaactga aatttgacca gatattgttg taaatagaaa atctggcttg 120
taggtgg 127

<210> SEQ ID NO 70
<211> LENGTH: 200
<212> TYPE: DNA
<213> ORGANISM: Yarrowia lipolytica

<400> SEQUENCE: 70 gtttttttgat caatgatcca atggctttca catacccccc cacgcctata attaaaacac 60
agagaaatat aatctaactt aataaatatt acggagaatc tttcgagtgt tcagcagaaa 120
tatagccatt gtaacaaaag ccggctatcg accgctttat cgaagaatat ttcccgcccc 180
ccagtggcca aacgatatcg 200

<210> SEQ ID NO 71
<211> LENGTH: 200
<212> TYPE: DNA
<213> ORGANISM: Yarrowia lipolytica

<400> SEQUENCE: 71
ctatccgaag atcaagagcg aagcaagttg taagtccagg acatgtttcc cgcccacgcg 60
agtgatttat aacacctctc ttttttgaca cccgctcgcc ttgaaattca tgtcacataa 120

-continued attatagtca acgacgtttg aataacttgt cttgtagttc gatgatgatc atatgattac 180
attaatagta attactgtat 200

<210> SEQ ID NO 72
<211> LENGTH: 200
<212> TYPE: DNA
<213> ORGANISM: Yarrowia lipolytica

<400> SEQUENCE: 72
acttcgagct aatccagtag cttacgttac ccaggggcag gtcaactggc tagccacgag 60
tctgtcccag gtcgcaattt agtgtaataa acaatatata tattgagtct aaagggaatt 120
gtagctattg tgattgtgtg attttcgtct tgctggttct tattgtgtcc cattcgtttc 180
atcctgatga ggacccctgg 200

<210> SEQ ID NO 73
<211> LENGTH: 200
<212> TYPE: DNA
<213> ORGANISM: Yarrowia lipolytica

<400> SEQUENCE: 73
gctatttaca gcatgtgtaa tgaggaatat aacgttgatt gaattgtttg tgaaaaatgt 60
agaaaatttc agtgaagttg tgttttctat atagtaagca cttttggtac aagtatctgc 120
acatccctgc atgttacaag cctgatcatg cagggcaata ttctgactat aaatatacct 180
cgatatttta gcaagctata 200

<210> SEQ ID NO 74
<211> LENGTH: 300
<212> TYPE: DNA
<213> ORGANISM: Yarrowia lipolytica

<400> SEQUENCE: 74
atgtggtgat tgctgttgtg caagcctttg ctcgttttct gctgtatgta atttaaagaa 60
cgattgtatg aatcgaagtc aaggtgagtg tagtttgaga agtgtaaccc cagtgtcata 120
gctgtgtact ccattcattg aagggtgtag tcgtgtttta ttgcatgagc gcctattact 180
cgtataagta actgttttgt aacacttcat gaacggagat ggtatgaaca gaagtaataa 240
tatcctggaa gtcagctgtg cccagaggtg tgtgtgggtg tggcatactt tgggacaaca 300

<210> SEQ ID NO 75
<211> LENGTH: 1503
<212> TYPE: DNA
<213> ORGANISM: Artificial sequence
<220> FEATURE:
<223> OTHER INFORMATION: tHMG CpO for Yarrowia lipolitica

<400> SEQUENCE: 75
atgacccagt ctgtgaaggt ggttgagaag cacgttccta tcgtcattga gaagcccagc 60
gagaaggagg aggacacctc ttctgaagac tccattgagc tgactgtcgg aaagcagccc 120
aagcccgtga ccgagacccg ttctctggac gacttggagg ctatcatgaa ggcaggtaag 180
accaagctcc tggaggacca cgaggttgtc aagctctctc tcgaaggcaa gctccctttg 240
tatgctcttg agaagcagct tggtgacaac acccgagctg ttggcatccg acgatctatc 300
atctcccagc agtctaatac caagactctt gagacctcaa agctccctta cctgcactac 360
gactacgacc gtgtttttgg agcctgttgc gagaacgtta ttggttacat gcctctcccc 420

-continued

```
gttggtgttg ctggccccat gaacattgat ggcaagaact accacattcc tatggccacc    480

actgagggtt gtcttgttgc ctcaaccatg cgaggttgca aggccatcaa cgccggtggc    540

ggtgttacca ctgtgcttac tcaggacggt atgacacgag gtccttgtgt ttccttcccc    600

tctctcaagc gggctggagc cgctaagatc tggcttgatt ccgaggaggg tctcaagtcc    660

atgcgaaagg ccttcaactc cacctctcga tttgctcgtc tccagtctct tcactctacc    720

cttgctggta acctgctgtt tattcgattc cgaaccacca ctggtgatgc catgggcatg    780

aacatgatct ccaagggcgt cgaacactct ctggccgtca tggtcaagga gtacggcttc    840

cctgatatgg acattgtgtc tgtctcgggt aactactgca ctgacaagaa gcccgcagcg    900

atcaactgga tcgaaggccg aggcaagagt gttgttgccg aagccaccat ccctgctcac    960

attgtcaagt ctgttctcaa aagtgaggtt gacgctcttg ttgagctcaa catcagcaag   1020

aatctgatcg gtagtgccat ggctggctct gtgggaggtt tcaatgcaca cgccgcaaac   1080

ctggtgaccg ccatctacct tgccactggc caggatcctg ctcagaatgt cgagtcttcc   1140

aactgcatca cgctgatgag caacgtcgac ggtaacctgc tcatctccgt ttccatgcct   1200

tctatcgagg tcggtaccat tggtggaggt actattttgg agccccaggg tgctatgctg   1260

gagatgcttg gcgtgcgagg tcctcacatc gagacccccg gtgccaacgc ccaacagctt   1320

gctcgcatca ttgcttctgg agttcttgca gcggagcttt cgctgtgttc tgctcttgct   1380

gccggccatc ttgtgcaaag tcatatgacc cacaaccgtt cccaggctcc tactccggcc   1440

aagcagtctc aggccgatct gcagcgtctc caaaacggtt cgaatatctg cattcggtca   1500

tag                                                                 1503
```

<210> SEQ ID NO 76
<211> LENGTH: 984
<212> TYPE: DNA
<213> ORGANISM: Artificial sequence
<220> FEATURE:
<223> OTHER INFORMATION: GGS CpO for Yarrowia lipolitica

<400> SEQUENCE: 76

```
atggattata acagcgcgga tttcaaggag atctggggca aggccgccga caccgcgctg     60

ctgggaccgt acaactacct cgccaacaac cggggccaca acatcagaga acacttgatc    120

gcagcgttcg gagcggttat caaggtggac aagagcgatc tcgaaaccat ttcgcacatc    180

accaagattt tgcataactc gtcgctgctt gttgatgacg tggaagacaa ctcgatgctc    240

cgacgaggcc tgccggcagc ccattgtctg tttggagtcc cccaaaccat caactccgcc    300

aactacatgt actttgtggc tctgcaggag gtgctcaagc tcaagtctta tgatgccgtc    360

tccattttca ccgaggaaat gatcaacttg catagaggtc agggtatgga tctctactgg    420

agagaaacac tcacttgccc ctcggaagac gagtatctgg agatggtggt gcacaagacc    480

ggaggactgt ttcggctggc tctgagactt atgctgtcgg tggcatcgaa acaggaggac    540

catgaaaaga tcaactttga tctcacacac cttaccgaca cactgggagt catttaccag    600

attctggatg attacctcaa cctgcagtcc acggaattga ccgagaacaa gggattctgc    660

gaagatatca gcgaaggaaa gttttcgttt ccgctgattc acagcatccg gaccaacccg    720

gataaccacg agattctcaa cattctcaaa cagcgaacaa gcgacgcttc actcaaaaag    780

tacgccgtgg actacatgag aacagaaacc aagagtttcg actactgcct caagagaatc    840

caggccatgt cactcaaggc aagttcgtac attgatgatc tcgcagcagc cggccacgat    900

gtctccaagt tgcgagccat tttgcattat tttgtgtcca cctctgactg tgaggagaga    960
```

aagtactttg aggatgcgca gtga 984

<210> SEQ ID NO 77
<211> LENGTH: 1446
<212> TYPE: DNA
<213> ORGANISM: Artificial sequence
<220> FEATURE:
<223> OTHER INFORMATION: UGT1 CpO for Yarrowia lipolitica

<400> SEQUENCE: 77
atggacgcca tggccaccac cgagaagaag ccccacgtca tcttcatccc cttccccgcc 60
cagtcccaca tcaaggccat gctcaagctc gcccagctcc tccaccacaa gggcctccag 120
atcacctttg tcaacaccga cttcatccac aaccagttcc tcgagtcctc cggcccccac 180
tgtctggacg gtgctcccgg tttccgattt gagactatcc ccgatggtgt ctcccactcc 240
cccgaggcct ccatccccat ccgagagtct ctgctccgat ccattgagac taacttcctc 300
gaccgattca ttgatctcgt caccaagctc cccgatcctc ccacctgtat catctccgac 360
ggtttcctgt ccgttttcac cattgatgct gccaagaagc tcggtatccc cgtcatgatg 420
tactggactc tggctgcctg tggtttcatg ggtttctacc acatccactc tctgatcgag 480
aagggctttg ctcctctcaa ggacgcctcc tacctcacca acggttacct cgacaccgtc 540
attgactggg tccccggtat ggagggtatc cgactcaagg acttcccccct cgactggtcc 600 accgacctca acgacaaggt tctcatgttc accaccgagg ctccccagcg atcccacaag 660
gtttcccacc acatcttcca caccttcgac gagctcgagc cctccatcat caagactctg 720
tctctgcgat acaaccacat ctacaccatt ggcccccctcc agctcctcct cgaccagatc 780
cccgaggaga agaagcagac cggtatcacc tctctgcacg gctactctct cgtcaaggaa 840
gagcccgagt gcttccagtg gctccagtcc aaggagccca actccgttgt ctacgtcaac 900
tttggctcca ccaccgtcat gtctctcgag gacatgaccg agtttggctg ggtctggcc 960 aactccaacc actacttcct gtggatcatc cgatccaacc tcgtcattgg cgagaacgcc 1020
gttctgcctc ccgagctcga ggagcacatc aagaagcgag gcttcattgc ctcttggtgc 1080
tcccaggaga aggttctcaa gcacccctcc gtcggtggtt tcctgaccca ctgcggctgg 1140
ggctccacca ttgagtctct gtccgctggt gtccccatga tctgctggcc ctactcctgg 1200
gaccagctca ccaactgccg atacatctgc aaggagtggg aggttggtct ggagatgggt 1260
accaaggtca agcgagatga ggtcaagcga ctcgtccagg agctcatggg cgagggtggt 1320
cacaagatgc gaaacaaggc caaggactgg aaggagaagg cccgaattgc cattgccccc 1380
aacggctctt cttctctcaa cattgacaag atggtcaagg agatcactgt tctcgctcga 1440
aactaa 1446

<210> SEQ ID NO 78
<211> LENGTH: 1383
<212> TYPE: DNA
<213> ORGANISM: Artificial sequence
<220> FEATURE:
<223> OTHER INFORMATION: UGT3 CpO for Yarrowia lipolitica

<400> SEQUENCE: 78
atggccgagc agcagaagat caagaagtct ccccacgttc tgctcatccc cttccctctg 60
cagggccaca tcaacccctt catccagttc ggcaagcgac tcatctccaa gggtgtcaag 120
accactctgg tcaccaccat ccacaccctc aactccactc tcaaccactc caacaccacc 180
accacctcca tcgagatcca ggccatctcc gacggctgtg acgagggtgg tttcatgtct 240
gctggtgagt cttacctcga gactttcaag caggtcggtt ccaagtctct ggctgacctc 300
atcaagaagc tccagtccga gggtaccacc attgacgcca tcatctacga ctccatgacc 360
gagtgggttc tcgatgtcgc catcgagttt ggtattgacg gtggctcctt cttcacccag 420
gcctgtgtcg tcaactctct ctactaccac gtccacaagg gtctgatctc tctgcccctc 480
ggcgagactg tctccgtccc cggtttcccc gttctgcagc gatgggagac tcctctcatt 540
ctccagaacc acgagcagat ccagtccccc tggtcccaga tgctcttcgg ccagttcgcc 600
aacattgacc aggcccgatg ggttttcacc aactccttct acaagctcga ggaagaggtc 660
attgagtgga cccgaaagat ctggaacctc aaggtcattg gccccaccct cccctccatg 720
tacctcgaca agcgactcga tgacgacaag gacaacggtt tcaacctcta caaggccaac 780
caccacgagt gcatgaactg gctcgacgac aagcccaagg agtccgttgt ctacgttgcc 840
tttggctctc tggtcaagca cggccccgag caggttgagg agatcacccg agctctgatt 900
gactccgatg tcaacttcct gtgggtcatc aagcacaagg aagagggtaa gctccccgag 960
aacctgtccg aggtcatcaa gaccggcaag ggcctcattg ttgcctggtg caagcagctc 1020
gacgttctcg cccacgagtc cgtcggctgc tttgtcaccc actgcggttt caactccacc 1080
ctcgaggcta tctctctcgg tgtccccgtt gttgccatgc cccagttctc cgaccagacc 1140
accaacgcca agctcctcga tgagattctc ggtgtcggtg tccgagtcaa ggctgacgag 1200
aacggtattg tccgacgagg taacctggct tcttgtatca agatgatcat ggaggaagag 1260
cgaggtgtca tcatccgaaa gaacgccgtc aagtggaagg atctggccaa ggttgctgtc 1320
cacgagggtg gctcttccga caacgacatt gtcgagtttg tctccgagct catcaaggcc 1380
taa 1383

<210> SEQ ID NO 79
<211> LENGTH: 1377
<212> TYPE: DNA
<213> ORGANISM: Artificial sequence
<220> FEATURE:
<223> OTHER INFORMATION: UGT4 CpO for Yarrowia lipolitica

<400> SEQUENCE: 79
atggagaaca agaccgagac taccgtccga cgacgacgac gaatcattct cttccccgtc 60
cccttccagg gccacatcaa ccccattctg cagctcgcca acgttctgta ctccaagggc 120
ttctccatca ccatcttcca caccaacttc aacaagccca agacctccaa ctacccccac 180
ttcactttcc gattcatcct cgacaacgac ccccaggacg agcgaatctc caacctgccc 240
acccacggtc ctctggctgg tatgcgaatc cccatcatca acgagcacgg tgctgacgag 300
ctccgacgag agctcgagct gctcatgctc gcctccgaag aggacgagga agtctcctgt 360
ctgatcaccg atgctctgtg gtactttgcc cagtccgtcg ccgactctct caacctgcga 420
cgactcgttc tcatgacctc ctctctgttc aacttccacg cccacgtttc tctgccccag 480
tttgacgagc tcggttacct cgaccccgat gacaagaccc gactcgagga gcaggcttcc 540
ggtttcccca tgctcaaggt caaggacatc aagtccgcct actccaactg gcagattctc 600
aaggagattc tcggcaagat gatcaagcag accaaggcct cctccggtgt catctggaac 660
tccttcaagg agctcgagga gtccgagctc gagactgtca tccgagagat ccccgctccc 720
tctttcctca tcccccctgcc caagcacctc accgcttcct cctcttctct gctcgaccac 780
gaccgaaccg tctttcagtg gctcgaccag cagcccccctt cctccgtcct ctacgtttcc 840

-continued

```
ttcggctcca cctccgaggt cgacgagaag gacttcctcg agattgctcg aggcctcgtt    900

gactccaagc agtccttcct gtgggttgtc cgacccggct ttgtcaaggg ctccacctgg    960

gttgagcccc tgcccgatgg tttcctcggt gagcgaggcc gaattgtcaa gtgggtcccc   1020

cagcaggaag ttctggccca cggtgccatt ggtgccttct ggacccactc cggctggaac   1080

tccactctcg agtccgtctg cgagggtgtc cccatgatct tctccgactt tggcctcgac   1140

cagcccctca acgcccgata catgtccgat gttctcaagg tcggtgtcta cctcgagaac   1200

ggctgggagc gaggtgagat tgccaacgcc atccgacgag tcatggtcga cgaggaaggt   1260

gagtacatcc gacagaacgc ccgagtcctc aagcagaagg ccgatgtctc tctcatgaag   1320

ggtggttctt cttacgagtc tctcgagtct ctcgtttcct acatctcttc tttgtaa      1377
```

<210> SEQ ID NO 80
<211> LENGTH: 2232
<212> TYPE: DNA
<213> ORGANISM: Artificial sequence
<220> FEATURE:
<223> OTHER INFORMATION: tCPS_SR CpO for Yarrowia lipolitica

<400> SEQUENCE: 80

```
atgtgcaagg ctgtttccaa ggagtactcc gatctgctcc agaaggacga ggcctctttc     60

accaagtggg acgacgacaa ggtcaaggac cacctcgaca ccaacaagaa cctctacccc    120

aacgacgaga tcaaggagtt tgtcgagtcc gtcaaggcca tgttcggctc catgaacgac    180

ggcgagatta atgtctctgc ttacgacacc gcctgggttg ctctggtcca ggatgtcgac    240

ggttccggct ctcctcagtt cccttcctct ctcgagtgga tcgccaacaa ccagctgtcc    300

gacggttctt ggggtgacca cctgctcttc tctgctcacg accgaatcat caacaccctg    360

gcctgtgtca ttgctctgac ctcttggaac gtccacccct ccaagtgcga gaagggtctg    420

aacttcctcc gagagaacat ctgcaagctc gaggacgaga acgccgagca catgcccatt    480

ggcttcgagg tcaccttccc ctctctgatt gacattgcca agaagctcaa cattgaggtc    540

cccgaggaca cccccgctct caaggagatc tacgctcgac gagacatcaa gctcaccaag    600

atccccatgg aggttctcca caaggtcccc accactctcc tccactctct cgagggtatg    660

cccgatctcg agtgggagaa gctgctcaag ctgcagtgca aggacggctc tttcctcttc    720

tccccctctt ccactgcctt cgccctcatg cagaccaagg acgagaagtg tctccagtac    780

ctcaccaaca ttgtcaccaa gttcaacggt ggtgtcccca acgtctaccc cgttgacctc    840

tttgagcaca tctgggttgt tgaccgactc cagcgactcg gtatcgcccg atacttcaag    900

tccgagatca aggactgtgt cgagtacatc aacaagtact ggaccaagaa cggtatctgc    960

tgggcccgaa acacccacgt ccaggacatt gacgacaccg ccatgggctt ccgagttctg   1020

cgagcccacg gctacgatgt cacccccgat gtctttcgac agtttgagaa ggacggcaag   1080

tttgtctgtt tcgccggtca gtccacccag gccgtcaccg gtatgttcaa cgtctaccga   1140

gcttctcaga tgctcttccc cggtgagcga atcctcgagg acgccaagaa gttctcctac   1200

aactacctca aggagaagca gtccaccaac gagctgctcg acaagtggat cattgccaag   1260

gatctgcccg gtgaggttgg ctacgccctc gacatcccct ggtacgcctc tctgccccga   1320

ctggagactc gatactacct cgagcagtac ggtggtgagg acgatgtctg gatcggtaag   1380

accctgtacc gaatgggcta cgtttccaac aacacctacc tcgagatggc caagctcgac   1440

tacaacaact acgttgccgt cctccagctc gagtggtaca ccatccagca gtggtacgtc   1500
```

-continued

```
gacattggta tcgagaagtt cgagtccgac aacatcaagt ccgtccttgt ctcctactac   1560

ctcgctgctg cctccatctt cgagcccgag cgatccaagg agcgaattgc ctgggccaag   1620

accaccatcc tcgtcgacaa gatcacctcc atcttcgact cctcccagtc ctccaaggaa   1680

gatatcaccg ccttcattga caagttccga aacaagtcct cctccaagaa gcactccatc   1740

aacggcgagc cctggcacga ggtcatggtt gctctcaaga aaactctcca cggctttgcc   1800

ctcgacgctc tgatgaccca ctctcaggac atccaccccc agctccacca ggcctgggag   1860

atgtggctca ccaagctcca ggacggtgtt gatgtcactg ctgagctcat ggtccagatg   1920

atcaacatga ccgccggccg atgggtttcc aaggagctcc tcacccaccc ccagtaccag   1980

cgactctcca ctgtcaccaa ctctgtctgc cacgacatca ccaagctcca caacttcaag   2040

gagaactcca ccaccgtcga ctccaaggtc caggagctgg tccagctcgt tttctccgac   2100

acccccgatg atctcgacca ggacatgaag cagaccttcc tgactgtcat gaaaactttc   2160

tactacaagg cctggtgcga ccccaacacc atcaacgacc acatctccaa ggtctttgag   2220

attgtgattt aa                                                         2232
```

```
<210> SEQ ID NO 81
<211> LENGTH: 2274
<212> TYPE: DNA
<213> ORGANISM: Artificial sequence
<220> FEATURE:
<223> OTHER INFORMATION: tKS-SR CpO for Yarrowia lipolitica

<400> SEQUENCE: 81

atgacctccc acggcggcca gaccaacccc accaacctca tcattgacac caccaaggag     60

cgaatccaga agcagttcaa gaacgtcgag atctccgttt cctcctacga caccgcctgg    120

gtcgccatgg tcccctctcc caactccccc aagtctccct gcttccccga gtgtctcaac    180

tggctcatca acaaccagct caacgacggc tcttggggtc tggtcaacca cacccacaac    240

cacaaccacc ccctcctcaa ggactctctc tcttccactc tcgcctgcat tgttgctctc    300

aagcgatgga acgttggcga ggaccagatc aacaagggtc tgtctttcat tgagtccaac    360

ctcgcctccg ccaccgagaa gtcccagccc tcccccattg gctttgatat catcttcccc    420

ggtctgctcg agtacgccaa gaacctcgat atcaacctgc tctccaagca gaccgacttc    480

tctctcatgc tgcacaagcg agagctcgag cagaagcgat gccactccaa cgagatggac    540

ggctacctgg cctacatttc cgagggtctg ggtaacctct acgactggaa catggtcaag    600

aagtaccaga tgaagaacgg ttccgttttc aactccccct ctgccaccgc tgctgccttc    660

atcaaccacc agaaccccgg ctgtctcaac tacctcaact ctctgctcga caagtttggt    720

aacgccgtcc ccactgtcta cccccacgat ctcttcatcc gactctccat ggtcgacacc    780

attgagcgac tcggtatttc ccaccacttc cgagtcgaga tcaagaacgt tctcgatgag    840

acttaccgat gctgggttga gcgagatgag cagatcttca tggacgttgt cacctgtgct    900

ctggccttcc gactcctccg aatcaacggt tacgaggttt cccccgaccc cctcgccgag    960

atcaccaacg agctggctct caaggacgag tacgccgccc tcgagactta ccacgcttct   1020

cacattctgt accaagagga tctgtcctcc ggcaagcaga ttctcaagtc cgccgacttc   1080

ctcaaggaga tcatctccac tgactccaac cgactctcca agctcatcca caaggaagtc   1140

gagaacgctc tcaagttccc catcaacacc ggtctggagc gaatcaacac ccgacgaaac   1200

atccagctct acaacgtcga caacacccga attctcaaga ccacctacca ctcttccaac   1260

atctccaaca ccgactacct gcgactcgcc gtcgaggact tctacacctg ccagtccatc   1320
```

```
taccgagagg agctcaaggg tctggagcga tgggttgtcg agaacaagct cgaccagctc   1380
aagtttgccc gacaaaagac tgcctactgc tacttctccg ttgctgccac cctctcttct   1440
cccgagctct ccgacgcccg aatctcttgg gccaagaacg gtatcctgac cactgttgtc   1500
gacgacttct ttgacattgg tggcaccatt gacgagctga ccaacctcat ccagtgcgtc   1560
gagaagtgga acgtcgacgt tgacaaggac tgttgttccg agcacgtccg aatcctcttc   1620
ctggctctca aggacgccat ctgctggatc ggtgacgagg ccttcaagtg gcaggctcga   1680
gatgtcactt cccacgtcat ccagacctgg ctcgagctca tgaactccat gctgcgagag   1740
gccatctgga cccgagatgc ctacgtcccc accctcaacg agtacatgga gaacgcctac   1800
gtcagctttg ctctcggtcc cattgtcaag cccgccatct actttgtcgg tcccaagctg   1860
tccgaggaga ttgtcgagtc ctccgagtac cacaacctct tcaagctcat gtccacccag   1920
ggccgactcc tcaacgatat ccactccttc aagcgagagt tcaaggaagg taagctcaac   1980
gccgttgctc tgcacctgtc caacggtgag tccggcaagg tcgaggaaga ggtcgtcgag   2040
gagatgatga tgatgatcaa gaacaagcga aaggagctca tgaagctcat cttcgaggag   2100
aacggctcca ttgtcccccg agcctgcaag gacgccttct ggaacatgtg ccacgtcctc   2160
aacttcttct acgccaacga cgacggtttc accggcaaca ccattctcga caccgtcaag   2220
gacatcatct acaaccctct ggttctggtc aacgagaacg aggagcagag gtaa         2274
```

<210> SEQ ID NO 82
<211> LENGTH: 1578
<212> TYPE: DNA
<213> ORGANISM: Artificial sequence
<220> FEATURE:
<223> OTHER INFORMATION: KAH_4 CpO for Yarrowia lipolitica

<400> SEQUENCE: 82

```
atggagtctc tggttgtcca caccgtcaac gccatctggt gcattgtcat tgtcggtatc     60
ttctccgtcg gctaccacgt ctacggccga gctgttgtcg agcagtggcg aatgcgacga    120
tctctcaagc tccagggtgt caagggtcct cctccctcca tcttcaacgg taacgtttcc    180
gagatgcagc gaatccagtc cgaggccaag cactgctccg gtgacaacat catctcccac    240
gactactctt cttctctgtt cccccacttt gaccactggc gaaagcagta cggccgaatc    300
tacacctact ccactggcct caagcagcac ctctacatca accaccccga gatggtcaag    360
gagctctccc agaccaacac cctcaacctc ggccgaatca cccacatcac caagcgactc    420
aaccccattc tcggtaacgg tatcatcacc tccaacggcc cccactgggc ccaccagcga    480
cgaatcattg cctacgagtt cacccacgac aagatcaagg gtatggtcgg tctgatggtc    540
gagtccgcca tgcccatgct caacaagtgg gaggagatgg tcaagcgagg tggtgagatg    600
ggctgtgaca tccgagtcga cgaggacctc aaggatgtct ccgctgacgt cattgccaag    660
gcctgtttcg gctcttcctt ctccaagggc aaggccatct tctccatgat ccgagatctg    720
ctcaccgcca tcaccaagcg atccgtcctc ttccgattca acggtttcac cgacatggtt    780
ttcggctcca agaagcacgg tgacgttgac attgacgctc tcgagatgga gctcgagtcc    840
tccatctggg agactgtcaa ggagcgagag attgagtgca aggacaccca caagaaggac    900
ctcatgcagc tcattctcga gggtgccatg cgatcttgtg acggtaacct gtgggacaag    960
tctgcttacc gacgattcgt tgtcgacaac tgcaagtcca tctactttgc cggccacgac   1020
tccaccgccg tttccgtttc ttggtgcctc atgctgctcg ctctcaaccc ctcttggcag   1080
```

-continued

```
gtcaagatcc gagatgagat tctgtcctcc tgcaagaacg gtatccccga cgccgagtcc   1140

atccccaacc tcaagaccgt caccatggtc atccaggaga ctatgcgact ctaccctccc   1200

gctcccattg tcggccgaga ggcctccaag gacattcgac tcggtgatct ggttgtcccc   1260

aagggtgtct gtatctggac cctcatcccc gctctgcacc gagatcccga gatctggggt   1320

cccgacgcca acgacttcaa gcccgagcga ttctccgagg gtatctccaa ggcctgcaag   1380

taccccccagt cctacatccc ctttggcctc ggcccccgaa cctgtgtcgg caagaacttt   1440

ggtatgatgg aggtcaaggt cctcgtttct ctgattgtct ccaagttctc cttcactctg   1500

tctcccacct accagcactc tccctcccac aagctgctcg tcgagcccca gcacggtgtt   1560

gtcatccgag ttgtataa                                                 1578
```

<210> SEQ ID NO 83
<211> LENGTH: 1578
<212> TYPE: DNA
<213> ORGANISM: Artificial sequence
<220> FEATURE:
<223> OTHER INFORMATION: KO_Gib CpO for Yarrowia lipolitica

<400> SEQUENCE: 83

```
atgtccaagt ccaactccat gaactccacc tcccacgaga ctctcttcca gcagctcgtt     60

ctcggcctcg accgaatgcc cctcatggac gtccactggc tcatctacgt tgcctttggt    120

gcctggctct gctcctacgt catccacgtt ctgtcctctt cctccactgt caaggtcccc    180

gtcgtcggtt accgatccgt tttcgagccc acctggctcc tccgactgcg attcgtctgg    240

gagggtggtt ccatcattgg ccagggctac aacaagttca aggactccat cttccaggtc    300

cgaaagctcg gtaccgacat tgtcatcatc cctcccaact acattgacga ggtccgaaag    360

ctctcccagg acaagacccg atccgtcgag cccttcatca acgactttgc cggccagtac    420

acccgaggta tggtctttct gcagtccgat ctccagaacc gagtcatcca gcagcgactc    480

acccccaagc ttgtctctct caccaaggtc atgaaggaag agctcgacta cgctctgacc    540

aaggagatgc ccgacatgaa gaacgacgag tgggttgagg tcgacatctc ttccatcatg    600

gtccgactca tctctcgaat ctccgcccga gttttcctcg gccccgagca ctgccgaaac    660

caggagtggc tcaccaccac cgccgagtac tccgagtctc tcttcatcac cggcttcatc    720

ctccgagttg tcccccacat tctccgaccc ttcattgctc ctctgctgcc ctcttaccga    780

accctgctgc gaaacgtttc ttccggccga cgagtcattg gtgatatcat ccgatcccag    840

cagggtgacg gtaacgagga catcctctct tggatgcgag atgctgccac tggtgaggag    900

aagcagatcg acaacattgc ccagcgaatg ctcattctgt ctctcgcctc catccacacc    960

accgccatga ccatgaccca cgccatgtac gatctgtgtg cctgccccga gtacattgag   1020

cccctccgag atgaggtcaa gtccgtcgtt ggtgcttctg gctgggacaa gaccgctctc   1080

aaccgattcc acaagctcga ctctttcctc aaggagtccc agcgattcaa ccccgttttc   1140

ctgctcacct tcaaccgaat ctaccaccag tccatgaccc tctccgatgg taccaacatc   1200

ccctccggta cccgaattgc tgtcccctct cacgccatgc tccaggactc cgcccacgtc   1260

cccggtccca ctcctcccac tgagttcgac ggtttccgat actccaagat ccgatccgac   1320

tccaactacg cccagaagta cctcttctcc atgaccgact cttccaacat ggcctttggc   1380

tacggtaagt acgcctgccc cggccgattc tacgcctcca acgagatgaa gctgactctg   1440

gccattctgc tcctccagtt tgagttcaag ctccccgacg gtaagggccg accccgaaac   1500

atcaccatcg actccgacat gatccccgac ccccgagctc gactctgtgt ccgaaagcga   1560
```

tctctgcgtg acgagtaa 1578

<210> SEQ ID NO 84
<211> LENGTH: 2133
<212> TYPE: DNA
<213> ORGANISM: Artificial sequence
<220> FEATURE:
<223> OTHER INFORMATION: CPR_3 CpO for Yarrowia lipolitica

<400> SEQUENCE: 84
atgtcctcct cttcttcttc ttccacctcc atgattgatc tcatggctgc catcatcaag 60
ggtgagcccg tcattgtctc cgaccccgcc aacgcctccg cctacgagtc cgttgctgcc 120
gagctgtcct ccatgctcat cgagaaccga cagtttgcca tgatcgtcac cacctccatt 180
gctgttctca ttggctgcat tgtcatgctc gtctggcgac gatctggctc cggtaactcc 240
aagcgagtcg agcccctcaa gcccctggtc atcaagcccc gagaagagga gatcgacgac 300
ggccgaaaga aggtcaccat cttctttggc acccagaccg gtactgctga gggcttcgcc 360
aaggctctcg gtgaggaagc caaggctcga tacgaaaaga cccgattcaa gattgtcgac 420
ctcgatgatt acgctgccga tgacgacgag tacgaggaga agctcaagaa agaggacgtt 480
gccttcttct tcctcgccac ctacggtgac ggtgagccca ccgacaacgc tgcccgattc 540
tacaagtggt tcaccgaggg taacgaccga ggcgagtggc tcaagaacct caagtacggt 600
gttttcggtc tgggcaaccg acagtacgag cacttcaaca aggttgccaa ggttgtcgac 660
gacatcctcg tcgagcaggg tgcccagcga ctcgtccagg tcggcctcgg tgatgatgac 720
cagtgcatcg aggacgactt cactgcctgg cgagaggctc tgtggcccga gctcgacacc 780
attctgcgag aggaaggtga caccgccgtt gccaccccct acaccgccgc cgtcctcgag 840
taccgagtct ccatccacga ctccgaggat gccaagttca acgacatcaa catggccaac 900
ggtaacggct acaccgtctt tgacgcccag caccccctaca aggccaacgt cgccgtcaag 960
cgagagctcc acacccccga gtccgaccga tcttgtatcc acctcgagtt tgacattgct 1020
ggttccggtc tgacctacga gactggtgac cacgttggtg tcctctgtga caacctgtcc 1080
gagactgtcg acgaggctct gcgactcctc gacatgtccc ccgacactta cttctctctg 1140
cacgccgaga aagaggacgg tactcccatc tcttcttctc tgccccctcc cttccctccc 1200
tgcaacctgc gaaccgctct gacccgatac gcctgcctcc tctcttctcc caagaagtct 1260
gctctcgttg ctctggccgc ccacgcctcc gaccccaccg aggctgagcg actcaagcac 1320
ctcgcctctc ccgctggcaa ggacgagtac tccaagtggg ttgtcgagtc ccagcgatct 1380
ctgctcgagg tcatggccga gttcccctcc gccaagcccc ctctcggtgt tttcttcgcc 1440
ggtgttgctc cccgactcca gccccgattc tactccatct cctcttcccc caagatcgcc 1500
gagactcgaa tccacgttac ctgtgctctg gtctacgaga agatgcccac cggccgaatc 1560
cacaagggtg tctgctccac ctggatgaag aacgccgttc cctacgagaa gtccgagaac 1620
tgttcctctg ctcccatctt tgtccgacag tccaacttca agctccccctc cgactccaag 1680 gtccccatca tcatgattgg ccccggtacc ggcctcgccc ccttccgagg cttcctgcag 1740
gagcgactcg ccctcgtcga gtccggtgtc gagctcggcc cctccgtcct cttctttggc 1800
tgccgaaacc gacgaatgga cttcatctac gaagaggagc tccagcgatt cgtcgagtcc 1860
ggtgctctcg ccgagctctc cgttgccttc tcccgagagg gtcccaccaa ggagtacgtc 1920
cagcacaaga tgatggacaa ggcctccgac atctggaaca tgatctccca gggcgcctac 1980

-continued

| | |
|---|---|
| ctctacgtct gcggtgacgc caagggtatg gcccgagatg tccaccgatc tctgcacacc | 2040 |
| attgcccagg agcagggctc catggactcc accaaggccg agggtttcgt caagaacctc | 2100 |
| cagacctccg gccgatacct ccgagatgtc tgg | 2133 |

UDP-GLYCOSYLTRANSFERASES

CROSS-REFERENCE TO RELATED APPLICATIONS

This application is a Continuation of U.S. patent application Ser. No. 16/777,427, filed Jan. 30, 2020, which is a Divisional of U.S. patent application Ser. No. 15/558,133, filed Sep. 13, 2017, which is a National Stage entry of International Application No. PCT/EP2016/055734, filed Mar. 16, 2016, which claims priority to U.S. Provisional Application No. 62/133,606, filed Mar. 16, 2015. The disclosure of the priority applications are incorporated in their entirety herein by reference.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2919208-460002_ST25.txt" created on 26 Jan. 2021, and 159,491 bytes in size) is submitted concurrently with the instant application, and the entire contents of the Sequence Listing are incorporated herein by reference.

BACKGROUND OF THE INVENTION

Field of the Invention

The present invention relates to a recombinant host comprising a recombinant nucleic acid sequence encoding a variant UDP-glycosyltransferase (UGT) polypeptide. The invention also relates to a process for the preparation of a glycosylated diterpene using such a recombinant host and to a fermentation broth which may be the result of such a process. The invention further relates to a glycosylated diterpene obtained by such a process or obtainable from such a fermentation broth and to a composition comprising two or more such glycosylated diterpenes. In addition the invention relates to a foodstuff, feed or beverage which comprises such a glycosylated diterpene or a such composition. The invention also relates to a method for converting a first glycosylated diterpene into a second glycosylated diterpene using the above-mentioned recombinant host. Furthermore, the invention relates to variant UGT polypeptides, to nucleic acid sequences encoding such polypeptides, to a nucleic acid construct comprising such a polynucleotide sequence and to a method for producing the variant UGT polypeptides using the above-mentioned recombinant host.

Description of Related Art

The leaves of the perennial herb, *Stevia rebaudiana* Bert., accumulate quantities of intensely sweet compounds known as steviol glycosides. Whilst the biological function of these compounds is unclear, they have commercial significance as alternative high potency sweeteners.

These sweet steviol glycosides have functional and sensory properties that appear to be superior to those of many high potency sweeteners. In addition, studies suggest that stevioside can reduce blood glucose levels in Type II diabetics and can reduce blood pressure in mildly hypertensive patients.

Steviol glycosides accumulate in *Stevia* leaves where they may comprise from 10 to 20% of the leaf dry weight. Stevioside and rebaudioside A are both heat and pH stable and suitable for use in carbonated beverages and many other foods. Stevioside is between 110 and 270 times sweeter than sucrose, rebaudioside A between 150 and 320 times sweeter than sucrose. In addition, rebaudioside D is also a high-potency diterpene glycoside sweetener which accumulates in *Stevia* leaves. It may be about 200 times sweeter than sucrose. Rebaudioside M is a further high-potency diterpene glycoside sweetener. It is present in trace amounts in certain *stevia* variety leaves, but has been suggested to have a superior taste profile.

Steviol glycosides have traditionally been extracted from the *Stevia* plant. In *Stevia*, (−)-kaurenoic acid, an intermediate in gibberellic acid (GA) biosynthesis, is converted into the tetracyclic dipterepene steviol, which then proceeds through a multi-step glycosylation pathway to form the various steviol glycosides. However, yields may be variable and affected by agriculture and environmental conditions. Also, *Stevia* cultivation requires substantial land area, a long time prior to harvest, intensive labour and additional costs for the extraction and purification of the glycosides.

SUMMARY

More recently, interest has grown in producing steviol glycosides using fermentative processes. WO2013/110673 and WO2015/007748 describe microorganisms that may be used to produce at least the steviol glycosides rebaudioside A and rebaudioside D.

Further improvement of such microoganisms is desirable in order that higher amounts of steviol glycosides may be produced and/or additional or new steviol glycosides and/or higher amounts of specific steviol glycosides and/or mixtures of steviol glycosides having desired ratios of different steviol glycosides.

In *Stevia rebaudiana*, steviol is synthesized from GGPP, which is formed by the deoxyxylulose 5-phosphate pathway. The activity of two diterpene cyclases (−)-copalyl diphosphate synthase (CPS) and (−)-kaurene synthase (KS) results in the formation of (−)-Kaurene which is then oxidized in a three step reaction by (−)-kaurene oxidase (KO) to form (−)-kaurenoic acid.

In *Stevia rebaudiana* leaves, (−)-kaurenoic acid is then hydroxylated, by ent-kaurenoic acid 13-hydroxylase (KAH) to form steviol. Steviol is then glycosylated by a series of UDP-glycosyltransferases (UGTs) leading to the formation of a number of steviol glycosides. Specifically, these molecules can be viewed as a steviol molecule, with its carboxyl hydrogen atom replaced by a glucose molecule to form an ester, and an hydroxyl hydrogen with combinations of glucose and rhamnose to form an acetal.

These pathways may be reconstructed in recombinant hosts, for example yeasts such as *Saccharomyces* and *Yarrowia*.

The invention relates to the identification of new variant UDP-glycosyltransferase (UGT) polypeptides, typically having improved properties in comparison to those that are currently known. These polypeptides may be used to generate recombinant hosts that produce higher amounts of steviol glycosides and/or additional or new steviol glycosides and/or higher amounts of specific steviol glycosides and/or mixtures of steviol glycosides having desired ratios of different steviol glycosides.

Thus, the invention also relates to a recombinant host capable of producing a glycosylated diterpene (i.e. a diterpene glycoside such as a steviol glycoside), such as steviolmonoside, steviolbioside, stevioside, rebaudioside A, rebaudioside B, rebaudioside C, rebaudioside D, rebaudioside E, rebaudioside F, rebaudioside M, rubusoside, dulcoside A, steviol-13-monoside, steviol-19-monoside or 13-[(β-D-Glucopyranosyl)oxy)kaur-16-en-18-oic acid 2-O-β-D-glucopyranosyl-β-D-glucopyranosyl ester steviol-19-diside, Accordingly, the invention relates to a recombinant host comprising a recombinant nucleic acid sequence, typically having UDP-glycosyltransferase (UGT) activity such as UGT2 activity, encoding a polypeptide having at least about:

- a. 85% identity to the amino acid sequence set forth in SEQ ID NO: 1;
- b. 85% identity to the amino acid sequence set forth in SEQ ID NO: 3;
- c. 85% identity to the amino acid sequence set forth in SEQ ID NO: 6;
- d. 85% identity to the amino acid sequence set forth in SEQ ID NO: 9;
- e. 85% identity to the amino acid sequence set forth in SEQ ID NO: 11;
- f. 85% identity to the amino acid sequence set forth in SEQ ID NO: 14;
- g. 85% identity to the amino acid sequence set forth in SEQ ID NO: 17;
- h. 85% identity to the amino acid sequence set forth in SEQ ID NO: 20;
- i. 85% identity to the amino acid sequence set forth in SEQ ID NO: 22; or
- j. 85% identity to the amino acid sequence set forth in SEQ ID NO: 25.

The invention also relates to:

- a process for the preparation of a glycosylated diterpene which comprises fermenting a recombinant host of the invention in a suitable fermentation medium, and optionally recovering the glycosylated diterpene;
- a fermentation broth comprising a glycosylated diterpene obtainable by the process of the invention;
- a glycosylated diterpene obtained by such a process or obtainable from such a fermentation broth;
- a composition comprising two or more such diterpenes;
- a foodstuff, feed or beverage which comprises such a glycosylated diterpene;
- a method for converting a first glycosylated diterpene into a second glycosylated diterpene, which method comprises:
  - contacting said first glycosylated diterpene with a recombinant host of the invention, a cell free extract derived from such a recombinant host or an enzyme preparation derived from either thereof;
  - thereby to convert the first glycosylated diterpene into the second glycosylated diterpene.
- a polypeptide having UGT2 activity, wherein said polypeptide is selected from the group consisting of:
- (a) a polypeptide comprising an amino acid sequence as set out in any one of SEQ ID NOs: 1, 3, 6, 9, 11, 14, 17, 20, 22 or 25; or
- (b) a polypeptide comprising an amino acid sequence having at least about 85% sequence identity with the amino acid sequence of any one of SEQ ID NOs: 1, 3, 6, 9, 11, 14, 17, 20, 22 or 25; or
- (c) a polypeptide encoded by a polynucleotide comprising the polynucleotide sequence as set out in any one SEQ ID NOs: 2, 4, 5, 7, 8, 10, 12, 13, 15, 16, 18, 19, 21, 23, 24 or 26; or
- (d) a polypeptide encoded by a polynucleotide comprising a polynucleotide sequence having at least 50% sequence identity to the polypeptide coding sequence in any one SEQ ID NOs: 2, 4, 5, 7, 8, 10, 12, 13, 15, 16, 18, 19, 21, 23, 24 or 26; or
- (e) a polypeptide encoded by a polynucleotide which hybridises, preferably under at least low stringency conditions, with the complementary strand of any one SEQ ID NOs: 2, 4, 5, 7, 8, 10, 12, 13, 15, 16, 18, 19, 21, 23, 24 or 26; or
- (f) a polypeptide encoded by a polynucleotide which hybridises, preferably under at least low stringency conditions, with the complementary strand of a polynucleotide having at least 50% sequence identity to any one SEQ ID NOs: 2, 4, 5, 7, 8, 10, 12, 13, 15, 16, 18, 19, 21, 23, 24 or 26; or
- (g) a fragment of a polypeptide as defined in (a), (b), (c), (d), (e) or (f).
  - a polynucleotide sequence coding for such a polypeptide;
  - a nucleic acid construct comprising such a polynucleotide sequence; and
  - a method of producing the polypeptide of the invention, comprising:
- (a) cultivating a recombinant host of the invention under conditions conducive to the production of the polypeptide by the host cell, and optionally,
- (b) recovering the polypeptide.

BRIEF DESCRIPTION OF THE DRAWINGS

FIG. 12 sets out the production of rebaudioside M in *Saccharomyces* strains expressing different variants of UGT2, as a percentage of the rebaudioside M production in a *Saccharomyces* strain expressing UGT2_1a.

FIG. 29 sets out the production of rebaudioside M in *Yarrowia* strains expressing different variants of UGT2, as a percentage of the rebaudioside M production in a *Yarrowia* strain expressing UGT2_1a.

DESCRIPTION OF THE SEQUENCE LISTING

Figure 1:
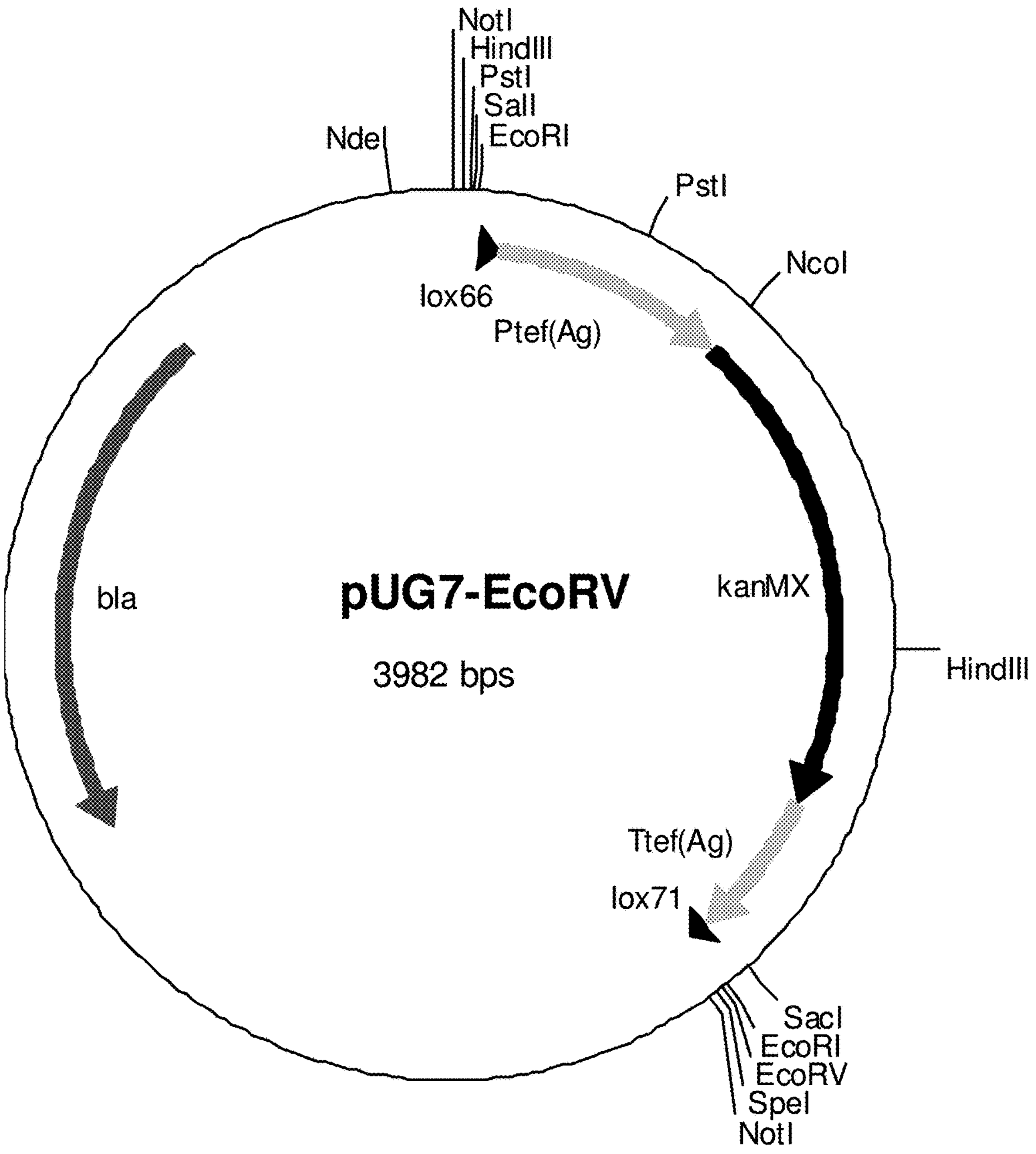
FIG. 1 sets out a schematic representation of the plasmid pUG7-EcoRV.

A description of the sequences is set out in Table 13. Sequences described herein may be defined with reference to the sequence listing or with reference to any database accession numbers set out herein, for example in Table 13.

DETAILED DESCRIPTION OF THE INVENTION

Throughout the present specification and the accompanying claims, the words “comprise”, “include” and “having” and variations such as “comprises”, “comprising”, “includes” and “including” are to be interpreted inclusively. That is, these words are intended to convey the possible inclusion of other elements or integers not specifically recited, where the context allows.

The articles “a” and “an” are used herein to refer to one or to more than one (i.e. to one or at least one) of the grammatical object of the article. By way of example, “an element” may mean one element or more than one element.

Herein, “rebaudioside” may be shortened to ““reb”. That is rebaudioside A and rebA, for example, are intended to indicate the same molecule.

The term “recombinant” when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. The term “recombinant” is synonymous with “genetically modified”.

The invention relates to new variant polypeptides having UDP-glycosyltransferase (UGT) activity. For the purposes of this invention, a polypeptide having UGT activity is one which has glycosyltransferase activity (EC 2.4), i.e. that can act as a catalyst for the transfer of a monosaccharide unit from an activated nucleotide sugar (also known as the “glycosyl donor”) to a glycosyl acceptor molecule, usually an alcohol. The glycosyl donor for a UGT is typically the nucleotide sugar uridine diphosphate glucose (uracil-diphosphate glucose, UDP-glucose). A polypeptide of the invention typically has UGT activity and a polynucleotide sequence of the invention typically encodes such a polypeptide. Typically, the polypeptides of the invention are variant polypeptides having UGT2-type activity.

According to the invention, there is thus provided a polypeptide, typically one having UGT activity, wherein said polypeptide is selected from the group consisting of:

(a) a polypeptide comprising an amino acid sequence as set out in any one of SEQ ID NOs: 1, 3, 6, 9, 11, 14, 17, 20, 22 or 25; or (b) a polypeptide comprising an amino acid sequence having at least about 85% sequence identity with the amino acid sequence of any one of SEQ ID NOs: 1, 3, 6, 9, 11, 14, 17, 20, 22 or 25; or (c) a polypeptide encoded by a polynucleotide comprising the polynucleotide sequence as set out in any one SEQ ID NOs: 2, 4, 5, 7, 8, 10, 12, 13, 15, 16, 18, 19, 21, 23, 24 or 26; or (d) a polypeptide encoded by a polynucleotide comprising a polynucleotide sequence having at least 50% sequence identity to the polypeptide coding sequence in any one SEQ ID NOs: 2, 4, 5, 7, 8, 10, 12, 13, 15, 16, 18, 19, 21, 23, 24 or 26; or (e) a polypeptide encoded by a polynucleotide which hybridizes, preferably under at least low stringency conditions, with the complementary strand of any one SEQ ID NOs: 2, 4, 5, 7, 8, 10, 12, 13, 15, 16, 18, 19, 21, 23, 24 or 26; or (f) a polypeptide encoded by a polynucleotide which hybridizes, preferably under at least low stringency conditions, with the complementary strand of a polynucleotide having at least 50% sequence identity to any one SEQ ID NOs: 2, 4, 5, 7, 8, 10, 12, 13, 15, 16, 18, 19, 21, 23, 24 or 26; or (g) a fragment of a polypeptide as defined in (a), (b), (c), (d), (e) or (f).

Such a polypeptide may comprise an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to any one of SEQ ID NOs: 1, 3, 6, 9, 11, 14, 17, 20, 22 or 25.

Thus, the invention relates to:

- a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 1;
- a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO 3;
- a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 6;
- a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 9;
- a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 11;
- a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 14;
- a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 17;
- a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 20;
- a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 22; and
- a polypeptide, typically having UGT activity, which comprises an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to SEQ ID NO: 25.

As used herein, the term "polypeptide" refers to a molecule comprising amino acid residues linked by peptide bonds and containing more than five amino acid residues. The amino acids are identified by either the single-letter or three-letter designations. The term "protein" as used herein is synonymous with the term "polypeptide" and may also refer to two or more polypeptides. Thus, the terms "protein", "peptide" and "polypeptide" can be used interchangeably. Polypeptides may optionally be modified (e.g., glycosylated, phosphorylated, acylated, farnesylated, prenylated, sulfonated, and the like) to add functionality. Polypeptides exhibiting activity may be referred to as enzymes. It will be understood that, as a result of the degeneracy of the genetic code, a multitude of nucleotide sequences encoding a given polypeptide may be produced.

A polypeptide of the invention may comprise a signal peptide and/or a propeptide sequence. In the event that a polypeptide of the invention comprises a signal peptide and/or a propeptide, sequence identity may be calculated over the mature polypeptide sequence.

Figure 31:
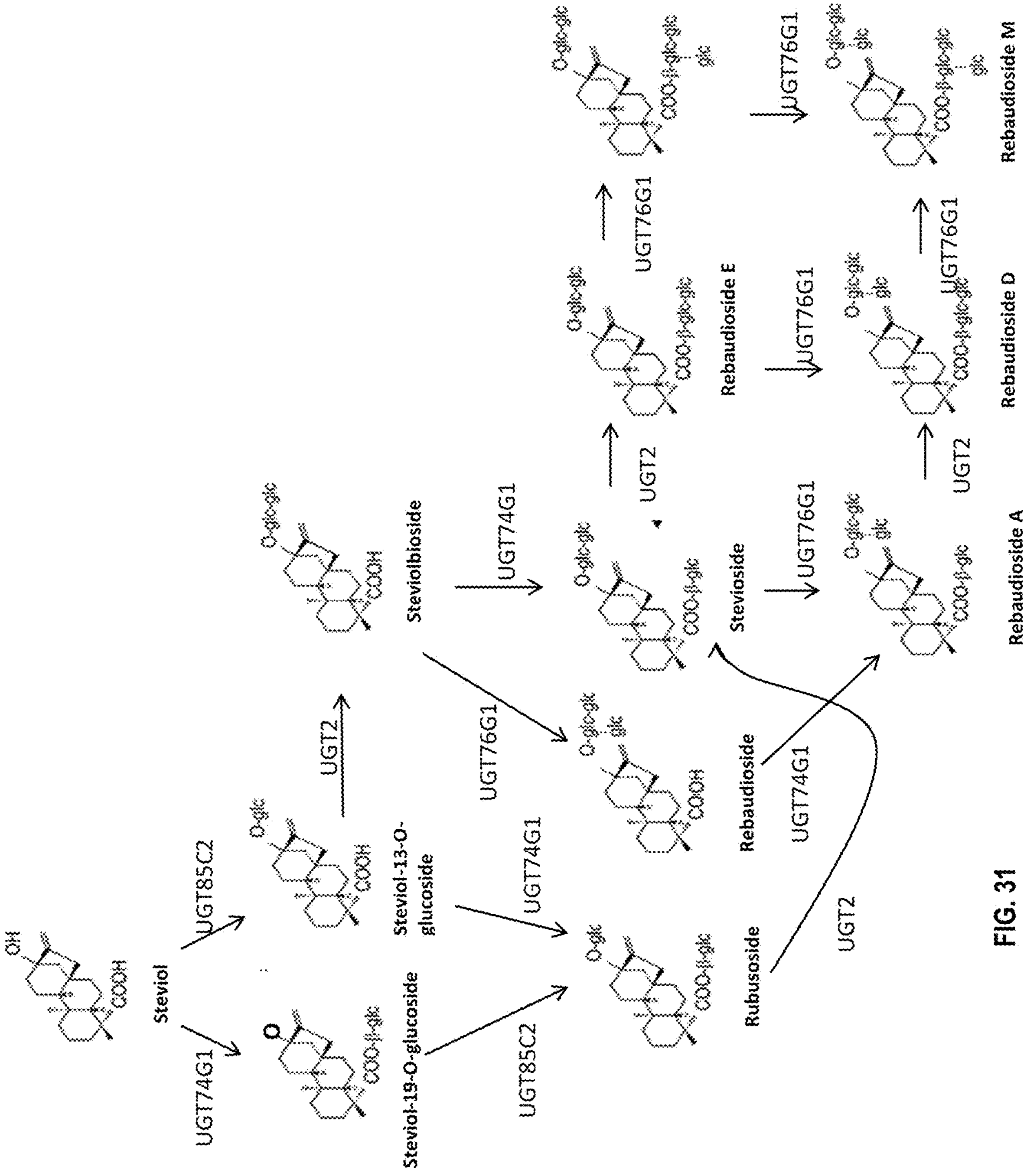
FIG. 31 sets out sets out a schematic diagram of the potential pathways leading to biosynthesis of steviol glycosides.
Figure 32:
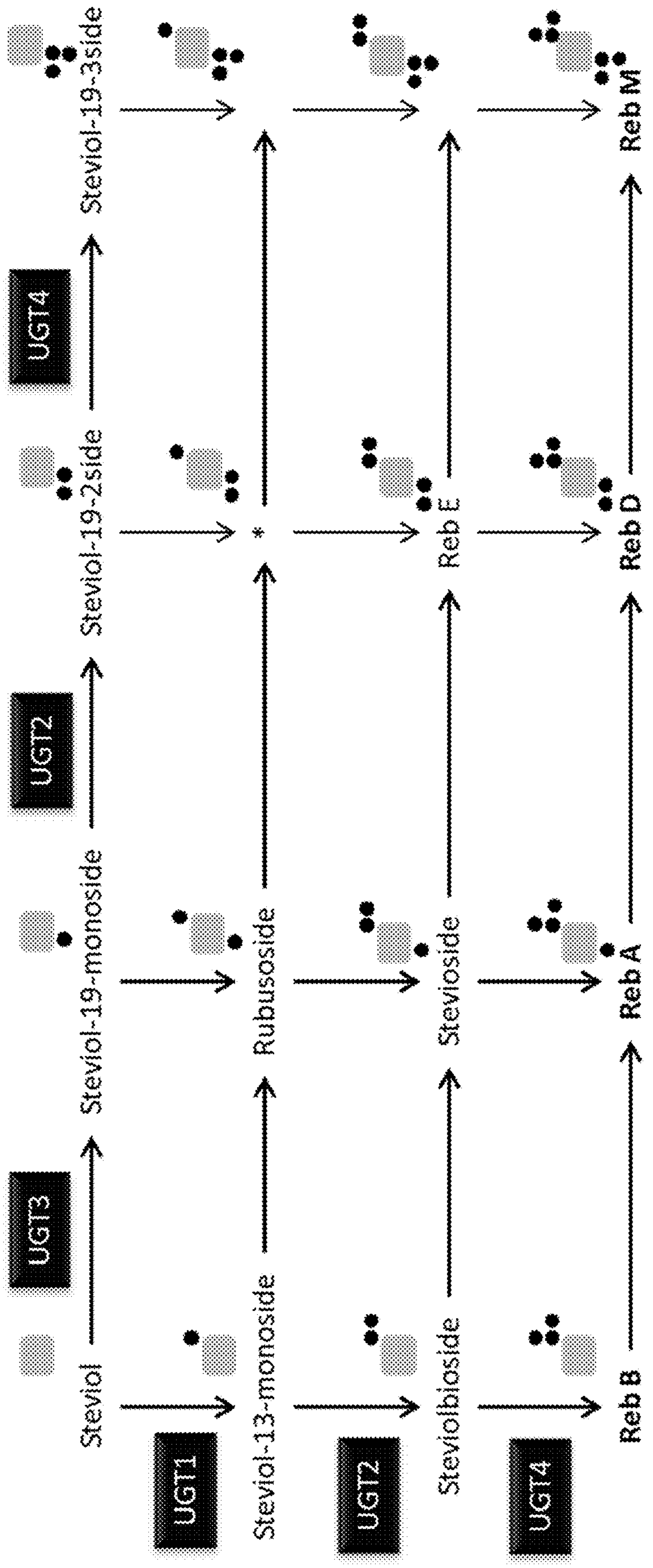
FIG. 32 sets out sets out a schematic diagram of the potential pathways leading to biosynthesis of steviol glycosides. The compound shown with an asterisk is 13-[(β-D-Glucopyranosyl)oxy)kaur-16-en-18-oic acid 2-O-β-D-glucopyranosyl-β-D-glucopyranosyl ester

A polypeptide of the invention typically has UGT activity and more preferably has UGT2 activity. FIGS. 31 and 32 illustrate a non-exhaustive list of reactions that may be catalyzed by a polypeptide having UGT2.

A polypeptide having UGT2 activity is one which functions as a uridine 5'-diphospho glucosyl: steviol-13-O-glucoside transferase (also referred to as a steviol-13-monoglucoside 1,2-glucosylase), transferring a glucose moiety to the C-2' of the 13-O-glucose of the acceptor molecule, steviol-13-O-glucoside. Typically, a suitable UGT2 polypeptide also functions as a uridine 5'-diphospho glucosyl: rubusoside transferase transferring a glucose moiety to the C-2' of the 13-O-glucose of the acceptor molecule, rubusoside.

A polypeptide having UGT2 activity may also catalyze reactions that utilize steviol glycoside substrates other than steviol-13-O-glucoside and rubusoside, e.g., a functional UGT2 polypeptide may utilize stevioside as a substrate, transferring a glucose moiety to the C-2' of the 19-O-glucose residue to produce rebaudioside E. A functional UGT2 polypeptide may also utilize rebaudioside A as a substrate, transferring a glucose moiety to the C-2' of the 19-O-glucose residue to produce rebaudioside D.

A polypeptide having UGT2 activity may also catalyze reactions that utilize steviol-19-glucoside or rubusoside as a substrate, e.g., a functional UGT2 polypeptide may utilize steviol-19-glucoside or rubusoside as a substrate, transferring a glucose moiety to the 19 position to produce steviol-19-2side or 13-[(β-D-Glucopyranosyl)oxy)kaur-16-en-18-oic acid 2-O-β-D-glucopyranosyl-β-D-glucopyranosyl ester respectively.

However, a functional UGT2 polypeptide typically does not transfer a glucose moiety to steviol compounds having a 1,3-bound glucose at the C-13 position, i.e., transfer of a glucose moiety to steviol 1,3-bioside and 1,3-stevioside typically does not occur.

A polypeptide having UGT2 activity may also transfer sugar moieties from donors other than uridine diphosphate glucose. For example, a polypeptide having UGT2 activity act as a uridine 5'-diphospho D-xylosyl: steviol-13-O-glucoside transferase, transferring a xylose moiety to the C-2' of the 13-O-glucose of the acceptor molecule, steviol-13-O-glucoside. As another example, a polypeptide having UGT2 activity may act as a uridine 5'-diphospho L-rhamnosyl: steviol-13-O-glucoside transferase, transferring a rhamnose moiety to the C-2' of the 13-O-glucose of the acceptor molecule, steviol.

One or more of the above-described activities may be used to define a polypeptide having UGT2 activity. A polypeptide of the invention may have improved UGT2 activity in respect of one or more of the above-described activities in comparison with the UGT2_1a polypeptide (SEQ ID NO: 27).

A polypeptide of the invention may be used to steer production of steviol glycosides in a recombinant cell to a desired steviol glycoside, such as rebaudioside A, rebaudioside D or rebaudioside M. For example, a UGT2 polypeptide which preferentially catalyzes conversion of steviol-13-monoside to steviolbioside and/or conversion of rubusoside to stevioside may help to steer production towards rebaudiosideA, whereas a UGT2 polypeptide which preferentially catalyzes conversion of stevioside to rebE or rubusoside to a compound with an additional sugar at the 19 position may help to steer production towards rebaudioside M. That is to say preference for addition of a sugar moiety at the 13 position may help steer production towards rebaudioside A, whereas preference for addition of a sugar moiety at the 19 position may help steer production towards rebaudioside M.

The invention further provides a polynucleotide sequence coding for a polypeptide as described herein.

Such a polynucleotide sequence may be selected from the group consisting of:

(a) a polynucleotide sequence comprising any one of SEQ ID NOs: 2, 4, 5, 7, 8, 10, 12, 13, 15, 16, 18, 19, 21, 23, 24 or 26 or comprising a polynucleotide sequence having at least 30% sequence identity with the polynucleotide sequence of any one of SEQ ID NOs: 2, 4, 5, 7, 8, 10, 12, 13, 15, 16, 18, 19, 21, 23, 24 or 26; or (b) a polynucleotide sequence which hybridizes, preferably under at least low stringency conditions, with the complementary strand of any one SEQ ID NOs: 2, 4, 5, 7, 8, 10, 12, 13, 15, 16, 18, 19, 21, 23, 24 or 26; or (c) a polynucleotide sequence which hybridizes, preferably under at least low stringency conditions with the complementary strand of a polynucleotide having at least 30% sequence identity to any one of any one SEQ ID NOs: 2, 4, 5, 7, 8, 10, 12, 13, 15, 16, 18, 19, 21, 23, 24 or 26;

(d) a polynucleotide sequence which is degenerate as a result of the degeneracy of the genetic code to a polynucleotide sequence as defined in any one of (a), (b) or (c); or (e) a polynucleotide sequence which is the complement of a nucleotide sequence as defined in (a), (b), (c) or (d).

A polynucleotide sequence of the invention may have a sequence identity of at least 40%, at least 50%, at least 60%, preferably at least 70%, more preferably at least 80%, most preferably at-least 90%, most preferably at least 93%, most preferably at least about 95%, most preferably at least about 96%, most preferably at least about 97%, even most preferably at least about 98%, and even more preferred at least 99% to any one of any one SEQ ID NOs: 2, 4, 5, 7, 8, 10, 12, 13, 15, 16, 18, 19, 21, 23, 24 or 26.

The term "nucleic acid" as used in the present invention refers to a nucleotide polymer including at least 5 nucleotide units. A nucleic acid refers to a ribonucleotide polymer (RNA), deoxynucleotide polymer (DNA) or a modified form of either type of nucleic acid or synthetic form thereof or mixed polymers of any of the above. Nucleic acids may include either or both naturally-occurring and modified nucleic acids linked together by naturally-occurring and/or non-naturally occurring nucleic acid linkages. The nucleic acid molecules may be modified chemically or biochemically or may contain non-natural or derivatized nucleic acid bases, as will be readily appreciated by those of skill in the art. Such modifications include, for example, labels, methylation, substitution of one or more of the naturally occurring nucleic acids with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) The term nucleic acid is also intended to include any topological conformation, including single-stranded (sense strand and antisense strand), double-stranded, partially duplexed, triplex, hairpinned, circular and padlocked conformations. Also included are synthetic molecules that mimic nucleic acids in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for antisense therapy, hybridization probes and PCR primers. The term "nucleic acid", "polynucleotide" and "polynucleotide sequence" can be used interchangeably herein.

As used herein, the term "hybridization" means the pairing of substantially complementary strands of oligomeric compounds. One mechanism of pairing involves hydrogen bonding, which may be Watson-Crick, Hoogsteen or reversed Hoogsteen hydrogen bonding, between complementary nucleotide bases (nucleotides) of the strands of oligomeric compounds. For example, adenine and thymine are complementary nucleic acids which pair through the formation of hydrogen bonds. Hybridization can occur under varying circumstances. "Stringency hybridization" or "hybridizes under low stringency, medium stringency, high stringency, or very high stringency conditions" is used herein to describe conditions for hybridization and washing, more specifically conditions under which an oligomeric compound will hybridize to its target sequence, but to a minimal number of other sequences. So, the oligomeric compound will hybridize to the target sequence to a detectably greater degree than to other sequences. Guidance for performing hybridization reactions can be found in Current Protocols in Molecular Biology, John Wiley & Sons, N.Y. (1989), 6.3.1-6:3.6. Aqueous and non-aqueous methods are described in that reference and either can be used. Stringency conditions are sequence-dependent and will be different in different circumstances. Generally, stringency conditions are selected to be about 5° C. lower than the thermal melting point ($T_m$) for the oligomeric compound at a defined ionic strength and pH. The $T_m$ is the temperature (under defined ionic strength and pH) at which 50% of an oligomeric compound hybridizes to a perfectly matched probe. Stringency conditions may also be achieved with the addition of destabilizing agents such as formamide.

Examples of specific hybridization conditions are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5M sodium phosphate, 7% SDS at 65° C., followed by one or more washes at 0.2×SSC, 1% SDS at 65° C.

In general, high stringency conditions, such as high hybridization temperature and optionally low salt concentrations, permit only hybridization between sequences that are highly similar, whereas low stringency conditions, such as low hybridization temperature and optionally high salt concentrations, allow hybridization when the sequences are less similar.

The invention also provides a nucleic acid construct comprising the polynucleotide sequence of the invention.

The term “nucleic acid construct” refers to as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term “expression cassette” when the nucleic acid construct contains all the control sequences required for expression of a coding sequence, wherein said control sequences are operably linked to said coding sequence.

A nucleic acid of the invention may be an expression vector, wherein a polynucleotide sequence of the invention is operably linked to at least one control sequence for the expression of the polynucleotide sequence in a host cell.

The term “operably linked” as used herein refers to two or more nucleic acid sequence elements that are physically linked and are in a functional relationship with each other. For instance, a promoter is operably linked to a coding sequence if the promoter is able to initiate or regulate the transcription or expression of a coding sequence, in which case the coding sequence should be understood as being “under the control of” the promoter. Generally, when two nucleic acid sequences are operably linked, they will be in the same orientation and usually also in the same reading frame. They usually will be essentially contiguous, although this may not be required.

An expression vector comprises a polynucleotide coding for a polypeptide of the invention, operably linked to the appropriate control sequences (such as a promoter, and transcriptional and translational stop signals) for expression and/or translation in vitro, or in the host cell of the polynucleotide.

The expression vector may be any vector (e.g., a plasmid or virus), which can be conveniently subjected to recombinant DNA procedures and can bring about the expression of the polynucleotide. The choice of the vector will typically depend on the compatibility of the vector with the cell into which the vector is to be introduced. The vectors may be linear or closed circular plasmids. The vector may be an autonomously replicating vector, i.e., a vector, which exists as an extra-chromosomal entity, the replication of which is independent of chromosomal replication, e.g., a plasmid, an extra-chromosomal element, a mini-chromosome, or an artificial chromosome.

Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell. A vector of the invention may comprise one or more selectable markers, which permit easy selection of transformed cells.

The invention also provides a recombinant host which comprises a recombinant nucleic acid sequence encoding a polypeptide of the invention.

That is to say, a recombinant host of the invention may comprise, for example, a recombinant nucleic acid sequence encoding a polypeptide having at least about:

a. 85% identity to the amino acid sequence set forth in SEQ ID NO: 1;
b. 85% identity to the amino acid sequence set forth in SEQ ID NO: 3;
c. 85% identity to the amino acid sequence set forth in SEQ ID NO: 6;
d. 85% identity to the amino acid sequence set forth in SEQ ID NO: 9;
e. 85% identity to the amino acid sequence set forth in SEQ ID NO: 11;
f. 85% identity to the amino acid sequence set forth in SEQ ID NO: 14;
g. 85% identity to the amino acid sequence set forth in SEQ ID NO: 17;
h. 85% identity to the amino acid sequence set forth in SEQ ID NO: 20;
i. 85% identity to the amino acid sequence set forth in SEQ ID NO: 22; or
j. 85% identity to the amino acid sequence set forth in SEQ ID NO: 25.

A recombinant host of the invention may comprise any polynucleotide encoding a polypeptide of the invention as described herein. A recombinant host of the invention is typically capable of expressing a polypeptide of the invention.

Typically, a recombinant host of the invention is capable of producing a glycosylated diterpene, such as a steviol glycoside. For example, a recombinant host of the invention may be capable of producing one or more of, for example, steviol-13-monoside, steviol-19-monoside, 13-[(β-D-Glucopyranosyl)oxy)kaur-16-en-18-oic acid 2-O-β-D-glucopyranosyl-β-D-glucopyranosyl ester, rubusoside, stevioside, steviol-19-diside, steviolbioside, rebA, rebE, rebD or rebM.

A recombinant host according to the invention may comprise one or more recombinant nucleotide sequence(s) encoding one of more of:

a polypeptide having ent-copalyl pyrophosphate synthase activity;

a polypeptide having ent-Kaurene synthase activity;

a polypeptide having ent-Kaurene oxidase activity; and a polypeptide having kaurenoic acid 13-hydroxylase activity.

For the purposes of this invention, a polypeptide having ent-copalyl pyrophosphate synthase (EC 5.5.1.13) is capable of catalyzing the chemical reaction:

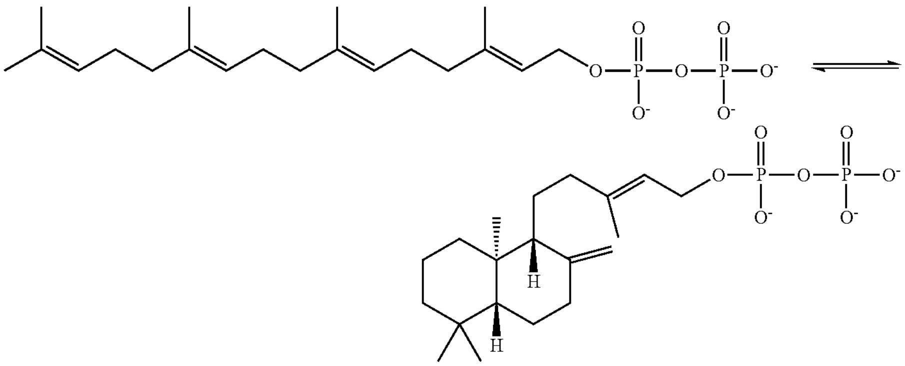

This enzyme has one substrate, geranylgeranyl pyrophosphate, and one product, ent-copalyl pyrophosphate. This enzyme participates in gibberellin biosynthesis. This enzyme belongs to the family of isomerase, specifically the class of intramolecular lyases. The systematic name of this enzyme class is ent-copalyl-diphosphate lyase (decyclizing). Other names in common use include having ent-copalyl pyrophosphate synthase, ent-kaurene synthase A, and ent-kaurene synthetase A.

Suitable nucleic acid sequences encoding an ent-copalyl pyrophosphate synthase may for instance comprise a sequence as set out in SEQ ID. NO: 1, 3, 5, 7, 17, 19, 59, 61, 141, 142, 151, 152, 153, 154, 159, 160, 182 or 184 of WO2015/007748.

For the purposes of this invention, a polypeptide having ent-kaurene synthase activity (EC 4.2.3.19) is a polypeptide that is capable of catalyzing the chemical reaction:

ent-copalyl diphosphate ⇌ ent kaurene+diphosphate

Hence, this enzyme has one substrate, ent-copalyl diphosphate, and two products, ent-kaurene and diphosphate.

This enzyme belongs to the family of lyases, specifically those carbon-oxygen lyases acting on phosphates. The systematic name of this enzyme class is ent-copalyl-diphosphate diphosphate-lyase (cyclizing, ent-kaurene-forming). Other names in common use include ent-kaurene synthase B, ent-kaurene synthetase B, ent-copalyl-diphosphate diphosphate-lyase, and (cyclizing). This enzyme participates in diterpenoid biosynthesis.

Suitable nucleic acid sequences encoding an ent-Kaurene synthase may for instance comprise a sequence as set out in SEQ ID. NO: 9, 11, 13, 15, 17, 19, 63, 65, 143, 144, 155, 156, 157, 158, 159, 160, 183 or 184 of WO2015/007748.

ent-copalyl diphosphate synthases may also have a distinct ent-kaurene synthase activity associated with the same protein molecule. The reaction catalyzed by ent-kaurene synthase is the next step in the biosynthetic pathway to gibberellins. The two types of enzymic activity are distinct, and site-directed mutagenesis to suppress the ent-kaurene synthase activity of the protein leads to build up of ent-copalyl pyrophosphate.

Accordingly, a single nucleotide sequence used in the invention may encode a polypeptide having ent-copalyl pyrophosphate synthase activity and ent-kaurene synthase activity. Alternatively, the two activities may be encoded two distinct, separate nucleotide sequences.

For the purposes of this invention, a polypeptide having ent-kaurene oxidase activity (EC 1.14.13.78) is a polypeptide which is capable of catalysing three successive oxidations of the 4-methyl group of ent-kaurene to give kaurenoic acid. Such activity typically requires the presence of a cytochrome P450.

Suitable nucleic acid sequences encoding an ent-Kaurene oxidase may for instance comprise a sequence as set out in SEQ ID. NO: 21, 23, 25, 67, 85, 145, 161, 162, 163, 180 or 186 of WO2015/007748.

For the purposes of the invention, a polypeptide having kaurenoic acid 13-hydroxylase activity (EC 1.14.13) is one which is capable of catalyzing the formation of steviol (ent-kaur-16-en-13-ol-19-oic acid) using NADPH and $O_2$. Such activity may also be referred to as ent-ka 13-hydroxylase activity.

Suitable nucleic acid sequences encoding a kaurenoic acid 13-hydroxylase may for instance comprise a sequence as set out in SEQ ID. NO: 27, 29, 31, 33, 69, 89, 91, 93, 95, 97, 146, 164, 165, 166, 167 or 185 of WO2015/007748.

A recombinant host of the invention may comprise a recombinant nucleic acid sequence encoding a polypeptide having NADPH-cytochrome p450 reductase activity. That is to say, a recombinant host of the invention may be capable of expressing a nucleotide sequence encoding a polypeptide having NADPH-cytochrome p450 reductase activity. For the purposes of the invention, a polypeptide having NADPH-Cytochrome P450 reductase activity (EC 1.6.2.4; also known as NADPH:ferrihemoprotein oxidoreductase, NADPH:hemoprotein oxidoreductase, NADPH:P450 oxidoreductase, P450 reductase, POR, CPR, CYPOR) is typically one which is a membrane-bound enzyme allowing electron transfer to cytochrome P450 in the microsome of the eukaryotic cell from a FAD- and FMN-containing enzyme NADPH:cytochrome P450 reductase (POR; EC 1.6.2.4).

A recombinant host according to any one of the preceding claims which comprises a one or more recombinant nucleic acid sequences encoding one or more of:

(i) a polypeptide having UGT74G1 activity (UGT3 activity);

(ii) a polypeptide having UGT85C2 activity (UGT1 activity); and (iii) a polypeptide having UGT76G1 activity (UGT4 activity).

FIGS. 31 and 32 set out schematic diagram of the potential pathways leading to biosynthesis of steviol glycosides.

A recombinant host of the invention will typically comprise at least one recombinant nucleic acid encoding a polypeptide having UGT1 activity, at least one recombinant nucleic acid encoding a polypeptide having UGT2 activity, at least one recombinant nucleic acid encoding a polypeptide having UGT3 activity and at least one recombinant nucleic acid encoding a polypeptide having UGT4 activity. One nucleic acid may encode two or more of such polypeptides.

A nucleic acid encoding a polypeptide of the invention may be used to steer production of steviol glycosides in a recombinant cell to a desired steviol glycoside, such as rebaudioside A, rebaudioside D or rebaudioside M. For example, a recombinant nucleic acid which encodes a UGT2 polypeptide which preferentially catalyzes conversion of steviol-13-monoside to steviolbioside and/or conversion of rubusoside to stevioside may help to steer production towards rebaudiosideA, whereas a recombinant nucleic acid which encodes a UGT2 polypeptide which preferentially catalyzes conversion of stevioside to rebE or rubusoside to a compound with an additional sugar at the 19 position may help to steer production towards rebaudioside M. That is to say preference for addition of a sugar moiety at the 13 position may help steer production towards rebaudioside A, whereas preference for addition of a sugar moiety at the 19 position may help steer production towards rebaudioside M.

A recombinant host of the invention may comprises a nucleotide sequence encoding a polypeptide capable of catalyzing the addition of a C-13-glucose to steviol. That is to say, a recombinant host of the invention may comprise a UGT which is capable of catalyzing a reaction in which steviol is converted to steviolmonoside.

Such a recombinant host of the invention may comprise a nucleotide sequence encoding a polypeptide having the activity shown by UDP-glycosyltransferase (UGT) UGT85C2, whereby the nucleotide sequence upon transformation of the host confers on that host the ability to convert steviol to steviolmonoside.

UGT85C2 activity is transfer of a glucose unit to the 13-OH of steviol. Thus, a suitable UGT85C2 may function as a uridine 5'-diphospho glucosyl: steviol 13-OH transferase, and a uridine 5'-diphospho glucosyl: steviol-19-O-glucoside 13-OH transferase. A functional UGT85C2 polypeptides may also catalyze glucosyl transferase reactions that utilize steviol glycoside substrates other than steviol and steviol-19-O-glucoside. Such sequences may be referred to as UGT1 sequences herein.

A recombinant host of the invention may comprise a nucleotide sequence encoding a polypeptide having UGT activity may comprise a nucleotide sequence encoding a polypeptide capable of catalyzing the addition of a C-13-glucose to steviol or steviolmonoside. That is to say, a recombinant of the invention may comprise a UGT which is capable of catalyzing a reaction in which steviolmonoside is converted to steviolbioside. Accordingly, such a recombinant host may be capable of converting steviolmonoside to steviolbioside. Expression of such a nucleotide sequence may confer on the host the ability to produce at least steviolbioside.

A recombinant microorganism of the invention also comprises a nucleotide sequence encoding a polypeptide having UGT activity may comprise a nucleotide sequence encoding a polypeptide capable of catalyzing the addition of a C-19-glucose to steviolbioside. That is to say, a microorganism of the invention may comprise a UGT which is capable of catalyzing a reaction in which steviolbioside is converted to stevioside. Accordingly, such a microorganism may be capable of converting steviolbioside to stevioside. Expression of such a nucleotide sequence may confer on the microorganism the ability to produce at least stevioside.

A microorganism of the invention may thus also comprise a nucleotide sequence encoding a polypeptide having the activity shown by UDP-glycosyltransferase (UGT) UGT74G1, whereby the nucleotide sequence upon transformation of the microorganism confers on the cell the ability to convert steviolbioside to stevioside.

Suitable UGT74G1 polypeptides may be capable of transferring a glucose unit to the 13-OH or the 19-COOH, respectively, of steviol. A suitable UGT74G1 polypeptide may function as a uridine 5'-diphospho glucosyl: steviol 19-COOH transferase and a uridine 5'-diphospho glucosyl: steviol-13-O-glucoside 19-COOH transferase. Functional UGT74G1 polypeptides also may catalyze glycosyl transferase reactions that utilize steviol glycoside substrates other than steviol and steviol-13-O-glucoside, or that transfer sugar moieties from donors other than uridine diphosphate glucose. Such sequences may be referred to herein as UGT3 sequences.

A recombinant host of the invention may comprise a nucleotide sequence encoding a polypeptide capable of catalyzing glucosylation of the C-3' of the glucose at the C-13 position of stevioside. That is to say, a recombinant host of the invention may comprise a UGT which is capable of catalyzing a reaction in which stevioside to rebaudioside A. Accordingly, such a recombinant host may be capable of converting stevioside to rebaudioside A. Expression of such a nucleotide sequence may confer on the host the ability to produce at least rebaudioside A.

A recombinant microorganism of the invention may thus also comprise a nucleotide sequence encoding a polypeptide having the activity shown by UDP-glycosyltransferase (UGT) UGT76G1, whereby the nucleotide sequence upon transformation of the microorganism confers on the cell the ability to convert stevioside to rebaudioside A.

A suitable UGT76G1 adds a glucose moiety to the C-3' of the C-13-O-glucose of the acceptor molecule, a steviol 1,2 glycoside. Thus, UGT76G1 functions, for example, as a uridine 5'-diphospho glucosyl: steviol 13-O-1,2 glucoside C-3' glucosyl transferase and a uridine 5'-diphospho glucosyl: steviol-19-O-glucose, 13-O-1,2 bioside C-3' glucosyl transferase. Functional UGT76G1 polypeptides may also catalyze glucosyl transferase reactions that utilize steviol glycoside substrates that contain sugars other than glucose, e.g., steviol rhamnosides and steviol xylosides. Such sequences may be referred to herein as UGT4 sequences.

A recombinant host of the invention typically comprises nucleotide sequences encoding polypeptides having all four UGT activities described above. A given nucleic acid may encode a polypeptide having one or more of the above activities. For example, a nucleic acid encode for a polypeptide which has two, three or four of the activities set out above. Preferably, a recombinant host of the invention comprises UGT1, UGT2 and UGT3 and UGT4 activity. Suitable UGT1, UGT3 and UGT4 sequences are described in in Table 1 of WO2015/007748.

A recombinant host of the invention may comprise a recombinant nucleic acid sequence encoding an additional polypeptide having UGT2 activity. That is to say, a recombinant host of the invention may comprise a nucleic acid sequence encoding a variant UGT2 of the invention and one or more additional, different, variant of the invention or any another, different, UGT2.

Use of a nucleic acid sequence encoding a UGT2_1 b, UGT2_2 b, UGT2_3 b, UGT2_4 b, UGT2_5 b, UGT2_6 b, UGT2_7 b, UGT2_8 b, UGT2_9 b or UGT2_10 b polypeptide (or related polypeptide as described herein) may be useful in improving rebA production.

Use of a nucleic acid sequence encoding a UGT2_7 b polypeptide (or related polypeptide as described herein) may be useful in improving rebM production.

In a recombinant host of the invention, the ability of the host to produce geranylgeranyl diphosphate (GGPP) may be upregulated. Upregulated in the context of this invention implies that the recombinant host produces more GGPP than an equivalent non-recombinant host.

Accordingly, a recombinant host of the invention may comprise one or more nucleotide sequence(s) encoding hydroxymethylglutaryl-CoA reductase, farnesyl-pyrophosphate synthetase and geranylgeranyl diphosphate synthase, whereby the nucleotide sequence(s) upon transformation of the microorganism confer(s) on the microorganism the ability to produce elevated levels of GGPP. Thus, a recombinant host according to the invention may comprise one or more recombinant nucleic acid sequence(s) encoding one or more of hydroxymethylglutaryl-CoA reductase, farnesyl-pyrophosphate synthetase and geranylgeranyl diphosphate synthase.

Accordingly, a recombinant host of the invention may comprise nucleic acid sequences encoding one or more of:

a polypeptide having hydroxymethylglutaryl-CoA reductase activity;

a polypeptide having farnesyl-pyrophosphate synthetase activity;

a polypeptide having geranylgeranyl diphosphate synthase activity.

A host or host cell as defined herein is an organism suitable for genetic manipulation and one which may be cultured at cell densities useful for industrial production of a target product. A suitable host may be a microorganism, for example one which may be maintained in a fermentation device. A host cell may be a host cell found in nature or a host cell derived from a parent host cell after genetic manipulation or classical mutagenesis.

As used herein, a recombinant host is one which is genetically modified or transformed/transfected with one or more of the nucleotide sequences as defined herein. The presence of the one or more such nucleotide sequences alters the ability of the microorganism to produce diterpene glycosides, in particular one or more steviol glycosides. A non-recombinant host, i.e. one that is not transformed/transfected or genetically modified, typically does not comprise one or more of the nucleotide sequences enabling the cell to produce a diterpene glycoside. Hence, a non-recombinant host is typically a host that does not naturally produce a diterpene glycoside, although a host which naturally produces a diterpene or diterpene glycoside and which has been modified according to the invention (and which thus has an altered ability to produce a diterpene glycoside) is considered a recombinant host according to the invention.

In particular, it may be possible that the enzymes selected from the group consisting of ent-copalyl pyrophosphate synthase, ent-Kaurene synthase, ent-Kaurene oxidase, and kaurenoic acid 13-hydroxylase, UGTs, hydroxymethylglutaryl-CoA reductase, farnesyl-pyrophosphate synthetase, geranylgeranyl diphosphate synthase and NADPH-cytochrome p450 reductase are native to the host and that transformation with one or more of the nucleotide sequences encoding these enzymes may not be required to confer the host cell the ability to produce a diterpene glycoside. A preferred host according to the present invention may be a recombinant host which is naturally capable of producing GGPP (i.e. in its non-recombinant form).

Further improvement of diterpene glycoside production by the host microorganism may be obtained by classical strain improvement.

A host cell may be a prokaryotic, archaebacterial or eukaryotic host cell.

A prokaryotic host cell may, but is not limited to, a bacterial host cell. An eukaryotic host cell may be, but is not limited to, a yeast, a fungus, an amoeba, an algae, an animal, an insect host cell.

An eukaryotic host cell may be a fungal host cell. “Fungi” include all species of the subdivision Eumycotina (Alexopoulos, C. J., 1962, In: Introductory Mycology, John Wiley & Sons, Inc., New York). The term fungus thus includes among others filamentous fungi and yeast.

“Filamentous fungi” are herein defined as eukaryotic microorganisms that include all filamentous forms of the subdivision Eumycotina and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocallimastix, Neurospora, Paecilomyces, Penicillium, Piromyces, Phanerochaete* Podospora, Pycnoporus, *Rhizopus, Schizophyllum, Sordaria, Talaromyces, Rasmsonia, Thermoascus, Thielavia, Tolypocladium, Trametes* and *Trichoderma*. Preferred filamentous fungal strains that may serve as host cells belong to the species *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora* thermophyla. Reference host cells for the comparison of fermentation characteristics of transformed and untransformed cells, include e.g. *Aspergillus niger* CBS120.49, CBS 513.88, *Aspergillus oryzae* ATCC16868, ATCC 20423, IFO 4177, ATCC 1011, ATCC 9576, ATCC14488-14491, ATCC 11601, ATCC12892, *Aspergillus fumigatus* AF293 (CBS101355), *P. chrysogenum* CBS 455.95, *Penicillium citrinum* ATCC 38065, *Penicillium chrysogenum* P2, *Acremonium chrysogenum* ATCC 36225, ATCC 48272, *Trichoderma reesei* ATCC 26921, ATCC 56765, ATCC 26921, *Aspergillus sojae* ATCC11906, *Chrysosporium lucknowense* ATCC44006 and derivatives of all of these strains. Particularly preferred as filamentous fungal host cell are *Aspergillus niger* CBS 513.88 and derivatives thereof.

An eukaryotic host cell may be a yeast cell. Preferred yeast host cells may be selected from the genera: *Saccharomyces* (e.g., *S. cerevisiae, S. bayanus, S. pastorianus, S. carlsbergensis*), Brettanomyces, *Kluyveromyces, Candida* (e.g., *C. krusei, C. revkaufi, C. pulcherrima, C. tropicalis, C. utilis*), *Issatchenkia* (eg. *I. orientalis*) *Pichia* (e.g., *P. pastoris*), *Schizosaccharomyces, Hansenula, Kloeckera, Pachysolen, Schwanniomyces, Trichosporon, Yarrowia* (e.g., *Y. lipolytica* (formerly classified as *Candida lipolytica*)), Yamadazyma.

Prokaryotic host cells may be bacterial host cells. Bacterial host cell may be Gram negative or Gram positive bacteria. Examples of bacteria include, but are not limited to, bacteria belonging to the genus *Bacillus* (e.g., *B. subtilis, B. amyloliquefaciens, B. licheniformis, B. puntis, B. megaterium, B. halodurans, B. pumilus*), *Acinetobacter, Nocardia, Xanthobacter, Escherichia* (e.g., *E. coli* (e.g., strains DH 1 OB, StbI2, DH5-alpha, DB3, DB3.1), DB4, DB5, JDP682 and ccdA-over (e.g., U.S. application Ser. No. 09/518, 188))), *Streptomyces, Erwinia, Klebsiella, Serratia* (e.g., S. marcessans), *Pseudomonas* (e.g., *P. aeruginosa*), *Salmonella* (e.g., *S. typhimurium, S. typhi*). Bacteria also include, but are not limited to, photosynthetic bacteria (e.g., green non-sulfur bacteria (e.g., *Choroflexus* bacteria (e.g., *C. aurantiacus*), *Chloronema* (e.g., *C. gigateum*)), green sulfur bacteria (e.g., *Chlorobium* bacteria (e.g., *C. limicola*), *Pelodictyon* (e.g., *P. luteolum*), purple sulfur bacteria (e.g., *Chromatium* (e.g., *C. okenii*)), and purple non-sulfur bacteria (e.g., *Rhodospirillum* (e.g., *R. rubrum*), *Rhodobacter* (e.g. *R. sphaeroides, R. capsulatus*), and *Rhodomicrobium* bacteria (e.g., *R. vanellii*)).

Host cells may be host cells from non-microbial organisms. Examples of such cells, include, but are not limited to, insect cells (e.g., *Drosophila* (e.g., *D. melanogaster*), *Spodoptera* (e.g., *S. frugiperda* Sf9 or Sf21 cells) and Trichoplusa (e.g., High-Five cells); nematode cells (e.g., *C. elegans* cells); avian cells; amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells).

The invention further provides a method for producing a polypeptide of the invention comprising:

(a) cultivating a recombinant host cell of the invention under conditions conducive to the production of the polypeptide by the host cell, and optionally, (b) recovering the polypeptide.

A recombinant host according to the present invention may be able to grow on any suitable carbon source known in the art and convert it to a glycosylated diterpene, e.g. a steviol glycoside. The recombinant host may be able to convert directly plant biomass, celluloses, hemicelluloses, pectines, rhamnose, galactose, fucose, maltose, maltodextrines, ribose, ribulose, or starch, starch derivatives, sucrose, lactose and glycerol. Hence, a preferred host expresses enzymes such as cellulases (endocellulases and exocellulases) and hemicellulases (e.g. endo- and exo-xylanases, arabinases) necessary for the conversion of cellulose into glucose monomers and hemicellulose into xylose and arabinose monomers, pectinases able to convert pectines into glucuronic acid and galacturonic acid or amylases to convert starch into glucose monomers. Preferably, the host is able to convert a carbon source selected from the group consisting of glucose, xylose, arabinose, sucrose, lactose and glycerol. The host cell may for instance be a eukaryotic host cell as described in WO03/062430, WO06/009434, EP1499708B1, WO2006096130 or WO04/099381.

Thus, in a further aspect, the invention also provides a process for the preparation of a glycosylated diterpene, such as a steviol glycoside, which comprises fermenting a recombinant host of the invention which is capable of producing at least one glycosylated diterpene in a suitable fermentation medium, and optionally recovering the glycosylated diterpene.

The glycosylated terpene, for example a steviol glycoside, may be stevio-19-monoside, steviol-19-diside, steviol-19-3side, steviol-13-monoside, rubusoside, 13-[(δ-D-Glucopyranosyl)oxy)kaur-16-en-18-oic acid 2-O-β-D-glucopyranosyl-β-D-glucopyranosyl ester, steviolbioside, stevioside, rebaudioside E, rebaudioside B, rebaudioside A, rebaudioside D or rebaudioside M. Thus, the invention provides a process for the production of one or more such steviol glycosides.

The fermentation medium used in the process for the production of a glycosylated diterpene may be any suitable fermentation medium which allows growth of a particular eukaryotic host cell. The essential elements of the fermentation medium are known to the person skilled in the art and may be adapted to the host cell selected.

Preferably, the fermentation medium comprises a carbon source selected from the group consisting of plant biomass, celluloses, hemicelluloses, pectines, rhamnose, galactose, fucose, fructose, maltose, maltodextrines, ribose, ribulose, or starch, starch derivatives, sucrose, lactose, fatty acids, triglycerides and glycerol. Preferably, the fermentation medium also comprises a nitrogen source such as urea, or an ammonium salt such as ammonium sulphate, ammonium chloride, ammonium nitrate or ammonium phosphate.

The fermentation process according to the present invention may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. A SSF process may be particularly attractive if starch, cellulose, hemicelluose or pectin is used as a carbon source in the fermentation process, where it may be necessary to add hydrolytic enzymes, such as cellulases, hemicellulases or pectinases to hydrolyse the substrate.

The recombinant host used in the process for the preparation of a glycosylated diterpene may be any suitable recombinant host as defined herein above. It may be advantageous to use a recombinant eukaryotic recombinant host according to the invention in the process since most eukaryotic cells do not require sterile conditions for propagation and are insensitive to bacteriophage infections. In addition, eukaryotic host cells may be grown at low pH to prevent bacterial contamination.

The recombinant host according to the present invention may be a facultative anaerobic microorganism. A facultative anaerobic recombinant host can be propagated aerobically to a high cell concentration. This anaerobic phase can then be carried out at high cell density which reduces the fermentation volume required substantially, and may minimize the risk of contamination with aerobic microorganisms.

The fermentation process for the production of a glycosylated diterpene according to the present invention may be an aerobic or an anaerobic fermentation process.

An anaerobic fermentation process may be herein defined as a fermentation process run in the absence of oxygen or in which substantially no oxygen is consumed, preferably less than 5, 2.5 or 1 mmol/L/h, and wherein organic molecules serve as both electron donor and electron acceptors. The fermentation process according to the present invention may also first be run under aerobic conditions and subsequently under anaerobic conditions.

The fermentation process may also be run under oxygen-limited, or micro-aerobical, conditions. Alternatively, the fermentation process may first be run under aerobic conditions and subsequently under oxygen-limited conditions. An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used.

The production of a glycosylated diterpene in the process according to the present invention may occur during the growth phase of the host cell, during the stationary (steady state) phase or during both phases. It may be possible to run the fermentation process at different temperatures.

The process for the production of a glycosylated diterpene may be run at a temperature which is optimal for the recombinant host. The optimum growth temperature may differ for each transformed recombinant host and is known to the person skilled in the art. The optimum temperature might be higher than optimal for wild type organisms to grow the organism efficiently under non-sterile conditions under minimal infection sensitivity and lowest cooling cost. Alternatively, the process may be carried out at a temperature which is not optimal for growth of the recombinant host.

The process for the production of a glycosylated diterpene according to the present invention may be carried out at any suitable pH value. If the recombinant host is a yeast, the pH in the fermentation medium preferably has a value of below 6, preferably below 5,5, preferably below 5, preferably below 4,5, preferably below 4, preferably below pH 3,5 or below pH 3,0, or below pH 2,5, preferably above pH 2. An advantage of carrying out the fermentation at these low pH values is that growth of contaminant bacteria in the fermentation medium may be prevented.

Such a process may be carried out on an industrial scale. The product of such a process is one or more glycosylated diterpenes, such as one or more steviol glycosides, for example one or more of 13-[(β-D-Glucopyranosyl)oxy)kaur-16-en-18-oic acid 2-O-β-D-glucopyranosyl-β-D-glucopyranosyl ester, steviolbioside, stevioside, rebaudioside E, rebaudioside B, rebaudioside A, rebaudioside D or rebaudioside M.

Recovery of glycosylated diterpene(s) from the fermentation medium may be performed by known methods in the art, for instance by distillation, vacuum extraction, solvent extraction, or evaporation.

In the process for the production of a glycosylated diterpene according to the invention, it may be possible to achieve a concentration of above 5 mg/l fermentation broth, preferably above 10 mg/l, preferably above 20 mg/l, preferably above 30 mg/l fermentation broth, preferably above 40 mg/l, more preferably above 50 mg/l, preferably above 60 mg/l, preferably above 70, preferably above 80 mg/l, preferably above 100 mg/l, preferably above 1 g/l, preferably above 5 g/l, preferably above 10 g/l, for example above 20 g/l, but usually up to a concentration of about 200 g/l, such as up to about 150 g/l, such as up to about 100 g/l, for example up to about 70 g/l. Such concentrations may be concentration of the total broth or of the supernatant.

The invention further provides a fermentation broth comprising a glycosylated diterpene obtainable by the process of the invention for the preparation of a glycosylated diterpene.

In the event that one or more glycosylated diterpenes is expressed within the microorganism, such cells may need to be treated so as to release them. Preferentially, at least one glycosylated diterpene, such as a steviol glycoside, for example rebA or rebM, is produced extracellularly.

The invention also provides a glycosylated diterpene obtained by a process according to the invention for the preparation of a glycosylated diterpene or obtainable from a fermentation broth of the invention. Such a glycosylated diterpene may be a non-naturally occurring glycosylated diterpene, that is to say one which is not produced in plants.

Also provided is a composition comprising two or more glycosylated diterpenes obtainable by a process of the invention for the preparation of a glycosylated diterpene or obtainable from a fermentation broth of the invention. In such a composition, one or more of the glycosylated diterpenes may be a non-naturally occurring glycosylated diterpene, that is to say one which is not produced in plants.

Furthermore, the invention provides a method for converting a first glycosylated diterpene into a second glycosylated diterpene, which method comprises:

contacting said first glycosylated diterpene with a recombinant host of the invention, a cell free extract derived from such a recombinant host or an enzyme preparation derived from either thereof;

thereby to convert the first glycosylated diterpene into the second glycosylated diterpene.

In such a method, the second glycosylated diterpene may be steviol-19-diside, steviolbioside, stevioside, RebE, RebD or 13-[(β-D-Glucopyranosyl)oxy)kaur-16-en-18-oic acid 2-O-β-D-glucopyranosyl-β-D-glucopyranosyl ester.

In such a method, the first glycosylated diterpene may be steviol-13-monoside, steviol-19-monoside, rubusoside, stevioside, rebaudioside A or 13-[(β-D-Glucopyranosyl)oxy)kaur-16-en-18-oic acid 2-O-β-D-glucopyranosyl-β-D-glucopyranosyl ester and the second glycosylated diterpene is steviol-19-diside, steviolbioside, stevioside, RebE, RebD or 13-[(β-D-Glucopyranosyl)oxy)kaur-16-en-18-oic acid 2-O-β-D-glucopyranosyl-β-D-glucopyranosyl ester.

These are the first and second steviol glycosides in relation to a reaction catalysed by a polypeptide of the invention having UGT2 activity.

That is to say, the invention relates to a method of bioconversion or biotransformation.

A steviol glycoside or composition produced by the fermentation process according to the present invention may be used in any application known for such compounds. In particular, they may for instance be used as a sweetener, for example in a food or a beverage. According to the invention therefore, there is provided a foodstuff, feed or beverage which comprises a glycosylated diterpene such as a steviol glycoside or a composition of the invention.

For example a glycosylated diterpene or a composition of the invention may be formulated in soft drinks, as a tabletop sweetener, chewing gum, dairy product such as yoghurt (eg. plain yoghurt), cake, cereal or cereal-based food, nutraceutical, pharmaceutical, edible gel, confectionery product, cosmetic, toothpastes or other oral cavity composition, etc. In addition, a glycosylated diterpene or a composition of the invention can be used as a sweetener not only for drinks, foodstuffs, and other products dedicated for human consumption, but also in animal feed and fodder with improved characteristics.

Accordingly, the invention provides, inter alia, a foodstuff, feed or beverage which comprises a diterpene or glycosylated prepared according to a process of the invention.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

The glycosylated diterpene, for example a steviol glycoside, or a composition of the invention can be used in dry or liquid forms. It can be added before or after heat treatment of food products. The amount of the sweetener depends on the purpose of usage. It can be added alone or in the combination with other compounds.

Compounds produced according to the method of the invention may be blended with one or more further non-calorific or calorific sweeteners. Such blending may be used to improve flavour or temporal profile or stability. A wide range of both non-calorific and calorific sweeteners may be suitable for blending with a glycosylated diterpene or a composition of the invention. For example, non-calorific sweeteners such as mogroside, monatin, aspartame, acesulfame salts, cyclamate, sucralose, saccharin salts or erythritol. Calorific sweeteners suitable for blending with a glycosylated diterpene or a composition of the invention include sugar alcohols and carbohydrates such as sucrose, glucose, fructose and HFCS. Sweet tasting amino acids such as glycine, alanine or serine may also be used.

A glycosylated diterpene or a composition of the invention can be used in the combination with a sweetener suppressor, such as a natural sweetener suppressor. It may be combined with an umami taste enhancer, such as an amino acid or a salt thereof.

A glycosylated diterpene or a composition of the invention can be combined with a polyol or sugar alcohol, a carbohydrate, a physiologically active substance or functional ingredient (for example a carotenoid, dietary fiber, fatty acid, saponin, antioxidant, nutraceutical, flavonoid, isothiocyanate, phenol, plant sterol or stanol (phytosterols and phytostanols), a polyols, a prebiotic, a probiotic, a phytoestrogen, soy protein, sulfides/thiols, amino acids, a protein, a vitamin, a mineral, and/or a substance classified based on a health benefits, such as cardiovascular, cholesterol-reducing or anti-inflammatory.

A composition with a glycosylated diterpene or a composition of the invention may include a flavoring agent, an aroma component, a nucleotide, an organic acid, an organic acid salt, an inorganic acid, a bitter compound, a protein or protein hydrolyzate, a surfactant, a flavonoid, an astringent compound, a vitamin, a dietary fiber, an antioxidant, a fatty acid and/or a salt.

A glycosylated diterpene or a composition of the invention may be applied as a high intensity sweetener to produce zero calorie, reduced calorie or diabetic beverages and food products with improved taste characteristics. Also it can be used in drinks, foodstuffs, pharmaceuticals, and other products in which sugar cannot be used.

In addition, a glycosylated diterpene or a composition of the invention may be used as a sweetener not only for drinks, foodstuffs, and other products dedicated for human consumption, but also in animal feed and fodder with improved characteristics.

The examples of products where a glycosylated diterpene or a composition of the invention can be used as a sweetening compound can be as alcoholic beverages such as vodka, wine, beer, liquor, sake, etc; natural juices, refreshing drinks, carbonated soft drinks, diet drinks, zero calorie drinks, reduced calorie drinks and foods, yogurt drinks, instant juices, instant coffee, powdered types of instant beverages, canned products, syrups, fermented soybean paste, soy sauce, vinegar, dressings, mayonnaise, ketchups, curry, soup, instant bouillon, powdered soy sauce, powdered vinegar, types of biscuits, rice biscuit, crackers, bread, chocolates, caramel, candy, chewing gum, jelly, pudding, preserved fruits and vegetables, fresh cream, jam, marmalade, flower paste, powdered milk, ice cream, sorbet, vegetables and fruits packed in bottles, canned and boiled beans, meat and foods boiled in sweetened sauce, agricultural vegetable food products, seafood, ham, sausage, fish ham, fish sausage, fish paste, deep fried fish products, dried seafood products, frozen food products, preserved seaweed, preserved meat, tobacco, medicinal products, and many others. In principal it can have unlimited applications.

The sweetened composition comprises a beverage, non-limiting examples of which include non-carbonated and carbonated beverages such as colas, ginger ales, root beers, ciders, fruit-flavored soft drinks (e.g., citrus-flavored soft drinks such as lemon-lime or orange), powdered soft drinks, and the like; fruit juices originating in fruits or vegetables, fruit juices including squeezed juices or the like, fruit juices containing fruit particles, fruit beverages, fruit juice beverages, beverages containing fruit juices, beverages with fruit flavorings, vegetable juices, juices containing vegetables, and mixed juices containing fruits and vegetables; sport drinks, energy drinks, near water and the like drinks (e.g., water with natural or synthetic flavorants); tea type or favorite type beverages such as coffee, cocoa, black tea, green tea, oolong tea and the like; beverages containing milk components such as milk beverages, coffee containing milk components, cafe au lait, milk tea, fruit milk beverages, drinkable yogurt, lactic acid bacteria beverages or the like; and dairy products.

Generally, the amount of sweetener present in a sweetened composition varies widely depending on the particular type of sweetened composition and its desired sweetness. Those of ordinary skill in the art can readily discern the appropriate amount of sweetener to put in the sweetened composition.

A glycosylated diterpene or a composition of the invention can be used in dry or liquid forms. It can be added before or after heat treatment of food products. The amount of the sweetener depends on the purpose of usage. It can be added alone or in the combination with other compounds.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

Thus, compositions of the present invention can be made by any method known to those skilled in the art that provide homogenous even or homogeneous mixtures of the ingredients. These methods include dry blending, spray drying, agglomeration, wet granulation, compaction, co-crystallization and the like.

In solid form a glycosylated diterpene or a composition of the invention can be provided to consumers in any form suitable for delivery into the comestible to be sweetened, including sachets, packets, bulk bags or boxes, cubes, tablets, mists, or dissolvable strips. The composition can be delivered as a unit dose or in bulk form.

For liquid sweetener systems and compositions convenient ranges of fluid, semi-fluid, paste and cream forms, appropriate packing using appropriate packing material in any shape or form shall be invented which is convenient to carry or dispense or store or transport any combination containing any of the above sweetener products or combination of product produced above.

The composition may include various bulking agents, functional ingredients, colorants, flavors.

The terms “sequence homology” or “sequence identity” are used interchangeably herein. For the purpose of this invention, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at ncbi.nlm.nih.gov.

Embodiments of the Invention

1. A recombinant host comprising a recombinant nucleic acid sequence encoding a polypeptide having at least about:
   a. 85% identity to the amino acid sequence set forth in SEQ ID NO: 1;
   b. 85% identity to the amino acid sequence set forth in SEQ ID NO: 3;
   c. 85% identity to the amino acid sequence set forth in SEQ ID NO: 6;
   d. 85% identity to the amino acid sequence set forth in SEQ ID NO: 9;
   e. 85% identity to the amino acid sequence set forth in SEQ ID NO: 11;
   f. 85% identity to the amino acid sequence set forth in SEQ ID NO: 14;
   g. 85% identity to the amino acid sequence set forth in SEQ ID NO: 17;
   h. 85% identity to the amino acid sequence set forth in SEQ ID NO: 20;
   i. 85% identity to the amino acid sequence set forth in SEQ ID NO: 22; or
   j. 85% identity to the amino acid sequence set forth in SEQ ID NO: 25.
2. A recombinant host according to embodiment 1 which is capable of producing a glycosylated diterpene, such as a steviol glycoside.
3. A recombinant host according to embodiment 1 or 2 which comprises one or more recombinant nucleotide sequence(s) encoding:
   a polypeptide having ent-copalyl pyrophosphate synthase activity;
   a polypeptide having ent-Kaurene synthase activity;
   a polypeptide having ent-Kaurene oxidase activity; and
   a polypeptide having kaurenoic acid 13-hydroxylase activity.
4. A recombinant host according to any one of the preceding embodiments, which comprises a recombinant nucleic acid sequence encoding a polypeptide having NADPH-cytochrome p450 reductase activity.
5. A recombinant host according to any one of the preceding embodiments which comprises a recombinant nucleic acid sequence encoding one or more of:
   (i) a polypeptide having UGT74G1 (UGT3) activity;
   (ii) a polypeptide having UGT85C2 (UGT1) activity; and
   (iii) a polypeptide having UGT76G1 (UGT4) activity.
6. A recombinant host according to any one of the preceding embodiments which comprises a recombinant nucleic acid sequence encoding an additional polypeptide having UGT2 activity.
7. A recombinant host according to any one of the preceding embodiments, wherein the host belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia, Yamadazyma* or *Escherichia.*
8. A recombinant host according to embodiment 7, wherein the recombinant host is a *Saccharomyces cerevisiae* cell, a *Yarrowia lipolitica* cell, a *Candida krusei* cell, an *Issatchenkia orientalis* or an *Escherichia coli* cell.
9. A recombinant host according to any one of the preceding embodiments, wherein the ability of the host to produce geranylgeranyl diphosphate (GGPP) is upregulated.
10. A recombinant host according to any one of the preceding embodiments, comprising one or more recombinant nucleic acid sequence(s) encoding hydroxymethylglutaryl-CoA reductase, farnesyl-pyrophosphate synthetase and geranylgeranyl diphosphate synthase.

11. A recombinant host according to any one of the preceding embodiments which comprises a nucleic acid sequence encoding one or more of:
a polypeptide having hydroxymethylglutaryl-CoA reductase activity;
a polypeptide having farnesyl-pyrophosphate synthetase activity;
a polypeptide having geranylgeranyl diphosphate synthase activity.

12. A process for the preparation of a glycosylated diterpene which comprises fermenting a recombinant host according to any one of embodiments 2 to 11 in a suitable fermentation medium, and optionally recovering the glycosylated diterpene.

13. A process according to any one of embodiment 12 for the preparation of a glycosylated diterpene, wherein the process is carried out on an industrial scale.

14. A fermentation broth comprising a glycosylated diterpene obtainable by the process according to embodiment 12 or 13.

15. A glycosylated diterpene obtained by a process according to embodiment 12 or 13 or obtainable from a fermentation broth according to embodiment 14.

16. A composition comprising two or more glycosylated diterpenes obtained by a process according to embodiment 12 or 13 or obtainable from a fermentation broth according to embodiment 14.

17. A foodstuff, feed or beverage which comprises a glycosylated diterpene according to embodiment 15 or a composition according to embodiment 16.

18. A method for converting a first glycosylated diterpene into a second glycosylated diterpene, which method comprises:
contacting said first glycosylated diterpene with a recombinant host according to any one of embodiments 1 to 11, a cell free extract derived from such a recombinant host or an enzyme preparation derived from either thereof;
thereby to convert the first glycosylated diterpene into the second glycosylated diterpene.

19. A method according to embodiment 18, wherein the second glycosylated diterpene is steviol-19-diside, steviolbioside, stevioside, RebE, RebD or 13-[(β-D-Glucopyranosyl)oxy)kaur-16-en-18-oic acid 2-O-β-D-glucopyranosyl-β-D-glucopyranosyl ester.

20. A method according to claim 19, wherein the first glycosylated diterpene is steviol-13-monoside, steviol-19-monoside, rubusoside, stevioside, rebaudioside A or 13-[(β-D-Glucopyranosyl)oxy)kaur-16-en-18-oic acid 2-O-β-D-glucopyranosyl-β-D-glucopyranosyl ester and the second glycosylated diterpene is steviol-19-diside, steviolbioside, stevioside, RebE, RebD or 13-[(β-D-Glucopyranosyl)oxy)kaur-16-en-18-oic acid 2-O-β-D-glucopyranosyl-β-D-glucopyranosyl ester.

21. A polypeptide having UGT2 activity, wherein said polypeptide is selected from the group consisting of:
(a) a polypeptide comprising an amino acid sequence as set out in any one of SEQ ID NOs: 1, 3, 6, 9, 11, 14, 17, 20, 22 or 25; or
(b) a polypeptide comprising an amino acid sequence having at least about 85% sequence identity with the amino acid sequence of any one of SEQ ID NOs: 1, 3, 6, 9, 11, 14, 17, 20, 22 or 25; or
(c) a polypeptide encoded by a polynucleotide comprising the polynucleotide sequence as set out in any one SEQ ID NOs: 2, 4, 5, 7, 8, 10, 12, 13, 15, 16, 18, 19, 21, 23, 24 or 26; or
(d) a polypeptide encoded by a polynucleotide comprising a polynucleotide sequence having at least 30% sequence identity to the polypeptide coding sequence in any one SEQ ID NOs: 2, 4, 5, 7, 8, 10, 12, 13, 15, 16, 18, 19, 21, 23, 24 or 26; or
(e) a polypeptide encoded by a polynucleotide which hybridises, preferably under at least low stringency conditions, with the complementary strand of any one SEQ ID NOs: 2, 4, 5, 7, 8, 10, 12, 13, 15, 16, 18, 19, 21, 23, 24 or 26; or
(f) a polypeptide encoded by a polynucleotide which hybridises, preferably under at least low stringency conditions, with the complementary strand of a polynucleotide having at least 30% sequence identity to any one SEQ ID NOs: 2, 4, 5, 7, 8, 10, 12, 13, 15, 16, 18, 19, 21, 23, 24 or 26; or
(g) a fragment of a polypeptide as defined in (a), (b), (c), (d), (e) or (f).

22. A polypeptide according to embodiment 21, comprising a polypeptide having an amino acid sequence having at least about 86% sequence identity, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity to any one of SEQ ID NOs: 1, 3, 6, 9, 11, 14, 17, 20, 22 or 25.

23. A polynucleotide sequence coding for a polypeptide according to embodiment 21 or 22.

24. A polynucleotide sequence according to embodiment 23, wherein the polynucleotide sequence is selected from the group consisting of:
(a) a polynucleotide sequence comprising any one of SEQ ID NOs: 2, 4, 5, 7, 8, 10, 12, 13, 15, 16, 18, 19, 21, 23, 24 or 26 or comprising a polynucleotide sequence having at least 30% sequence identity with the polynucleotide sequence of any one of SEQ ID NOs: 2, 4, 5, 7, 8, 10, 12, 13, 15, 16, 18, 19, 21, 23, 24 or 26; or
(b) a polynucleotide sequence which hybridises, preferably under at least low stringency conditions, with the complementary strand of any one SEQ ID NOs: 2, 4, 5, 7, 8, 10, 12, 13, 15, 16, 18, 19, 21, 23, 24 or 26; or
(c) a polynucleotide sequence which hybridises, preferably under at least low stringency conditions with the complementary strand of a polynucleotide having at least 30% sequence identity to any one of any one SEQ ID NOs: 2, 4, 5, 7, 8, 10, 12, 13, 15, 16, 18, 19, 21, 23, 24 or 26;
(d) a polynucleotide sequence which is degenerate as a result of the degeneracy of the genetic code to a polynucleotide sequence as defined in any one of (a), (b) or (c); or
(e) a polynucleotide sequence which is the complement of a nucleotide sequence as defined in (a), (b), (c) or (d).

25. A polynucleotide sequence according to embodiment 5, having a sequence identity of at least 60%, preferably at least 70%, more preferably at least 80%, most preferably at-least 90%, most preferably at least 93%, most preferably at least about 95%, most preferably at least about 96%, most preferably at least about 97%, even most preferably at least about 98%, and even more preferred at least 99% to any one of any one SEQ ID NOs: 2, 4, 5, 7, 8, 10, 12, 13, 15, 16, 18, 19, 21, 23, 24 or 26.

26. A nucleic acid construct comprising the polynucleotide sequence of any one of embodiments 23 to 25.
27. A nucleic acid construct according to embodiment 26 which is an expression vector, wherein the polynucleotide sequence according to any one of embodiments 23 to 25 is operably linked to at least one control sequence for the expression of the polynucleotide sequence in a host cell.
28. A method of producing the polypeptide of embodiment 21 or 22, comprising:
   (a) cultivating a host cell according to embodiment 1 under conditions conducive to the production of the polypeptide by the host cell, and optionally,
   (b) recovering the polypeptide.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

Examples

Example 1: Over-expression of ERG20, BTS1 and tHMG in *S. cerevisiae*

For over-expression of ERG20, BTS1 tHMG1, expression cassettes were designed to be integrated in one locus using technology described in WO2013/076280. To amplify the 5' and 3' integration flanks for the integration locus, suitable primers and genomic DNA from a CEN.PK yeast strain (van Dijken et al. Enzyme and Microbial Technology 26 (2000) 706-714) was used. The different genes were ordered as cassettes (containing homologous sequence, promoter, gene, terminator, homologous sequence) at DNA2.0. The genes in these cassettes were flanked by constitutive promoters and terminators. See Table 1. Plasmid DNA from DNA2.0 containing the ERG20, tHMG1 and BTS1 cassettes were dissolved to a concentration of 100 ng/μl. In a 50 μl PCR mix 20 ng template was used together with 20 pmol of the primers. The material was dissolved to a concentration of 0.5 μg/μl.

TABLE 1

Composition of the over-expression constructs

| Promoter | ORF | Terminator |
|---|---|---|
| Eno2 (SEQ ID NO: 30) | ERG20 (SEQ ID NO: 31) | Adh1 (SEQ ID NO: 32) |
| Fba1 (SEQ ID NO: 33) | tHMG1 (SEQ ID NO: 34) | Adh2 (SEQ ID NO: 35) |
| Tef1 (SEQ ID NO: 36) | BTS1 (SEQ ID NO: 37) | Gmp1 (SEQ ID NO: 38) |

For amplification of the selection marker, the pUG7-EcoRV construct (FIG. 1) and suitable primers were used. The KanMX fragment was purified from gel using the Zymoclean Gel DNA Recovery kit (ZymoResearch). Yeast strain Cen.PK113-3C was transformed with the fragments listed in Table 2.

TABLE 2

| DNA fragments used for transformation of ERG20, tHMG1 and BTS1 Fragment |
|---|
| 5'YPRcTau3 |
| ERG20 cassette |
| tHMG1 cassette |
| KanMX cassette |
| BTS1 cassette |
| 3'YPRcTau3 |

Figure 2:
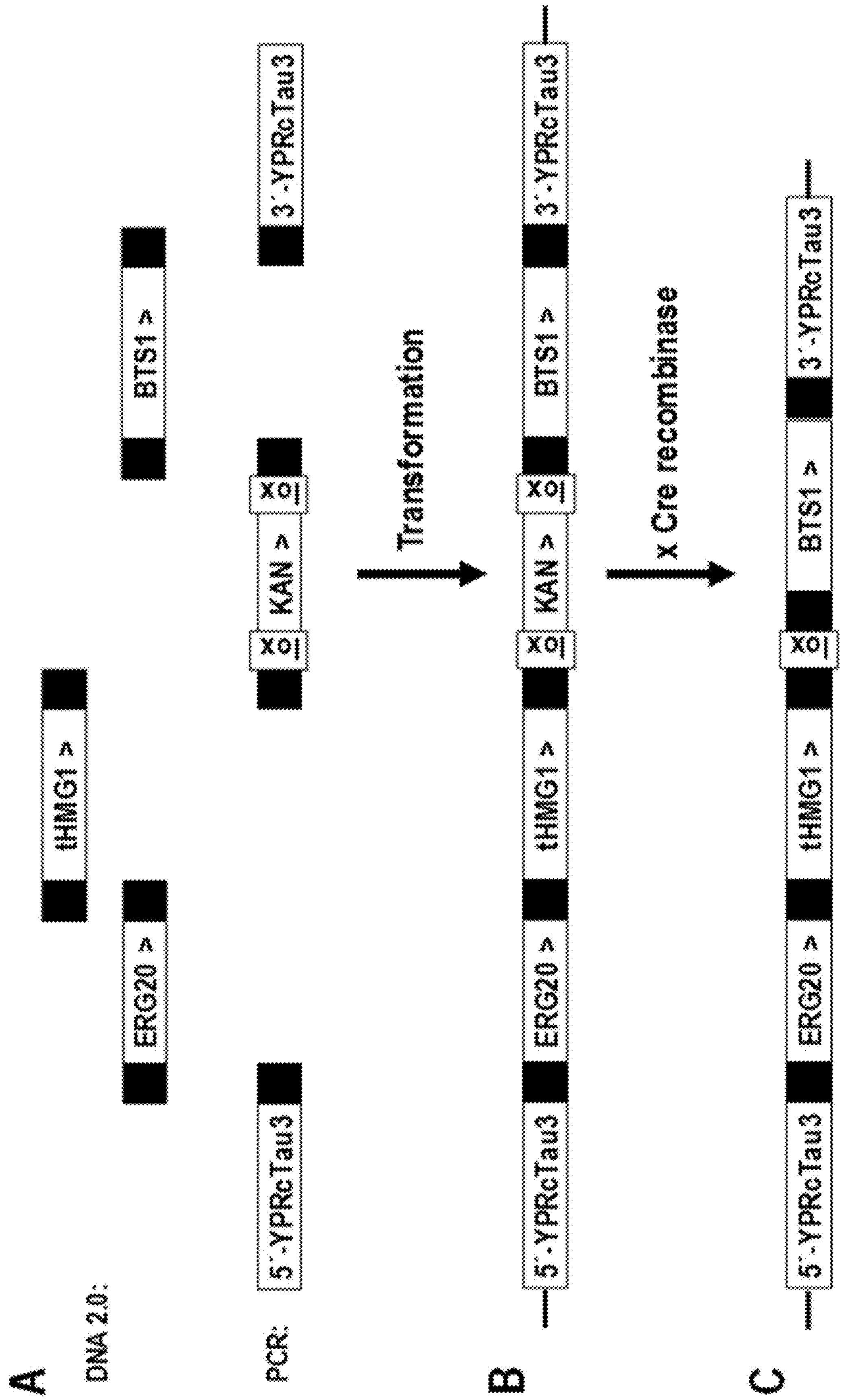
FIG. 2 sets out a schematic representation of the method by which the ERG20, tHMG1 and BTS1 over-expression cassettes are designed (A) and integrated (B) into the yeast genome. (C) shows the final situation after removal of the KANMX marker by the Cre recombinase.

After transformation and recovery for 2.5 hours in YEPhD (yeast extract phytone peptone glucose; BBL Phytone Peptone from BD) at 30° C. the cells were plated on YEPhD agar with 200 μg/ml G418 (Sigma). The plates were incubated at 30° C. for 4 days. Correct integration was established with diagnostic PCR and sequencing. Over-expression was confirmed with LC/MS on the proteins. The schematic of the assembly of ERG20, tHMG1 and BTS1 is illustrated in FIG. 2. This strain is named STV002.

Expression of CRE-recombinase in this strain led to out-recombination of the KanMX marker. Correct out-recombination, and presence of ERG20, tHMG and BTS1 was established with diagnostic PCR.

Example 2. Knock Down of Erg9

For reducing the expression of Erg9, an Erg9 knock down construct was designed and used that contains a modified 3' end, that continues into the TRP1 promoter driving TRP1 expression.

Figure 3:
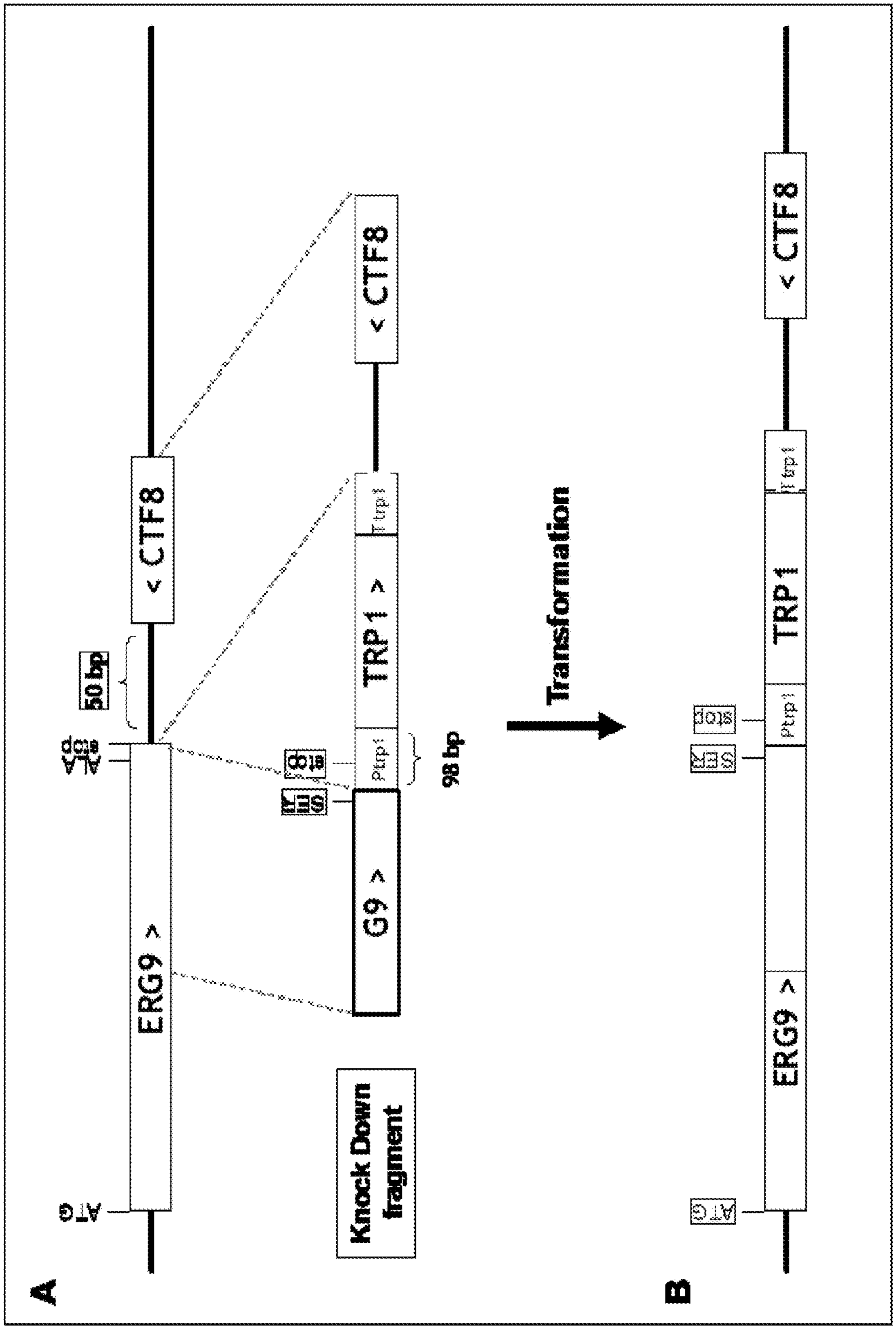
FIG. 3 sets out a schematic representation of the ERG9 knock down construct. This consists of a 500 bp long 3' part of ERG9, 98 bp of the TRP1 promoter, the TRP1 open reading frame and terminator, followed by a 400 bp long downstream sequence of ERG9. Due to introduction of a XbaI site at the end of the ERG9 open reading frame the last amino acid changes into Ser and the stop codon into Arg. A new stop codon is located in the TPR1 promoter, resulting in an extension of 18 amino acids.

The construct containing the Erg9-KD fragment was transformed to *E. coli* TOP10 cells. Transformants were grown in 2PY(2 times Phytone peptone Yeast extract), sAMP medium. Plasmid DNA was isolated with the QIAprep Spin Miniprep kit (Qiagen) and digested with SalI-HF (New England Biolabs). To concentrate, the DNA was precipitated with ethanol. The fragment was transformed to *S. cerevisiae*, and colonies were plated on mineral medium (Verduyn et al, 1992. Yeast 8:501-517) agar plates without tryptophan. Correct integration of the Erg9-KD construct was confirmed with diagnostic PCR and sequencing. The schematic of performed transformation of the Erg9-KD construct is illustrated in FIG. 3. The strain was named STV003.

Example 3. Over-Expression of UGT2 1a

For over-expression of UGT2_1a, technology was used as described in patent application nos. WO2013/076280 and WO2013/144257. The UGT2_1a was ordered as a cassette (containing homologous sequence, promoter, gene, terminator, homologous sequence) at DNA2.0. For details, see Table 3. To obtain the fragments containing the marker and Cre-recombinase, technology was used as described in patent application no. WO2013/135728. The NAT marker, conferring resistance to nourseothricin was used for selection.

TABLE 3

Composition of the over-expression construct

| Promoter | ORF | Terminator |
|---|---|---|
| Pgk1 (SEQ ID NO: 39) | UGT2_1a (SEQ ID NO: 28) | Adh2 (SEQ ID NO: 35) |

Suitable primers were used for amplification. To amplify the 5' and 3' integration flanks for the integration locus, suitable primers and genomic DNA from a CEN.PK yeast strain was used.

*S. cerevisiae* yeast strain STV003 was transformed with the fragments listed in Table 4, and the transformation mix was plated on YEPhD agar plates containing 50 μg/ml nourseothricin (Lexy NTC from Jena Bioscience).

TABLE 4

| DNA fragments used for transformation of UGT2 1a |
|---|
| Fragment |
| 5'Chr09.01 |
| UGT2_1a cassette |
| NAT-CR |
| RE |
| 3'Chr09.01 |

Figure 4:
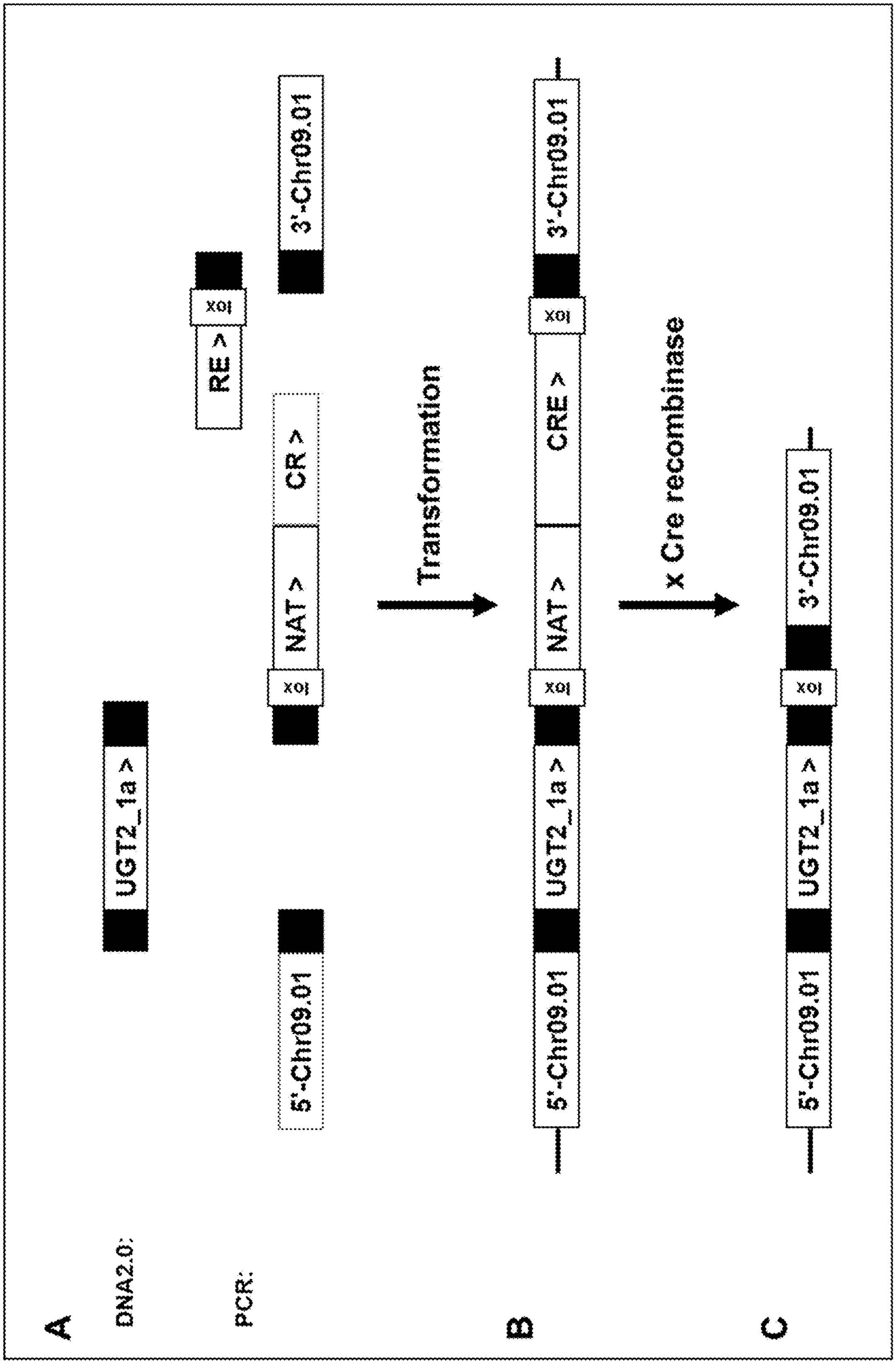
FIG. 4 sets out a schematic representation of how UGT2 is integrated into the genome. A. different fragments used in transformation; B. situation after integration; C. situation after expression of Cre recombinase).

Expression of the CRE recombinase is activated by the presence of galactose. To induce the expression of the CRE recombinase, transformants were restreaked on YEPh Galactose medium. This resulted in out-recombination of the marker(s) located between lox sites. Correct integration of the UGT2_1a and out-recombination of the NAT marker was confirmed with diagnostic PCR. The resulting strain was named STV004. The schematic of the performed transformation of the UGT2_1a construct is illustrated in FIG. 4.

Example 4. Over-Expression of Production Pathway to RebA: CPS, KS, KO, KAH, CPR, UGT1, UGT3 and UGT4

All pathway genes leading to the production of RebA were designed to be integrated in one locus using technology described in patent application nos. WO2013/076280 and WO2013/144257. To amplify the 5' and 3' integration flanks for the integration locus, suitable primers and genomic DNA from a CEN.PK yeast strain was used. The different genes were ordered as cassettes (containing homologous sequence, promoter, gene, terminator, homologous sequence) at DNA2.0 (see Table 5 for overview). The DNA from DNA2.0 was dissolved to 100 ng/μl. This stock solution was further diluted to 5 ng/μl, of which 1 μl was used in a 50 μl-PCR mixture. The reaction contained 25 pmol of each primer. After amplification, DNA was purified with the NucleoSpin 96 PCR Clean-up kit (Macherey-Nagel) or alternatively concentrated using ethanol precipitation.

TABLE 5

Sequences used for production pathway to RebA

| Promoter | ORF | SEQ ID | Terminator |
|---|---|---|---|
| Kl prom 12.pro (SEQ ID NO: 40) | trCPS_SR | 41 | Sc ADH2.ter (SEQ ID NO: 35) |
| Sc PGK1.pro (SEQ ID NO: 39) | trKS_SR | 42 | Sc TAL1.ter (SEQ ID NO: 43) |
| Sc ENO2.prp (SEQ ID NO: 30) | KO_Gibfu | 44 | Sc TPI1.ter (SEQ ID NO: 45) |

TABLE 5-continued

Sequences used for production pathway to RebA

| Promoter | ORF | SEQ ID | Terminator |
|---|---|---|---|
| Ag lox_TEF1.pro (SEQ ID NO: 46) | KANMX | 47 | Ag TEF1_lox.ter (SEQ ID NO: 48) |
| Sc TEF1.pro (SEQ ID NO: 36) | KAH_4 | 49 | Sc GPM1.ter (SEQ ID NO: 38) |
| Kl prom 6.pro (SEQ ID NO: 50) | CPR_3 | 51 | Sc PCD1.ter (SEQ ID NO: 52) |
| Kl prom 3.pro (SEQ ID NO: 53) | UGT1_SR | 54 | Sc TDH1.ter (SEQ ID NO: 55) |
| Kl prom 2.pro (SEQ ID NO: 56) | UGT3_SR | 57 | Sc ADH1.ter (SEQ ID NO: 32) |
| Sc FBA1.pro (SEQ ID NO: 33) | UGT4_SR | 58 | Sc ENO1.ter (SEQ ID NO: 59) |

All fragments for the pathway to RebA, the marker and the flanks (see overview in Table 6) were transformed to *S. cerevisiae* yeast strain STV004. After overnight recovery in YEPhD at 20° C. the transformation mixes were plated on YEPhD agar containing 200 μg/ml G418. These were incubated 3 days at 25° C. and one night at RT.

TABLE 6

| DNA fragments used for transformation of CPS, KS, KO, KanMX, KAH, CPR, UGT1, UGT3 and UGT4 Fragment |
|---|
| 5'INT1 |
| CPS cassette |
| KS cassette |
| KO cassette |
| KanMX cassette |
| KAH cassette |
| CPR cassette |
| UGT1 cassette |
| UGT3 cassette |
| UGT4 cassette |
| 3'INT1 |

Figure 5:
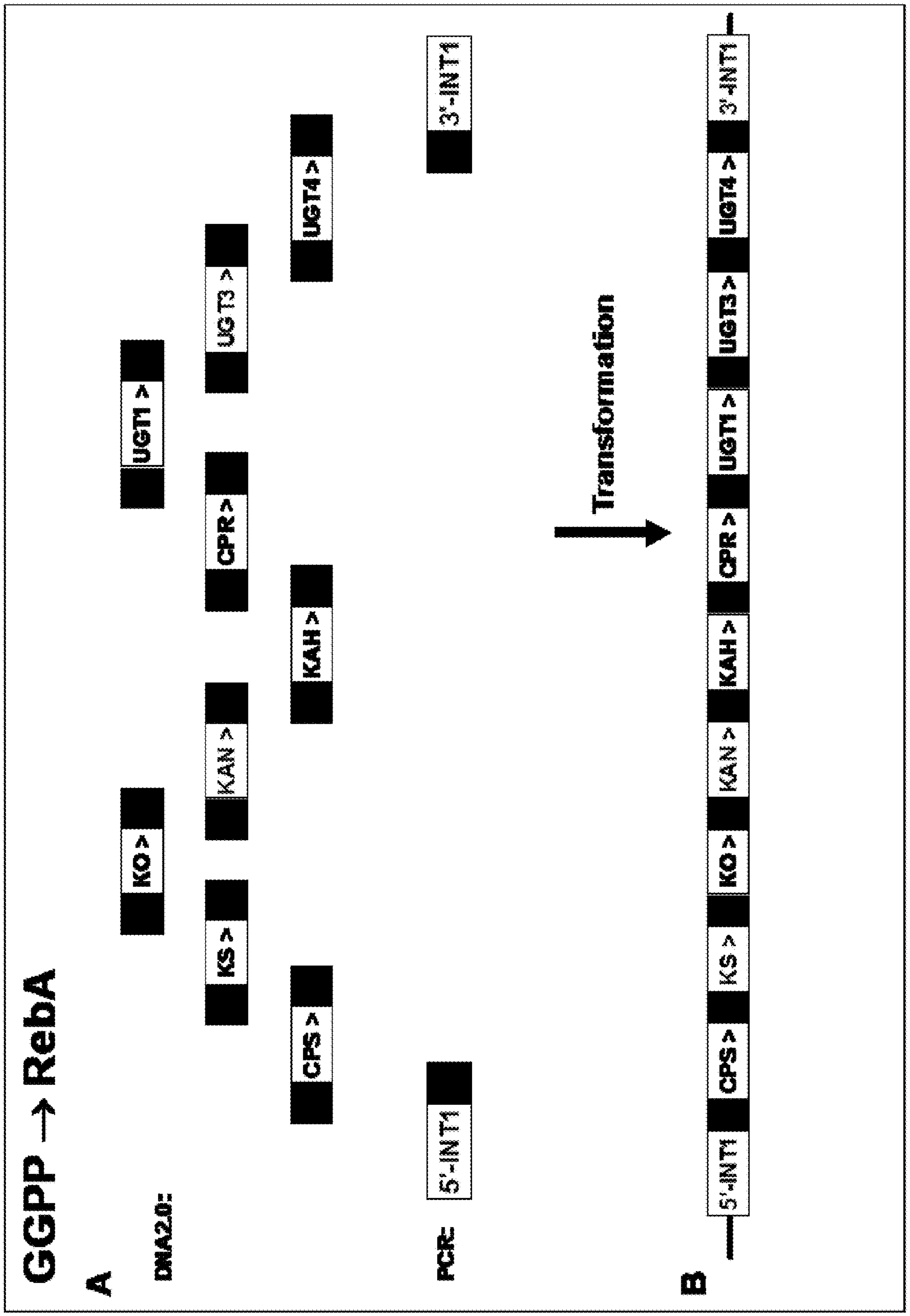
FIG. 5 sets out a schematic representation of how the pathway from GGPP to Steviol is integrated into the genome. A. different fragments used in transformation; B. situation after integration.

Correct integration was confirmed with diagnostic PCR and sequence analysis (3500 Genetic Analyzer, Applied Biosystems). The sequence reactions were done with the BigDye Terminator v3.1 Cycle Sequencing kit (Life Technologies). Each reaction (10 μl) contained 50 ng template and 3.2 pmol primer. The products were purified by ethanol/EDTA precipitation, dissolved in 10 μl HiDi formamide and applied onto the apparatus. The strain was named STV006. The schematic of how the pathway from GGPP to RebA is integrated into the genome is illustrated in FIG. 5. Table 7 sets out the strains used in Examples 1 to 5.

TABLE 7

Table of strains

| Strain | Background | Genotype |
|---|---|---|
| Cen.PK113-3C | — | MATa URA3 HIS3 LEU2 trp1-289 MAL2-8C SUC2 |
| STV002 | Cen.PK113-3C | MATa URA3 HIS3 LEU2 trp1-289 MAL2-8C SUC2 YPRcTau3::ERG20, tHMG1, KanMX, BTS1 |
| STV003 | STV002 | MATa URA3 HIS3 LEU2 trp1-289 MAL2-8C SUC2 YPRcTau3::ERG20, tHMG1, KanMX, BTS1 ERG9::ERG9-KD TRP1 |

TABLE 7-continued

| Table of strains | | |
|---|---|---|
| Strain | Background | Genotype |
| STV004 | STV003 | MATa URA3 HIS3 LEU2 trp1-289 MAL2-8C SUC2 YPRcTau3::ERG20, tHMG1, BTS1 ERG9::ERG9-KD TRP1 Chr09.01::UGT2_1a |
| STV006 | STV004 | MATa URA3 HIS3 LEU2 trp1-289 MAL2-8C SUC2 YPRcTau3::ERG20, tHMG1, BTS1 ERG9::ERG9-KD TRP1 Chr09.01::UGT2_1a INT1::CPS, KS, KO, KanMX, KAH, CPR, UGT1, UGT3, UGT4 |

Example 5. Removal of the KanMX Selection Marker of STV006

Figure 6:
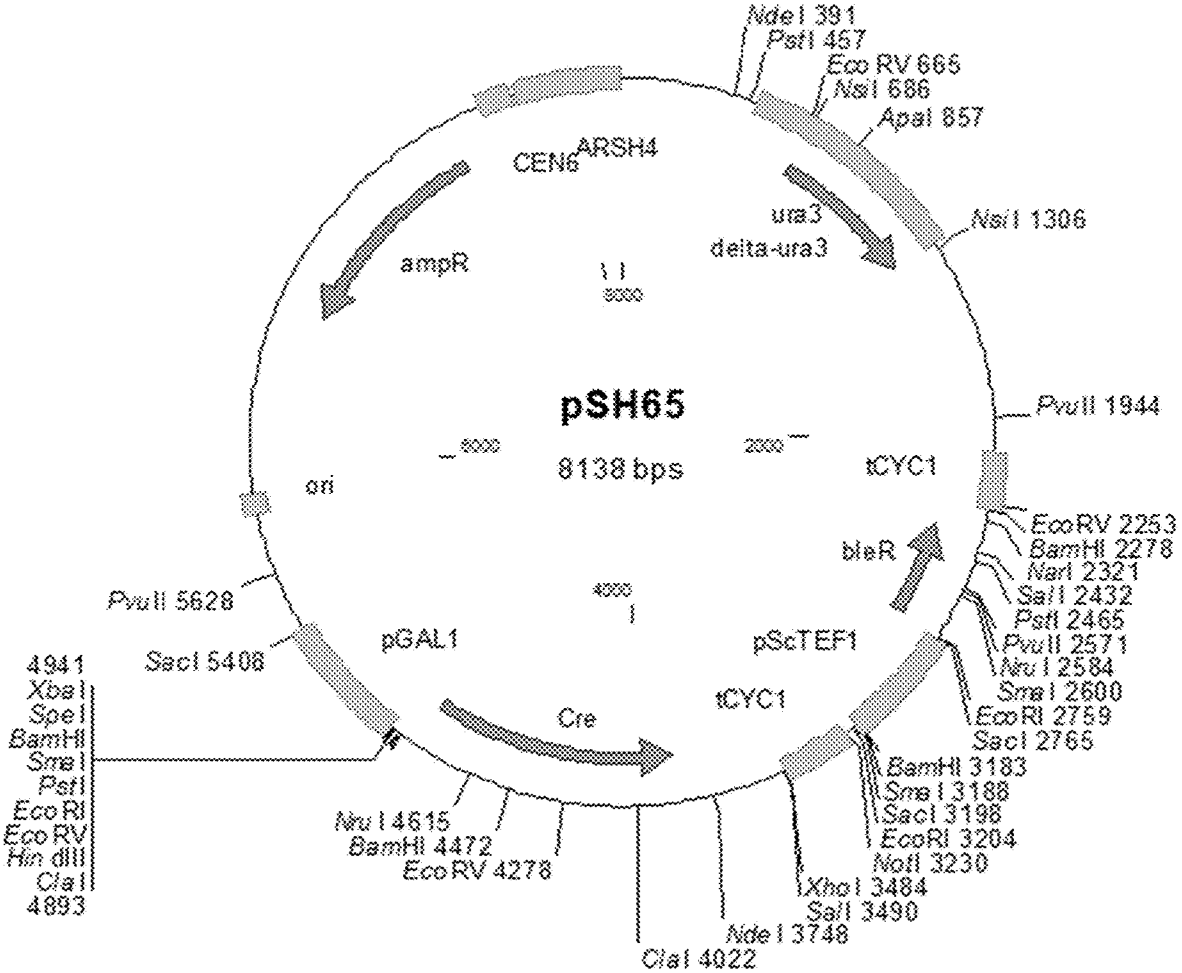
FIG. 6 sets out the pSH65 plasmid, carrying the CRE gene, which is used for removal of the antibiotic marker.

To remove the KanMX marker present in the strain, the plasmid pSH65, containing CRE recombinase (FIG. 6), was transformed to STV006. Transformants were first selected on YEPD containing 20 μg/ml Phleomycin (Invitrogen) and then restreaked on YEP Galactose medium to induce CRE recombinase expression. Correct out-recombination of the marker was established by diagnostic PCR. RebA production of this marker-free strain was confirmed in a production experiment. The marker free version of STV006 was called STV008.

Example 6. Removal of UGT2 1a in STV008 by the NAT Selection Marker

Figure 7:
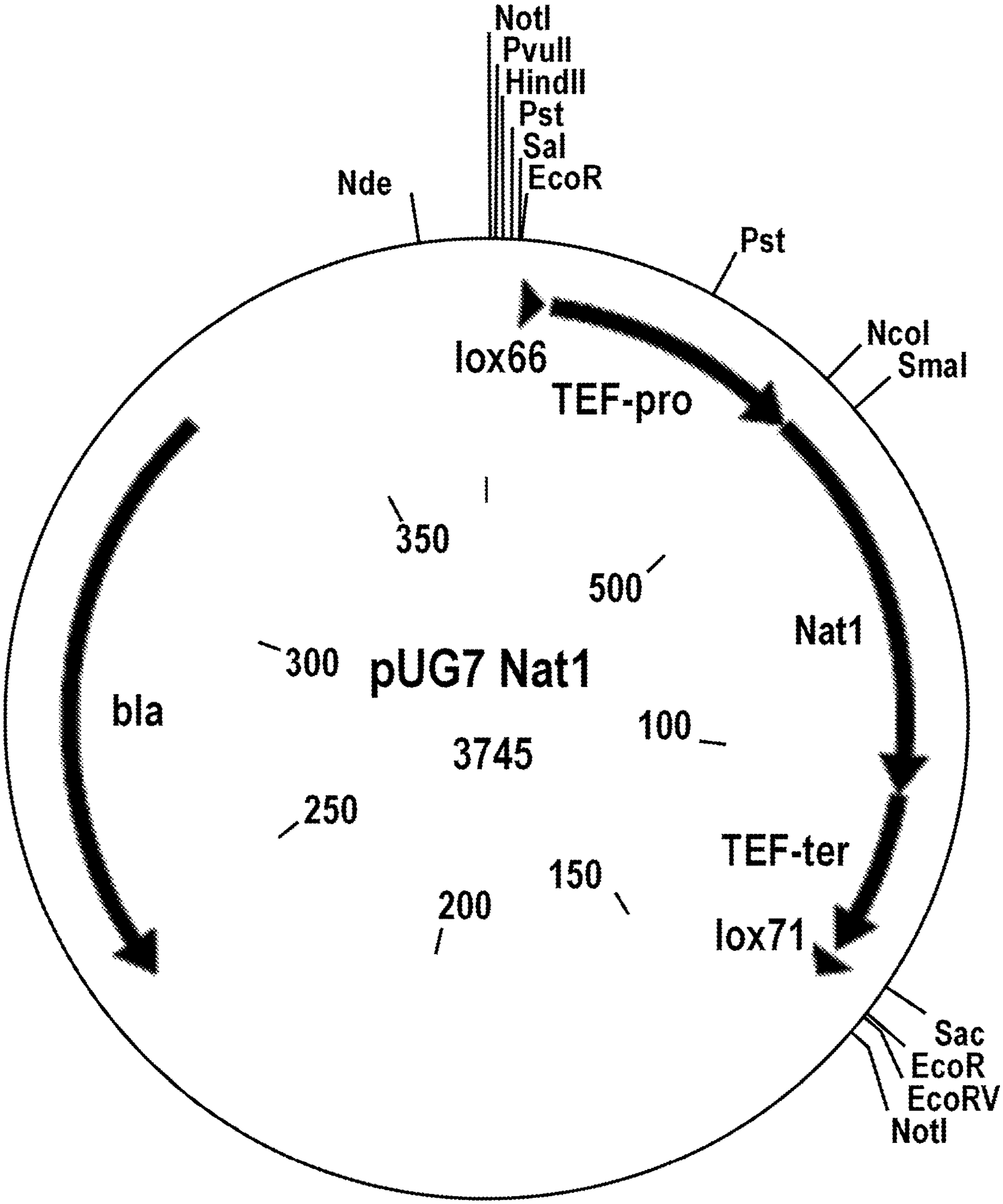
FIG. 7 sets out the map of plasmid pUG7-NAT.
Figure 8:
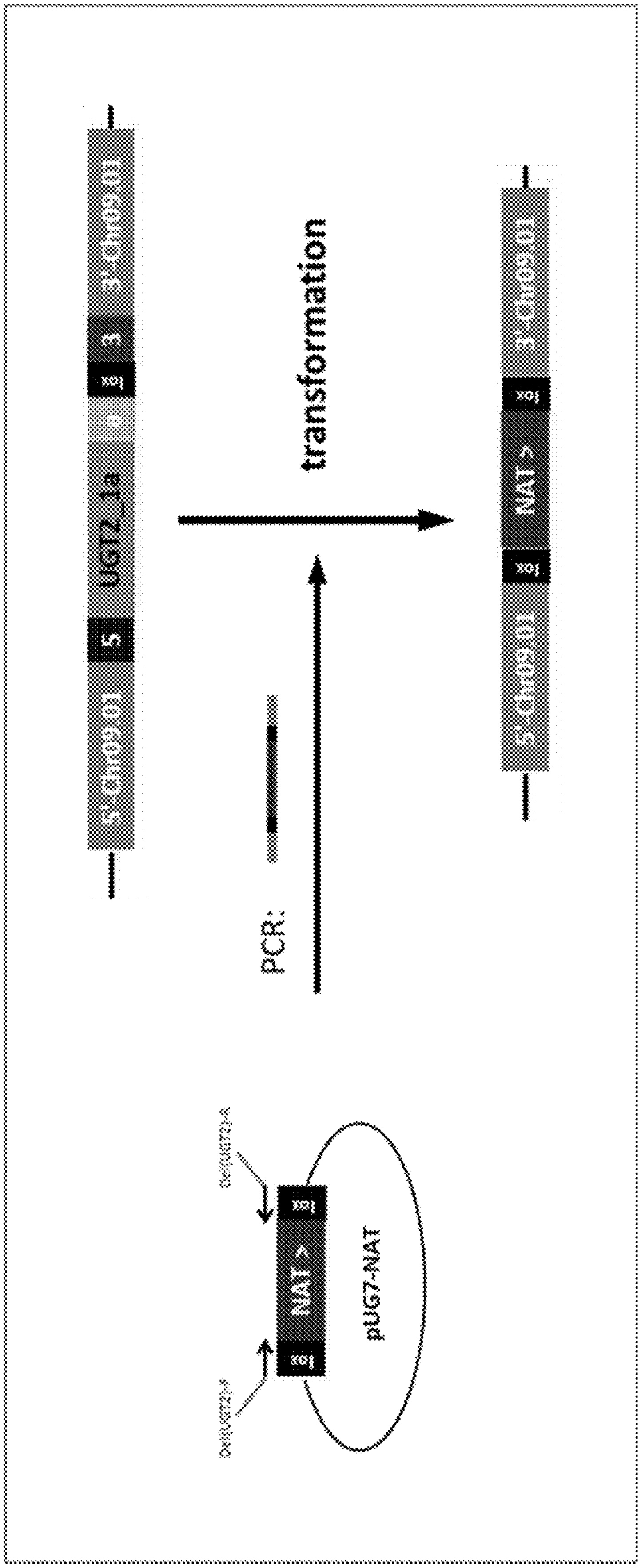
FIG. 8 sets out the replacement of UGT2_1a from STV008 with the Nat selection marker.

To remove the UGT2_1a, located at the Chr09.01 locus of STV008, the nourseothricin selection (NAT) marker and surrounding lox sites were amplified from the plasmid pUG7-NAT (FIG. 7) with primers containing additional 50 nt sequences homologous to the Chr09.01 integration flanks (FIG. 8). The PCR product was purified with the NucleoSpin Gel and PCR Clean-up kit (Macherey-Nagel) and transformed to STV008. Transformants were selected on YEPD containing 50 μg/ml nourseothricin (Lexy NTC from Jena Bioscience). Correct integration of the NAT marker and absence of UGT2_1a was confirmed by diagnostic PCR. This new strain was named STV009.

Example 7. Removal of the Nat Selection Marker of STV009

Figure 9:
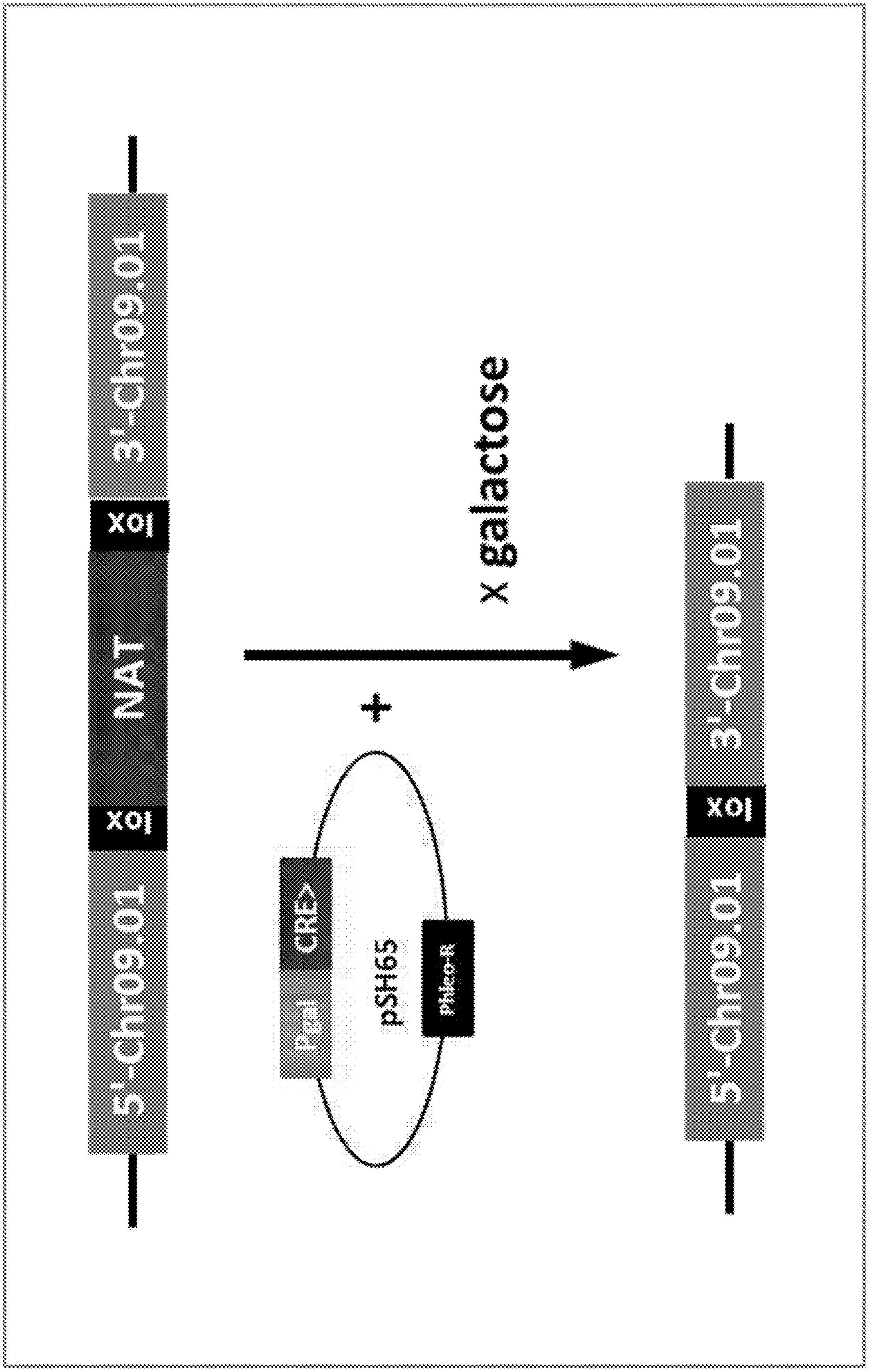
FIG. 9 sets out the removal of the NAT marker from STV008.

To be able to use the same integration locus for testing the UGT2 variants the NAT marker had to be removed from strain STV009 (FIG. 9). Therefore the CRE recombinase, located on the plasmid pSH65, was transformed to STV009 and transformants selected on YEPD containing 20 μg/ml Phleomycin. Colonies were restreaked on YEP Galactose agar plates. The plates were incubated at 30° C. Removal of the NAT marker by CRE recombinase was demonstrated by diagnostic PCR. In a production experiment it was shown that the STV009ΔNAT strain accumulates the same amount of rubusoside as its parent, STV009. The new strain was called STV053.

Example 8. Integration of UGT2 Gene Variants at the Chr09.01 Locus

Figure 10:
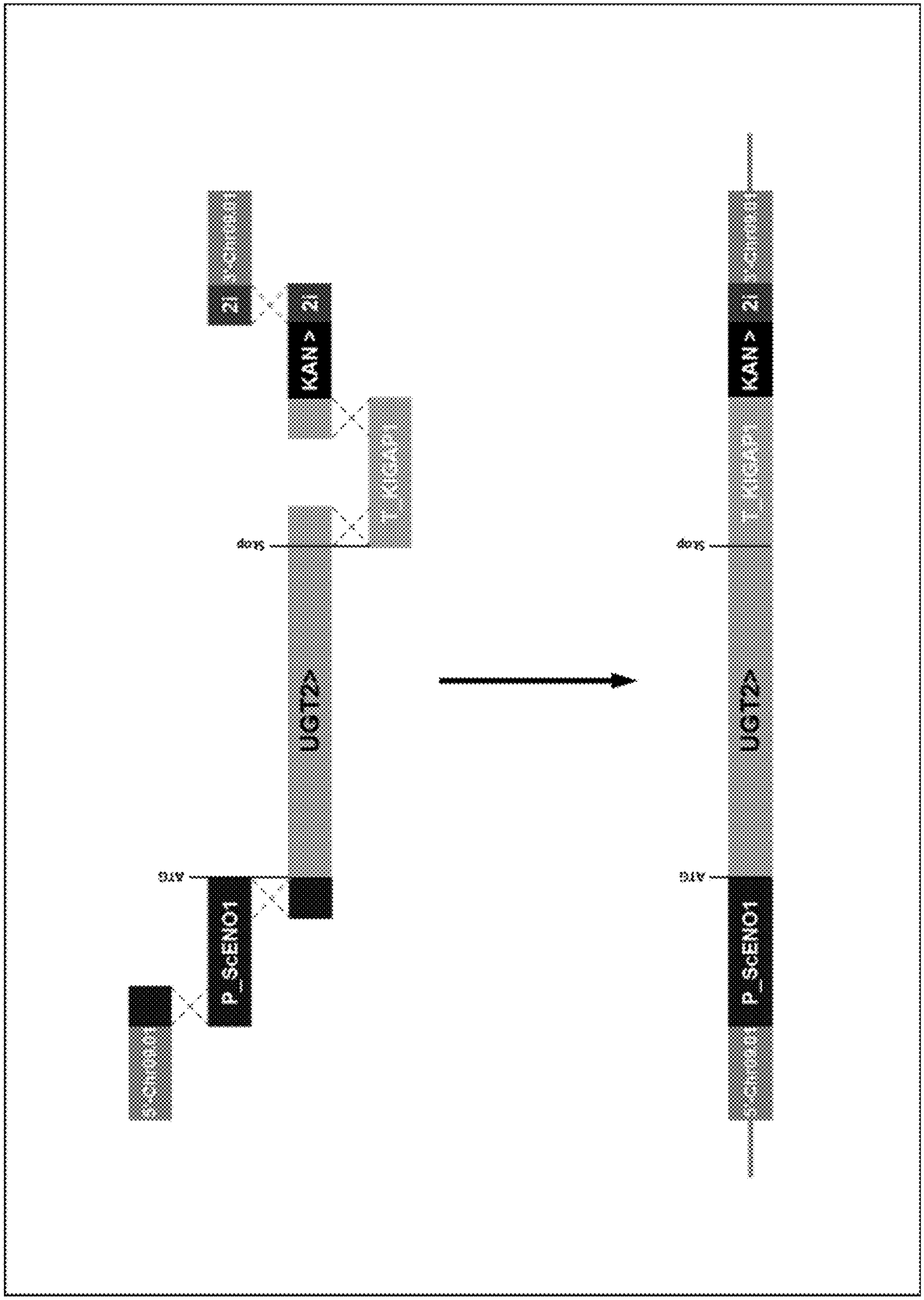
FIG. 10 sets out the integration of UGT2 genes at the Chr09.01 locus.

Different gene variants encoding UGT2 activity (SEQ ID NOs: 4, 7, 10, 12, 15, 18, 21, 23 and 28) were each separately integrated into the Chr09.01 locus by using several separate DNA fragments, containing 50 bp flanking homology segments for recombination (FIG. 10).

The 5'- and 3'-Chr09.01 integration flanks were amplified with suitable primers from genomic DNA from a CEN.PK yeast strain (van Dijken et al. Enzyme and Microbial Technology 26 (2000) 706-714). For the 5'-flank the reverse primer contained an extended 50 bp sequence homologous to promoter sequence to be used, namely the ScENO1 promoter (SEQ ID NO: 60). The forward primer for the 3'-flank contained a 50 bp linker extension.

The KanMX selection marker was amplified from the pUG7-EcoRV construct. The forward primer contained an additional 50 bp sequence homologous to the KIGAP1 (SEQ ID NO: 61) terminator. The reverse primer also possessed a 50 bp linker extension.

The different UGT2 gene variants were ordered at SGI-DNA. Their open reading frame was upstream flanked by 50 bp of the pScENO1 promoter (SEQ ID NO: 60) and downstream by 50 bp of the Klgap1T terminator (SEQ ID NO: 61). The genes were amplified from the SGI-DNA constructs by using primers annealing to these promoter and terminator sequences.

The PCR products were purified using the NucleoSpin 96 PCR Clean-up kit (Macherey-Nagel). Equimolar amounts of 5'-Chr09.01 flank, ENO1 promoter, UGT2 gene, KIGAP1 terminator, KanMX selection marker and 3'-Chr09.01 flank were combined for each UGT2 variant to be tested. One additional mixture was made containing the UGT2_1a. These mixtures were transformed to STV053 and plated on YEPD containing 200 μg/mIG418.

For each UGT2 variant, several replicate transformants were tested in a production experiment.

Example 9. Production of Rebaudioside a with *S. cerevisiae*

A pre-culture was inoculated with colony material from YEPD agar. The pre-culture was grown in 200 μl mineral medium with glucose as carbon source. The pre-culture was incubated 72 hours in an Infors incubator at 27° C., 750 rpm and 80% humidity.

40 μl of pre-culture was used to inoculate 2.5 ml mineral medium with glucose as carbon source. The main cultures were incubated 120 hours in an Infors incubator at 27° C., 550 rpm, 80% humidity. The cultures were well homogenized by pipetting up and down and 1 ml of culture was transferred to a 96-well plate. The 96-well plate was incubated for 15 minutes at 95° C. in a waterbath and cooled down to room temperature. To each well 0.5 ml of acetonitril was added and homogenized by pipetting up and down. The cell debris was pelleted by centrifugation at 3000×g for 10 minutes. The supernatant was diluted 200 times in 33% acetonitril.

Figure 11:
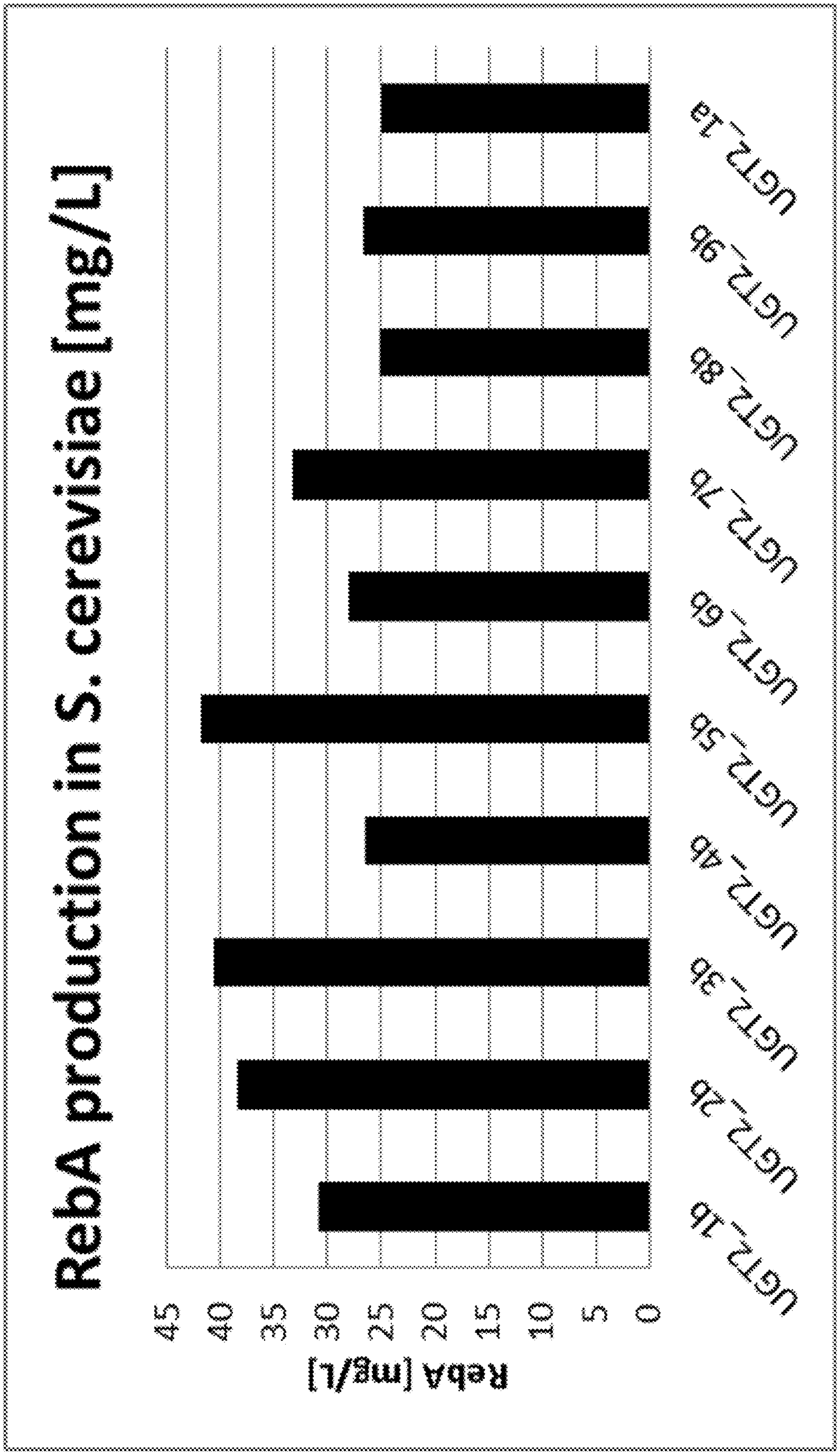
FIG. 11 sets out the production of rebaudioside A in *Saccharomyces* strains carrying different variants of UGT2

Samples were analyzed for RebA using LC/MS. RebA (RV0141-94, DAE Pyung Co. Ltd) was used as standard. We found that the strains that had the particular UGT2 gene variants as described, produced higher titers of RebA compared to the strain containing the UGT2_1a as set out in Table 8 and FIG. 11.

TABLE 8

| Rebaudioside A production in *Saccharomyces* strains expressing UGT2 variant enzymes | |
|---|---|
| UGT2 variant | RebA (mg/L) |
| UGT2_1b | 30.8 |
| UGT2_2b | 38.4 |
| UGT2_3b | 40.6 |
| UGT2_4b | 26.5 |
| UGT2_5b | 41.8 |
| UGT2_6b | 28.1 |
| UGT2_7b | 33.3 |
| UGT2_8b | 25.2 |
| UGT2_9b | 26.7 |
| UGT2_1a | 25.0 |

Example 10: Production of Rebaudioside M with *S. cerevisiae*

A pre-culture was inoculated with colony material from YEPD agar. The pre-culture was grown in 200 µl mineral medium with glucose as carbon source. The pre-culture was incubated 72 hours in an Infors incubator at 27° C., 750 rpm and 80% humidity.

40 µl of pre-culture was used to inoculate 2.5 ml mineral medium with glucose as carbon source. The main cultures were incubated 120 hours in an Infors incubator at 27° C., 550 rpm, 80% humidity. The cultures were well homogenized by pipetting up and down and 1 ml of culture was transferred to a 96-well plate. The 96-well plate was incubated for 15 minutes at 95° C. in a waterbath and cooled down to room temperature. To each well 0.5 ml of acetonitril was added and homogenized by pipetting up and down. The cell debris was pelleted by centrifugation at 3000×g for 10 minutes. The supernatant was diluted 200 times in 33% acetonitril.

The presence of RebM was confirmed by LC and MS analyzed with a LTQ orbitrap (Thermo), equipped with a Acella LC and a Waters Acquity UPLC BEH amide 1.7 µm 2.1*150 mm column. Eluentia used for the separation were A: 10 mM Ammonium acetate in MilliQ water, B: Acetonitrile, and the gradient started at 65% A and was kept here for 1.5 minutes, then increased to 95% B in 0.5 minutes and kept here for 0.5 minutes before regeneration for 1.5 min at 65% A. The flow-rate was 0.6 ml/min and the column temperature was kept at 50 C. Mass spectral analysis was performed in electrospray negative ionization mode, scanning from m/z 100-1800 at a resolution of 7500. Reb M elutes at tr=0.72 min, just after reb D at tr=0.63. Reb M is characterized by a deprotonated molecule of m/z 1289.5286. The elemental composition could be estimated using accurate mass analysis.

Figure 12:
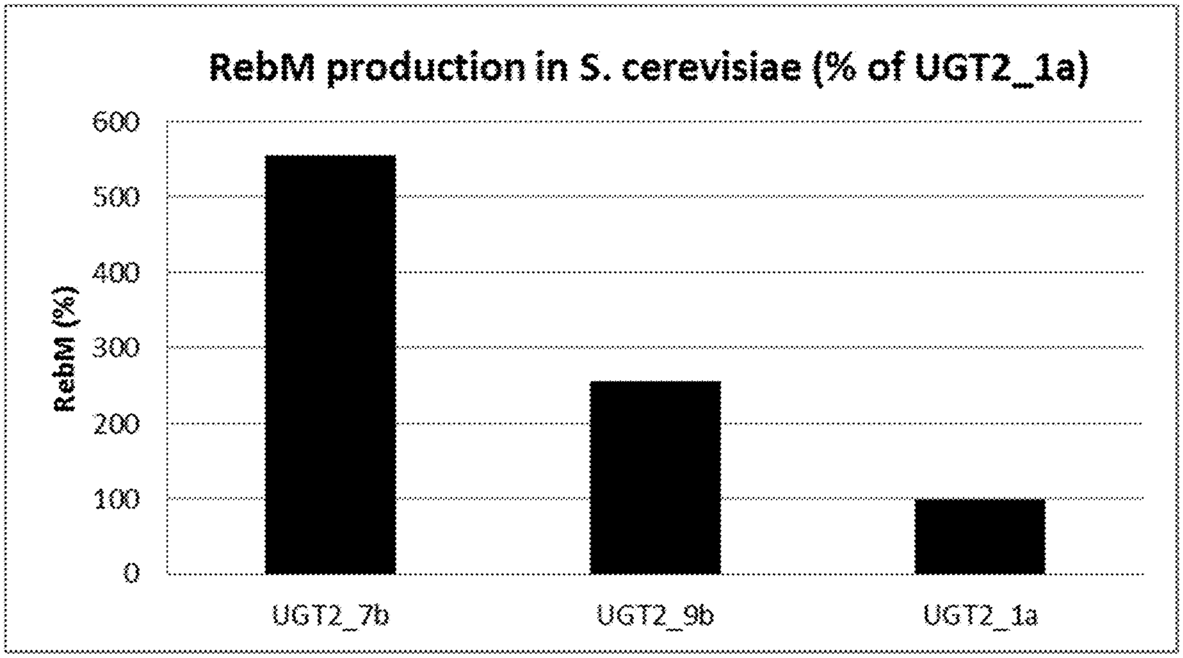

We found that the strains that had the particular UGT2 gene variants as described, produced higher titers of RebM compared to the strain containing the UGT2_1a as set out in FIG. 12 and Table 9.

TABLE 9

| Rebaudioside M production in *Saccharomyces* strains expressing UGT2 variant enzymes, compared in percentages to UGT2 1a. | |
|---|---|
| UGT2 variant | RebM (relative to UGT2_1a) |
| UGT2_7b | 555 |
| UGT2_9b | 256 |
| UGT2_1a | 100 |

Example 11: Description of Steviol Glycoside Production Strain ML14094 (MAT-A Lineage)

Two *Yarrowia lipolytica* strains of mating types MATA and MATB were engineered for steviol glycoside production. These strains were mated, the diploid sporulated, and spores with steviol glycoside production were selected. One of these spores was further developed for the production of steviol glycosides, including the production of rebaudioside A.

Step 1: Strain ML10371 (MAT-A, lys1-, ura3-, leu2-) was transformed with 5 defined DNA fragments. All transformations were carried out via a lithium acetate/PEG fungal transformation protocol method and transformants were selected on minimal medium, YPD+100 ug/ml nourseothricin or YPD+100 ug/ml hygromycin, as appropriate.

Figure 13:
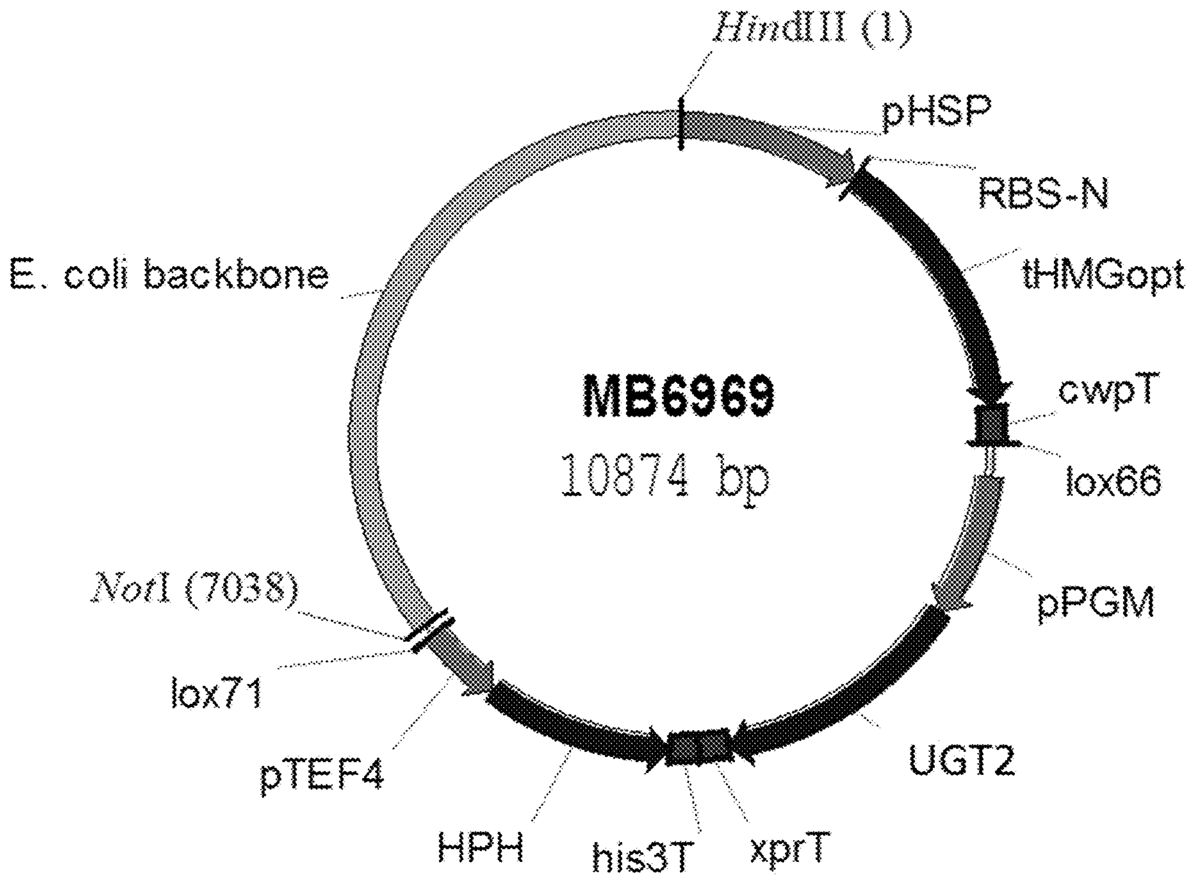
FIG. 13 sets out the map of plasmid MB6969, carrying genes tHMG and UGT2_1a FIG. 14 sets out the map of plasmid MB6856, carrying gene tHMG FIG. 15 sets out the map of plasmid MB6857, carrying gene tHMG FIG. 16 sets out the map of plasmid MB6948, carrying gene GGS FIG. 17 sets out the map of plasmid MB6958, carrying gene GGS FIG. 18 sets out the map of plasmid MB7015, carrying genes UGT1, UGT3 and UGT4

1) a 7.0 kb DNA fragment isolated by gel purification following HindIII/NotI digestion of plasmid MB6969 (FIG. 13). This construct encodes a synthetic construct for the overexpression of UGT2_1a (SEQ ID NO: 29) linked to the pPGM promoter (SEQ ID NO: 62) and xprT terminator (SEQ ID NO: 69) and the HPH hygromycin resistance gene, together flanked by lox sites (Güldener et al, 1996, Lambert et al, 2007), and a synthetic construct for the overexpression of the codon optimized *Y. lipolytica* hydroxymethylglutaryl-coenzyme A reductase open reading frame lacking the 5' membrane anchor sequence (tHMGopt: SEQ ID NO: 75) linked to the pHSP promoter (SEQ ID NO: 63) and cwpT terminator (SEQ ID NO: 70).

Figure 14:
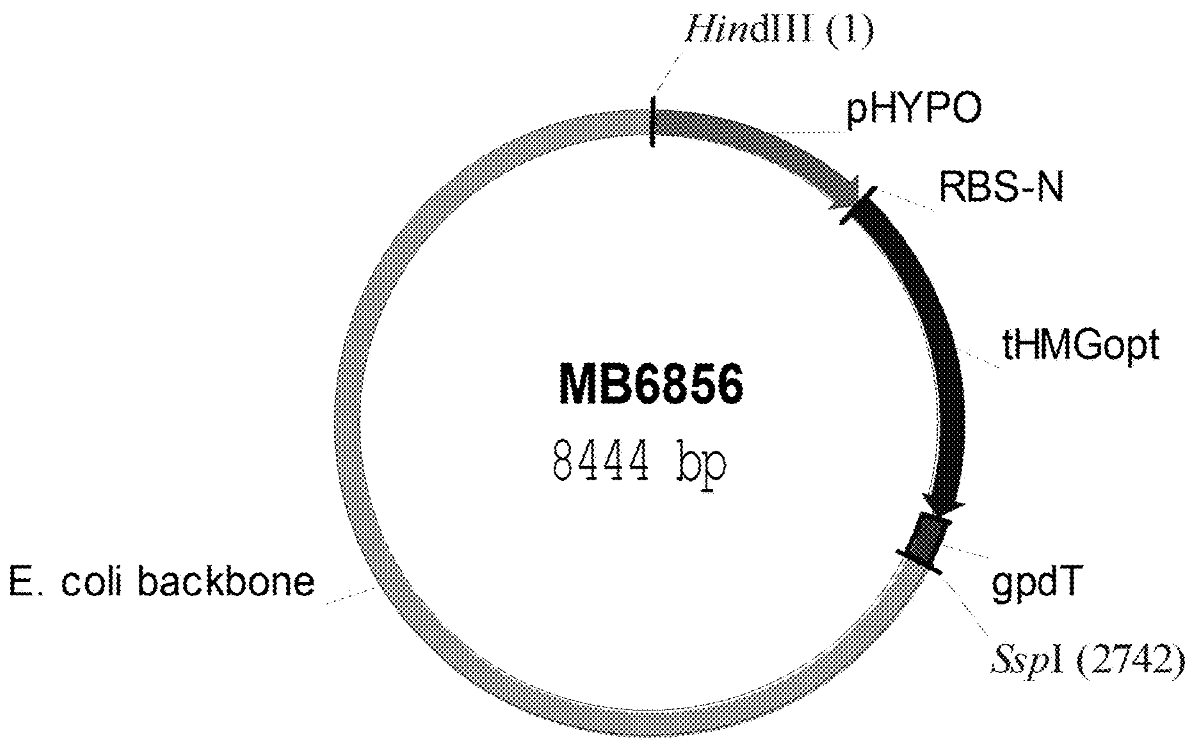

2) a 2.7 kb DNA fragment isolated by gel purification following HindIII/SspI digestion of MB6856 (FIG. 14). This construct encodes tHMGopt (SEQ ID NO: 75) linked to the pHYPO promoter (SEQ ID NO: 64) and gpdT terminator (SEQ ID NO: 71).

Figure 15:
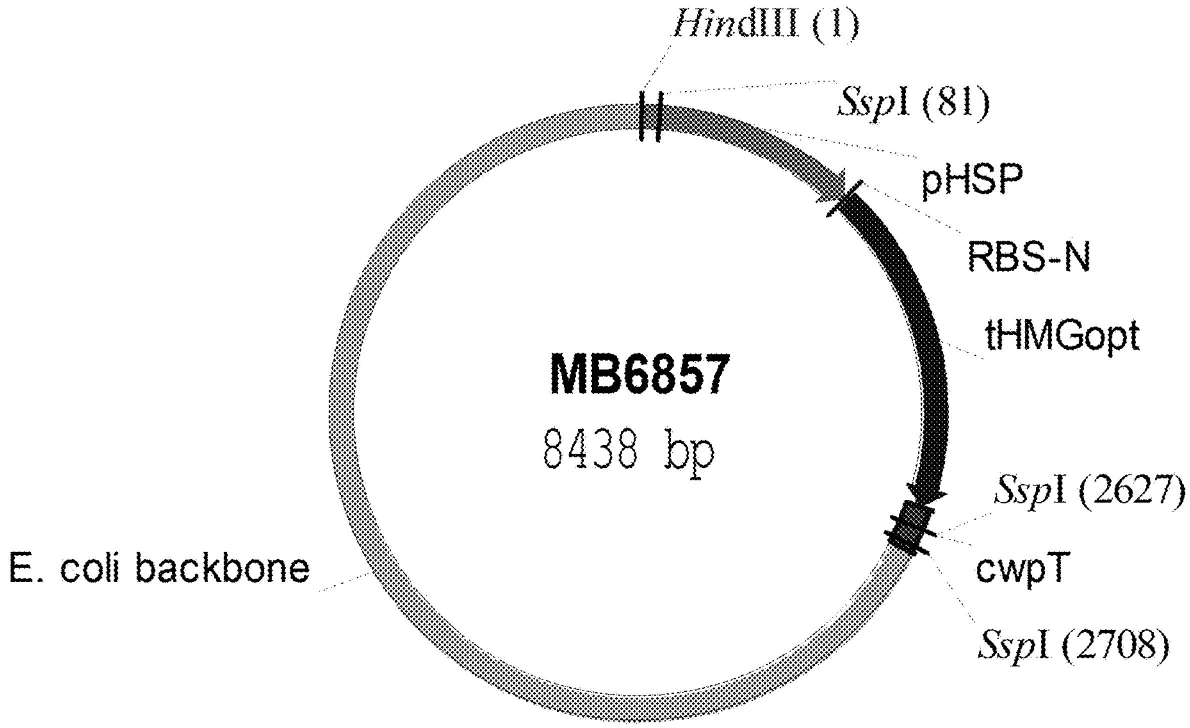

3) a 2.5 kb DNA fragment isolated by gel purification following SspI digestion of MB6857 (FIG. 15). This construct encodes tHMGopt (SEQ ID NO: 75) linked to the pHSP promoter (SEQ ID NO: 63) and cwpT terminator (SEQ ID NO: 70).

Figure 16:
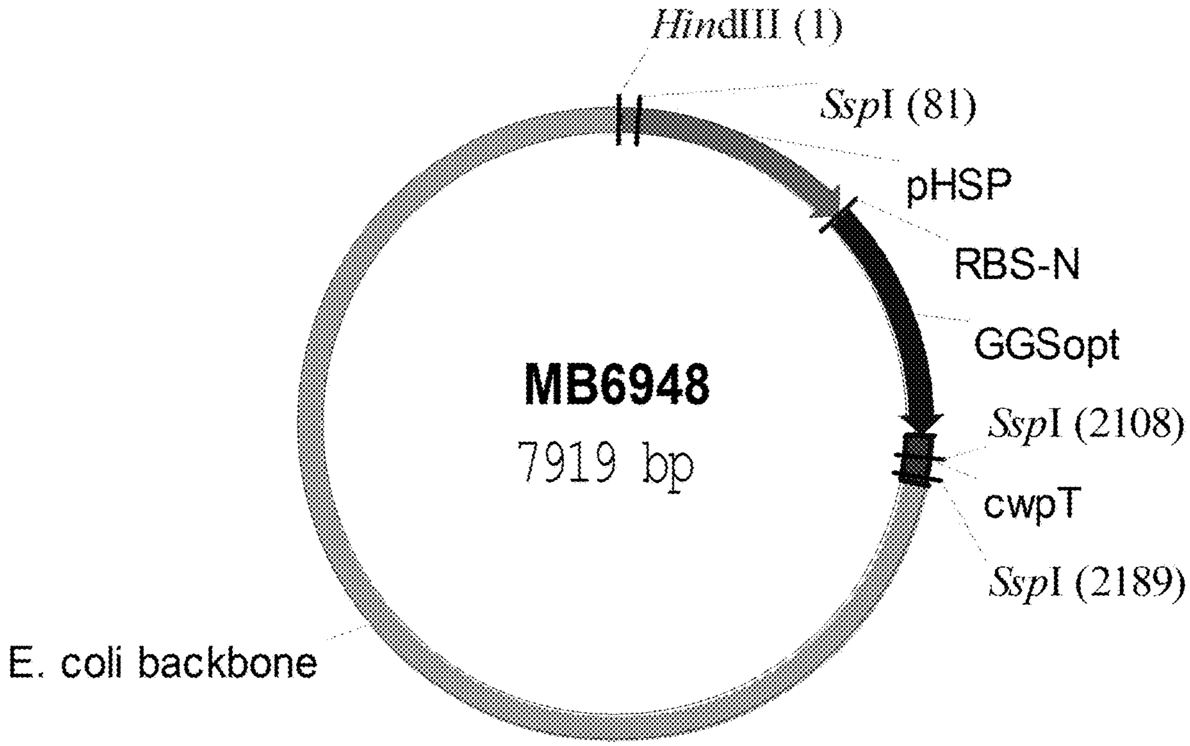

4) a 2.0 kb DNA fragment isolated by gel purification following SspI digestion of MB6948 (FIG. 16). This construct encodes a synthetic construct for the overexpression of the codon optimized *Y. lipolytica* geranyl-geranyl-pyrophosphate synthetase (GGSopt: SEQ ID NO: 76) linked to the pHSP promoter (SEQ ID NO: 63) and cwpT terminator (SEQ ID NO: 70).

Figure 17:
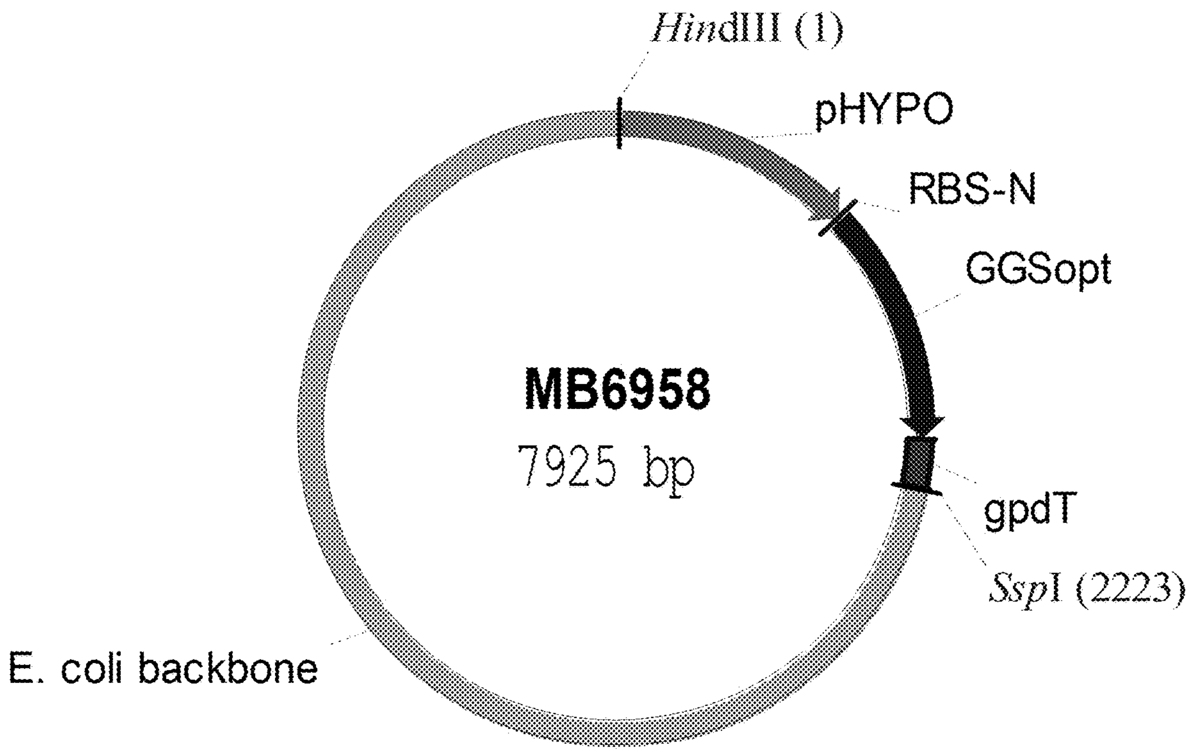

5) a 2.2 kb DNA fragment isolated by gel purification following HindIII/SspI digestion of MB6958 (FIG. 17). This construct encodes GGSopt (SEQ ID NO: 76) linked to the pHYPO promoter (SEQ ID NO: 64) and gpdT terminator (SEQ ID NO: 71). The resulting strain was denoted ML13462.

Figure 18:
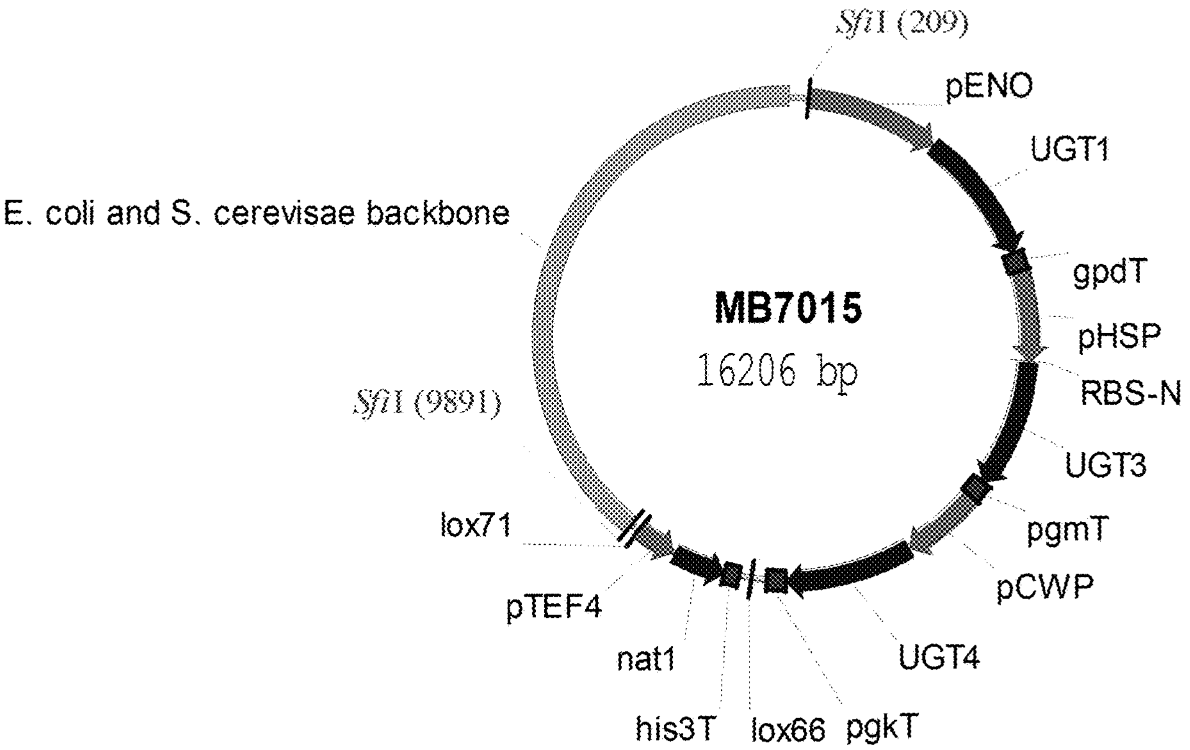

Step 2. Strain ML13462 was transformed with a 9.7 kb fragment isolated by gel purification following SfiI digestion of plasmid MB7015 (FIG. 18). This construct encodes a synthetic construct for the overexpression of UGT1 (SEQ ID NO: 77) linked to the pENO (SEQ ID NO: 65) promoter and gpdT terminator (SEQ ID NO: 71), UGT3 (SEQ ID NO: 78) linked to the pHSP promoter (SEQ ID NO: 63) and pgmT terminator (SEQ ID NO: 72), UGT4 (SEQ ID NO: 79) linked to the pCWP (SEQ NO: 66) promoter and pgkT terminator (SEQ ID NO: 73), and the lox-flanked nourseothricin resistance marker (NAT). Note that placement of lox sites allows for subsequent removal of nourseothricin resistance via CRE recombinase mediated recombination. A nourseothricin resistant isolate was denoted ML13500.

Figure 19:
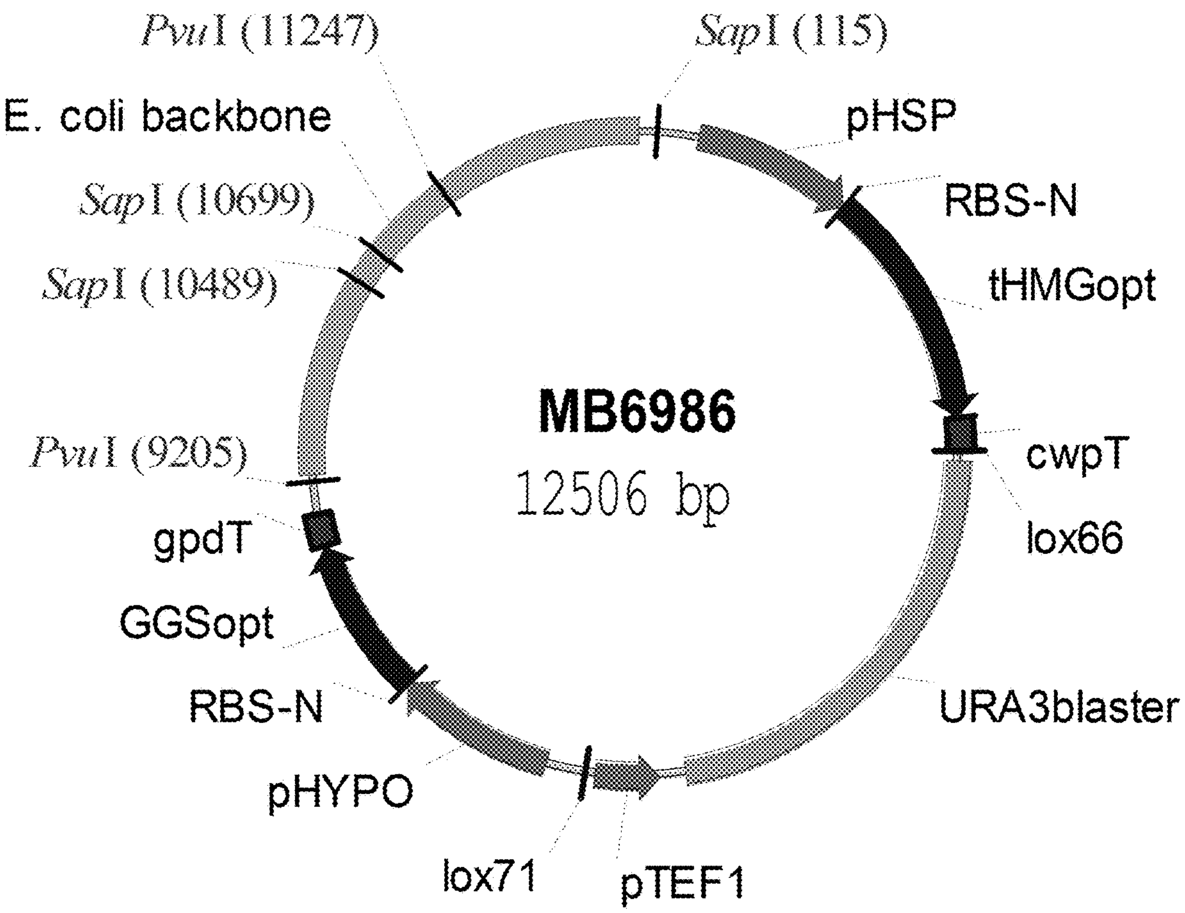
FIG. 19 sets out the map of plasmid MB6986, carrying genes tHMG and GGS

Step 3. Strain ML13500 was transformed with a 9.1 kb fragment isolated by gel purification following PvuI/SapI digestion of plasmid MB6986 (FIG. 19). This construct encodes tHMGopt (SEQ ID NO: 75) linked to the pHSP promoter (SEQ ID NO: 63) and cwpT terminator (SEQ ID NO: 70), the lox-flanked URA3blaster prototrophic marker, and GGSopt (SEQ ID NO: 76) linked to the pHYPO promoter (SEQ ID NO: 64) and gpdT terminator (SEQ ID NO: 71). Transformants were selected on minimal medium lacking uracil. One selected uracil prototroph was denoted ML13723.

Figure 20:
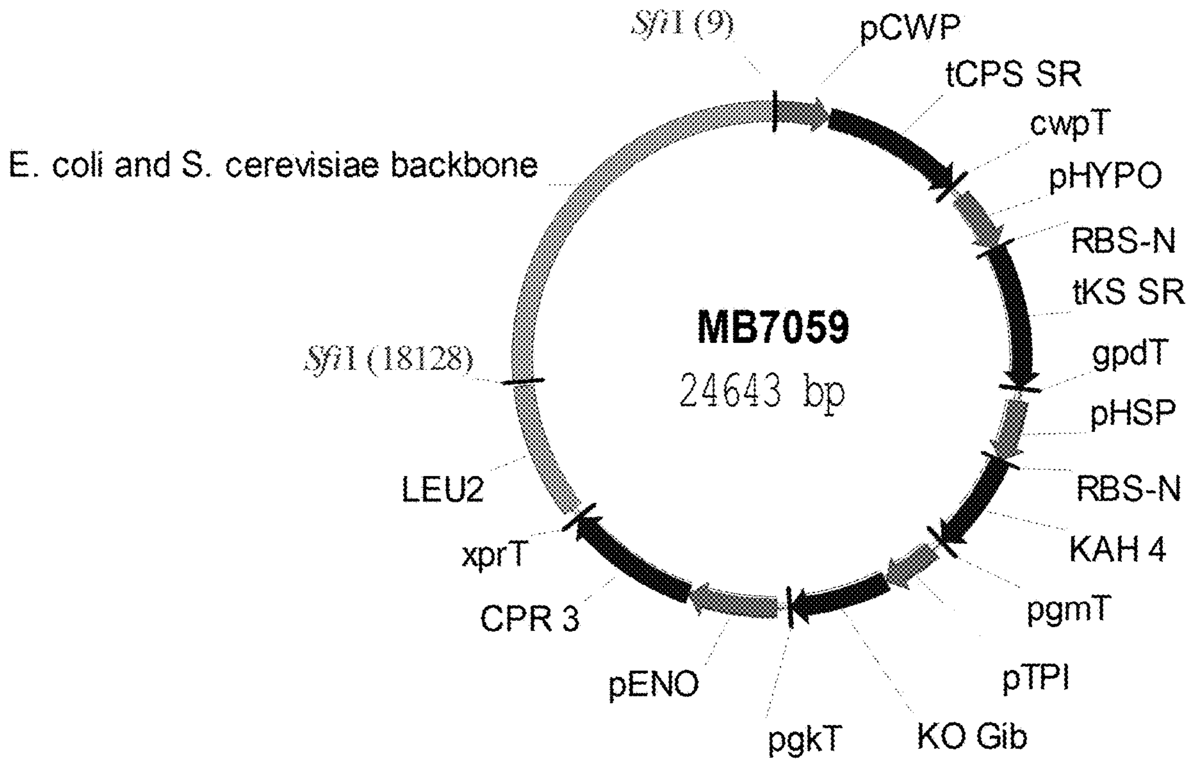
FIG. 20 sets out the map of plasmid MB7059, carrying genes tCPS_SR, tKS_SR, KAH_4, KO_Gib and CPR_3.

Step 4. Strain ML13723 was transformed with an 18.1 kb fragment isolated by gel purification following SfiI digestion of plasmid MB7059 (FIG. 20). MB7059 encodes the tCPS_SR (SEQ ID NO: 80) linked to pCWP promoter (SEQ ID NO: 66) and cwpT terminator (SEQ ID NO: 70), the tKS_SR (SEQ ID NO: 81) linked to the pHYPO promoter (SEQ ID NO: 64) and gpdT terminator (SEQ ID NO: 71), the KAH_4 (SEQ ID NO: 92) linked to the pHSP promoter (SEQ ID NO: 63) and pgmT terminator (SEQ ID NO: 72), the KO_Gib (SEQ ID NO: 83) linked to the pTPI promoter (SEQ ID NO: 67) and pgkT terminator (SEQ ID NO: 73), the CPR_3 (SEQ ID NO: 84) linked to the pENO promoter (SEQ ID NO: 65) and xprT terminator (SEQ ID NO: 69) and the native *Y. lipolytica* LEU2 locus. One selected rebaudioside A-producing transformant was denoted ML14032.

Step 5. Strain ML14032 was struck to YPD and grown overnight and then struck to 5-FOA plates to allow for recombination mediated loss of the URA3 marker introduced in Step 3. One selected 5-FOA resistant transformant was denoted ML14093.

Figure 21:
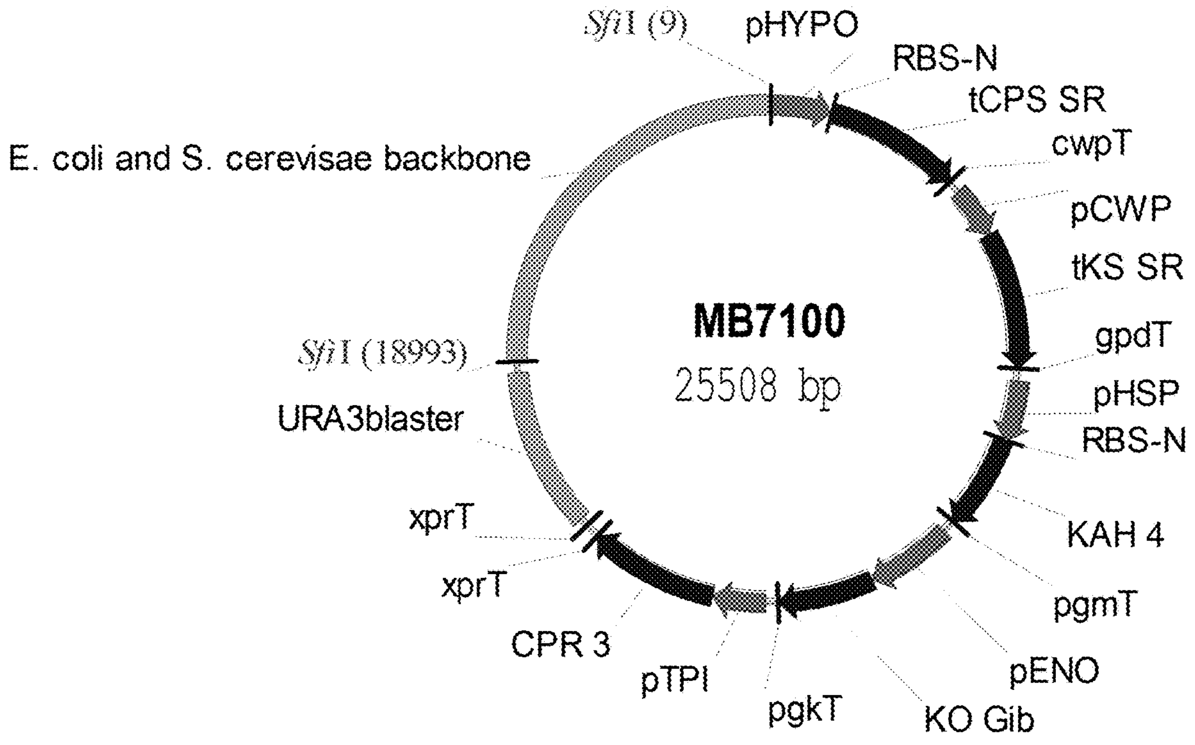
FIG. 21 sets out the map of plasmid MB7100, carrying genes tCPS_SR, tKS_SR, KAH_4, KO_Gib and CPR_3.

Step 6. Strain ML14093 was transformed with a 19.0 kb fragment isolated by gel purification following SfiI digestion of plasmid MB7100 (FIG. 21). MB7100 encodes the tCPS_SR (SEQ ID NO: 80) linked to the pHYPO promoter (SEQ ID NO: 64) and cwpT terminator (SEQ ID NO: 70), the tKS_SR (SEQ ID NO: 81) linked to the pCWP promoter (SEQ ID NO: 66) and gpdT terminator (SEQ ID NO: 71), the KAH_4 (SEQ ID NO: 82) linked to the pHSP promoter (SEQ ID NO: 63) and pgmT terminator (SEQ ID NO: 72), the KO_Gib (SEQ ID NO: 83) linked to the pENO promoter (SEQ ID NO: 65) and pgkT terminator (SEQ ID NO: 73), the CPR_3 (SEQ ID NO: 84) linked to the pTPI promoter (SEQ ID NO: 67) and xprT terminator (SEQ ID NO: 69) and URA3blaster prototrophic marker. Transformants were selected on minimal medium lacking uracil. One selected rebaudioside A producing uracil prototroph was denoted ML14094.

Example 12. Description of Steviol Glycoside Production Strain ML14087 (MAT-B Lineage)

Step 1. Strain ML13206 (MAT-B, ade1-, ure2-, leu2-) was transformed with 5 defined DNA fragments. All transformations were carried out via a lithium acetate/PEG fungal transformation protocol method and transformants were selected on minimal medium, YPD+100 ug/ml nourseothricin or YPD+100 ug/ml hygromycin, as appropriate.

1) a 7.0 kb DNA fragment isolated by gel purification following HindIII/NotI digestion of plasmid MB6969 (FIG. 13). This construct encodes a synthetic construct for the overexpression of the codon pair optimized (CpO) ORF of UGT2_1a (SEQ ID NO: 29) linked to the pPGM (SEQ ID NO: 62) promoter and xprT terminator (SEQ ID NO: 69) and the HPH hygromycin resistance gene, together flanked by lox sites (Güldener et al, 1996, Lambert et al, 2007), and a synthetic construct for the overexpression of the codon optimized *Y. lipolytica* hydroxymethylglutaryl-coenzyme A reductase open reading frame lacking the 5' membrane anchor sequence (tHMGopt: SEQ ID NO: 75) linked to the pHSP promoter (SEQ ID NO: 63) and cwpT terminator (SEQ ID NO: 70).

2) a 2.7 kb DNA fragment isolated by gel purification following HindIII/SspI digestion of MB6856 (FIG. 14). This construct encodes tHMGopt (SEQ ID NO: 75) linked to the pHYPO promoter (SEQ ID NO: 64) and gpdT terminator (SEQ ID NO: 71).

3) a 2.5 kb DNA fragment isolated by gel purification following SspI digestion of MB6857 (FIG. 15). This construct encodes tHMGopt (SEQ ID NO: 75) linked to the pHSP promoter (SEQ ID NO: 63) and cwpT terminator (SEQ ID NO: 70).

4) a 2.0 kb DNA fragment isolated by gel purification following SspI digestion of MB6948 (FIG. 16). This construct encodes a synthetic construct for the overexpression of the codon optimized *Y. lipolytica* geranyl-geranyl-pyrophosphate synthetase (GGSopt: SEQ ID NO: 76) linked to the pHSP promoter (SEQ ID NO: 63) and cwpT terminator (SEQ ID NO: 70).

5) a 2.2 kb DNA fragment isolated by gel purification following HindIII/SspI digestion of MB6958 (FIG. 17). This construct encodes GGSopt (SEQ ID NO: 76) linked to the pHYPO (SEQ ID NO: 64) promoter and gpdT terminator (SEQ ID NO: 71). The resulting strain was denoted ML13465.

Step 2. Strain ML13465 was transformed with 2 defined DNA fragments:

1). a 9.7 kb fragment isolated by gel purification following SfiI digestion of plasmid MB7015 (FIG. 18). This construct encodes a synthetic construct for the overexpression of UGT1 (SEQ ID NO: 77) linked to the pENO promoter (SEQ Id NO: 65) and gpdT (SEQ ID NO: 71) terminator, UGT3 (SEQ ID NO: 78) linked to the pHSP promoter (SEQ ID NO: 63) and pgmT terminator (SEQ ID NO: 72), UGT4 (SEQ ID NO: 79) linked to the pCWP promoter (SEQ ID NO: 66) and pgkT terminator (SEQ ID NO: 73), and the lox-flanked nourseothricin resistance marker (NAT). Note that placement of lox sites allows for subsequent removal of nourseothricin resistance via CRE recombinase mediated recombination.

Figure 22:
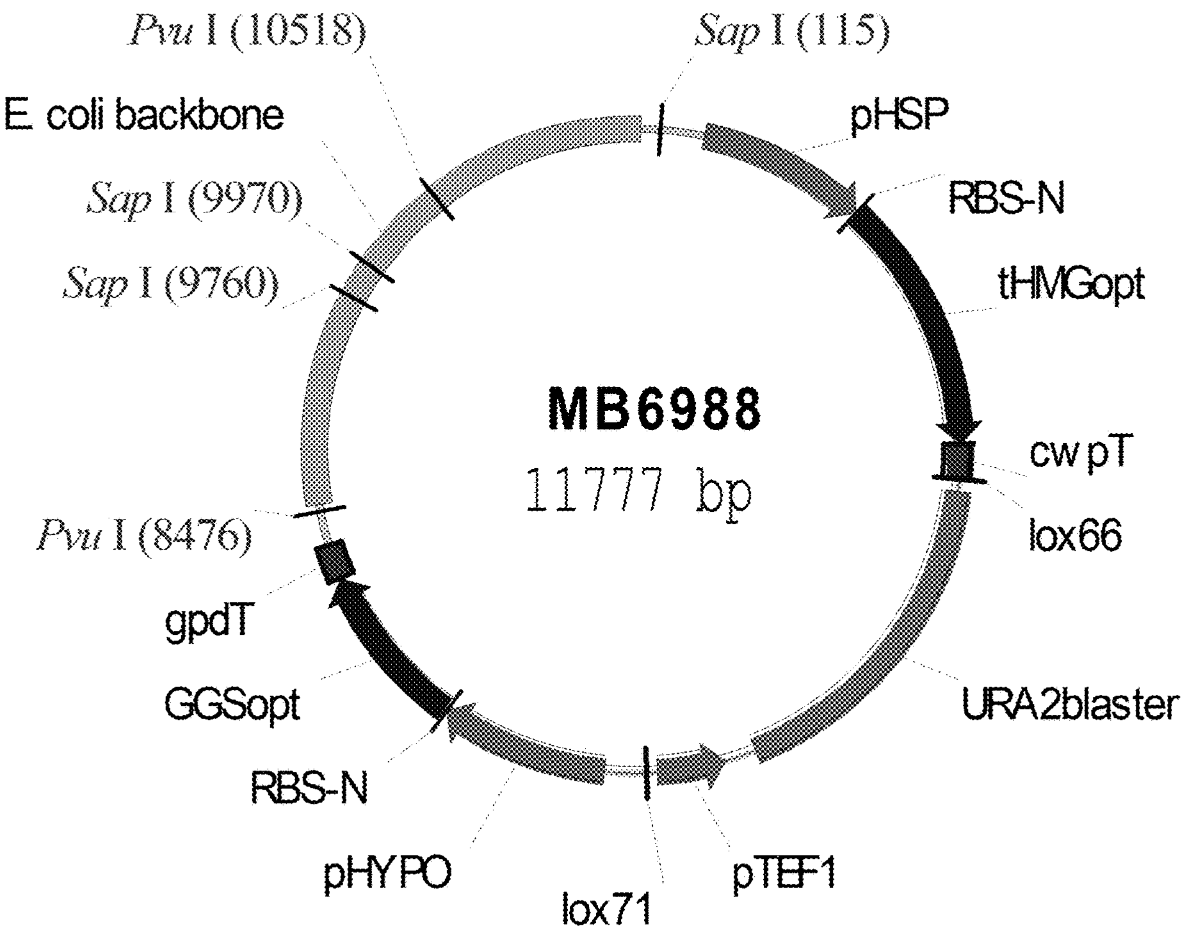
FIG. 22 sets out the map of plasmid MB6988, carrying genes tHMG and GGS FIG. 23 sets out the map of plasmid MB7044, carrying genes tCPS_SR, tKS_SR, KAH_4, KO_Gib and CPR_3.

2). a 9.1 kb fragment isolated by gel purification following PvuI/SapI digestion of plasmid MB6988 (FIG. 22). This construct encodes tHMGopt (SEQ ID NO: 75) linked to the pHSP promoter (SEQ ID NO: 63) and cwpT terminator (SEQ ID NO: 70), the lox-flanked URA2blaster prototrophic marker, and GGSopt (SEQ ID NO: 76) linked to the pHYPO promoter (SEQ ID NO: 64) and gpdT terminator (SEQ ID NO: 71). Strains were selected on YPD+100 ug/ml nourseothricin and replica plated to minimal medium lacking uracil. A nourseothricin resistant, uracil prototrophic isolate was denoted ML13490

Step 3. Strain ML13490 was struck to YPD and grown overnight and then struck to 5-FOA plates to allow for recombination mediated loss of the URA2 marker introduced in step 3 above. One selected 5-FOA resistant transformant was denoted ML13501.

Step 4. Strain ML13501 was transformed with a 9.1 kb fragment isolated by gel purification following PvuI/SapI digestion of plasmid MB6988 (FIG. 22). Transformants were selected on minimal medium lacking uracil. One selected uracil prototroph was denoted ML13724.

Figure 23:
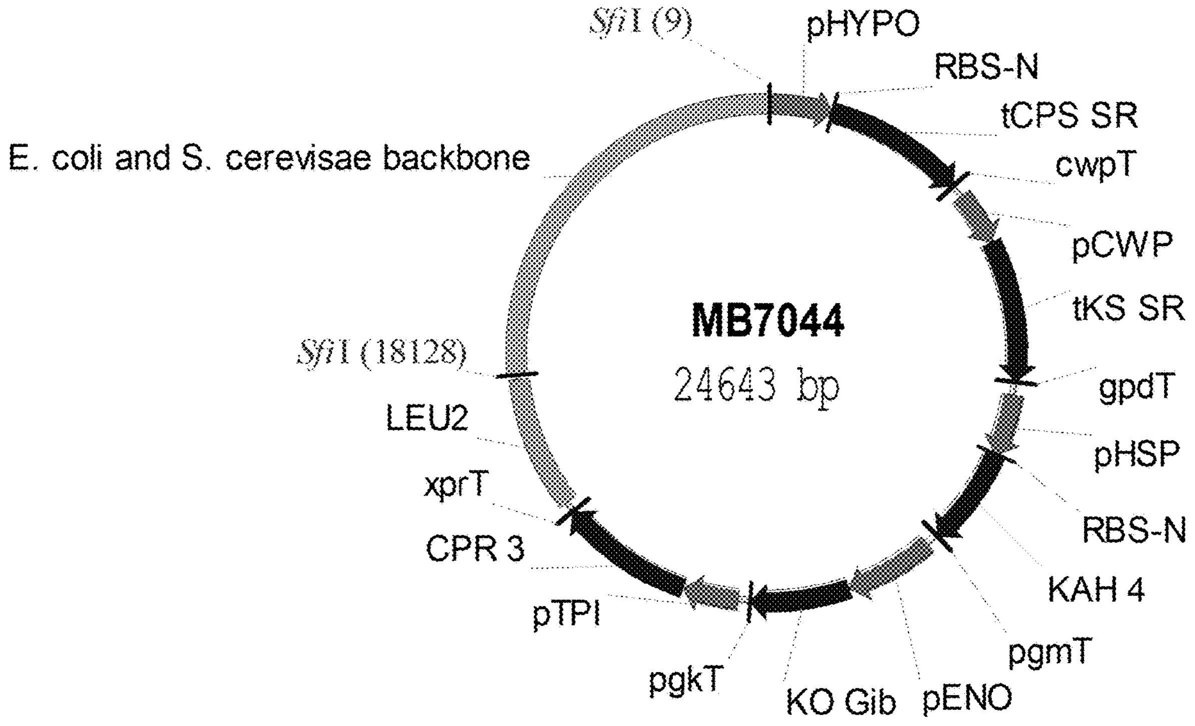

Step 5. Strain ML13724 was transformed with an 18.1 kb fragment isolated by gel purification following SfiI digestion of plasmid MB7044 (FIG. 23). MB7044 encodes the tCPS_SR (SEQ ID NO: 80) linked to the pHYPO promoter (SEQ ID NO: 64) and cwpT terminator (SEQ ID NO: 70), the tKS_SR (SEQ ID NO: 81) linked to the pCWP promoter (SEQ ID NO: 66) and gpdT terminator (SEQ ID NO: 70), the KAH_4 (SEQ ID NO: 82) linked to the pHSP promoter (SEQ ID NO: 63) and pgmT terminator (SEQ ID NO: 72), the KO_Gib (SEQ ID NO: 83) linked to the pENO promoter (SEQ ID NO: 65) and pgkT terminator (SEQ ID NO: 73), the CPR_3 (SEQ ID NO: 84) linked to the pTPI promoter (SEQ ID NO: 67) and xprT terminator (SEQ ID NO: 69) and the LEU2 locus. One selected rebaudioside A-producing transformant was denoted ML14044.

Step 6. Strain ML14044 was struck to YPD and grown overnight and then struck to 5-FOA plates to allow for recombination mediated loss of the URA2 marker introduced in Step 4 above. One selected 5'-FOA resistant transformant was denoted ML14076.

Figure 24:
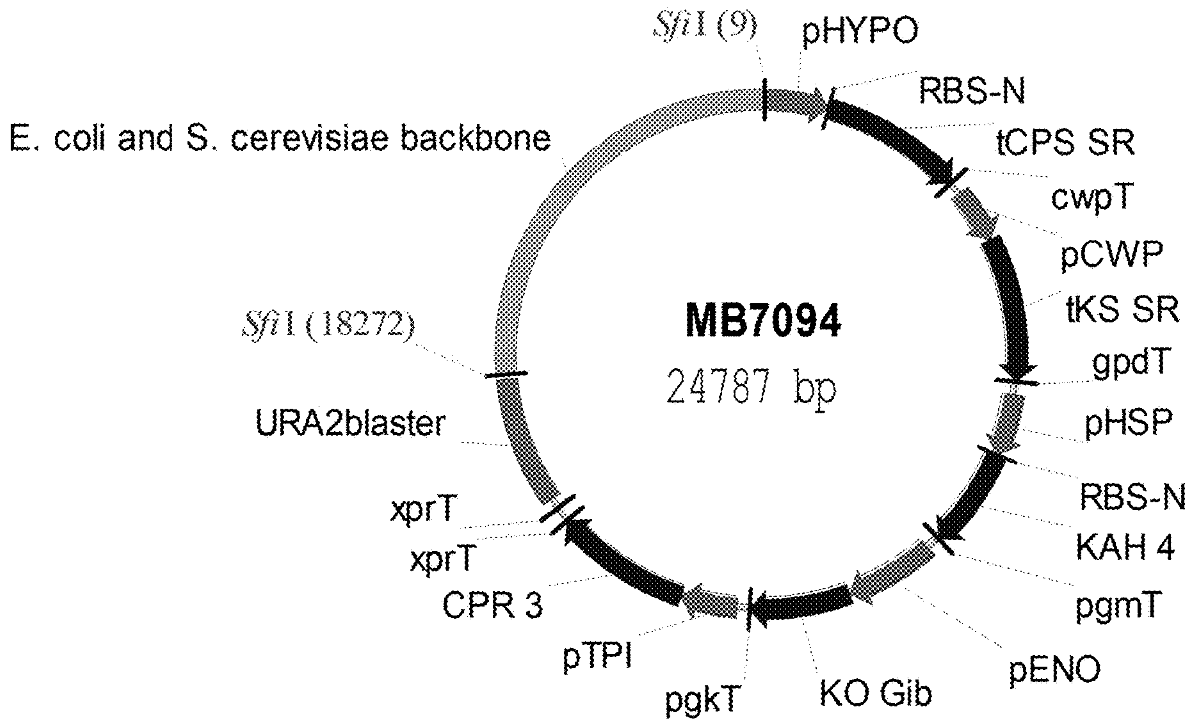
FIG. 24 sets out the map of plasmid MB7094, carrying genes tCPS_SR, tKS_SR, KAH_4, KO_Gib and CPR_3.

Step 7. Strain ML14076 was transformed with a 19.0 kb fragment isolated by gel purification following SfiI digestion of plasmid MB7094 (FIG. 24). MB7094 encodes the tCPS_SR (SEQ ID NO: 80) linked to the pHYPO promoter (SEQ ID NO: 64) and cwpT terminator (SEQ ID NO: 70), the tKS_SR (SEQ ID NO: 81) linked to the pCWP promoter (SEQ ID NO: 66) and gpdT terminator (SEQ ID NO: 71), the KAH_4 (SEQ ID NO: 82) linked to the pHSP promoter (SEQ ID NO: 63) and pgmT terminator (SEQ ID NO: 72), the KO_Gib (SEQ ID NO: 83) linked to the pENO promoter (SEQ ID NO: 65) and pgkT terminator (SEQ ID NO: 73), the CPR_3 (SEQ ID NO: 84) linked to the pTPI promoter (SEQ ID NO: 67) and xprT terminator (SEQ ID NO: 69) and URA2blaster prototrophic marker. Transformants were selected on minimal medium lacking uracil. One selected rebaudioside A producing uracil prototroph was denoted ML14087.

Example 13. Mating MATA and MATB Lineage and Selecting Steviol Glycoside-Producing Progeny Strains of opposite mating types (ML14094 and ML14087) with complementary nutritional deficiencies (ADE1+lys1- and ade1-LYS1+) were allowed to mate and then plated on selective media that would allow only diploids to grow (minimal media lacking both adenine and lysine). Diploid cells (ML14143) were then induced to undergo meiosis and sporulation by starvation, and the resulting haploid progenies were replica-plated to identify prototrophic isolates with hygromycin and nourseothricin resistance. One selected rebaudioside A-producing strain was denoted ML14737

Example 14. Making the Strain UGT2 1a-Free

Figure 25:
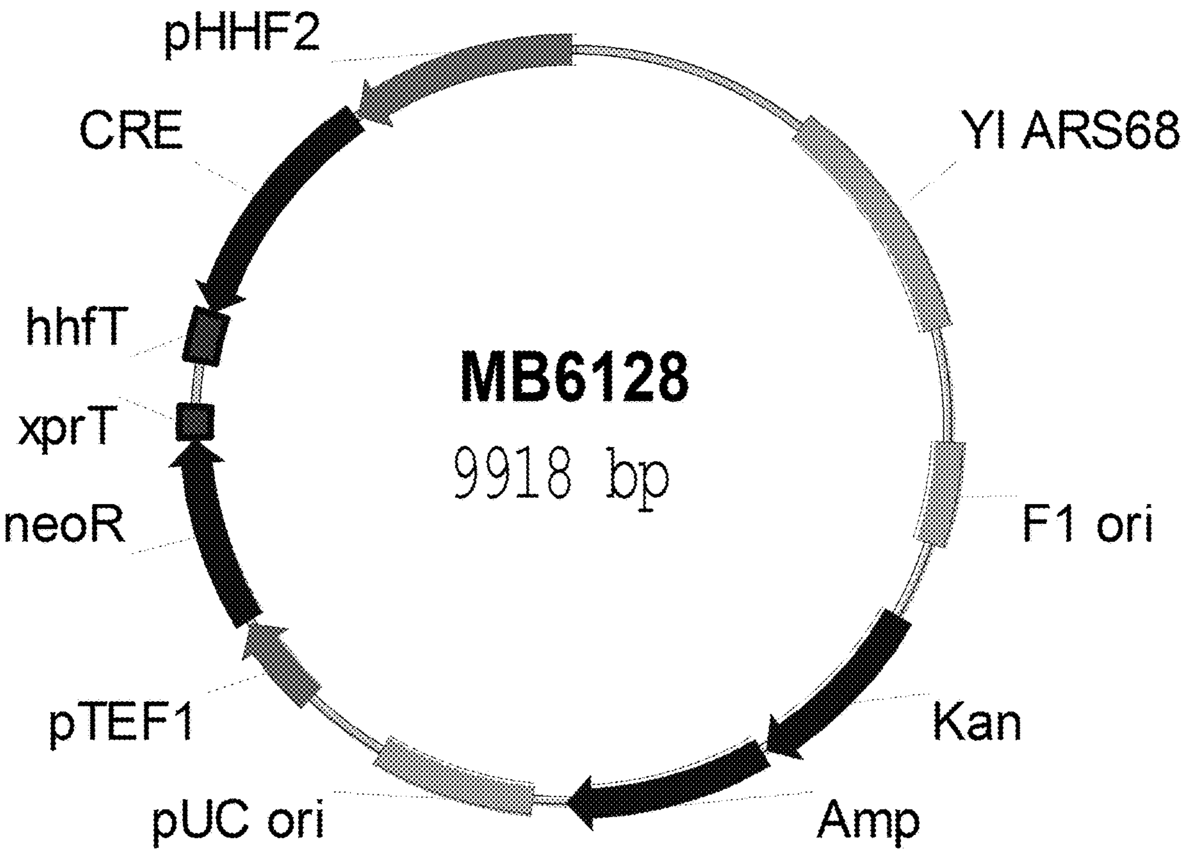
FIG. 25 sets out the map of plasmid MB6128, carrying CRE gene, which is used for removal of the antibiotic marker.

The hygromycin antibiotic marker and the nourseothricin antibiotic marker were removed from strain ML14737 after transformation with MB6128 (FIG. 25) which encodes a construct for constitutive overexpression of the CRE recombinase. CRE recombinase deletes the antibiotics markers by recombination over the Lox66 and Lox71 sites. An inactive Lox72 site is left in the genome (Güldener et al, 1996, Lambert et al, 2007). Plasmid MB6128 is a CEN plasmid which replicates episomally in *Yarrowia lipolytica* and which contains the CRE recombinase coding region under control of the native *Yarrowia lipolytica* pHHF promoter and hhfT terminator, and a neoR (encoding for G418 resistance) under the control of the native *Yarrowia lipolytica* pTEF1 promoter and xprT terminator. After selection of MB6128 transformants on YPD+G418 and screening for transformants that lost hygromycin and nourseothricin resistance by successful Cre-Lox recombination, the sensitive colonies were grown on non-selective medium to remove the MB6128 CEN plasmid (spontaneous loss of the CEN plasmid). The resulting antibiotic marker-free variant is denoted ML14869. This strain no longer produces rebaudioside A due to the loss of UGT2_1a along with the hygromycin resistance and produces the intermediate rubusoside instead.

Example 15. Transformation of UGT2 Genes

Figure 26:
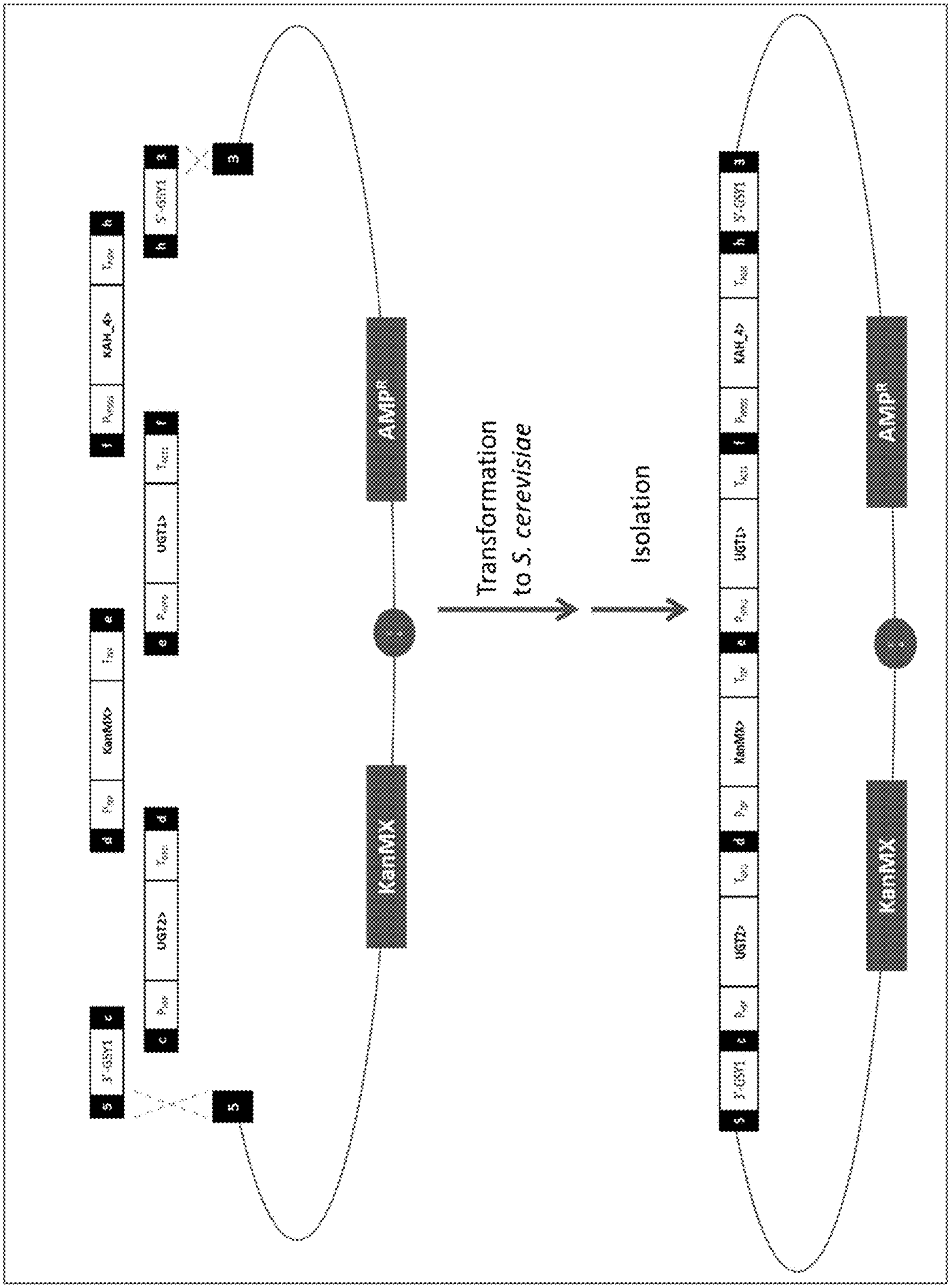
FIG. 26 sets out the method of assembly in a plasmid of genes UGT2, KanMX, UGT1 and KAH_4, flanked by gsyl integration flanks.

The UGT2 gene variants and UGT2_1a as control, were placed behind the *Yarrowia lipolytica* pHSP promoter (SEQ ID NO: 63) and combined with *Yarrowia lipolytica* terminator gpdT (SEQ ID NO: 71). Together with UGT1 (SEQ ID NO: 77), KAH_4 (SEQ ID NO: 82), the lox-flanked G418 resistance marker (KanMX) and *Yarrowia lipolytica* GSY1 integration flanks, each UGT2 was assembled into a construct on the CEN plasmid p417[5-3] in *Saccharomyces cerevisiae* (see FIG. 26).

TABLE 10

Promoters, ORFs and Terminators used in construction of strains with UGT2 variants

| Promoter | ORF | Terminator |
|---|---|---|
| pHSP (SEQ ID NO: 63) | UGT2 (SEQ ID NO: 5, 8, 13, 16, 19, 24, 26 and 29) | gpdT (SEQ ID NO: 71) |
| Ag_TEF1 | KanMX | Ag_TEF1 |
| pHYPO (SEQ ID NO: 64) | UGT1 (SEQ ID NO: 77) | act1T (SEQ ID NO: 74) |
| pYP001 (SEQ ID NO: 68) | KAH_4 (SEQ ID NO: 82) | pgmT (SEQ ID NO: 72) |

Figure 27:
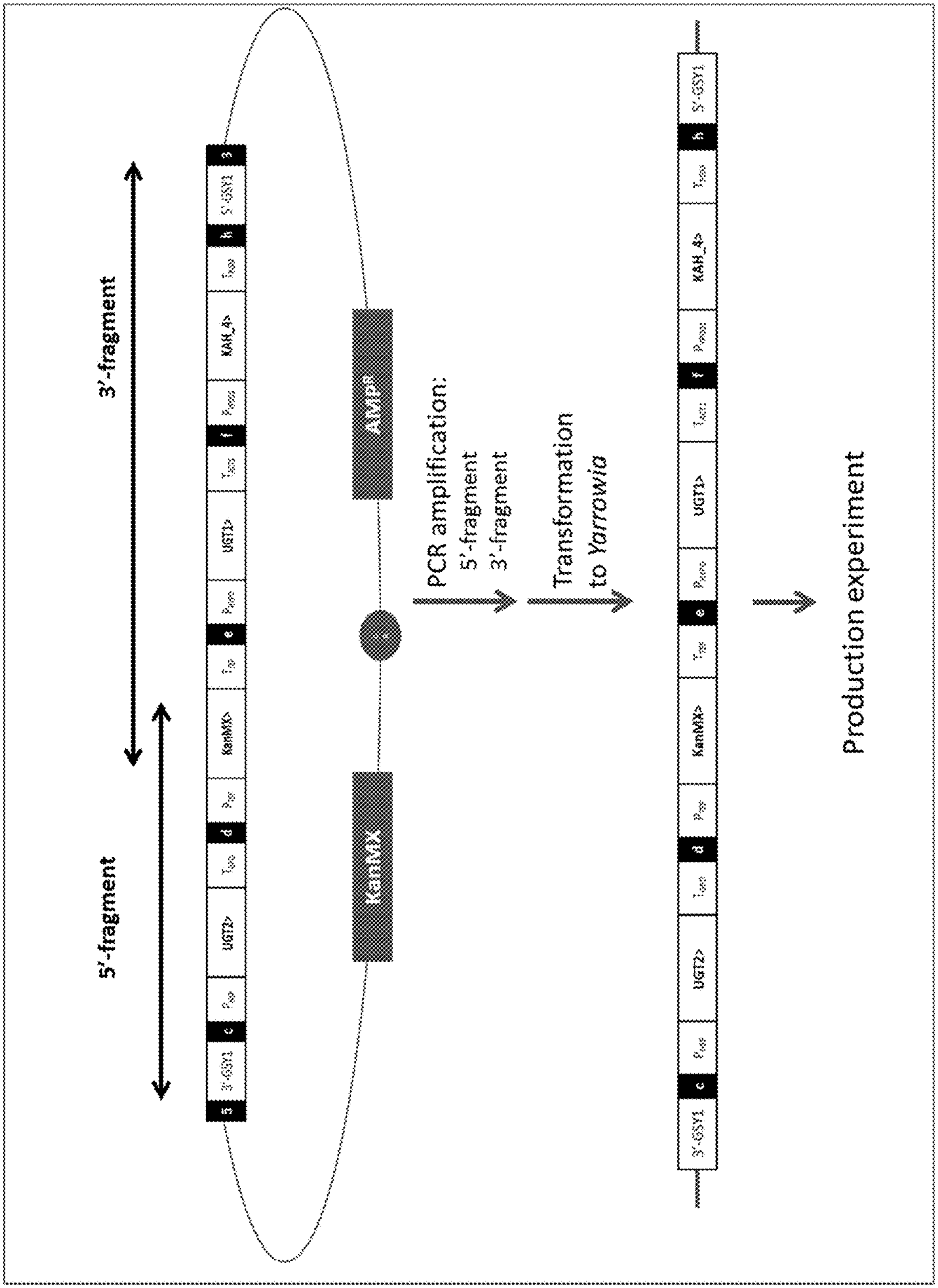
FIG. 27 sets out the method of amplification of the plasmid of FIG. 26, and transformation to *Yarrowia*.

These constructs, one for each UGT2, were used as template in PCRs to amplify the 5'-part and the 3'-part (see FIG. 27). This 5'-part consists of everything between the beginning of the 3'-GSY1 integration flank and the end of the KanMX open reading frame. The 3'-part consists of everything between the second codon of the KanMX open reading frame and the end of the 5'-GSY1 integration flank.

For the UGT2 testing each 5'-part and 3'-part combination was transformed to strain ML14869. Transformants were selected on YPD medium containing G418. From each transformation 12 colonies were selected for a production experiment.

Example 16. Production of RebA with *Y. lipolytica*

A pre-culture was inoculated with colony material from YEPh-D agar. The pre-culture was grown in 200 µl YEP with glucose as carbon source. The pre-culture was incubated 72 hours in an Infors incubator at 27° C., 750 rpm and 80% humidity. 40 µl of pre-culture was used to inoculate 2.5 ml YEP with glucose as carbon source. The main cultures were incubated 120 hours in an Infors incubator at 27° C., 550 rpm, 80% humidity. After 120 h the main culture was spun down at 2750 rpm for 10 min. From the supernatant 100 µl was taken and diluted 2.5 times in 55% acetonitrile. Further dilutions were made in 33% acetonitrile.

Figure 28:
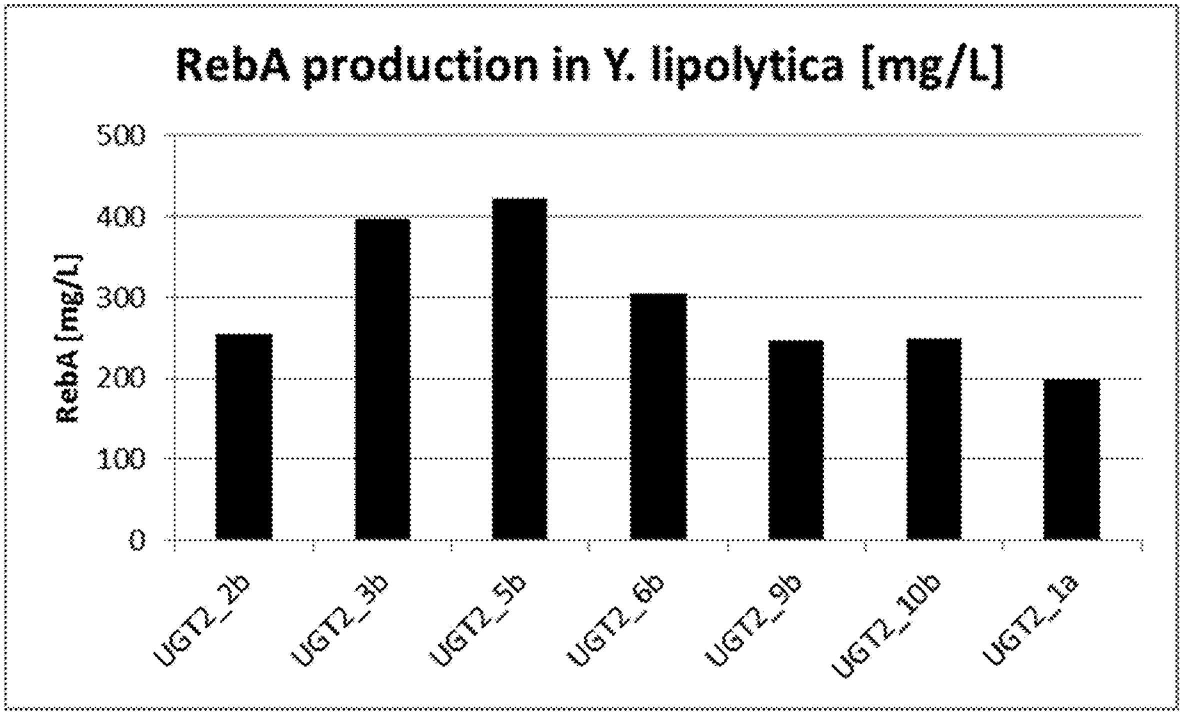
FIG. 28 sets out the production of rebaudioside A in *Yarrowia* strains expressing different variants of UGT2.

The results are set out in in FIG. 28 and Table 11. It can be seen that the strains that express the variant UGT2s produce higher titers of RebA.

TABLE 11

| Rebaudioside A production in *Yarrowia* strains expressing UGT2 variant enzymes | |
|---|---|
| Sample | RebA (mg/L) |
| UGT2_2b | 254 |
| UGT2_3b | 396 |
| UGT2_5b | 422 |
| UGT2_9b | 246 |
| UGT2_10b | 249 |
| UGT2_1a | 198 |

Example 17. Production of RebM with *Y. lipolytica*

A pre-culture was inoculated with colony material from YEPh-D agar. The pre-culture was grown in 200 µl YEP with glucose as carbon source. The pre-culture was incubated 72 hours in an Infors incubator at 27° C., 750 rpm and 80% humidity. 40 µl of pre-culture was used to inoculate 2.5 ml YEP with glucose as carbon source. The main cultures were incubated 120 hours in an Infors incubator at 27° C., 550 rpm, 80% humidity. After 120 h the main culture was spun down at 2750 rpm for 10 min. From the supernatant 100 µl was taken and diluted 2.5 times in 55% acetonitrile. Further dilutions were made in 33% acetonitrile.

Figure 29:
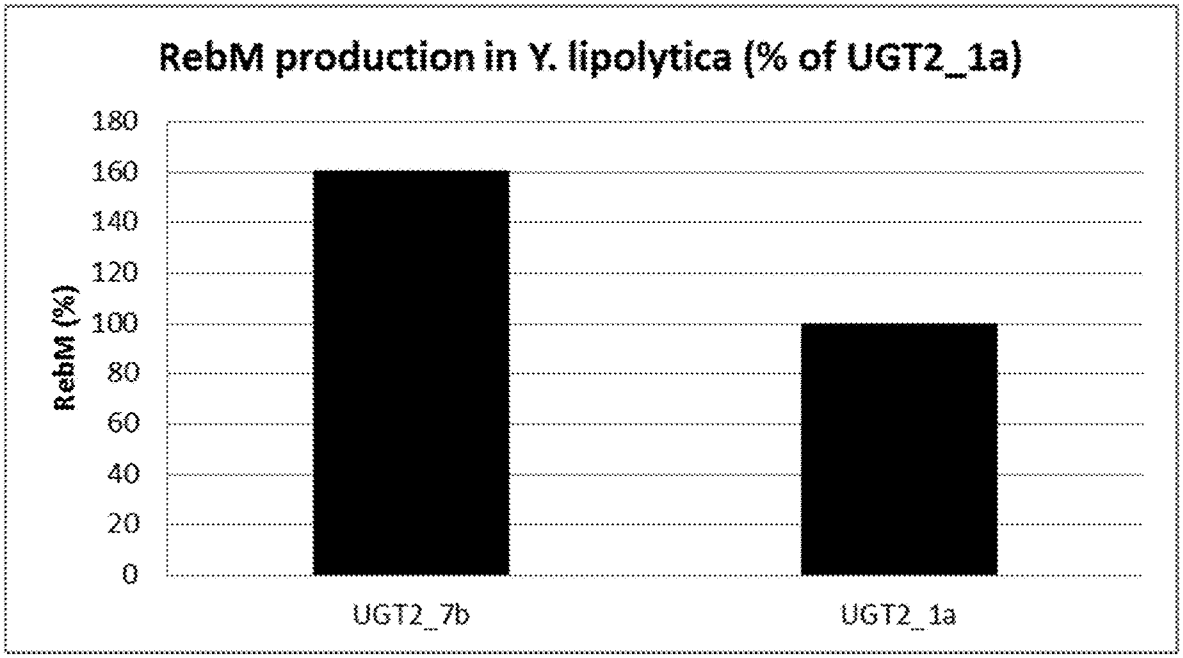

The results are set out in in FIG. 29 and Table 12. It can be seen that the strains that express the variant UGT2s produce higher titers of RebM.

TABLE 12

| Rebaudioside M production in *Yarrowia* strains expressing UGT2 variant enzymes | |
|---|---|
| Sample | RebM (mg/L) |
| UGT2_7b | 37.5 |
| UGT2_1a | 23.3 |

Example 18

In order to evaluate the effect of different variants of UGT2 on steviol glycoside production in bioreactors, two of the strains described in example 15 were selected. One strain expresses UGT2_6 b and the other strain expresses UGT2_7 b. The fermentation protocol applied was a fed-batch fermentation and whole broth samples were taken daily for the analysis of steviol glycosides with LC/MS.

Figure 30:
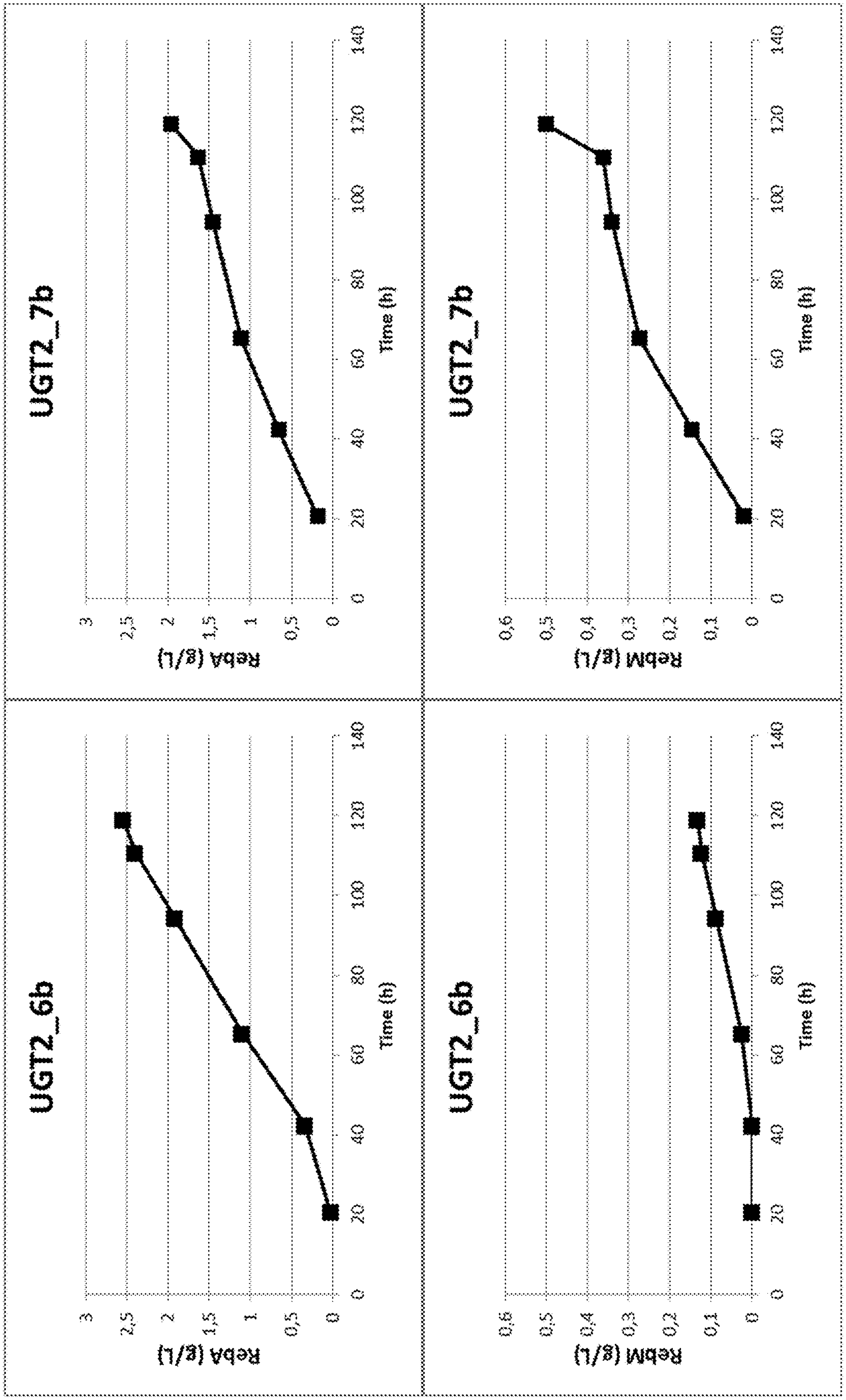
FIG. 30. RebA (top panels) and RebM (bottom panels) production in strains expressing either UGT2_6 b (left panels) or UGT2_7 b (right panels).

As can be seen in FIG. 30, the strain expressing UGT2_6 b makes more RebA compared to the strain expressing the UGT2_7 b. However, the strain expressing the UGT2_7 b produces substantially more RebM compared to the strain expressing the UGT2_6 b. Both strains make more RebA than RebM. At the end of the fermentation, with the strain expressing UGT2_6 b the RebA concentration is 20 fold higher than the RebM concentration, whereas in the strain expressing the UGT2_7 b, this is four fold higher. The different product ratio's reflect the intrinsic differences of the UGT2 properties, where the UGT2_7 b has a higher activity of glycosylation of the glucose on the 19-position compared to the UGT2_6 b. Products of the glycosylation reaction on the 19-position, such as RebE and RebD, from stevioside and RebA respectively, are further converted to RebM by the activity of UGT4, see FIG. 32.

This illustrates that production can be effectively steered to the product of interest by using the different variants of UGT2 here described.

TABLE 13

| Description of the sequence listing | |
|---|---|
| SEQ ID NO | Description |
| SEQ ID NO: 1 | UGT2_1b amino acid |
| SEQ ID NO: 2 | UGT2_1b CpO for *S. cerevisiae* |
| SEQ ID NO: 3 | UGT2_2b amino acid |
| SEQ ID NO: 4 | UGT2_2b CpO for *S. cerevisiae* |
| SEQ ID NO: 5 | UGT2_2b CpO for *Y. lipolitica* |
| SEQ ID NO: 6 | UGT2_3b amino acid |
| SEQ ID NO: 7 | UGT2_3b CpO for *S. cerevisiae* |
| SEQ ID NO: 8 | UGT2_3b CpO for *Y. lipolitica* |
| SEQ ID NO: 9 | UGT2_4b amino acid |
| SEQ ID NO: 10 | UGT2_4b CpO for *S. cerevisiae* |
| SEQ ID NO: 11 | UGT2_5b amino acid |
| SEQ ID NO: 12 | UGT2_5b CpO for *S. cerevisiae* |
| SEQ ID NO: 13 | UGT2_5b CpO for *Y. lipolitica* |
| SEQ ID NO: 14 | UGT2_6b amino acid |
| SEQ ID NO: 15 | UGT2_6b CpO for *S. cerevisiae* |
| SEQ ID NO: 16 | UGT2_6b CpO for *Y. lipolitica* |
| SEQ ID NO: 17 | UGT2_7b amino acid |
| SEQ ID NO: 18 | UGT2_7b CpO for *S. cerevisiae* |
| SEQ ID NO: 19 | UGT2_7b CpO for *Y. lipolitica* |
| SEQ ID NO: 20 | UGT2_8b amino acid |
| SEQ ID NO: 21 | UGT2_8b CpO for *S. cerevisiae* |
| SEQ ID NO: 22 | UGT2_9b amino acid |
| SEQ ID NO: 23 | UGT2_9b CpO for *S. cerevisiae* |
| SEQ ID NO: 24 | UGT2_9b CpO for *Y. lipolitica* |
| SEQ ID NO: 25 | UGT2_10b amino acid |
| SEQ ID NO: 26 | UGT2_10b CpO for *Y. lipolitica* |
| SEQ ID NO: 27 | UGT2_1a amino acid |
| SEQ ID NO: 28 | UGT2_1a CpO for *S. cerevisiae* |
| SEQ ID NO: 29 | UGT2_1a CpO for *Y. lipolitica* |
| SEQ ID NO: 30 | Eno2 promoter from *S. cerevisiae* |
| SEQ ID NO: 31 | ERG20 nucleic acid from *S. cerevisiae* |
| SEQ ID NO: 32 | Adh1 terminator from *S. cerevisiae* |
| SEQ ID NO: 33 | Fba1 promoter from *S. cerevisiae* |
| SEQ ID NO: 34 | tHMG nucleic acid from *S. cerevisiae* |
| SEQ ID NO: 35 | Adh2 terminator from *S. cerevisiae* |
| SEQ ID NO: 36 | Tef1 promoter from *S. cerevisiae* |
| SEQ ID NO: 37 | BTS1 nucleic acid from *S. cerevisiae* |
| SEQ ID NO: 38 | Gmp1 terminator from *S. cerevisiae* |
| SEQ ID NO: 39 | Pgk1 promoter from *S. cerevisiae* |
| SEQ ID NO: 40 | KI prom 12 promoter |
| SEQ ID NO: 41 | trCPS from *S. rebaudiana* CpO for *S. cerevisiae* |
| SEQ ID NO: 42 | trKS from *S. rebaudiana* CpO for *S. cerevisiae* |
| SEQ ID NO: 43 | TAL1 terminator from *S. cerevisiae* |
| SEQ ID NO: 44 | KO from *Giberella fujikuroi* CpO for S. |
| SEQ ID NO: 45 | Tpi1 terminator from *S. cerevisiae* |
| SEQ ID NO: 46 | Ag lox_TEF1.pro nucleic acid construct |
| SEQ ID NO: 47 | KANMX ORF CpO for *S. cerevisiae* |
| SEQ ID NO: 48 | Ag Tef1_lox.ter nucleic acid construct |
| SEQ ID NO: 49 | KAH_4 from *Arabidopsis thaliana* CpO for *S. cerevisiae* |
| SEQ ID NO: 50 | KI prom 6.pro promoter |
| SEQ ID NO: 51 | CPR_3 from *Arabidopsis thaliana* CpO for *S. cerevisiae* |
| SEQ ID NO: 52 | Pdc1 terminator from *S. cerevisiae* |
| SEQ ID NO: 53 | KI prom3 promoter |
| SEQ ID NO: 54 | UGT1 from *S. rebaudiana* CpO for *S. cerevisiae* |
| SEQ ID NO: 55 | Tdh1 terminator from *S. cerevisiae* |
| SEQ ID NO: 56 | KI prom 2 promoter |
| SEQ ID NO: 57 | UGT3 from *S. rebaudiana* CpO for *S. cerevisiae* |
| SEQ ID NO: 58 | UGT4 from *S. rebaudiana* CpO for *S. cerevisiae* |
| SEQ ID NO: 59 | Eno1 terminator from *S. cerevisiae* |
| SEQ ID NO: 60 | Eno1 promoter from *S. cerevisiae* |
| SEQ ID NO: 61 | Gap1T promoter from *K. lactis* |
| SEQ ID NO: 62 | PGM promoter from *Y. lipolitica* |
| SEQ ID NO: 63 | HSP promoter from *Y. lipolitica* |
| SEQ ID NO: 64 | HYPO promoter from *Y. lipolitica* |
| SEQ ID NO: 65 | ENO promoter from *Y. lipolitica* |
| SEQ ID NO: 66 | CWP promoter from *Y. lipolitica* |
| SEQ ID NO: 67 | TPI promoter from *Y. lipolitica* |
| SEQ ID NO: 68 | YP001 promoter from *Y. lipolitica* |
| SEQ ID NO: 69 | Xpr terminator from *Y. lipolitica* |
| SEQ ID NO: 70 | Cwp terminator from *Y. lipolitica* |
| SEQ ID NO: 71 | Gpd terminator from *Y. lipolitica* |
| SEQ ID NO: 72 | Pgm terminator from *Y. lipolitica* |
| SEQ ID NO: 73 | Pgk terminator from *Y. lipolitica* |
| SEQ ID NO: 74 | act1T terminator from *Y. lipolitica* |

TABLE 13-continued

Description of the sequence listing

| SEQ ID NO | Description |
|---|---|
| SEQ ID NO: 75 | tHMG CpO for *Y. lipolitica* |
| SEQ ID NO: 76 | GGS CpO for *Y. lipolitica* |
| SEQ ID NO: 77 | UGT1 CpO for *Y. lipolitica* |
| SEQ ID NO: 78 | UGT3 CpO for *Y. lipolitica* |
| SEQ ID NO: 79 | UGT4 CpO for *Y. lipolitica* |
| SEQ ID NO: 80 | tCPS from *S. rebaudiana* CpO for *Y. lipolitica* |
| SEQ ID NO: 81 | tKS from *S. rebaudiana* CpO for *Y. lipolitica* |
| SEQ ID NO: 82 | KAH_4 CpO for *Y. lipolitica* |
| SEQ ID NO: 83 | KO from *Gibberella fujikori* CpO for *Y. lipolitica* |
| SEQ ID NO: 84 | CPR_3 CpO for *Y. lipolitica* |

The invention claimed is:

1. A recombinant host comprising a recombinant nucleic acid sequence encoding a polypeptide having at least:

a. 91% identity to the amino acid sequence set forth in SEQ ID NO:1;
b. 92% identity to the amino acid sequence set forth in SEQ ID NO:3;
c. 92% identity to the amino acid sequence set forth in SEQ ID NO:6;
d. 91% identity to the amino acid sequence set forth in SEQ ID NO:9;
e. 92% identity to the amino acid sequence set forth in SEQ ID NO:11;
f. 89% identity to the amino acid sequence set forth in SEQ ID NO:14;
g. 88% identity to the amino acid sequence set forth in SEQ ID NO:20; or
h. 89% identity to the amino acid sequence set forth in SEQ ID NO:22.

2. The recombinant host according to claim 1 which is capable of producing a glycosylated diterpene.

3. The recombinant host according to claim 1, further comprising one or more recombinant nucleotide sequence(s) encoding:

a polypeptide having ent-copalyl pyrophosphate synthase activity;
a polypeptide having ent-Kaurene synthase activity;
a polypeptide having ent-Kaurene oxidase activity; and
a polypeptide having kaurenoic acid 13-hydroxylase activity.

4. The recombinant host according to claim 1, which comprises a recombinant nucleic acid sequence encoding a polypeptide having NADPH-cytochrome p450 reductase activity.

5. The recombinant host according to claim 1 which comprises a recombinant nucleic acid sequence encoding one or more of:

(i) a polypeptide having UGT74G1 (UGT3) activity;
(ii) a polypeptide having UGT85C2 (UGT1) activity; and
(iii) a polypeptide having UGT76G1 (UGT4) activity.

6. The recombinant host according to claim 1 which comprises a recombinant nucleic acid sequence encoding an additional polypeptide having UGT2 activity.

7. The recombinant host according to claim 1, wherein the host belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia, Yamadazyma*, or *Escherichia*.

8. The recombinant host according to claim 7, wherein the recombinant host is a *Saccharomyces cerevisiae* cell, a *Yarrowia lipolytica* cell, a *Candida krusei* cell, an *Issatchenkia orientalis* or an *Escherichia coli* cell.

9. The recombinant host according to claim 1, wherein the ability of the host to produce geranylgeranyl diphosphate (GGPP) is upregulated.

10. The recombinant host according to claim 1, comprising one or more recombinant nucleic acid sequence(s) encoding hydroxymethylglutaryl-CoA reductase, farnesyl-pyrophosphate synthetase and geranylgeranyl diphosphate synthase.

11. The recombinant host according to claim 1 which comprises a nucleic acid sequence encoding one or more of:

a polypeptide having hydroxymethylglutaryl-CoA reductase activity;
a polypeptide having farnesyl-pyrophosphate synthetase activity; and
a polypeptide having geranylgeranyl diphosphate synthase activity.

12. A process for the preparation of a glycosylated diterpene which comprises fermenting the recombinant host according to claim 2 in a suitable fermentation medium, and optionally recovering the glycosylated diterpene.

13. A method for converting a first glycosylated diterpene into a second glycosylated diterpene, which method comprises:

contacting said first glycosylated diterpene with:
a recombinant host comprising a recombinant nucleic acid sequence encoding a polypeptide having at least:
a. 91% identity to the amino acid sequence set forth in SEQ ID NO:1;
b. 92% identity to the amino acid sequence set forth in SEQ ID NO:3;
c. 92% identity to the amino acid sequence set forth in SEQ ID NO:6;
d. 91% identity to the amino acid sequence set forth in SEQ ID NO:9;
e. 92% identity to the amino acid sequence set forth in SEQ ID NO:11;
f. 89% identity to the amino acid sequence set forth in SEQ ID NO:14;
g. 88% identity to the amino acid sequence set forth in SEQ ID NO:20; or
h. 89% identity to the amino acid sequence set forth in SEQ ID NO:22;
a cell free extract derived from such a recombinant host, or an enzyme preparation derived from either thereof;
thereby to convert the first glycosylated diterpene into the second glycosylated diterpene.

14. The method according to claim 13, wherein the second glycosylated diterpene is steviol-19-diside, steviolbioside, stevioside, RebE, RebD or 13-[(β-D-Glucopyranosyl)oxy)kaur-16-en-18-oic acid 2-O-β-D-glucopyranosyl-β-D-glucopyranosyl ester.

15. The method according to claim 14, wherein the first glycosylated diterpene is steviol-13-monoside, steviol-19-monoside, rubusoside, stevioside, rebaudioside A or 13-[(β-D-Glucopyranosyl)oxy)kaur-16-en-18-oic acid 2-O-β-D-glucopyranosyl-β-D-glucopyranosyl ester and the second glycosylated diterpene is steviol-19-diside, steviolbioside, stevioside, RebE, RebD or 13-[(β-D-Glucopyranosyl)oxy)kaur-16-en-18-oic acid 2-O-β-D-glucopyranosyl-β-D-glucopyranosyl ester.

16. A nucleic acid construct comprising a polynucleotide sequence encoding a polypeptide having at least:

a. 91% identity to the amino acid sequence set forth in SEQ ID NO:1;
b. 92% identity to the amino acid sequence set forth in SEQ ID NO:3;
c. 92% identity to the amino acid sequence set forth in SEQ ID NO:6;
d. 91% identity to the amino acid sequence set forth in SEQ ID NO:9;
e. 92% identity to the amino acid sequence set forth in SEQ ID NO:11;
f. 89% identity to the amino acid sequence set forth in SEQ ID NO:14;
g. 88% identity to the amino acid sequence set forth in SEQ ID NO:20; or
h. 89% identity to the amino acid sequence set forth in SEQ ID NO:22.

17. The nucleic acid construct according to claim 16 which is an expression vector, wherein the polynucleotide sequence is operably linked to at least one control sequence for the expression of the polynucleotide sequence in a host cell.

18. A method of producing the nucleic acid construct of claim 16, comprising:
(i) cultivating a recombinant host cell comprising a recombinant nucleic acid sequence encoding a polypeptide having at least about:
a. 91% identity to the amino acid sequence set forth in SEQ ID NO:1;
b. 92% identity to the amino acid sequence set forth in SEQ ID NO:3;
c. 92% identity to the amino acid sequence set forth in SEQ ID NO:6;
d. 91% identity to the amino acid sequence set forth in SEQ ID NO:9;
e. 92% identity to the amino acid sequence set forth in SEQ ID NO:11;
f. 89% identity to the amino acid sequence set forth in SEQ ID NO:14;
g. 88% identity to the amino acid sequence set forth in SEQ ID NO:20; or
h. 89% identity to the amino acid sequence set forth in SEQ ID NO:22;
under conditions conducive to the production of the nucleic acid construct by the host cell, and optionally,
(ii) recovering the nucleic acid construct.

19. The recombinant host of claim 1, wherein the recombinant nucleic acid sequence encodes a polypeptide having at least 91% identity to the amino acid sequence set forth in SEQ ID NO:1.

20. The recombinant host of claim 1, wherein the recombinant nucleic acid sequence encodes a polypeptide having at least 92% identity to the amino acid sequence set forth in SEQ ID NO:3.

21. The recombinant host of claim 1, wherein the recombinant nucleic acid sequence encodes a polypeptide having at least 92% identity to the amino acid sequence set forth in SEQ ID NO:6.

22. The recombinant host of claim 1, wherein the recombinant nucleic acid sequence encodes a polypeptide having at least 91% identity to the amino acid sequence set forth in SEQ ID NO:9.

23. The recombinant host of claim 1, wherein the recombinant nucleic acid sequence encodes a polypeptide having at least 92% identity to the amino acid sequence set forth in SEQ ID NO:11.

24. The recombinant host of claim 1, wherein the recombinant nucleic acid sequence encodes a polypeptide having at least 89% identity to the amino acid sequence set forth in SEQ ID NO:14.

25. The recombinant host of claim 1, wherein the recombinant nucleic acid sequence encodes a polypeptide having at least 88% identity to the amino acid sequence set forth in SEQ ID NO:20.

26. The recombinant host of claim 1, wherein the recombinant nucleic acid sequence encodes a polypeptide having at least 89% identity to the amino acid sequence set forth in SEQ ID NO:22.

27. The method of claim 13, wherein the recombinant nucleic acid sequence encodes a polypeptide having at least 91% identity to the amino acid sequence set forth in SEQ ID NO:1.

28. The method of claim 13, wherein the recombinant nucleic acid sequence encodes a polypeptide having at least 92% identity to the amino acid sequence set forth in SEQ ID NO:3.

29. The method of claim 13, wherein the recombinant nucleic acid sequence encodes a polypeptide having at least 92% identity to the amino acid sequence set forth in SEQ ID NO:6.

30. The method of claim 13, wherein the recombinant nucleic acid sequence encodes a polypeptide having at least 91% identity to the amino acid sequence set forth in SEQ ID NO:9.

31. The method of claim 13, wherein the recombinant nucleic acid sequence encodes a polypeptide having at least 92% identity to the amino acid sequence set forth in SEQ ID NO:11.

32. The method of claim 13, wherein the recombinant nucleic acid sequence encodes a polypeptide having at least 89% identity to the amino acid sequence set forth in SEQ ID NO:14.

33. The method of claim 13, wherein the recombinant nucleic acid sequence encodes a polypeptide having at least 88% identity to the amino acid sequence set forth in SEQ ID NO:20.

34. The method of claim 13, wherein the recombinant nucleic acid sequence encodes a polypeptide having at least 89% identity to the amino acid sequence set forth in SEQ ID NO:22.

* * * * *